US009732322B2

(12) United States Patent
Dalton et al.

(10) Patent No.: US 9,732,322 B2
(45) Date of Patent: Aug. 15, 2017

(54) COMPOSITIONS FOR MESODERM DERIVED ISL1+ MULTIPOTENT CELLS (IMPS), EPICARDIAL PROGENITOR CELLS (EPCS) AND MULTIPOTENT C56C CELLS (C56CS) AND METHODS OF PRODUCING AND USING SAME

(71) Applicant: UNIVERSITY OF GEORGIA RESEARCH FOUNDATION, INC., Athens, GA (US)

(72) Inventors: Stephen Dalton, Athens, GA (US); David Reynolds, Kilsyth (AU)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 14/965,222

(22) Filed: Dec. 10, 2015

(65) Prior Publication Data
US 2016/0186140 A1    Jun. 30, 2016

Related U.S. Application Data

(60) Division of application No. 13/012,862, filed on Jan. 25, 2011, now abandoned, which is a continuation-in-part of application No. PCT/US2009/004334, filed on Jul. 27, 2009.

(60) Provisional application No. 61/137,058, filed on Jul. 25, 2008, provisional application No. 61/198,861, filed on Nov. 10, 2008, provisional application No. 61/215,621, filed on May 7, 2009, provisional application No. 61/385,641, filed on Sep. 23, 2010.

(51) Int. Cl.
*C12N 5/077* (2010.01)
*A61K 35/12* (2015.01)
*A61P 9/00* (2006.01)
*C12N 5/071* (2010.01)
*C12N 5/0735* (2010.01)
*C12N 5/0775* (2010.01)

(52) U.S. Cl.
CPC ......... *C12N 5/0657* (2013.01); *C12N 5/0606* (2013.01); *C12N 5/069* (2013.01); *C12N 5/0656* (2013.01); *C12N 5/0661* (2013.01); *C12N 5/0662* (2013.01); *C12N 5/0692* (2013.01); C12N 2501/105 (2013.01); C12N 2501/11 (2013.01); C12N 2501/115 (2013.01); C12N 2501/155 (2013.01); C12N 2501/16 (2013.01); C12N 2501/165 (2013.01); C12N 2501/195 (2013.01); C12N 2501/415 (2013.01); C12N 2501/727 (2013.01); C12N 2502/13 (2013.01); C12N 2506/02 (2013.01); C12N 2506/45 (2013.01); C12N 2533/78 (2013.01); C12N 2533/90 (2013.01)

(58) Field of Classification Search
CPC .. C12N 5/0657; C12N 5/0606; C12N 5/0656; C12N 5/0661; C12N 5/0662; C12N 5/069; C12N 5/0692; C12N 2501/105; C12N 2501/11; C12N 2501/115; C12N 2501/155; C12N 2501/16; C12N 2501/165; C12N 2501/195; C12N 2501/415; C12N 2501/727; C12N 2502/13; C12N 2506/02; C12N 2506/45; C12N 2533/78; C12N 2533/90
See application file for complete search history.

(56) References Cited

U.S. PATENT DOCUMENTS

| | | | |
|---|---|---|---|
| 4,557,264 A | 12/1985 | Hinsch | |
| 5,567,612 A | 10/1996 | Vacanti et al. | |
| 5,759,830 A | 6/1998 | Vacanti et al. | |
| 5,770,417 A | 6/1998 | Vacanti et al. | |
| 5,843,780 A | 12/1998 | Thomson | |
| 6,022,743 A | 2/2000 | Naughton et al. | |
| 6,306,424 B1 | 10/2001 | Vyakarnam et al. | |
| 6,331,298 B1 | 12/2001 | Ferguson et al. | |
| 6,333,029 B1 | 12/2001 | Vyakarnam et al. | |
| 6,365,149 B2 | 4/2002 | Vyakarnam et al. | |
| 6,509,369 B2 | 1/2003 | Scott et al. | |
| 6,534,084 B1 | 3/2003 | Vyakarnam et al. | |
| 6,599,323 B2 | 7/2003 | Melican et al. | |
| 6,626,950 B2 | 9/2003 | Brown et al. | |
| 6,642,048 B2 | 11/2003 | Xu et al. | |
| 6,656,488 B2 | 12/2003 | Yi et al. | |
| 6,793,945 B2 | 9/2004 | Bathurst et al. | |

(Continued)

FOREIGN PATENT DOCUMENTS

WO    2005014799 A1    2/2005
WO    2005065354 A2    7/2005
(Continued)

OTHER PUBLICATIONS

Cao et al. J. of Exp. Zoo., 311A: 368-376, 2009.*
(Continued)

Primary Examiner — Thaian N Ton
(74) Attorney, Agent, or Firm — Henry D. Coleman; R. Neil Sudol

(57) ABSTRACT

The present invention relates to inter alia, methods for the generation and maintenance of Mesoderm-derived ISL1+ Multipotent Progenitors (IMPs), the production of a number of pluripotent cells including and epicardial pluripotent cells (EPCs) and using these cells to produce endothelial cells, cardiomyocytes, smooth muscle cells, vascular cells and other cells and related methods as otherwise disclosed herein. The invention also relates to compositions comprising a population of cells.

3 Claims, 97 Drawing Sheets

(56) References Cited

U.S. PATENT DOCUMENTS

| | | | |
|---|---|---|---|
| 7,740,850 | B2 | 6/2010 | Zhu et al. |
| 2002/0072117 | A1 | 6/2002 | Xu et al. |
| 2004/0062753 | A1 | 4/2004 | Rezania et al. |
| 2004/0132729 | A1 | 7/2004 | Salituro et al. |
| 2004/0171623 | A1 | 9/2004 | Reynolds et al. |
| 2004/0209901 | A1 | 10/2004 | Adams et al. |
| 2004/0220393 | A1 | 11/2004 | Ward et al. |
| 2005/0148070 | A1 | 7/2005 | Thomson et al. |
| 2005/0233446 | A1 | 10/2005 | Parsons et al. |
| 2006/0030042 | A1 | 2/2006 | Brivanlou et al. |
| 2006/0246446 | A1 | 11/2006 | Evans et al. |
| 2007/0010011 | A1 | 1/2007 | Parsons et al. |
| 2009/0298169 | A1 | 12/2009 | Dalton et al. |
| 2010/0166713 | A1 | 7/2010 | Dalton et al. |

FOREIGN PATENT DOCUMENTS

| | | | |
|---|---|---|---|
| WO | 2006020919 | A2 | 2/2006 |
| WO | 2005086845 | A2 | 9/2006 |
| WO | 2007070964 | A1 | 6/2007 |
| WO | 2007143193 | A1 | 12/2007 |
| WO | 2008094597 | A2 | 8/2008 |

OTHER PUBLICATIONS

Breviniet al. Theriogenology, 74: 544-550, 2010.*
Paris et al. Theriogenology, 74: 516-524, 2010.*
Shiraki et al, Genes to Cells, 13:731-746, 2008.*
Wobus et al. (1997) J MoL Cell Cardiology 29:1525.*
Xu et al. (2002) Circulation Research 91:50.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Meijer et al., Trends in Pharmacological Sciences, 25(9): 471-480, 2004.*
Sato et al., Nature Med, 10(1): 55-63, 2004.*
Mikels et al., Oncogene, 25: 7461-7468, 2006.*
Dravid et al., Stem Cells, 23: 1489-1501, 2005.*
Ducy et al., Kidney International, 57: 2207-2214, 2000.*
Shimasaki et al., Endocrine Reviews, 25(1): 72-101, 2004.*
Laugwitz, et al. Nature, 2005;433:647-653 and Supplemental Table 2.
Nakano A, et al. Multipotent islet-1 cardiovascular progenitors in development and disease. Cold Spring Harbor Symposia on Quantitative Biology, 2008;73:297-306.
Schuldiner M, et al. Effects of Eight Growth Factors on the Differentiation of Cells Derived from Human Embryonic Stem Cells. Proceedings of the National Academy of Sciences USA, 2000;97:11307-11312.
Moretti A, et al. Multipotent embryonic Isl 1+ progenitor cells lead to cardiac, smooth muscle, and endothelial cell diversification. Cell, 2006;127:1151-1165.
Qyang Y, et al. The renewal and differentiation of Isl1+ cardiovascular progenitors are controlled by a Wnt/b-catenin pathway. Cell Stem Cell, 2007;1:165-179.
Stewart R, et al. Mechanisms of self-renewal in human embryonic stem cells. European Journal of Cancer, 2006;42:1257-1272.
Abu-Issa R, Kirby ML. Heart field: from mesoderm to heart tube. Annu Rev Cell Dev Biol, 2007;23:45-68.
Rossant J, Tam PP. Emerging asymmetry and embryonic patterning in early mouse development. Dev Cell, 2004;7:155-164.
Tam PP, et al. The allocation of epiblast cells to the embryonic heart and other mesodermal lineages: the role of ingression and tissue movement during gastrulation. Development, 1997;124:1631-1642.
Buckingham M, et al. Building the mammalian heart from two sources of myocardial cells. Nat Rev Genet, 2005;6:826-835.
Kelly RG, Buckingham ME. The anterior heart-forming field: voyage to the arterial pole of the heart. Trenda Genet, 2002;18:210-216.

Yang L, et al. Isl1Cre reveals a common Bmp pathway in heart and limb development. Development, 2006;133:1575-1585.
Laugwitz KL, et al. Islet1 cardiovascular progenitors: a single source for heart lineages? Development, 2008;135:193-205.
Manner J, et al. The origin, formation and developmental significance of the epicardium: a review. Cells Tissues Organs, 2001;169:89-103.
Olivey HE, et al. Coronary vessel development: the epicardium delivers. Trends Cardiovasc Med, 2004;14:247-251.
Mommersteeg MT, et al. The sinus venosus progenitors separate and and diversify from the first and second heart fields early in development. Cardiovasc Res, 2010;87:92-101.
Van Wijk B, et al. Epicardium and myocardium separate from a common precursor pool by crosstalk between bone morphogenetic protein- and fibroblast growth factor-signaling pathways. Circ Res, 2009;105:431-441.
Dettman RW, et al. Common epicardial origin of coronary vascular smooth muscle, perivascular fibroblasts, and intermyocardial fibroblasts in the avian heart. Dev Biol, 1998;193:169-181.
Mikawa T, Fischman DA. Retroviral analysis of cardiac morphogenesis: discontinuous formation of coronary vessels. Proc Natl Acad Sci USA, 1992;89:9504-9508.
Mikawa T, Gourdie RG. Pericardial mesoderm generates a population of coronary smooth muscle cells migrating into the heart along with ingrowth of the epicardial organ. Dev Biol, 1996;174:221-232.
Perez-Pomares JM, et al. Experimental studies on the spatiotemporal expression of WT1 and RALDH2 in the embryonic avian heart: a model for the regulation of myocardial and valvuloseptal development by epicardially derived cells (EPDCs). Dev Biol, 2002;247:307-326.
Cai CL, et al. A myocardial lineage derives from Tbx18 epicardial cells. Nature, 2008;454:104-108.
Limana F, et al. Idenfitication of myocardial and vascular precursor cells in human and mouse epicardium. Circ Res, 2007;101:1255-1265.
Zhou B, et al. Epicardial progenitors contribute to the cardiomyocyte lineage in the developing heart. Nature, 2008;454:109-113.
Christoffels VM, et al. Tbx18 and the fate of epicardial progenitors. Nature, 2009;458:E8-E9/discussion E9-E10.
Laflamme MA, et al. Cardiomyocytes derived from human embryonic stem cells in pro-survival factors enhance function of infarcted rat hearts. Nat Biotechnol, 2007;25:1015-1024.
Yang L, et al. Human cardiovascular progenitor cells develop from a KDR+ embryonic-stem-cell-derived population. Nature, 2008;453:524-528.
Lindsley RC, et al. Canonical Wnt signaling is required for development of embryonic stem cell-derived mesoderm. Development, 2006;133:3787-3796.
Van Wijk B, et al. Role of bone morphogenetic proteins in cardiac differentiation. Cardiovasc Res, 2007;74:244-255.
Mahlapuu M, et al. The forkhead transcription factor Foxf1 is required for differentiation of extra-embryonic and lateral plate mesoderm. Development, 2001;128:155-166.
Sakurai H, et al. Paraxial mesodermal progenitors derived from mouse embryonic stem cells contribute to muscle regeneration via differentiation into muscle satellite cells. Stem Cells, 2008;26:1865-1873.
Wilm B, et al. The forkhead genes, Foxc1 and Foxc2, regulate paraxial versus intermediate mesoderm cell fate. Dev Biol, 2004;271:176-189.
Ishii Y, et al. Induction of proepicardial marker gene expression by the liver bud. Development, 2007;134:3627-3637.
Park IH, et al. Reprogramming of human somatic cells to pluripotency with defined factors. Nature, 2008;451:141-146.
Zhou B, et al. Nkx2-5- and Isl1-expressing cardiac progenitors contribute to proepicardium. Biochem Biophys Res Commun, 2008;375:450-453.
Kruithof BP, et al. BMP and FGF regulate the differentiation of multipotential pericardial mesoderm into the myocardial or epicardial lineage. Dev Biol, 2006;295:507-522.

(56) References Cited

OTHER PUBLICATIONS

Kampmann E, Mey J. Retinoic acid enhances Erk phosphorylation in the chick retina. Neurosci Lett, 2007;426:18-22.
Li Z, et al. Role of ERK ½ signaling in neuronal differentiation of cultured embryonic stem cells. Dev Growth Differ, 2006;48:513-523.
Lu J, et al. All-trans retinoic acid promotes neural lineage entry by pluripotent embryonic stem cells via multiple pathways. BMC Cell Blol, 2009;10:57.
Smith J, et al. Retinoic acid induces nuclear accumulation of Raf1 during differentiation of HL-60 cells. Exp Cell Res, 2009;315:2241-2248.
Bell GW, et al. GEISHA, a whole-mount in situ hybridization gene expression screen in chicken embryos. Dev Dyn, 2004;229:677-687.
Darnell DK, et al. GEISHA: an in situ hybridization gene expression resource for the chicken embryo. Cytogenet Genome Res, 2007;:30-35.
Visel A, et al. GenePaint.org: an atlas of gene expression patterns in the mouse embryo. Nucleic Acids Res, 2004;32:D552-D556.
Kawaguchi M, et al. Serosal mesothelium retains vasculogenic potential. Dev Dyn, 2007;236:2973-2979.
Hidai H, et al. Cloning of capsulin, a basic helix-loop-helix factor expressed in progenitor cells of the pericardium and the coronary arteries. Mech Dev, 1998;73:33-43.
Hatcher CJ, et al. A role for Tbx5 in proepicardial cell migration during cardiogenesis. Physiol Genomics, 2004;18:129-140.
Norden J, et al. Wt1 and retinoic acid signaling in the subcoelomic mesenchyme control the development of the pleuropericardial membranes and the sinus horns. Circ Res, 2010;106:1212-1220.
Guadix JA, et al. In vivo and in vitro analysis of the vasculogenic potential of avian proepicardial and epicardial cells. Dev Dyn, 2006;235:1014-1025.
Van Tuyn J, et al. Epicardial cells of human adults can undergo an epithelial-to-mesenchymal transition and obtain characteristics of smooth muscle cells in vitro. Stem Cells, 2007;25:271-278.
Wilm B, et al. The serosal mesothelium is a major source of smooth muscle cells of the gut vasculature. Development, 2005;132:5317-5328.
Montesano R, et al. In vitro rapid organization of endothelial cells into capillary-like networks is promoted by collagen matrices. J Cell Biol, 1983;97:1648-1652.
Schechner JS, et al. In vivo formation of complex microvessels lined by human endothelial cells in an immunodeficient mouse. Proc Natl Acad Sci USA, 2000;97:9191-9196.
Paige SL, et al. Endogenous Wnt/beta-catenin signaling is required for cardiac differentiation in human embryonic stem cells. PLoS One, 2010;5:e11134.
Perez-Pomares JM, et al. Origin of coronary endothelial cells from epicardial mesothelium in avian embryos. Int J Dev Biol, 2002;46:1005-1013.
Poelmann RE, et al. Development of the cardiac coronary vascular endothelium, studied with antiendothelial antibodies, in chicken-quail chimeras. Circ Res, 1993;73:559-568.
Wang L, et al. Self-renewal of human embryonic stem cells requires insulin-like growth factor-1 receptor and ERBB2 receptor signaling. Blood, 2007;110:4111-4119.
Cavelters V, et al. In vivo visualization of 111-In labeled CD133+ peripheral blood stem cells after intracoronary administration in patients with chronic ischemic heart disease. Q J Nucl Med Mol Imaging, 2007;51:61-66.
Dalton S. Cardiac stem cells: at the heart of cell therapy. Regen Med, 2008;3:181-188.
Kucia M, et al. Trafficking of Normal Stem Cells and Metastasis of Cancer Stem Cells Involve Similar Mechanisms: Pivotal Role of the SDF-1—CXCR4 Axis. Stem Cells, 2005;23:879-894.
Olivey HE, et al. Transforming Growth Factor-beta Stimulates Epithelial Mesenchymal Transformation in the Proepicardium. Developmental Dynamics, 2006;235:50-59.

Phinney DG, et al. Concise Review: Mesenchymal Stem/Multipotent Stromal Cells: The State of Transdifferentiation and Modes of Tissue Repair—Current Views. Stem Cells, 2007;25:2896-2902.
Thomson JA, et al. Primate Embryonic Stem Cells. Current Topics in Developmental Biology, 1998;38:133-165.
Uccelli A, et al. Mesenchymal stem cells in health and disease. Nature, 2008;8:726-736.
Zhu X, et al. Early uptake of 99m-Tc-C2A in the acute phase of myocardial infarction as a prognostic indicator for follow-up cardiac dysfunction. Nuclear Medicine Communications, 2008;29:764-769.
Amit et al. Human Feeder Layers for Human Embryonic Stem Cells. Biology of Reproduction, 2003;68:2150-2156.
Carpenter et al. Charazation and Differentiation of Human Embryonic Stem Cells. Cloning and Stem Cells, 2003;5(1):79-88.
Carpenter et al. Properties of Four Human Embryonic Stem Cell Lines Maintained in a Feeder-Free Culture System. Developmental Dynamics, 2004;229:243-258.
Cheon, et al. Defomed Feeder-Free Culture System of Human Embryonic Stem Cells. Biology of Reproduction, 2006;74:611.
Cooper, et al. Biochemical properties of a keratan sulphate/chondroitin sulphate proteoglycan expressed in primate pluripotent stem cells. Journal of Anatomy, 2002;200:259-265.
Draper, et al. Surface antigens of human embryonic stem cells: changes upon differentiation in culture. Journal of Anatomy, 2002;200:249-258.
Ginis, et al. Differences between human and mouse embryonic stem cells. Developmental Biology, 2004;269:360-380.
Inzunza, et al. Derivation of Human Embryonic Stem Cell Lines in Serum Replacement Medium Using Postnatal Human Fibroblasts as Feeder Cells. Stem Cells, 2005;23:544-549.
Levenstein, et al. Basic Fibroblast Growth Factor Support of Human Embryonic Stem Cell Self-Renewal. Stem Cells, 2006;24:568-574.
Ludwig, et al. Derivation of human embryonic stem cells in defined conditions. Nature Biotechnology, 2006;24:185-187.
Miyamoto, et al. Human Placenta Feeder Layers Support Undifferentiated Growth of Primate Embryonic Stem Cells. Stem Cells, 2004;23:433-440.
OKA, et al. CD9 is Associated with Leukemia Inhibitory Factor-mediated Maintenance of Embryonic Stem Cells. Molecular Biology of the Cell, 2002;13:1274-1281.
Rathjen, et al. Formation of a primitive ectoderm like cell population, EPL cells, from ES cells in response to biologically derived factors. Journal of Cell Science, 1999;112:601-612.
Reubinoff, et al. Embryonic stem cell lines from human blastocysts: somatic differentiation in vitro. Nature Biotechnology, 2000;18:399-404.
Richards, et al. Comparative Evaluation of Various Human Feeders for Prolonged Undifferentiated Growth of Human Embryonic Stem Cells. Stem Cells, 2003;21:546-556.
Stojkovic, et al. An Autogeneic Feeder Cell System That Efficiently Supports Growth of Undifferentiated Human Embryonic Stem Cells. Stem Cells, 2005;23:306-314.
Takahashi, et al. Induction of Pluripotent Stem Cells from Mouse Embryonic and Adult Fibroblast Cultures by Defined Factors. Cell, 2006;126:663-676.
Tesar, et al. New cell lines from mouse epiblast share defining features with human embryonic stem cells. Nature, 2007;448:196-202.
Thomson, et al. Isolation of a primate embryonic stem cell line. Proceedings of the National Academy of Sciences USA, 1995;92:7844-7848.
Vacanti, et al. Selective cell Transplantation Using Bioabsorbable Artificial Polymers as Matricies. Journal of Pediatric Surgery, 1988;23:3-9.
Vunjak-Novakovic, et al. Dynamic Cell Seedings of Polymer Scaffolds for Cartilage Tissue Engineering. Biotechnology Prog, 1998;14:193-202.
Wang, et al. Derivation and Growing Human Embryonic Stem Cells on Feeders Derived from Themselves. Stem Cells, 2005;23:1221-1227.

(56) References Cited

OTHER PUBLICATIONS

Wang, et al. Self-renewal of human embryonic stem cells requires insulin-like growth factor-1 receptor and ERBB2 receptor signaling. Blood, 2007;110:4111-4119.

Xu, et al. Immortalized Fibroblast-Like Cells Derived from Human Embryonic Stem Cells Support Undifferentiated Cell Growth. Stem Cells, 2004;22:972-980.

Yang, et al. Novel cell immobilization method utilizing centrifugal force to achieve high-density hepatocyte culture in porous scaffold. J Biomed Mater Res, 2001;55(3):379-386.

Glover (Editor). DNA Cloning a Practical Approach vols. 1-2, 1985, IRL Press Limited, Oxford, England.

Hames and Higgins (Editors). Nucleic Acid Hybridisation a Practical Approach, 1985, IRL Press Limited, Oxford, England.

Maniatis, Fritsch and Sambrook. Molecular Cloning a Laboratory Manual, 1982, Cold Spring Harbor Laboratory, Cold Spring Harbor, New York.

Miller. Experiments in Molecular Genetics, 1972, Cold Spring Harbor Laboratory, Cold Spring Harbor, New York.

Old and Primrose. Principles of Gene Manipulation an Introdcution to Genetic Engineering, 1981, University of California Press, Berkeley, California.

Schleif and Wensink. Practical Methods in Molecular Biology, 1981, Springer-Verlag New York, Inc., New York, New York.

Rieger, Michaelis and Green. Glossary of Genetics Classical and Molecular Fifth Edition, 1991, Springer-Verlag, New York, New York.

Sambrook, Fritsch and Maniatis. Molecular Cloning a Laboratory Manual Second Edition, 1989, Cold Spring Harbor Laboratory Press, Plainview, New York.

Setlow and Hollaender (Editors). Genetic Engineering Principles and Methods vols. 1-4, 1979-1982, Plenum Press, New York, New York.

Thomson et al. Primate Embryonic Stem Cells. IN: Current Topics in Developmental Biology (1988, Academic Press, New York). vol. 38, pp. 133-165.

Wu (Editor). Methods in Enzymology vol. 68 Recombinant DNA, 1979, Academic Press (Elsevier Inc.) New York.

Wu (Editor). Methods in Enzymology vol. 218 Recombinant DNA Part 1, 1993, Academic Press (Elsevier Inc.) New York.

Wu, Grossman and Moldave (Editors). Methods in Enzymology vol. 65 Recombinant DNA Part C, 1980, Academic Press (Elsevier Inc.) New York.

Wu, Grossman and Moldave (Editors). Methods in Enzymology vol. 100 Recombinant DNA Part B, 1983, Academic Press (Elsevier Inc.) New York.

Wu, Grossman and Moldave (Editors). Methods in Enzymology vol. 101 Recombinant DNA Part C, 1983, Academic Press (Elsevier Inc.) New York.

Thomson JA, et al. Embryonic Stem Cell Lines Derived from Human Blastocysts. Science, 1998;282:1145-1147.

\* cited by examiner

FIGURE 6A
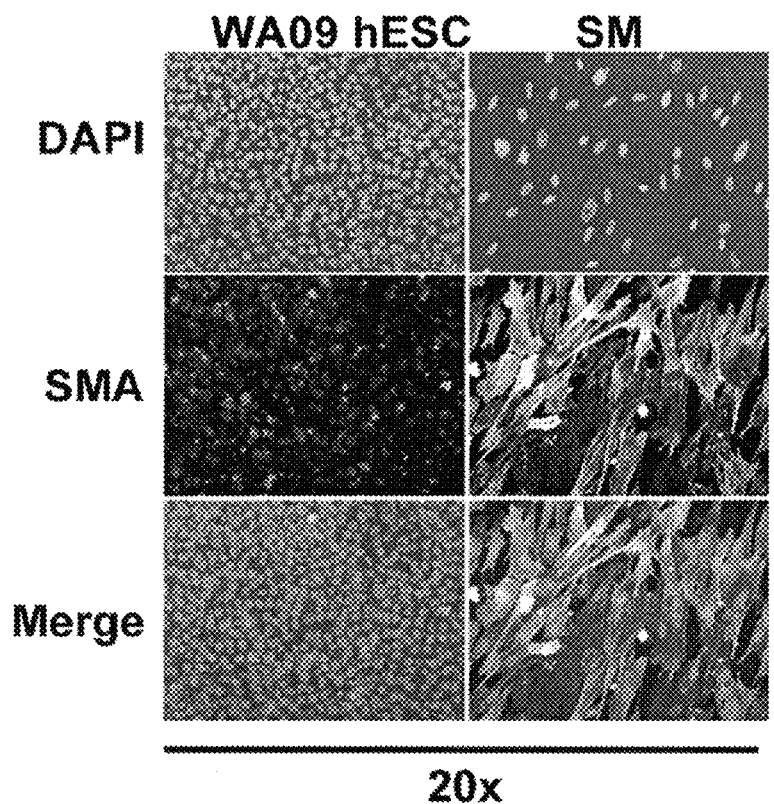
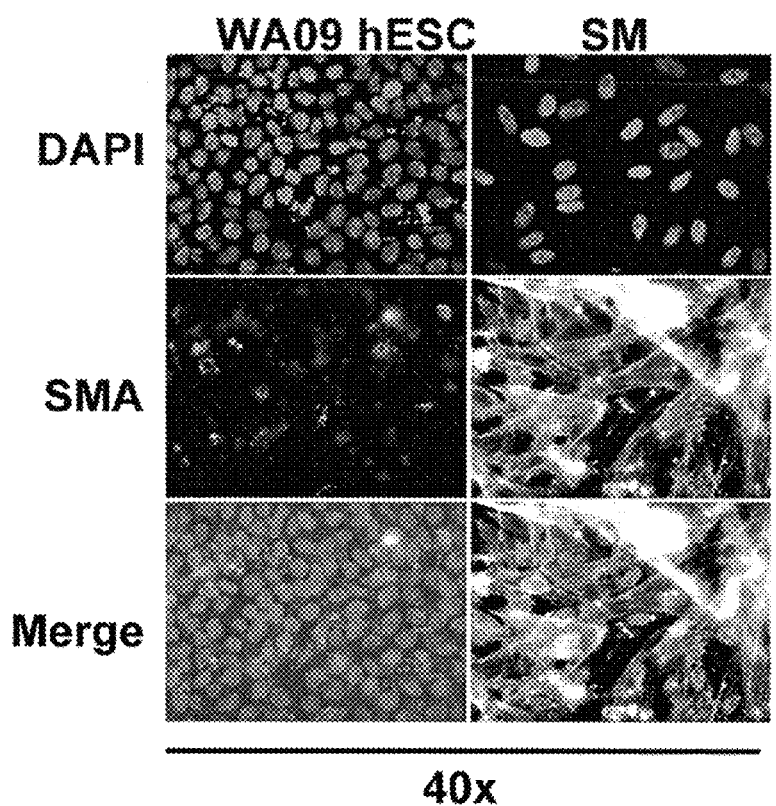

FIGURE 6C
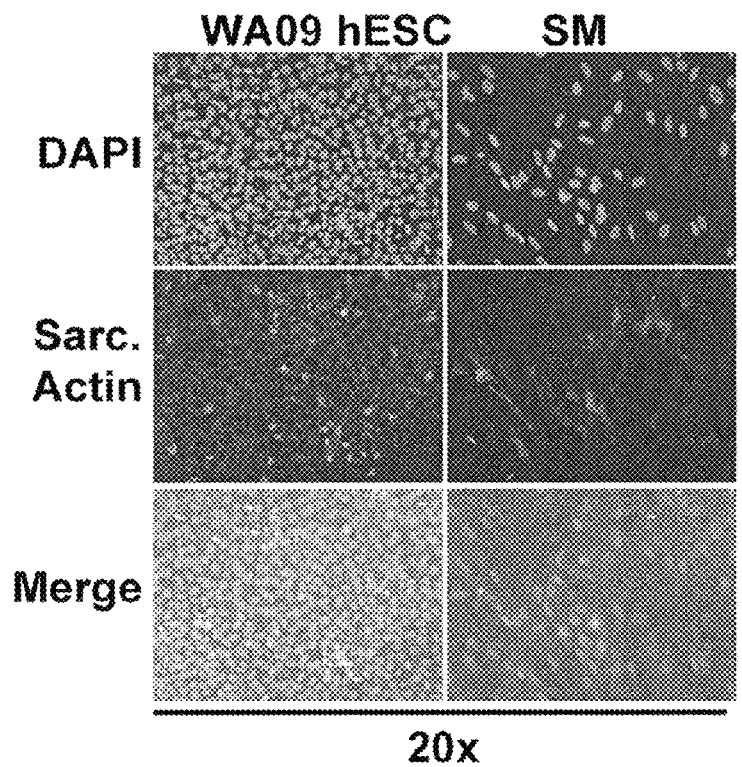
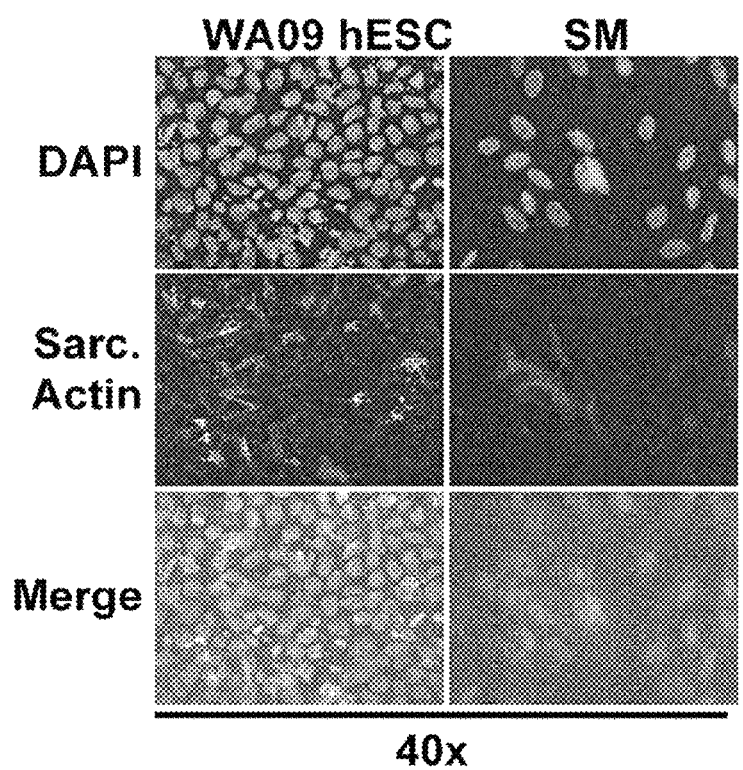

FIGURE 19

|  | day 0 (MMC) | day 2 | day 4 | day 6 |
|---|---|---|---|---|
| c-Kit | − | + | + | +/− |
| KDR/Flk-1 | − | − | − | − |
| CXCR4 | + | + | + | + |
| CD56 | + | + | + | + |
| CD31 | − | − | − | − |
| CD166 | +/− | + | + | + |
| CD105 | − | + | + | + |
| CD44 | − | + | + | + |
| CD133 | + | + | + | + |
| CD90 | + | + | + | + |

FIGURE 23
Experiment 1- Rat 1
0.1 hr
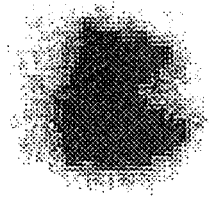
Lungs
2 hr
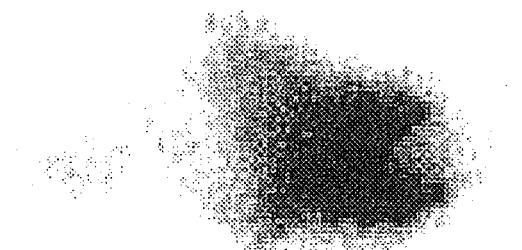
Liver  Lungs
24 hr
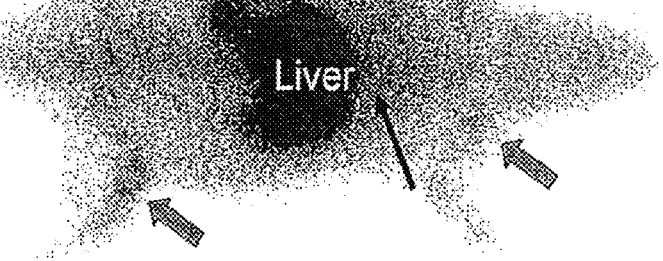
Spleen  Lungs
Liver

Figure 24
Experiment 1 - Rat 2
0.1 hr
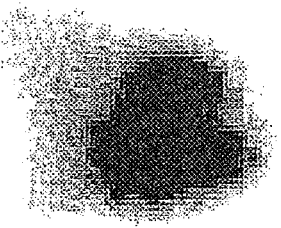
2 hr
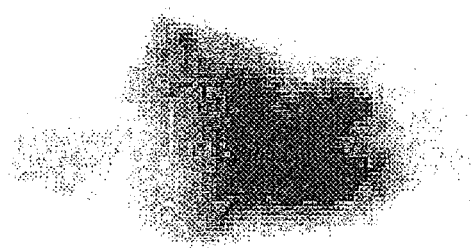
24 hr
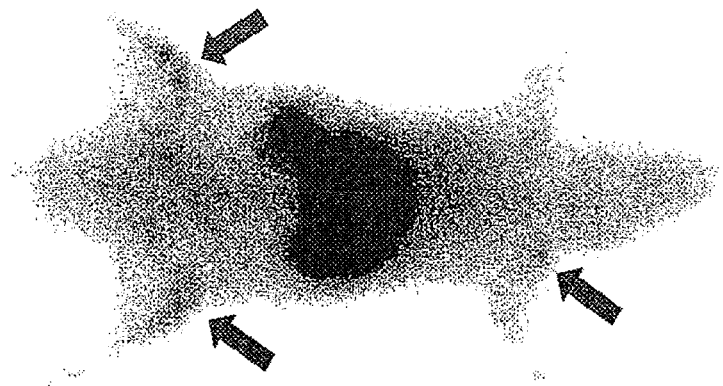

Experiment 2 - Rat 1
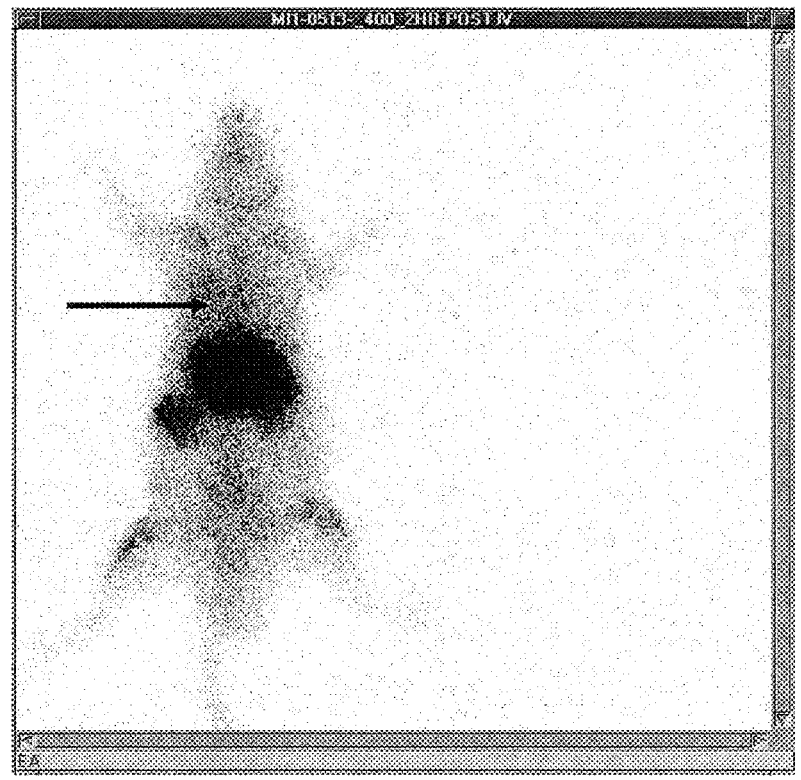
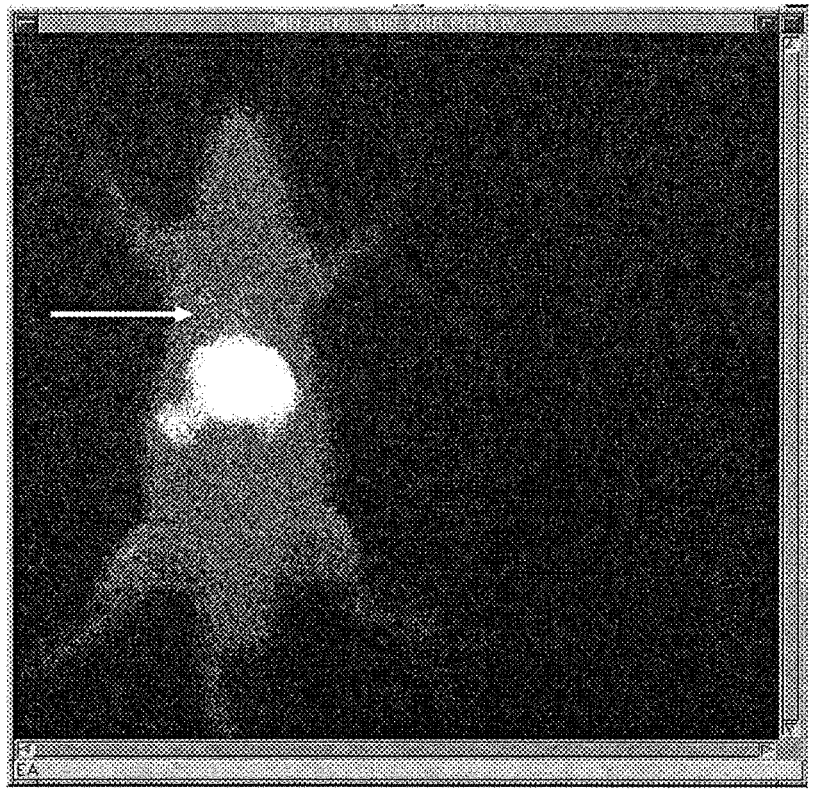

Experiment 2 - Rat 2

FIGURE 31
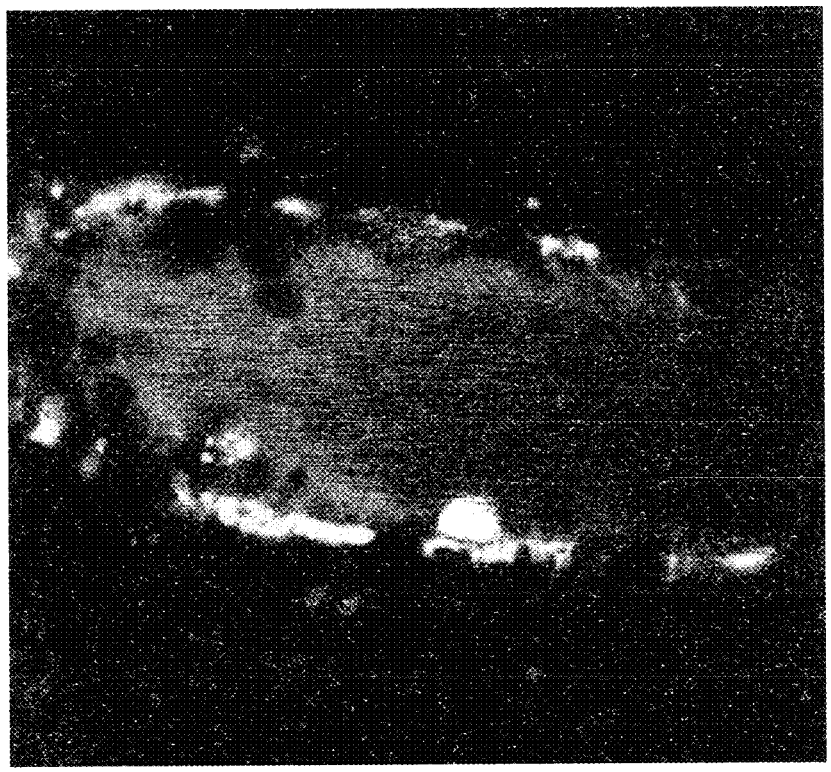
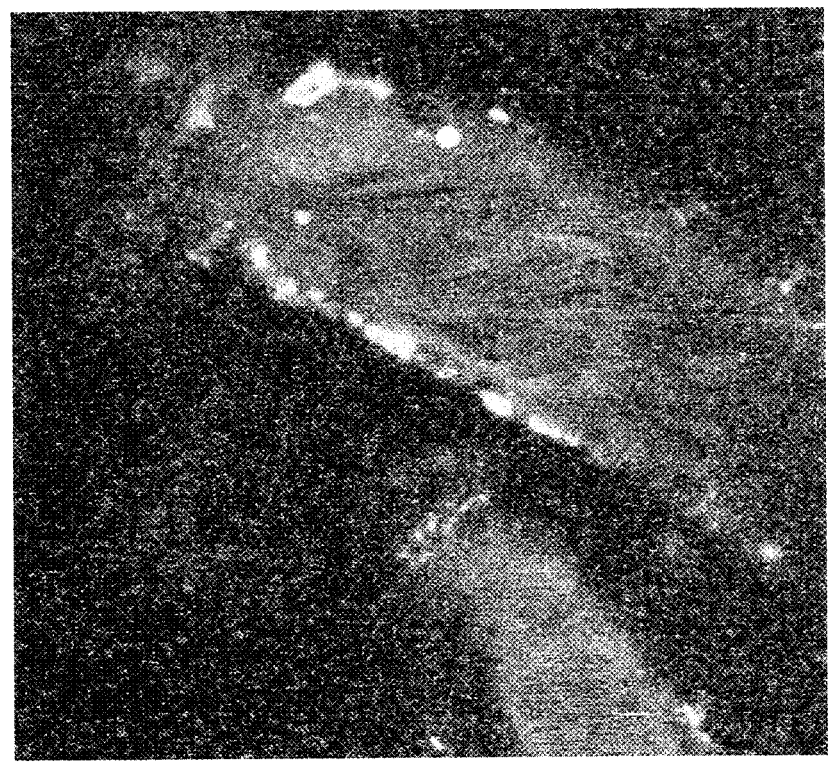

FIGURE 36

Smooth muscle
Endothelial cells
Cardiac fibroblasts
} Coronary vasculature
ie left anterior descending and
right coronary arteries D20 From hESC Epicardium

FIGURE 43
A.
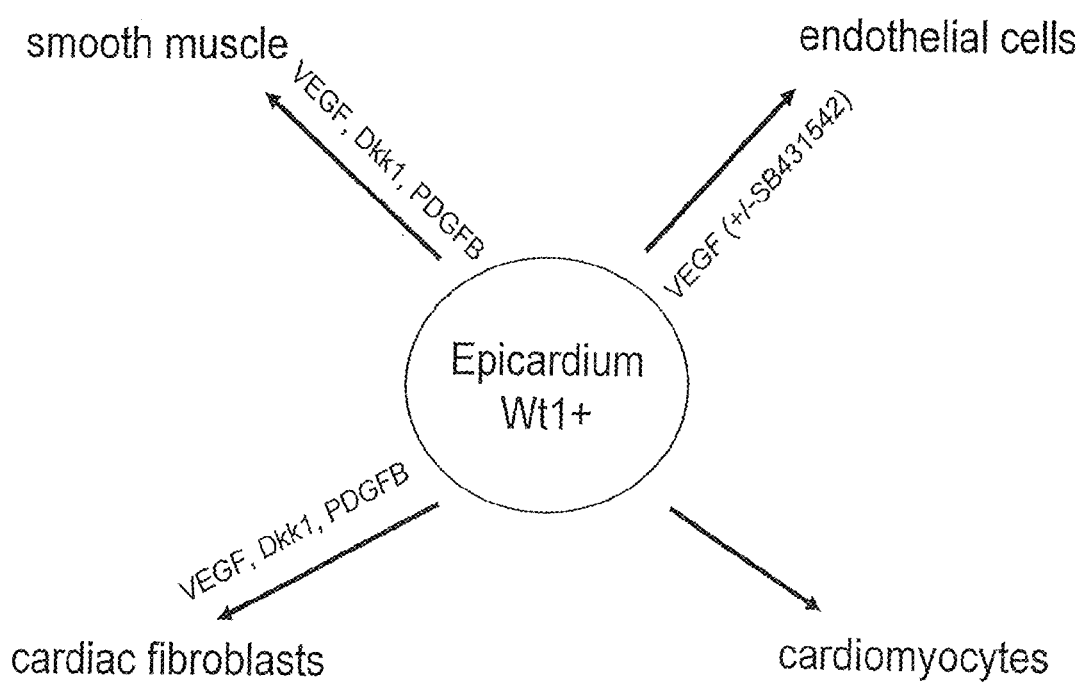
B.
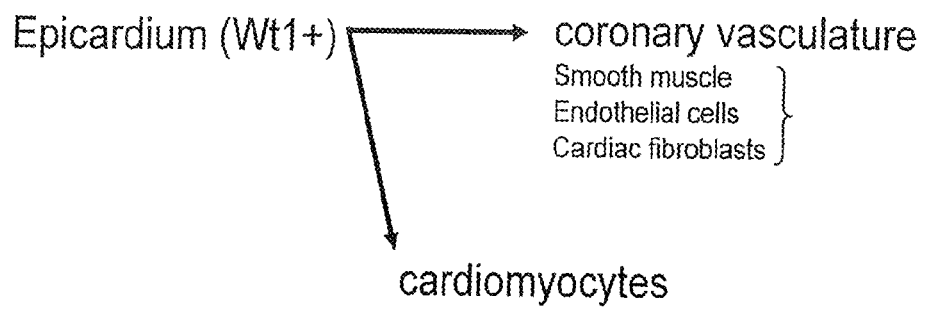

10%FBS

FIGURE 46

Table 1

| Probe Set ID | Log ratio | Gene Symbol |
|---|---|---|
| 205044_at | 10.6 | GABRP |
| 207147_at | 8.8 | DLX2 |
| 205932_s_at | 8.2 | MSX1 |
| 208502_s_at | 8.0 | PITX1 |
| 220138_at | 7.6 | HAND1 |
| 206104_at | 7.5 | ISL1 |
| 205590_at | 7.2 | RASGRP1 |
| 210002_at | 7.0 | GATA6 |
| 236163_at | 7.0 | LIX1 |
| 205517_at | 6.8 | GATA4 |
| 205935_at | 6.8 | FOXF1 |
| 209602_s_at | 6.8 | GATA3 |
| 205430_at | 6.7 | BMP5 |
| 208510_s_at | 6.7 | PPARG |
| 222917_s_at | 6.7 | TBX3 |
| 213139_at | 6.6 | SNAI2 |
| 213425_at | 6.6 | WNT5A |
| 220634_at | 6.5 | TBX4 |
| 214053_at | 6.4 | ERBB4 |
| 232712_at | 6.4 | FGF10 |
| 207558_s_at | 6.2 | PITX2 |
| 1559477_s_at | 6.2 | MEIS1 |
| 202409_at | 6.0 | IGF2 /// INS-IGF2 |
| 205555_s_at | 6.0 | MSX2 |
| 205990_s_at | 5.6 | WNT5A |
| 242940_x_at | 5.6 | DLX6 |
| 213707_s_at | 5.4 | DLX5 |
| 231798_at | 5.4 | NOG |
| 212977_at | 5.3 | CXCR7 |
| 240509_s_at | 5.2 | GREM2 |
| 221796_at | 5.1 | NTRK2 |
| 230865_at | 5.1 | LIX1 |
| 204602_at | 5.0 | DKK1 |
| 209961_s_at | 4.9 | HGF |
| 219908_at | 4.9 | DKK2 |
| 232231_at | 4.9 | RUNX2 |
| 209541_at | 4.8 | IGF1 |
| 1553131_a_at | 4.8 | GATA4 |
| 205289_at | 4.6 | BMP2 |
| 227812_at | 4.6 | TNFRSF19 |
| 231227_at | 4.6 | WNT5A |
| 208806_at | 4.5 | CHD3 |
| 207172_s_at | 4.4 | CDH11 |
| 221609_s_at | 4.4 | WNT6 |
| 231762_at | 4.4 | FGF10 |
| 209710_at | 4.2 | GATA2 |
| 220115_s_at | 4.2 | CDH10 |
| 223283_s_at | 4.2 | TSHZ1 |
| 1569362_at | 4.2 | ALCAM |
| 203131_at | 4.1 | PDGFRA |
| 44783_s_at | 4.1 | HEY1 |
| 211518_s_at | 4.0 | BMP4 |
| 217028_at | 4.0 | CXCR4 |
| 205290_s_at | 3.7 | BMP2 |
| 213943_at | 3.7 | TWIST1 |
| 206578_at | 2.9 | NKX2-5 |

Table 2

FIGURE 47

| Probe set ID | H9 D22 | iPS D22 | H1 D22 | H7 D22 | O2 D22 | Gene Symbol |
|---|---|---|---|---|---|---|
| 215076_s_at | 12.8 | 9.8 | 10.8 | 10.2 | 10.2 | COL3A1 |
| 210002_at | 12.4 | 8.2 | 10.8 | 8.3 | 7.6 | GATA6 |
| 221796_at | 10.7 | 8.5 | 6.6 | 6.2 | 8.5 | NTRK2 |
| 223282_at | 10.6 | 6.4 | 7.2 | 9.7 | 11.6 | TSHZ1 |
| 219682_s_at | 10 | 5.2 | 10.1 | 8.2 | 9.7 | TBX3 |
| 206104_at | 9.8 | 5.7 | 5.7 | 5.6 | 9.8 | ISL1 |
| 207016_s_at | 9.4 | 5.5 | 6 | 5 | 5.4 | ALDH1A2 |
| 213139_at | 8.9 | 6 | 6.8 | 6.7 | 6.9 | SNAI2 |
| 209540_at | 8.5 | 5.1 | 9.2 | 7.1 | 9.8 | IGF1 |
| 202410_x_at | 8.3 | 8.6 | 7.3 | 7.4 | 4.6 | IGF2 /// INS-IGF2 |
| 230865_at | 8 | 5 | 5 | 9.6 | 9.7 | LIX1 |
| 216953_s_at | 7.9 | 6.3 | 9.1 | 7.3 | 5.9 | WT1 |
| 236197_at | 7.7 | 3.9 | 6.7 | 7.2 | 5.1 | GATA5 |
| 209360_s_at | 7.4 | 6.4 | 4.1 | 4.9 | 5.6 | RUNX1 |
| 240715_at | 7.1 | 5.1 | 3.7 | 5.9 | 6.4 | TBX5 |
| 213943_at | 7 | 4.8 | 9.6 | 7.1 | 6.2 | TWIST1 |
| 210875_s_at | 6.8 | 2.8 | 4.8 | 5.9 | 7.5 | TCF8 |
| 242138_at | 6.8 | 2.5 | 4 | 2.4 | 7.6 | DLX1 |
| 209604_s_at | 6.7 | 6.9 | 6.7 | 5.4 | 6.9 | GATA3 |
| 208502_s_at | 6.6 | 9.4 | 6.7 | 6 | 5.5 | PITX1 |
| 40560_at | 6.4 | 5.1 | 5.2 | 6.6 | 5.9 | TBX2 |
| 206404_at | 6.2 | 3.3 | 5.2 | 2.6 | 5.9 | FGF9 |
| 219908_at | 6.2 | 6.9 | 5 | 9.6 | 6.8 | DKK2 |
| 213273_at | 6 | 4.9 | 4.2 | 4.6 | 4 | ODZ4 |
| 209199_s_at | 5.9 | 3.1 | 2.5 | 3.6 | 3.1 | MEF2C |
| 228915_at | 5.9 | 4.6 | 5.9 | 5.9 | 5.8 | DACH1 |
| 203131_at | 5.8 | 5.1 | 5.8 | 6.5 | 3.4 | PDGFRA |
| 209560_s_at | 5.8 | 4 | 5.4 | 4.2 | 3.7 | DLK1 |
| 236163_at | 5.8 | 5.9 | 4.4 | 6.1 | 5.1 | LIX1 |
| 201506_at | 5.6 | 4.7 | 5.8 | 6.8 | 4.9 | TGFBI |
| 203868_s_at | 5.6 | 4.9 | 5.9 | 4.9 | 4.3 | VCAM1 |
| 205080_at | 5.6 | 6.4 | 5.8 | 5.8 | 4.9 | RARB |
| 207558_s_at | 5.6 | 6.7 | 4.1 | 4.3 | 8.2 | PITX2 |
| 226143_at | 5.6 | 4.9 | 4.4 | 4.6 | 5.8 | RAI1 |
| 228121_at | 5.1 | 4.7 | 4.6 | 5.1 | 5.6 | TGFB2 |
| 207147_at | 4.8 | 8.8 | 8.7 | 4.1 | 8 | DLX2 |
| 218718_at | 4.8 | 4.1 | 4.7 | 4 | 4 | PDGFC |
| 220115_s_at | 4.8 | 3.9 | 4.7 | 6 | 4.9 | CDH10 |
| 231227_at | 4.8 | 4.9 | 4.4 | 2.9 | 3.7 | WNT5A |
| 205471_s_at | 4.7 | 3.4 | 6.2 | 4.7 | 6.3 | DACH1 |
| 207173_x_at | 4.7 | 5.2 | 5.2 | 7.4 | 5.9 | CDH11 |
| 212843_at | 4.7 | 4.2 | 3.8 | 6 | 3.5 | NCAM1 |
| 212977_at | 4.7 | 6.1 | 5.1 | 5.1 | 3.8 | CXCR7 |
| 227812_at | 4.6 | 5.6 | 6.3 | 9.7 | 5.4 | TNFRSF19 |
| 204602_at | 4.5 | 5.1 | 3.3 | 7.1 | 6.5 | DKK1 |
| 206392_s_at | 4.4 | 8.3 | 8.5 | 6.3 | 5.1 | RARRES1 |
| 207069_s_at | 4.2 | 4 | 4.1 | 4.7 | 4.7 | SMAD6 |
| 220634_at | 4.1 | 7 | 6.1 | 5.4 | 6.3 | TBX4 |
| 225442_at | 4.1 | 3.4 | 4.8 | 5 | 5.9 | DDR2 |
| 221029_s_at | 3.7 | 2.2 | 4.9 | 5.3 | 5.4 | WNT5B |
| 202273_at | 3.1 | 2 | 2.9 | 5.5 | 3.9 | PDGFRB |
| 209651_at | 3.1 | 3.9 | 3.3 | 3.1 | 3.9 | TGFB1I1 |

FIGURE 50
A
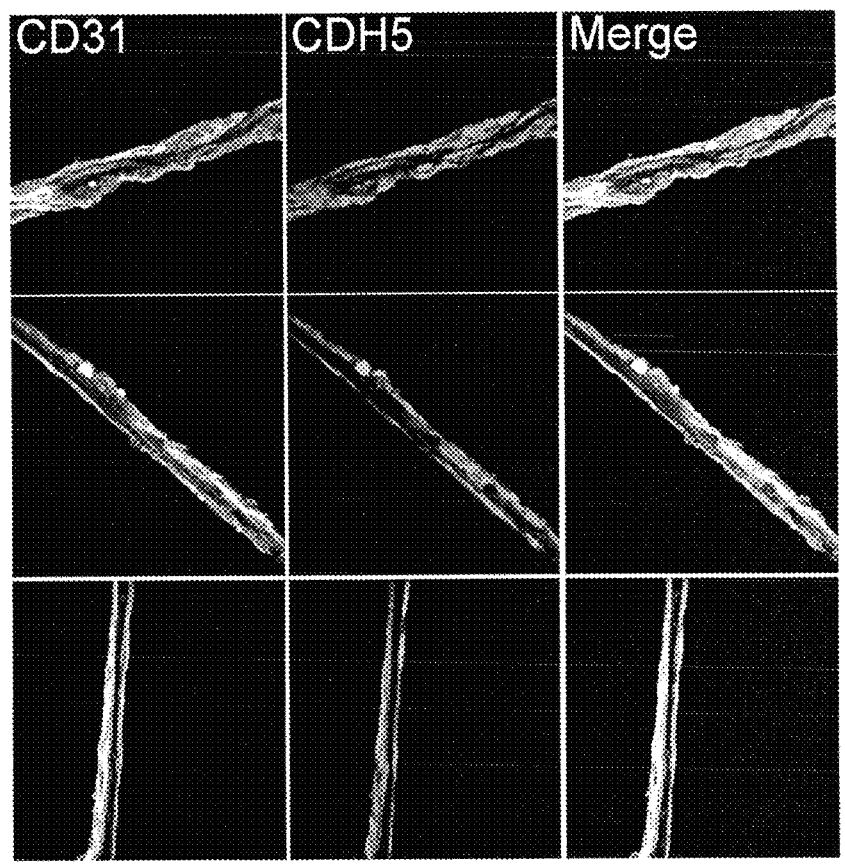
B
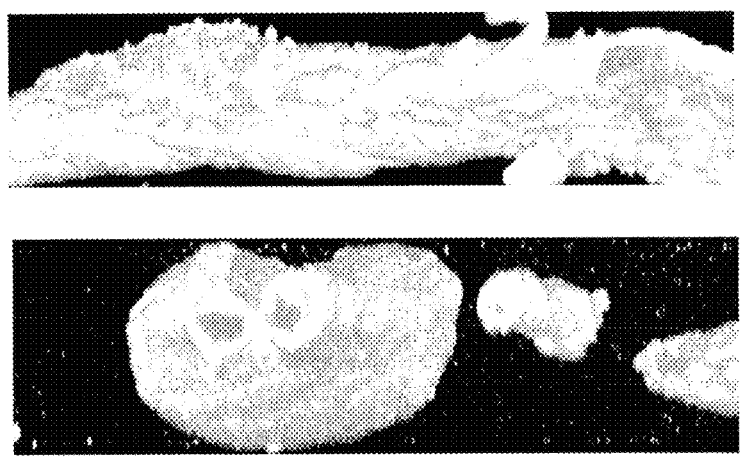

FIGURE 53
VIMENTIN
DAPI
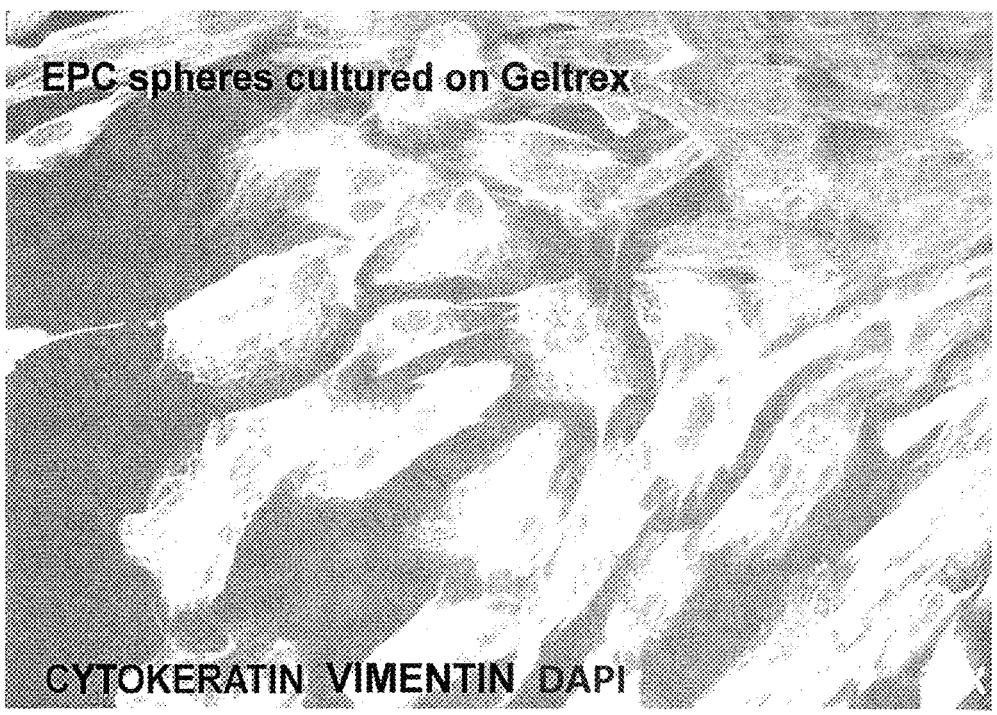

Figure 67
Table 3

| Gene Descriptor | Gene Symbol | Unigene |
|---|---|---|
| Snail homolog 2 | SNAI2 | Hs.360174 |
| T-box 3 | TBX3 | Hs.129895 |
| GATA binding protein 3 | GATA3 | Hs.524134 |
| Forkhead box C1 | FOXC1 | Hs.348883 |
| Msh homeobox 1 | MSX1 | Hs.424414 |
| Myeloid ecotropic viral integration site 1 homolog | MEIS1 | Hs.526754 |
| Aldehyde dehydrogenase 1 family, member A2 | ALDH1A2 | Hs.643455 |
| LIM homeobox 1 | LHX1 | Hs.443727 |
| Forkhead box A2 | FOXA2 | Hs.155651 |
| Forkhead box F1 | FOXF1 | Hs.155591 |
| Wingless-type MMTV integration site family, member 8A | WNT8A | Hs.591274 |
| Bone morphogenetic protein 4 | BMP4 | Hs.68879 |
| Cerberus 1, cysteine knot superfamily, homolog | CER1 | Hs.248204 |
| Wingless-type MMTV integration site family, member 5A | WNT5A | Hs.643085 |
| Frizzled homolog 10 | FZD10 | Hs.31664 |
| Wingless-type MMTV integration site family, member 4 | WNT4 | Hs.591521 |
| Platelet-derived growth factor receptor, alpha polypeptide | PDGFRA | Hs.74615 |
| Dapper, antagonist of beta-catenin, homolog 1 | DACT1 | Hs.48950 |
| Delta-like 3 (Drosophila) | DLL3 | Hs.127792 |
| Dickkopf homolog 1 | DKK1 | Hs.40499 |
| Mesoderm posterior 1 homolog | MESP1 | Hs.447531 |
| GATA binding protein 2 | GATA2 | Hs.367725 |
| Wingless-type MMTV integration site family, member 3 | WNT3 | Hs.445884 |
| Lymphoid enhancer-binding factor 1 | LEF1 | Hs.555947 |
| Bone morphogenetic protein 2 | BMP2 | Hs.73853 |
| Mesoderm posterior 2 homolog | MESP2 | Hs.37311 |
| Cadherin 11, type 2, OB-cadherin (osteoblast) | CDH11 | Hs.116471 |
| Platelet-derived growth factor receptor, beta polypeptide | PDGFRB | Hs.509067 |

Figure 76
a
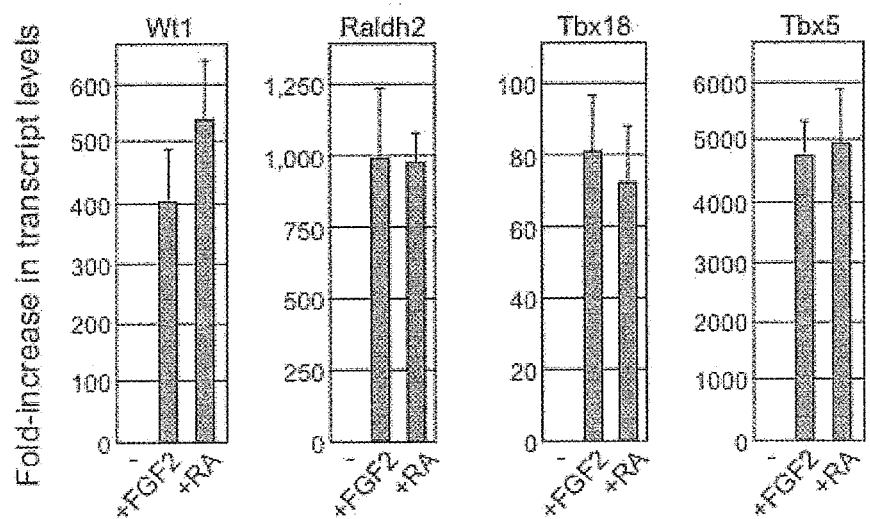
b
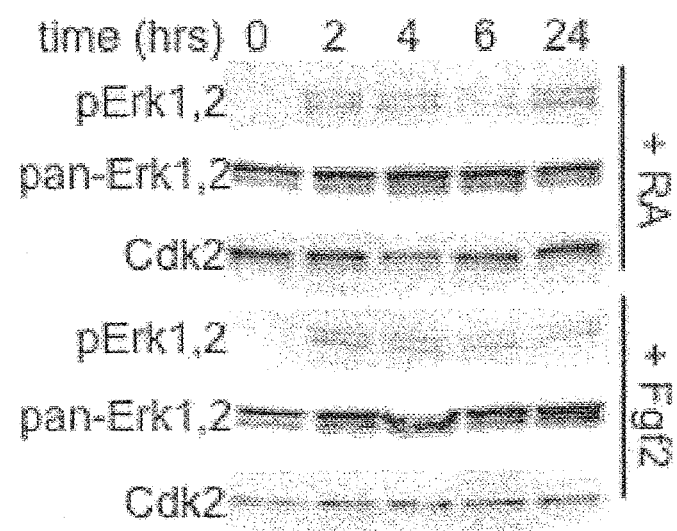

Figure 77
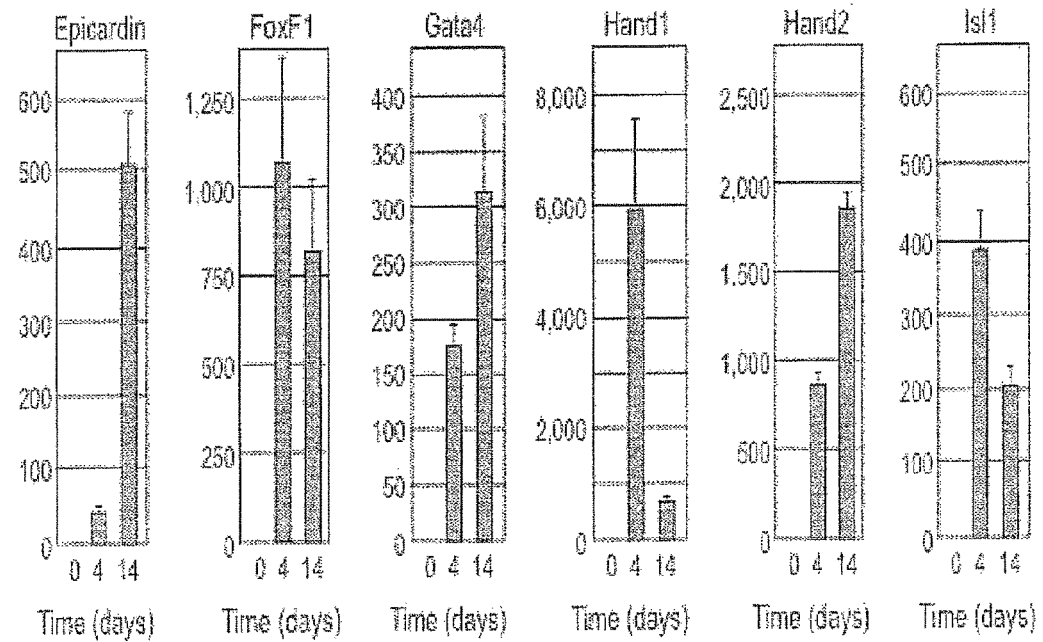
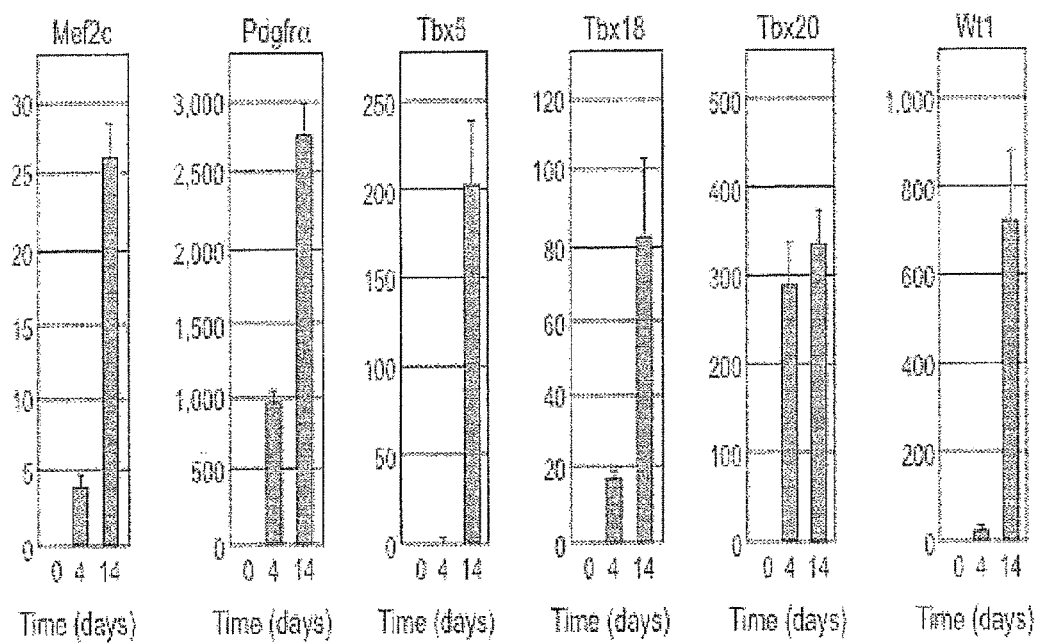

Figure 79
a
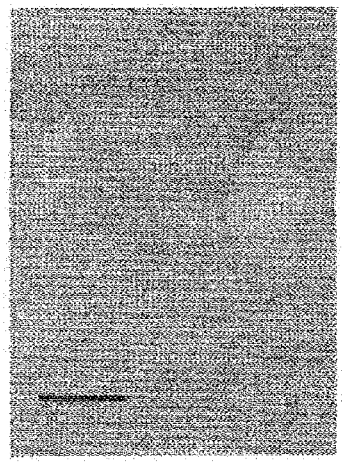
b 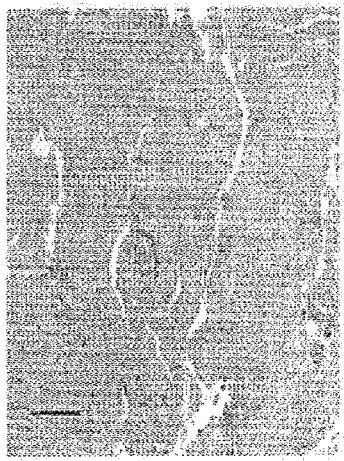 c 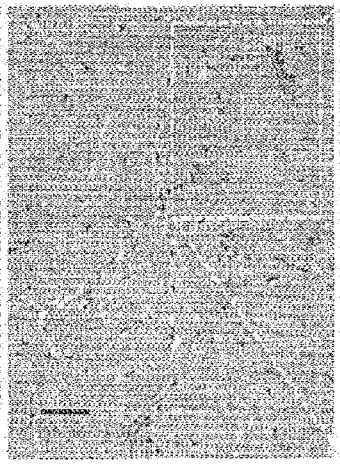 d 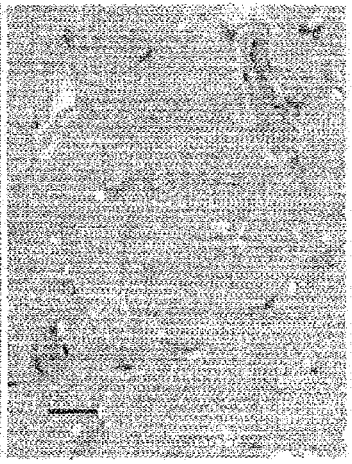

Figure 80

Table 4

| Probe Set ID | WA09 $Log_2$ | BG02 $Log_2$ | Gene Symbol |
|---|---|---|---|
| 214520_at | -0.2 | 0.7 | FOXC2 |
| 215122_at | 1.2 | -0.2 | TBX6 |
| 229638_at | -0.5 | 0.8 | IRX3 |
| 207680_x_at | -1.1 | 0.5 | PAX3 |
| 205646_s_at | -0.75 | 0.0 | PAX6 |
| 206228_at | -1.0 | -0.8 | PAX2 |

Figure 81

Table 5

| Antibody | Company | Catalogue # |
|---|---|---|
| Isl1 | R & D Systems | AF1837 |
| Nkx2.5 | R & D Systems | MAB2444 |
| KDR-APC | R & D Systems | FAB359A |
| Cadherin 11 | R & D Systems | AF1790 |
| Brachyury | R & D Systems | AF2085 |
| VE-Cadherin | R & D Systems | AF938 |
| CD31 | R & D Systems | BBA7 |
| FoxF1 | R & D Systems | AF4798 |
| Nanog | Cosmo Bio. | RCAB0004P-I |
| Oct4 | Santa Cruz Biotechnology | sc-8628 |
| Tbx5 | Santa Cruz Biotechnology | sc-48782 |
| Cdk2 (M2) | Santa Cruz Biotechnology | sc-163 |
| PDGFRβ-PE | BD Biosciences | 588621 |
| c-Kit-PE | BD Biosciences | 340529 |
| Smooth Muscle Actin | Sigma | A2547 |
| Calponin | Sigma | C2687 |
| ADLH1A2/RALDH2 | Sigma | HPA010022 |
| Tbx20 | Abcam | ab42468 |
| Irx3 | Abcam | ab57735 |
| Wilms Tumor 1 | Abcam | ab52933 |
| Snail | Abcam | ab85931 |
| Cytokeratin | Abcam | ab7753 |
| Vimentin | Abcam | ab16700 |
| E Cadherin | Invitrogen | 13-1700 |
| GFP | Invitrogen | A11122 |
| β-Catenin | BD Transduction Laboratories | 610154 |
| ZO-1 | BD Transduction Laboratories | 610966 |
| Von Willebrand Factor | Dako | A0082 |
| Smooth Muscle Actin | Dako | M0851 |
| p44/42 MAPK (Erk1/2) | Cell Signaling | 9102L |
| P-p44/42 MAPK (T202/Y204) | Cell Signaling | 9101S |

All fluorescent secondary antibodies used herein were Donkey α-species Alexa Fluors from Invitrogen or HRP conjugates from Dako

Figure 82

Table 6

| Gene | Applied Biosystems ID |
|---|---|
| AFP | Hs00173490_m1 |
| ALDH1A2/Raldh2 | Hs00180254_m1 |
| Epicardin/TCF21 | Hs00162646_m1 |
| Fgf10 | Hs00610298_m1 |
| FoxF1 | Hs00230962_m1 |
| GAPDH | Hs99999905_m1 |
| Gata4 | Hs00171403_m1 |
| Hand1 | Hs00231848_m1 |
| Hand2 | Hs00232769_m1 |
| HHex | Hs00242160_m1 |
| Isl1 | Hs00158126_m1 |
| Mef2c | Hs00231149_m1 |
| Nanog | Hs02387400_g1 |
| Nkx2.5 | Hs00231763_m1 |
| Pax6 | Hs00240871_m1 |
| PDGFRα | Hs00183486_m1 |
| Pitx2 | Hs00165626_m1 |
| Sox1 | Hs00534426_s1 |
| Sox17 | Hs00751752_s1 |
| T | Hs00610080_m1 |
| Tbx5 | Hs00361155_m1 |
| Tbx18 | Hs01385455_m1 |
| Tbx20 | Hs00396596_m1 |
| THBD | Hsoo264920_s1 |
| Wt1 | Hs01103754_m1 |
| Zic1 | Hs00602749_m1 |

COMPOSITIONS FOR MESODERM DERIVED ISL1+ MULTIPOTENT CELLS (IMPS), EPICARDIAL PROGENITOR CELLS (EPCS) AND MULTIPOTENT C56C CELLS (C56CS) AND METHODS OF PRODUCING AND USING SAME

RELATED APPLICATIONS AND GRANT SUPPORT

This application is a divisional of U.S. Ser. No. 13/012,862, filed Jan. 25, 2011, which is a continuation-in-part application of PCT/US 2009/004334 (Published as WO 2010/011352), filed Jul. 27, 2009, entitled "Compositions for Mesoderm Derived ISL1+ Multipotent Cells (IMPs), Epicardial Progenitor Cells (EPCs) and Multipotent CXCR4+CD56+ Cells (C56Cs) and Methods of Use, which claims the benefit of priority from provisional applications U.S. 61/137,058, filed Jul. 25, 2008, entitled "Methods and Composition of Matter for hESC-Derived Multipotent Progenitors of Mesoderm Origin", U.S. 61/198,861, filed Nov. 10, 2008, entitled "Applications for MMCs and C56Cs in Cell Therapy" and U.S. 61/215,621, filed May 7, 2009, entitled "Generation of a Multi-Potent Epicardial Progenitor Cells (EPCs) from Human Pluripotent Stem Cells", each of which applications is incorporated by reference in its entirety herein. The continuation-in-part application U.S. Ser. No. 13/012,862 also claims the benefit of priority of U.S. provisional application 61/385,641, filed Sep. 23, 2010, entitled "Efficient Differentiation of Human Pluripotent Cells Into Coronary Vascular Progenitor-Like Cells" which is also incorporated by reference in its entirety herein.

This invention was made with government support under National Institute of General Medical Sciences (GM75334) and National Heart, Lung and Blood Institute (HL089471). The government has certain rights in the invention.

FIELD OF THE INVENTION

The present invention relates to inter alia, methods for the generation and maintenance of mesoderm-derived ISL1+ Multipotent Progenitors (IMPs), compositions thereof, related methods for producing a variety of multipotent progenitor cells as otherwise described herein. Methods of using these cells in therapeutic methods are also disclosed. The present invention also relates to the discovery that human pluripotent stem cells, including embryonic stem cells (hESCs) and human induced pluripotent stem cells (hiPSCs), can be differentiated into Isl1+ multi-potent cardiovascular progenitors (IMPs), using similar methods.

Other methods for producing IMPs directly from pluripotent cells, EPCs from IMPs and smooth muscle cells, endoothelials cells, blood vessels and vascular cells are other aspects of the present invention presented herein. IMPs represent early mesoderm progenitors, characteristic of splanchnic mesoderm formed in the vertebrate embryo. Developmentally, this cells forms from pluripotent cells through a lateral plate mesoderm intermediate followed by transition to a splanchnic mesoderm cell.

The invention also relates to an efficient conversion of hESC and hiPSC-derived IMPs into a Wilm's tumor protein 1 positive (Wt1+) multi-potent progenitor, referred to as an epicardial progenitor cell (EPC). EPCs are capable of differentiation into smooth muscle cells, endothelial cells and cardiac fibroblasts and consequently, components of the coronary vasculature. Since the EPC is a progenitor for cells that comprise the coronary vascular system, it provides utility as a cell therapeutic, as a drug screening tool and as a research tool. These cells can also be differentiated into cardiomyocytes, among others, as is set forth in great detail herein.

Still a further invention relates to the discovery of a CD56+ multipotent migratory cell (MMC) that can be prepared directly from pluripotent stem cells, including hESCs and hiPSCs. MMCs are ectoderm derived neuroprogenitor cells capable of differentiation into multiple neuronal cell types including motor neurons and dopaminergic neurons. Methods of producing these cells, as well as using these cells in therapy, are alternatively described in the present invention.

Other methods for producing IMPs directly from pluripotent cells, EPCs from IMPs and smooth muscle cells, endoothelials cells, blood vessels and vascular cells are other aspects of the present invention which are presented herein.

BACKGROUND OF THE INVENTION

Human embryonic stem cells (hESC's) (markers for hESCs include SSEA3, SSEA4, TRA-1-60, TRA-1-81 antigens, Nanog, Oct4) are a pluripotent population of cells that can be differentiated into cells derived from all three embryonic germ layers and extraembryonic lineages. FIG. 33. This property of hESC's has important implications in cell therapy (e.g. diabetes, heart disease, neurodegenerative diseases), drug discovery and developmental modeling.

Other pluripotent cell types have been identified in mouse. Primitive ectoderm like (EPL; Rathjen et al., 1999, J. Cell Sci) cells were shown to form from mESC's with the ability to dedifferentiate into mESC's. Recently, a new mouse cell, post-implantation epiblast stem cells (EpiSC; Tesar et al., Nature 448: 196-202; 2007) was identified that shares characteristics of hESC's (Nanog+ Sox2+ Oct4+). All of these pluripotent cell types from mouse can generate the three embryonic germ layer in vitro or in a teratoma assay.

Epiblast stem cells (EpiScs) and induced pluripotent stem cells (iPS) fit into the broad pluripotent cell category and in concept, the technology described in the application could apply to these and other pluripotent cell types (ie, primate pluripotent cells). EpiSc epiblast stem cells are isolated from early post-implantation stage embryos and express Oct4 and are pluripotent (Tesar et al, Nature, Vol 448, p. 196 12 Jul. 2007). Induced pluripotent stem cells (iPS cells) are made by dedifferentiating adult skin fibroblasts or, other adult somatic cells, back to a pluripotent state by retroviral transduction of four genes (c-myc, Klf4, Sox2, Oct4) (Takahashi and Yamanaka, Cell 126, 663-676, Aug. 25, 2006).

The advantage of developing other non-ESC, self renewing, pluripotent/multipotent stem cells would help in improve developmental models, improve directed differentiation into adult cells and allow more efficient and less costly approaches to conventional methods.

Human pluripotent cells (such as human embryonic stem cells [hESCs] and induced pluripotent stem cells [iPS cells]) can be differentiated through a bi-potential mesendoderm (T+, MixL1+) precursor that can be further differentiated into a wide range of mesoderm lineages such as bone, blood, muscle and kidney. See FIG. 12. Different types of mesoderm precursors can be formed in embryonic development from mesendoderm. These include lateral plate mesoderm, splanchnic mesoderm, paraxial mesoderm and somatic mesoderm. Each of these mesoderm precursors gives rise to different types of mesoderm tissue (FIG. 12). IMP cells represent Isl1+ Nkx2.5+ splanchnic mesoderm, a type of mesoderm that forms the cardiovascular system and hematopoietic system.

The epicardium is derived from Isl1+ splanchnic mesoderm and constitutes the outer layer of the vertebrate heart. Embryologicaly, the epicardium is derived from a source of pro-epicardium though to originate in the septum traversum. Epicardium consists of a single layer of flat mesothelium that is connected to the mycocardium by sub-epicardial connective tissue (Manner et al., 2001, Cells Tissues Organs 169, 89-103). Formation of the epicardium over the developing heart coincides with the development of coronary blood vessels (Olivey et al., Trends in Cardiovasc Med 2004, 14, 247-251). Once the pro-epicardium comes into contact with the developing heart at around the time of beating, it spreads over the myocardium forming a new layer, the epicardium. The epicardium and related cells/tissue preceding the epicardium then gives rise to multiple cell types that together make up the coronary vasculature including smooth muscle cells, endothelial cells and cardiac fibroblasts. See FIG. 36. Epicardial cells also have the capacity to differentiate into cardiomyocytes (Zhou et al., 2008 Nature 454, 109-113). Soon after invading the myocardial surface, sub-populations of epicardial cells undergo an epithelial to mesenchymal transition and migrate into the sub-epicardial space. Some of these cells then have the capacity to further migrate into the compact zone of the myocardium. Coronary blood vessels form as angioblasts, derived from epicardium and/or other cells migrating into the heart, coalesce to form a primitive vascular plexus in the sub-epicardial space and in the myocardium. Eventually, these endothelial tubes coalesce to form larger vessels that become the coronary arteries and veins. The complement of cells comprising the coronary vasculature including smooth muscle and endothelial cells and, interspersed fibroblasts—all originating from progenitors in the pro-epicardium/epicardium. Epicardium is typically signified by expression of Wilm's tumor rotein 1 (WT1), T-box factor 18 (Tbx18), epicardin (Tcf21) and RALDH2 (Zhou et al., 2008; Cai et al., 2008, Nature 454, 104-108). The WT1+ epicardium is believed to form from an Isl1+ Nkx2.5+ precursor (Zhou et al., 2008). Progenitor cells expressing Wt1+ originating from the pro-epicardium/epicardium contribute to formation of the coronary vasculature. The EPC described herein represents a coronary vascular progenitor cell derived from human pluripotent cells.

As another aspect of this invention, conditions for the differentiation of human pluripotent cells into multipotent migratory cells (MMCs) have been described. MMCs form directly from adherant pluripotent cells in chemically defined media. MMCs are generated by treating human pluripotent cells with small molecule compounds to culture media. See FIG. 13. These compounds are known inhibitors of GSK3 activity (BIO) and TGFβ/Activin A/Nodal signaling (SB431542). By further treatment, MMCs can be differentiated into a wide range of cell types. By other treatments, MMCs can be converted to a CXCR4+ CD56+ population of cells (C56Cs, for CXCR4+/CD56+ cells), that up-regulate additional cell surface markers. In addition to expressing the cytokine receptor CXCR4 and CD56, C56Cs can up-regulate the stem cell marker c-Kit. C56Cs do not express markers for hematopoietic stem cells, such as CD45, or endothelial markers such as CD31.

Since C56Cs are produced from MMCs and express markers for receptors of cytokine signaling (CXCR4) known to be involved in stem cell 'homing' to ischemic-inflammatory tissue, it is possible that these cells may be capable of 'homing' to sites of tissue damage. Systemic administration by intravenous administration would be one way whereby these cells could home to damaged tissue and participate in repair processes. Once these cells have homed to damaged tissue, they may then promote tissue repair by paracrine mechanisms or by trans-differentiating into cells that participate directly in repair. These cells may also participate in the suppression of inflammatory responses and by immunomodulation (suppressing T cells, natural killer cell activity).

BRIEF DESCRIPTION OF THE FIGURES

FIGS. 6A, 6B, 6C: Generation of smooth muscle cells from (WA09-derived) IMP's following treatment with Wnt3a (25 ng/ml) and BMP4 (100 ng/ml) for 14 days. The cells were split at 1:4-1:6 ratio, fixed in 4% paraformadehyde and immunostained positively for A) smooth muscle actin (SMA) and B) smooth muscle calponin and negatively for the cardiomyocyte marker C) sarcomeric actin (Sarc. Actin). DNA was stained with dapi. Merge images are shown for SMA/Dapi, Calponin/Dapi and Sarc. Actin/Dapi. Images were taken at 20 and 40× magnification.

FIG. 19. Summary of cell surface markers on MMCs and C56Cs as determined by flow cytometry.

FIG. 23, 24. Experiment 1. 'Homing' of [$^{111}$In]oxime-labeled cells to the ischemic heart, bone and liver, lungs, spleen of 2 rats (FIG. 8—rat #1; FIG. 9—rat #2). C56Cs were labeled with [$^{111}$In]oxime then injected (~2×10$^6$ cells in 0.1 ml saline) into the tail vein of Sprague Dawley rats and then subject to 'live' nuclear imaging with a gamma camera 0.1, 2 and 24 hours post-infusion. Gray arrows indicate incorporation in bone: black arrow indicates incorporation into heart.

FIG. 25, 26. Experiment 2. 'Homing' of [$^{111}$In]oxime-labeled cells to the ischemic heart of 2 rats (FIG. 21—rat #1; FIG. 22—rat #2). C56Cs were labeled with [$^{111}$In]oxime then injected (~2×10$^6$ cells in 0.1 ml saline) into the tail vein of Sprague Dawley rats and then subject to 'live' nuclear imaging with a gamma camera 2 hours post-infusion. Arrows indicate incorporation into the heart.

Views of the short and long axis are shown. A thin, non-beating cardiac muscle wall is clearly seen in the region of ischemia.

Figure 28:
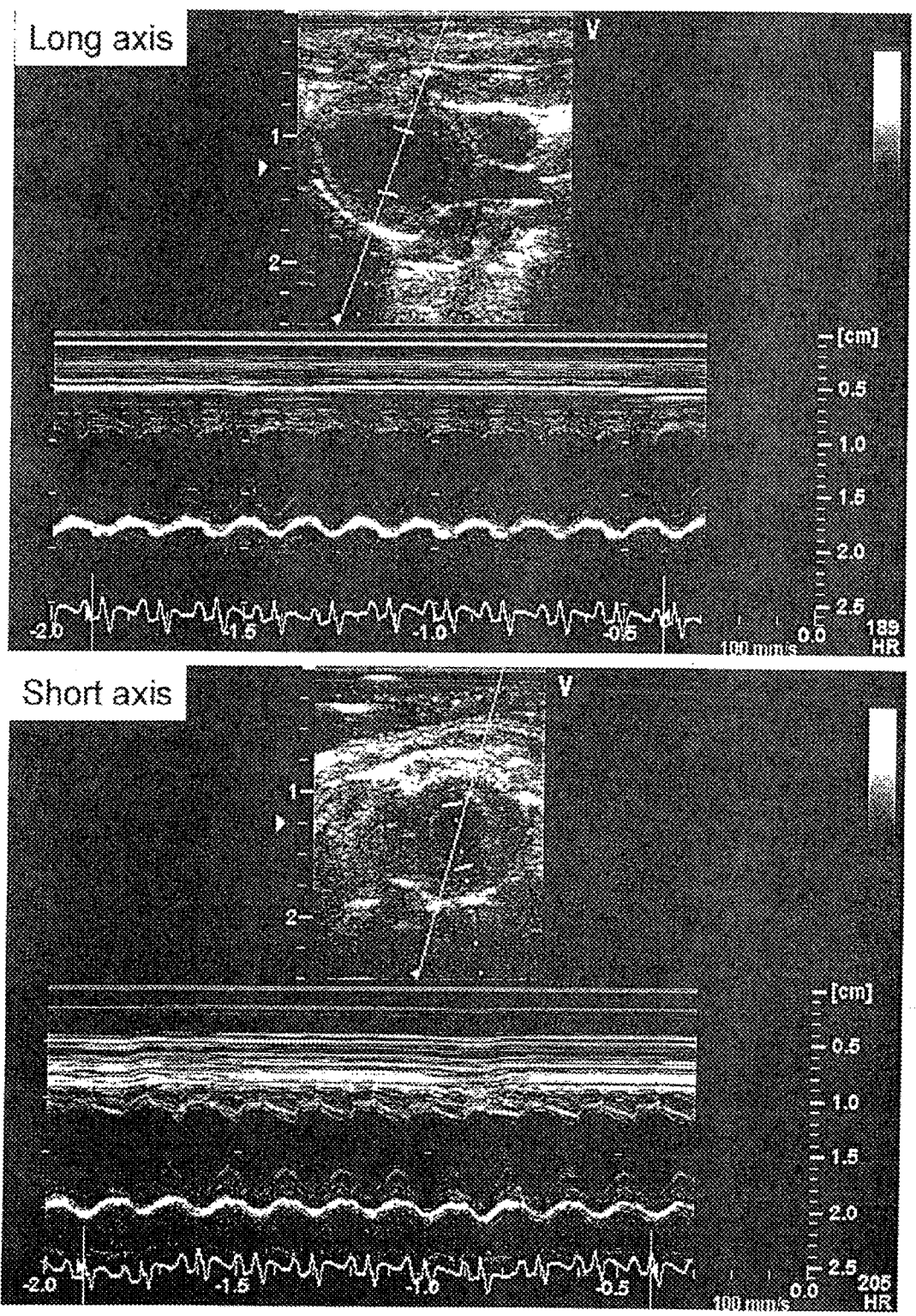

FIG. 28. Trans-thoracic echocardiography of an athymic rat with an acute myocardial infarction that received C56Cs (~2×10$^6$ cells per dose in 0.1 ml in saline) administered into the tail vein. A dose of cells were administered each day over a 3 day period post-infarction. Echocardiography was performed 2 weeks post-infusion. Views of the short and long axis are shown. A thickened, beating cardiac muscle wall is seen in contrast to the rat imaged in FIG. 25.

Figure 29:
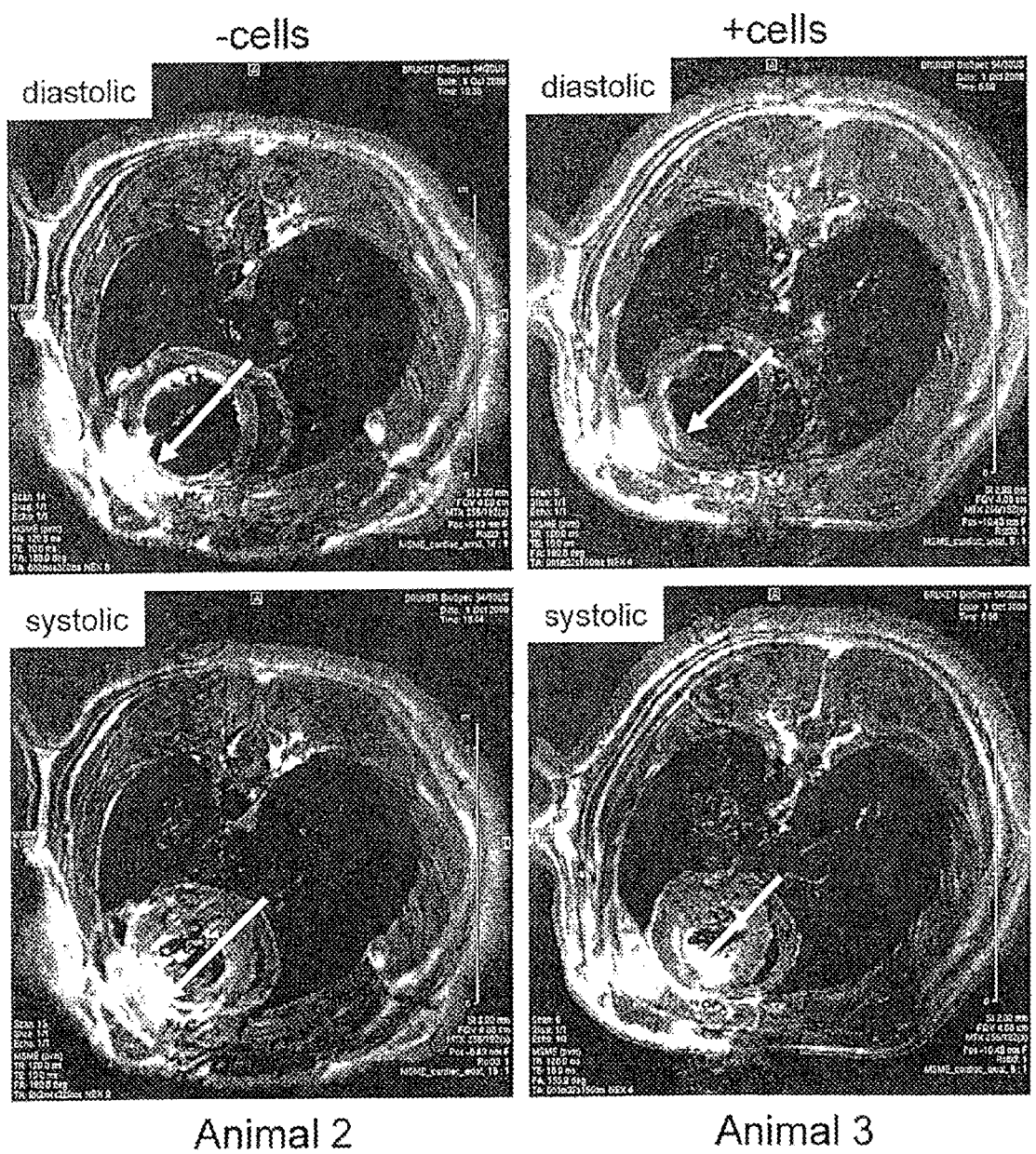

FIG. 29. High resolution MRI scans of athymic rats (shown in FIGS. 23,24) at 2 weeks following treatment with saline alone (−cells; animal 2) or C56Cs (+cells, animal 3). Diastolic and systolic views are shown from each of the 2 animals.

Figure 30:
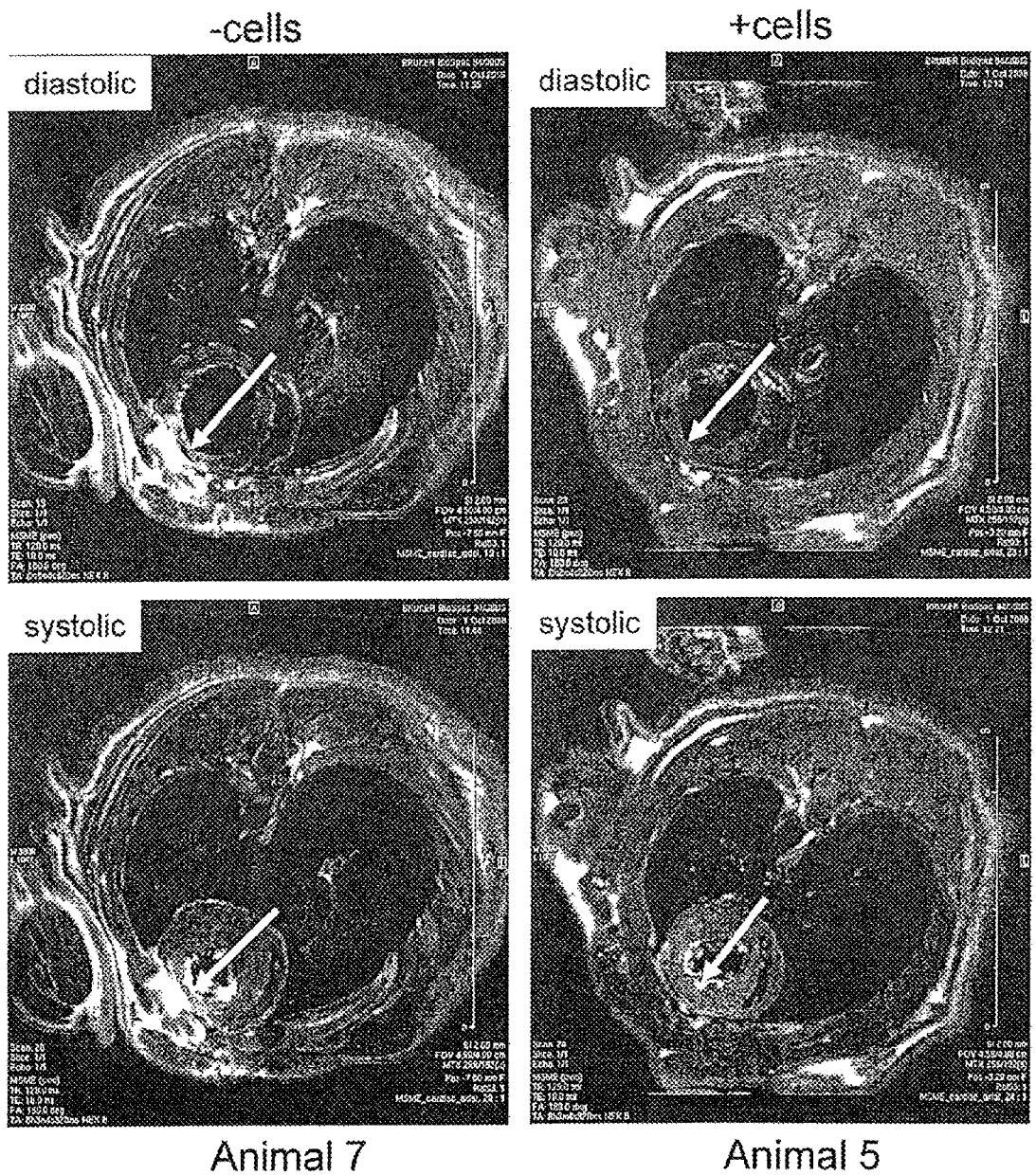

FIG. 30. High resolution MRI scans of athymic rats (3,4) at 2 weeks following treatment with saline alone (−cells, animal 7) or C56Cs (+cells, animal 5). Diastolic and systolic views are shown from each of the 2 animals.

FIG. 31. 2-photon confocal images of GFP+ cells that have localized to the photo-thrombotic cerebral stroke region. The vasculature shown in red results from Texas Red staining.

Figure 32:
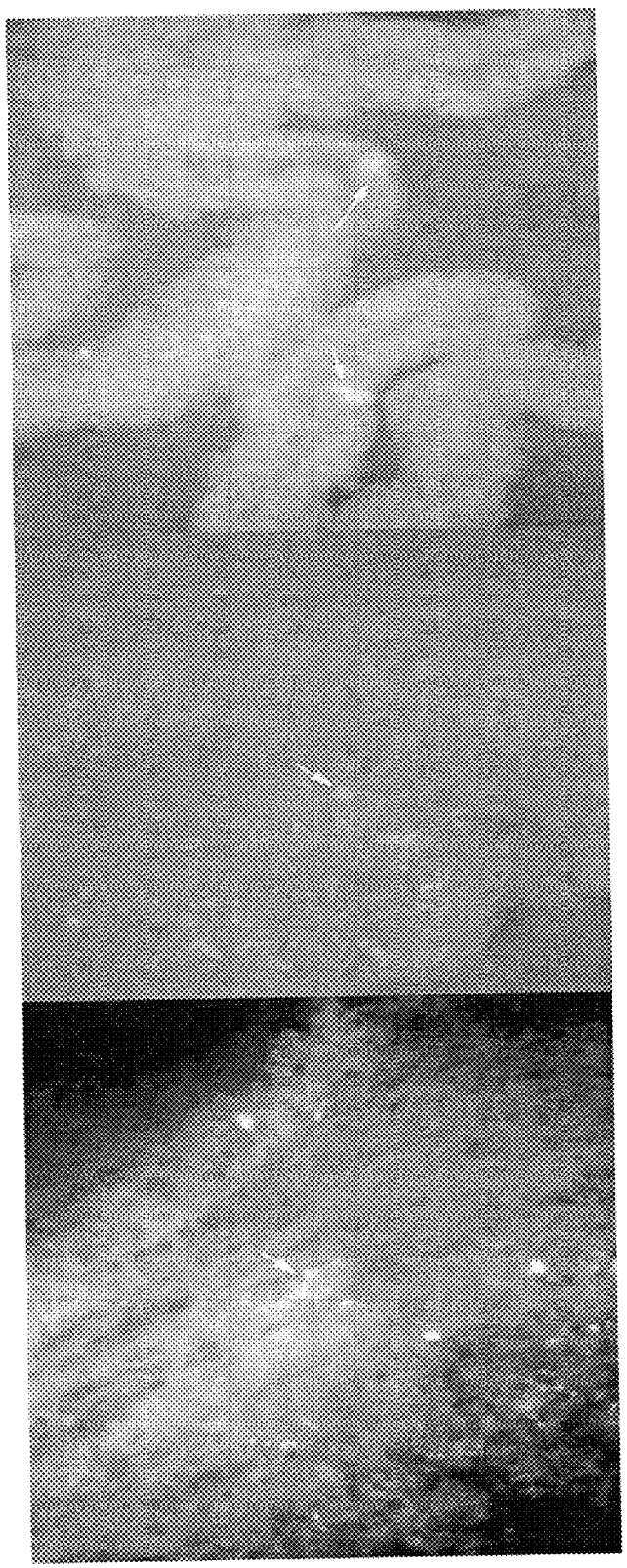

FIG. 32. Immuno-fluorescence staining of frozen brain sections taken from mice that had received a photo-thrombotic cerebral stroke. Images show localization of GFP+ infused C56C-derived cells near the penumbra and choroid plexus. Localization of GFP+ cells are indicated by arrows. Cells present in these sections exhibit multiple 'processes' indicative of dynamic behavior (observed by real time 2-photon imaging).

Figure 33:
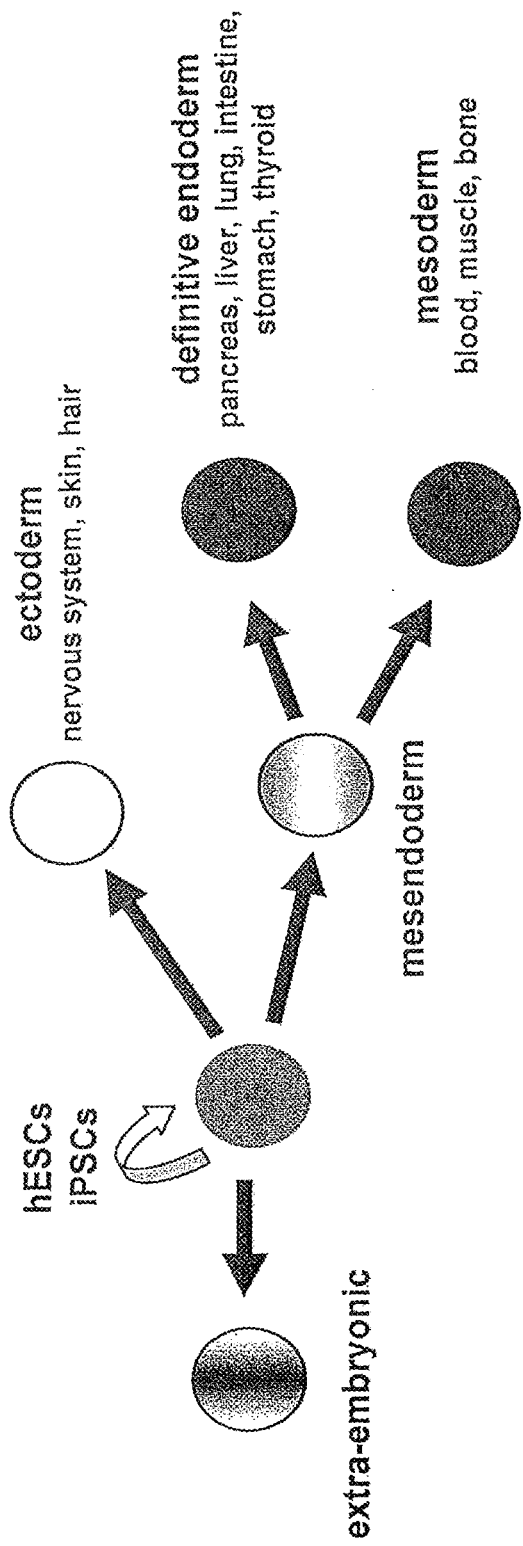

FIG. 33. Figure depicts the ability of human pluripotent stem cells (such as hESCs and hiPSCs) to differentiate into the three embryonic germ layers (ectoderm, mesoderm and definitive endoderm) and extra-embryonic lineages. Pluripotent cells are typically Oct4$^+$ and Nanog$^+$. Under the appropriate conditions, pluripotent cells can be maintained in a stable, self-renewing state.

Figure 34:
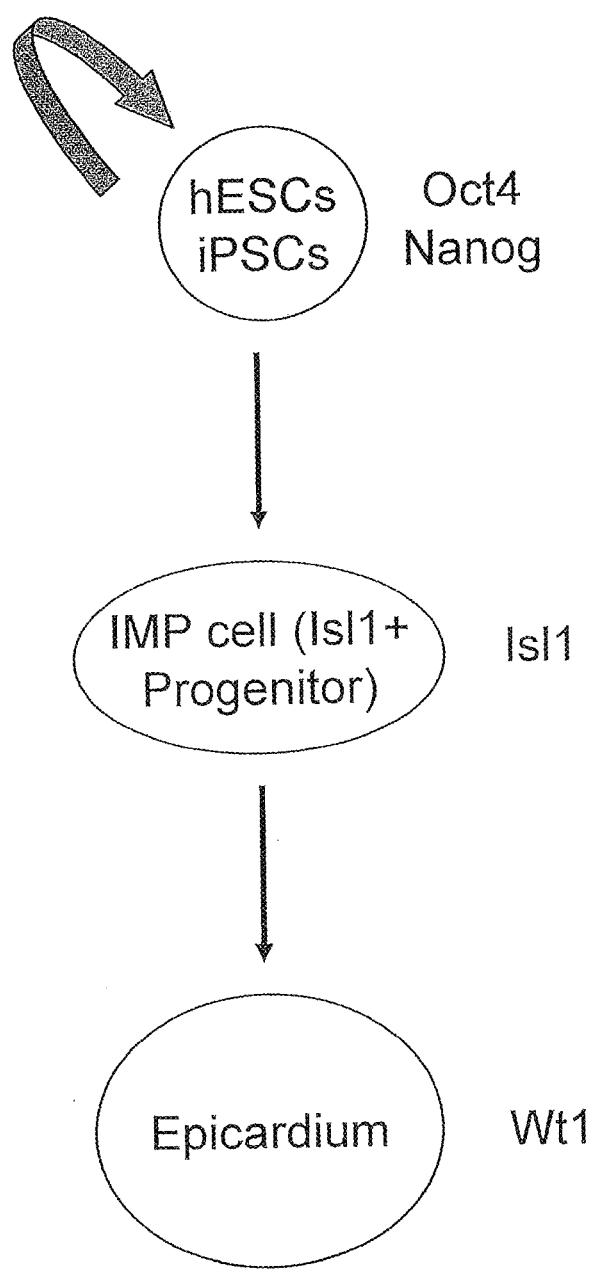

FIG. 34. A schematic illustrating the differentiation path of pluripotent cells (Oct4$^+$, Nanog$^+$) as they progress to IMP (Isl1+) cells and then to Wt1+ pro-epicardium/epicardium progenitors.

Figure 35:
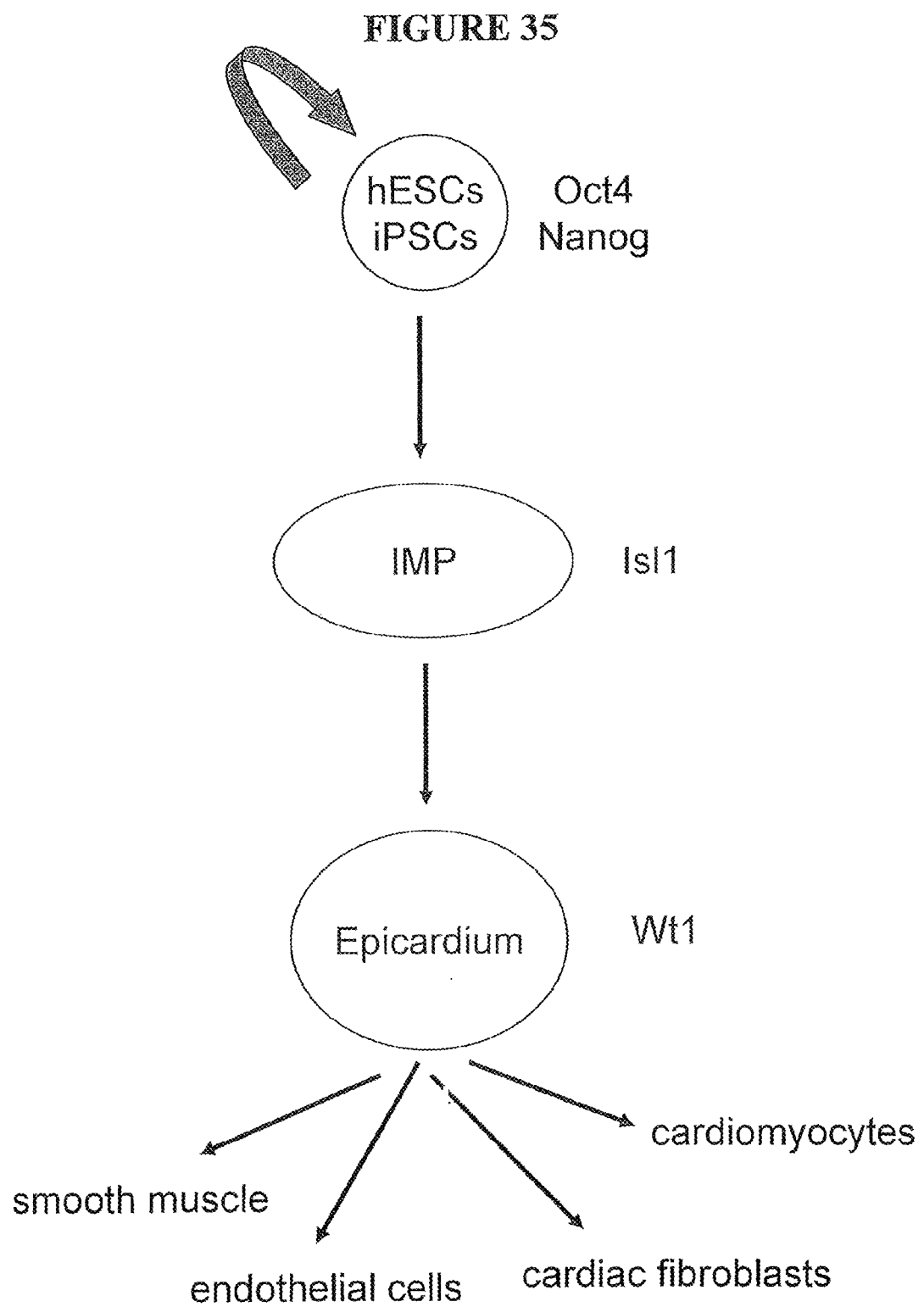

FIG. 35. Wt1+ pro-epicardium/epicardium can differentiate into smooth muscle, endothelial cells, cardiac fibroblasts and cardiomyocytes. They are therefore multipotent and able to generate to coronary vasculature and cardiac muscle.

FIG. 36. The primary cells involved in formation of the coronary vasculature and the major vessels of the coronary vasculature.

Figure 37:
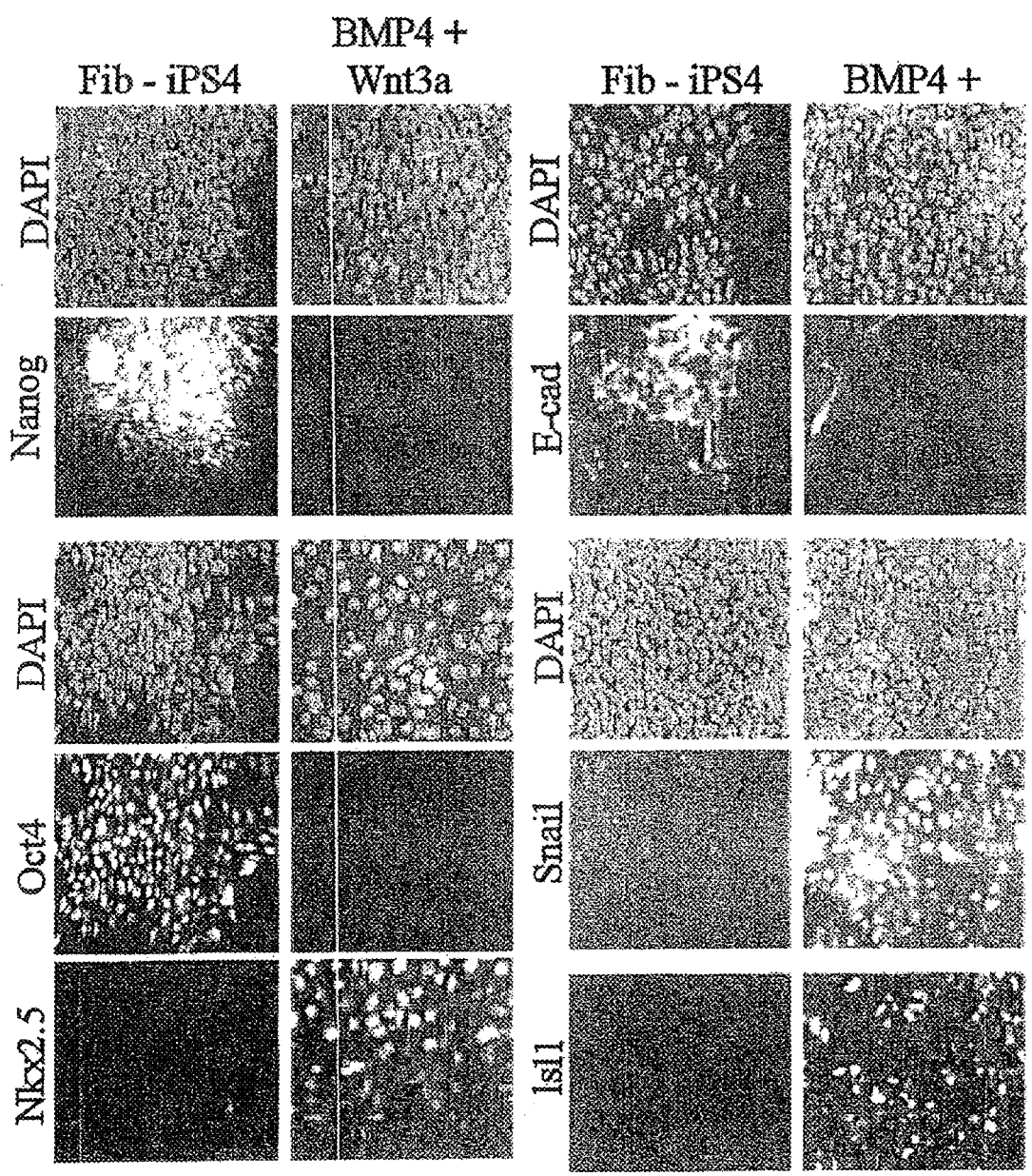

FIG. 37. Human iPSCs (Fib-iPS4) treated with BMP4 and Wnt3a differentiate to Islet 1 multipotent progenitors (IMPs, Isl1+) over a 4 day period. Immunostaining shows that following treatment with BMP4 and Wnt3a, hiPSCs lose expression of Nanog, Oct4 but, up-regulate Nkx2.5 and Isl1. As part of this process, hiPSCs go through an epithelial to mesenchymal transition (EMT), as indicated by down-regulation of E-cadherin and up-regulation of Snail.

Figure 38:
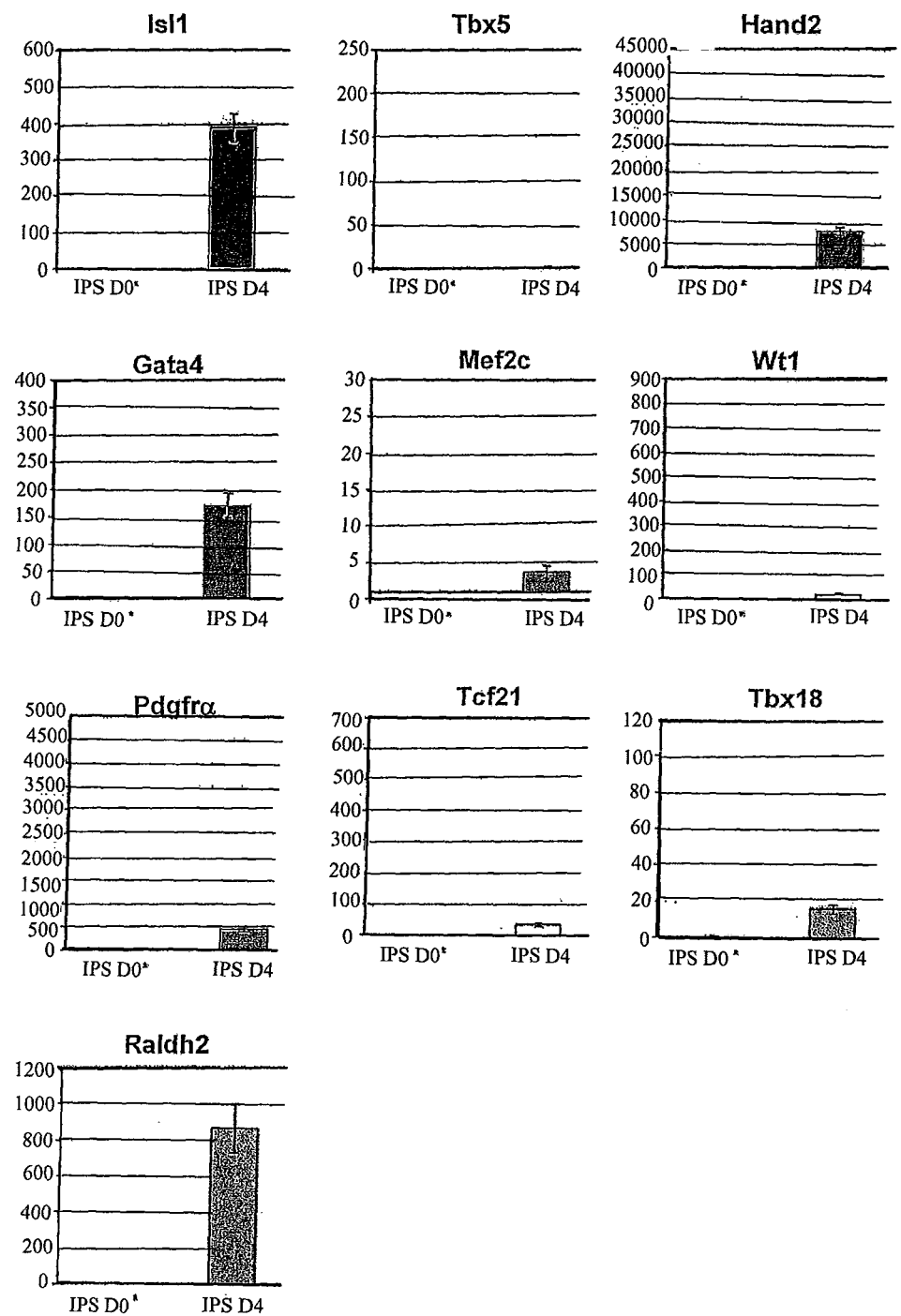

FIG. 38. hiPSCs (Fib-iPS4) and hiPSCs (Fib-iPS4) treated with BMP4 and Wnt3a for 4 days were analyzed by Q-PCR analysis for marker transcripts. Over this time period Isl1 and Hand 2 increase significantly. Assays were performed in triplicate. Error bars represent the standard error of the mean.

Figure 39:
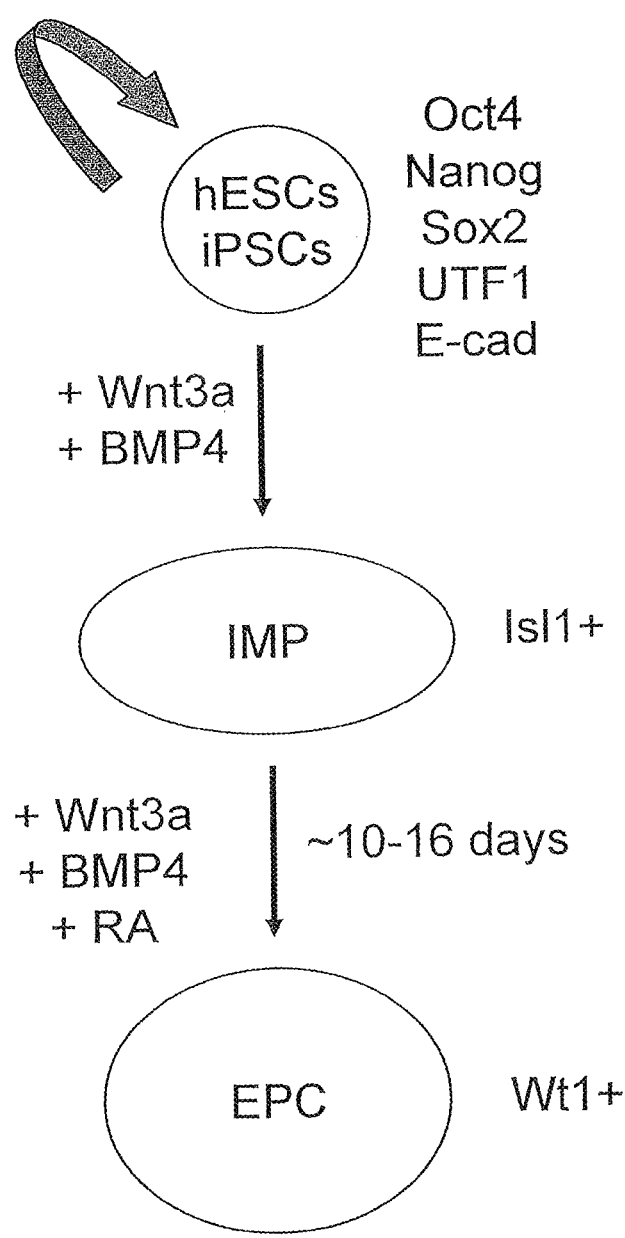

FIG. 39. Schematic showing the differentiation path of pluripotent cells (hESCs and hiPSCs etc.) first as they differentiate to IMP (Isl1+) cells and then to pro-epicardium/epicardium-like cells which we refer to as epicardial progenitor cells (EPCs, Wt1+). Factors added to defined media (DM) at each stage are indicated.

Figure 40:
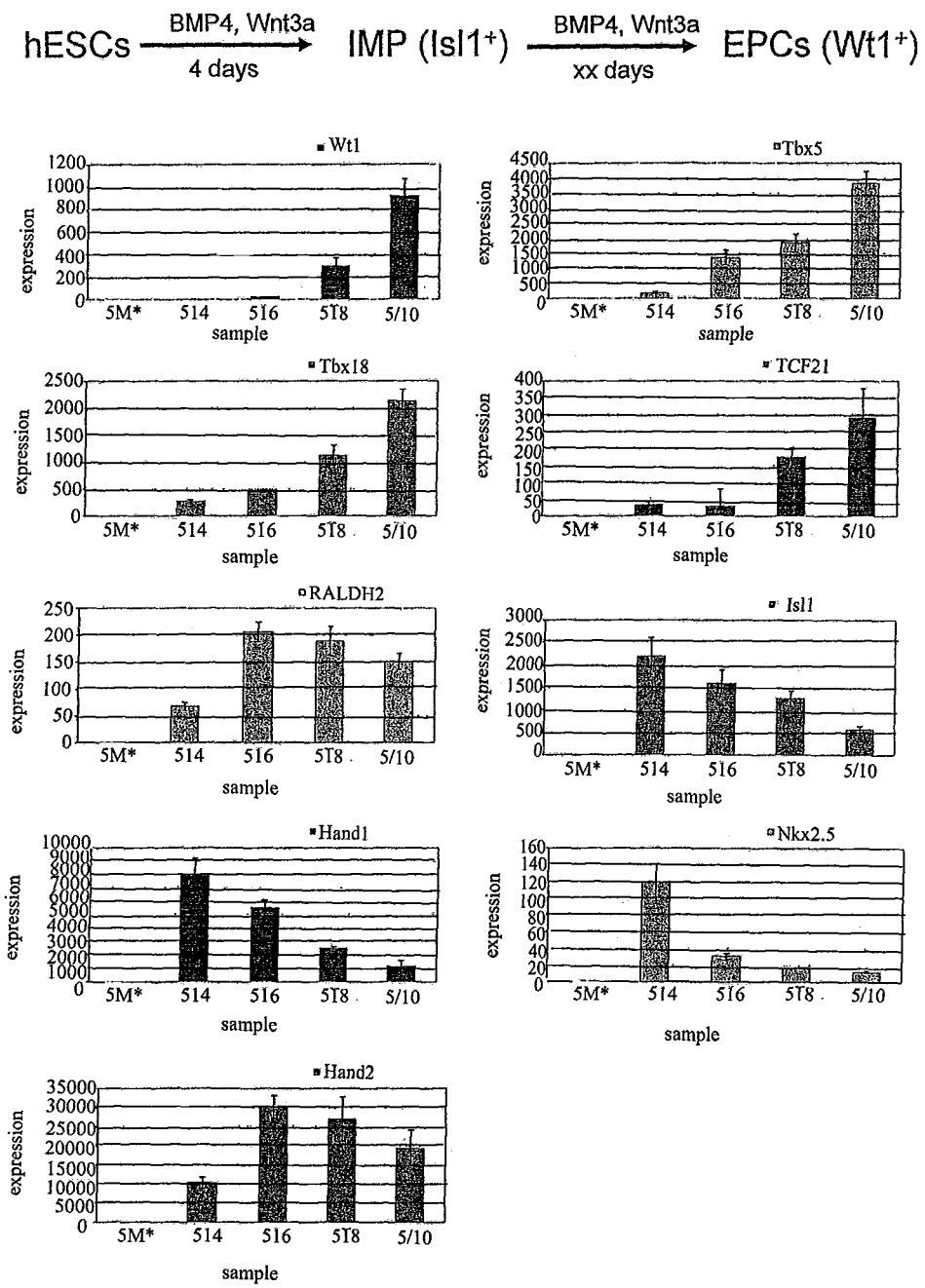

FIG. 40. IMP cells derived from hESCs (WA09) were treated with BMP4, Wnt3a and all-trans retinoic acid for the times indicated. As IMP cells transition towards EPCs they downregulate Isl1, Hand1 and Nkx2.5 but up-regulate other markers such as Raldh2, Tbx18, Tcf21 (epicardin) and Tbx5. q-PCR assays were performed in triplicates and shown as the standard error of the mean.

Figure 41:
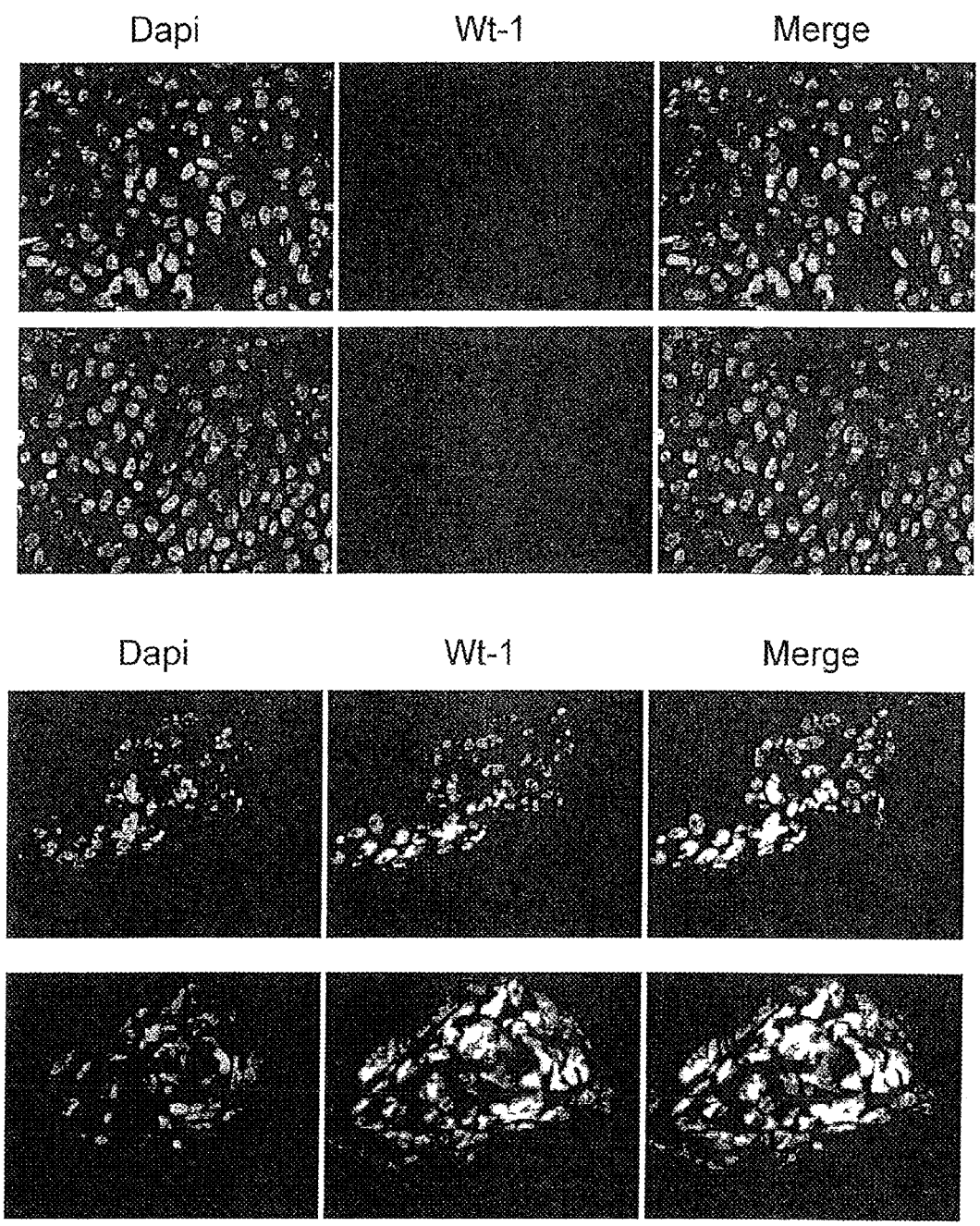

FIG. 41. Immunostaining analysis showing that EPCs express Wt1. 20× objective.

Figure 42:
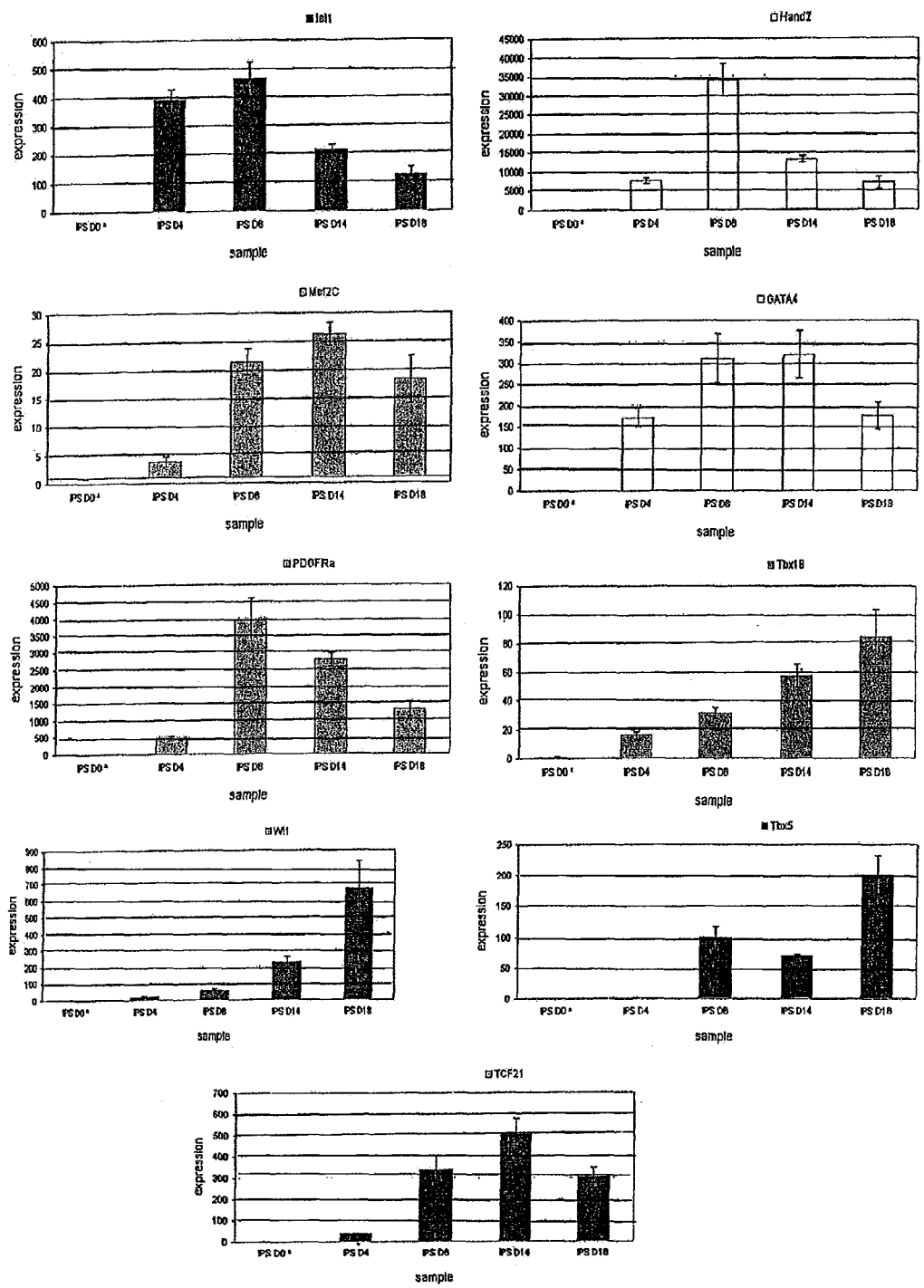

FIG. 42. IMP cells derived from hiPSCss (Fib-hPS4) were treated with BMP4, Wnt3a and all-trans retinoic acid for a period of 16 days. As IMP cells transition towards EPCs they down-regulate Isl1, but up-regulate Wt1, Tbx18 and Tbx5. q-PCR assays were performed in triplicates and shown as the standard error of the mean.

FIG. 43. A. Schematic showing possible differentiation outcomes for Wt1+ epicardium such as smooth muscle, endothelial cells, cardiac fibroblasts and cardiomyocytes. Potential factor treatment regimes for each are indicated. B. Shows that epicardium can differentiate to generate the coronary vasculature lineages (smooth muscle, endothelial cells, cardiac fibroblasts) and cardiomyocytes.

Figure 44A:
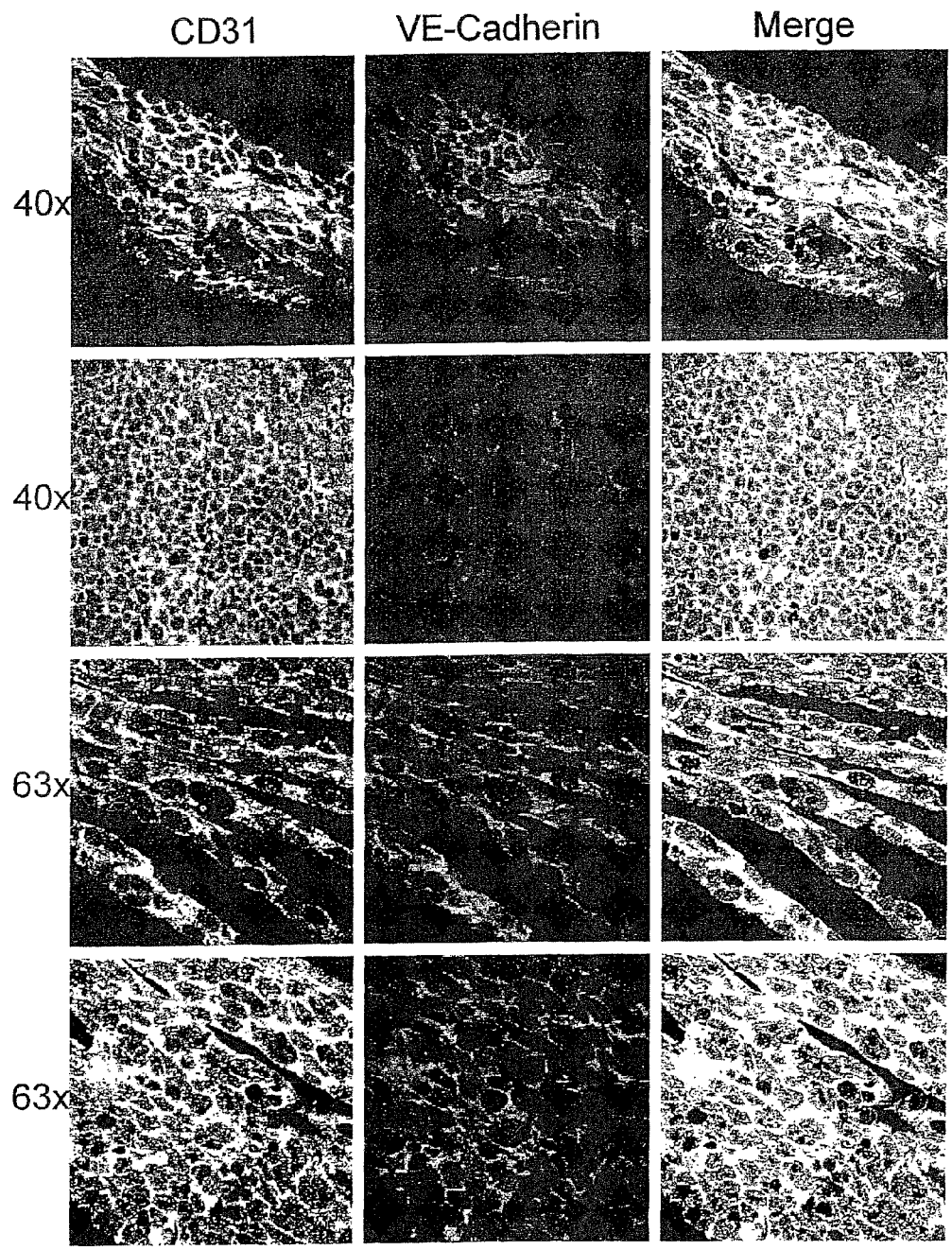

FIGS. 44A, 44 B. EPCs derived from hESCs (WA09) were passaged (1.25×10$^5$ cells/cm$^2$) into DM media −Activin +VEGFA for 12 days. The resultant cells were stained for (a) CD31 and VE-cadherin (CDH5) and (b) Pro-collagen and smooth muscle actin. Images were acquired at 40× and 63× magnification as indicated.

Figure 45:
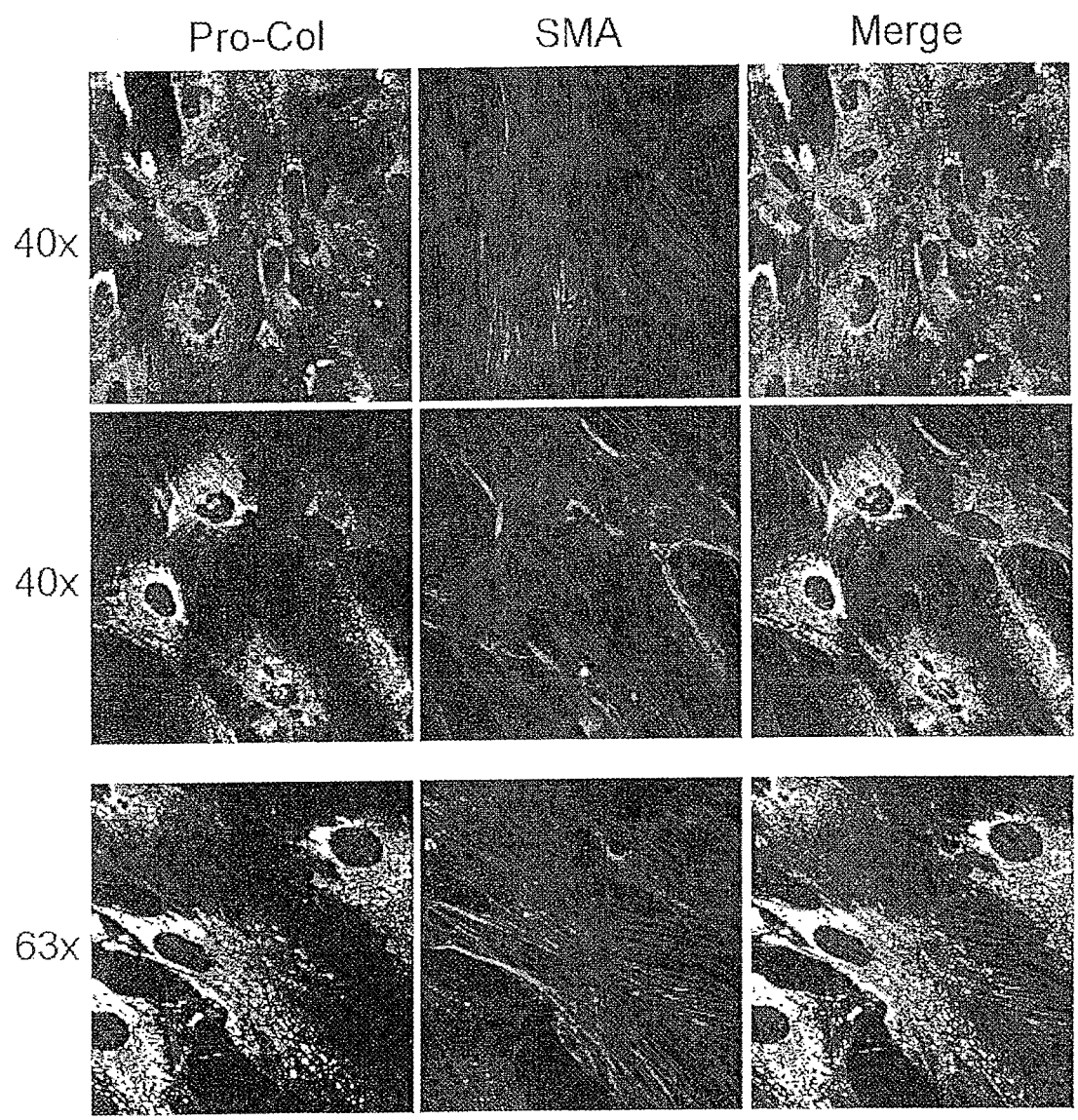

FIG. 45. EPCs derived from hESCs (WA09) were passaged (1.25×10$^5$ cells/cm$^2$) into 10% FBS, DMEM, 1× Pen/Strep, sodium pyruvate, L-Glutamine for 12 days. The resultant cultures were stained for Pro-collagen and smooth muscle actin.

FIG. 46, Table 1. Microarray profiling (Affymetrix Human Genome U133 Plus 2.0) of IMPs generated from hIPSCs (hFib2-iPS4) revealed a set of genes up-regulated >log 2$^3$, compared to the starting pluripotent cell population. Cells were differentiated through the IMP (Isl1+) stage (for 4 days) in defined media plus Wnt3a and BMP4.

FIG. 47, Table 2. Microarray profiling (Affymetrix Human Genome U133 Plus 2.0) of EPCs generated from hESCs (WA01, WA07, WA09, BG02) and hIPSCs (hFib2-iPS4) revealed a common set of genes up-regulated >log 2$^3$, compared to the starting pluripotent cell population. Cells were differentiated through the IMP (Isl1+) stage (for 4 days) and then towards EPCs for a further 16 days.

Figure 48:
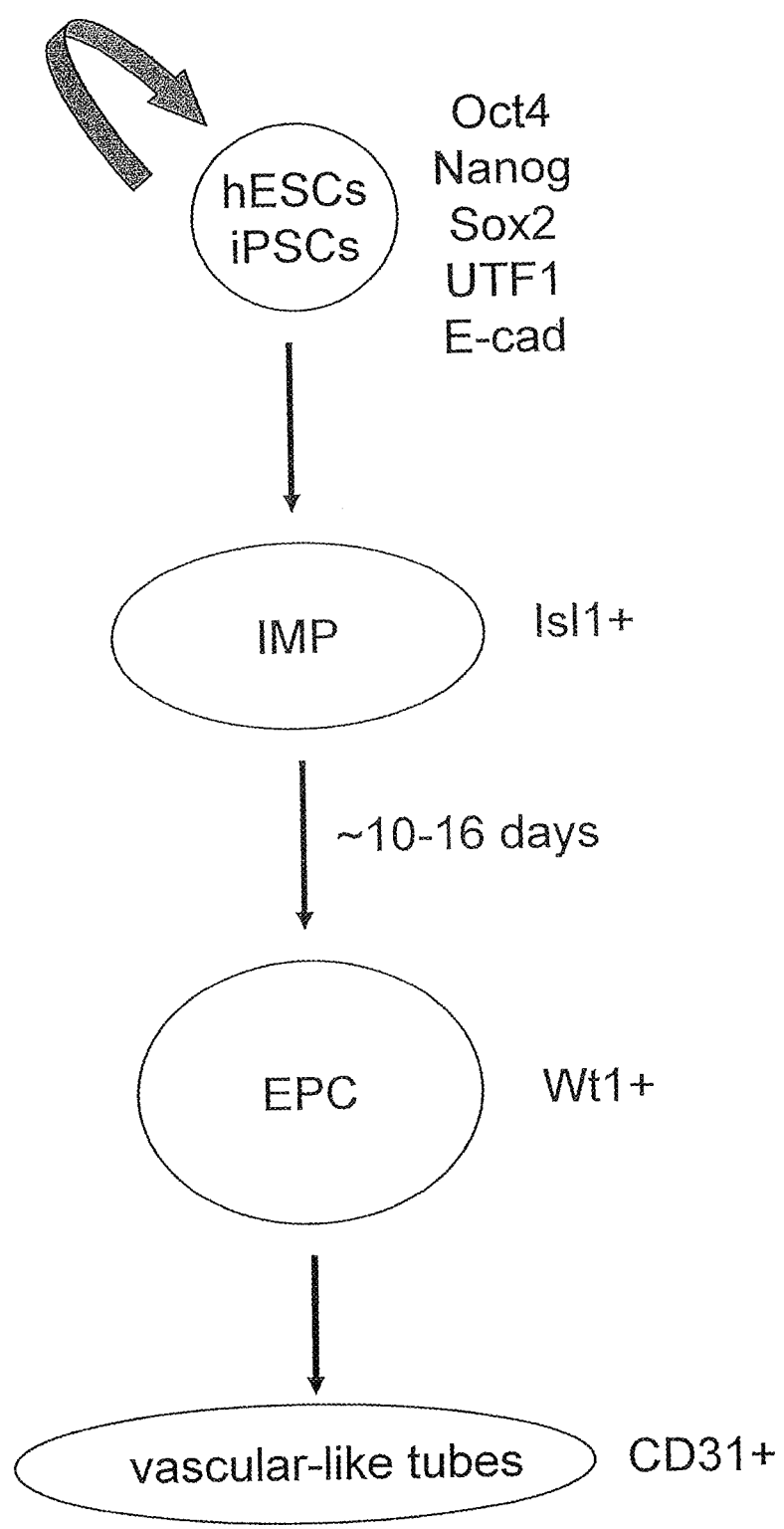

FIG. 48: Sequence of differentiation steps we use to define the progression of hESCs or hiPSCs to IMP cells (Isl1+) then EPCs (Wt1+) and then to vascular-like tubes (CD31+).

Figure 49:
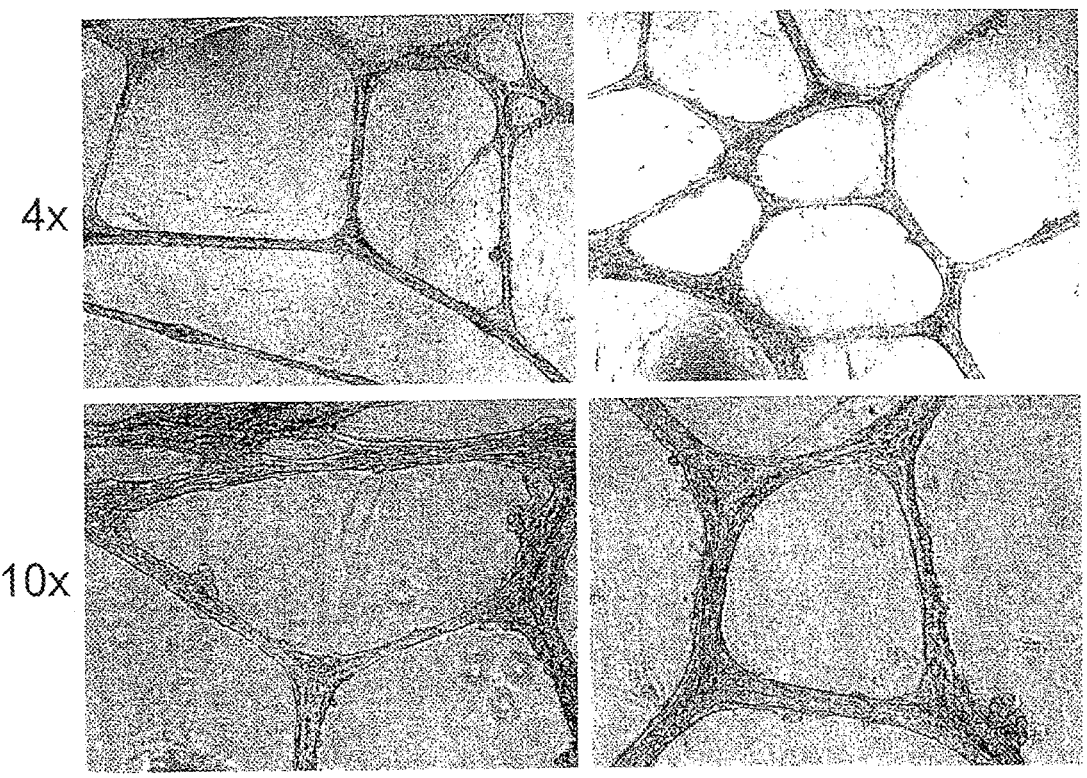

FIG. 49: Bright field images of endothelial tubes formed from epicardial progenitor cells (EPCs). The images are at 4× and 10× magnification as indicated.

FIG. 50: Confocal images of endothelial tubes from epicedial cells. A. Confocal images of tubes stained with CD31 (green) and CDH5 (red) in one focal plane revealing the presence of a lumen. All images were at a 40× magnification. B. Reconstruction of endothelial tubes from Z-stacked confocal images at 40× magnification. Yellow denotes overlap of CD31 and CDH5 expression.

Figure 51:
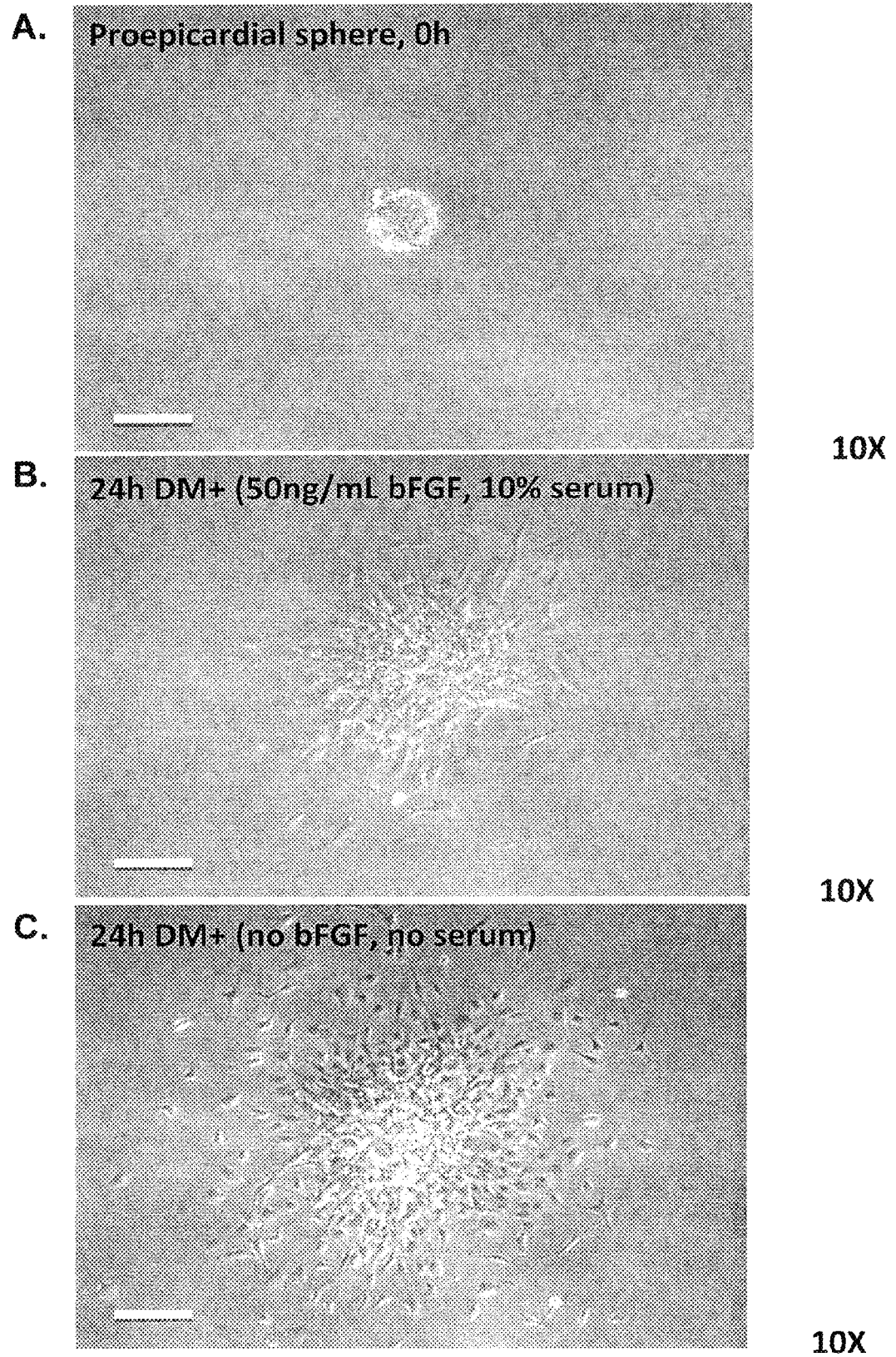

FIG. 51: Spheres were generated from EPCs and plated down on a collagen based matrix (Geltrex). A. Shows the adherence of the sphere at t=0. B. Plated spheres were cultured in bFGF+10% fetal calf serum (B) or, in the absence of serum and bFGF (C). Bright field images were taken 24 hrs post-plating of EPC spheres. Similar results were obtained when spheres were plated on collagen I matrix (not shown).

Figure 52:

FIG. 52. WA09 hESCs were plated on Geltrex and probed with antibodies for cytokeratin (red) and vimentin (green). DNA was detected by staining with DAPI. hESCs are +ve for the epithelial marker cytokeratin but negative for the mesenchymal marker vimentin.

FIG. 53. EPCs plated on Geltrex, as in FIG. 4, were fixed with PFA and stained with antibodies for cytokeratin (red) and vimentin (green). DNA was detected by staining with DAPI. Cells are +ve for vimentin (green) indicating they have undergone an epithelial to mesenchymal transition and are mesenchymal and migratory.

Figure 54:
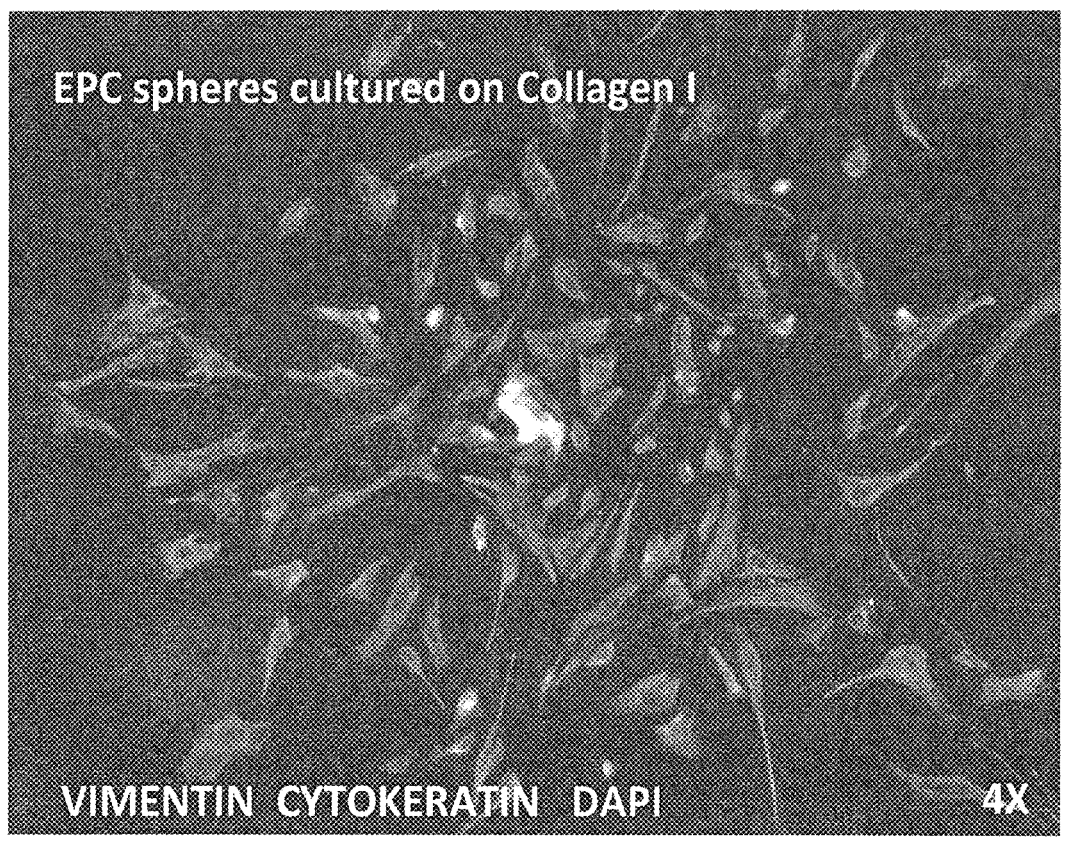

FIG. 54. EPCs were plated on collagen I matrix. Cells were fixed and stained with antibodies for cytokeratin (green) and vimentin (red). DNA was detected with DAPI. Cells are vimentin +ve, indicating they have undergone an epithelial to mesenchymal transition and are mesenchymal and migratory.

Figure 55:
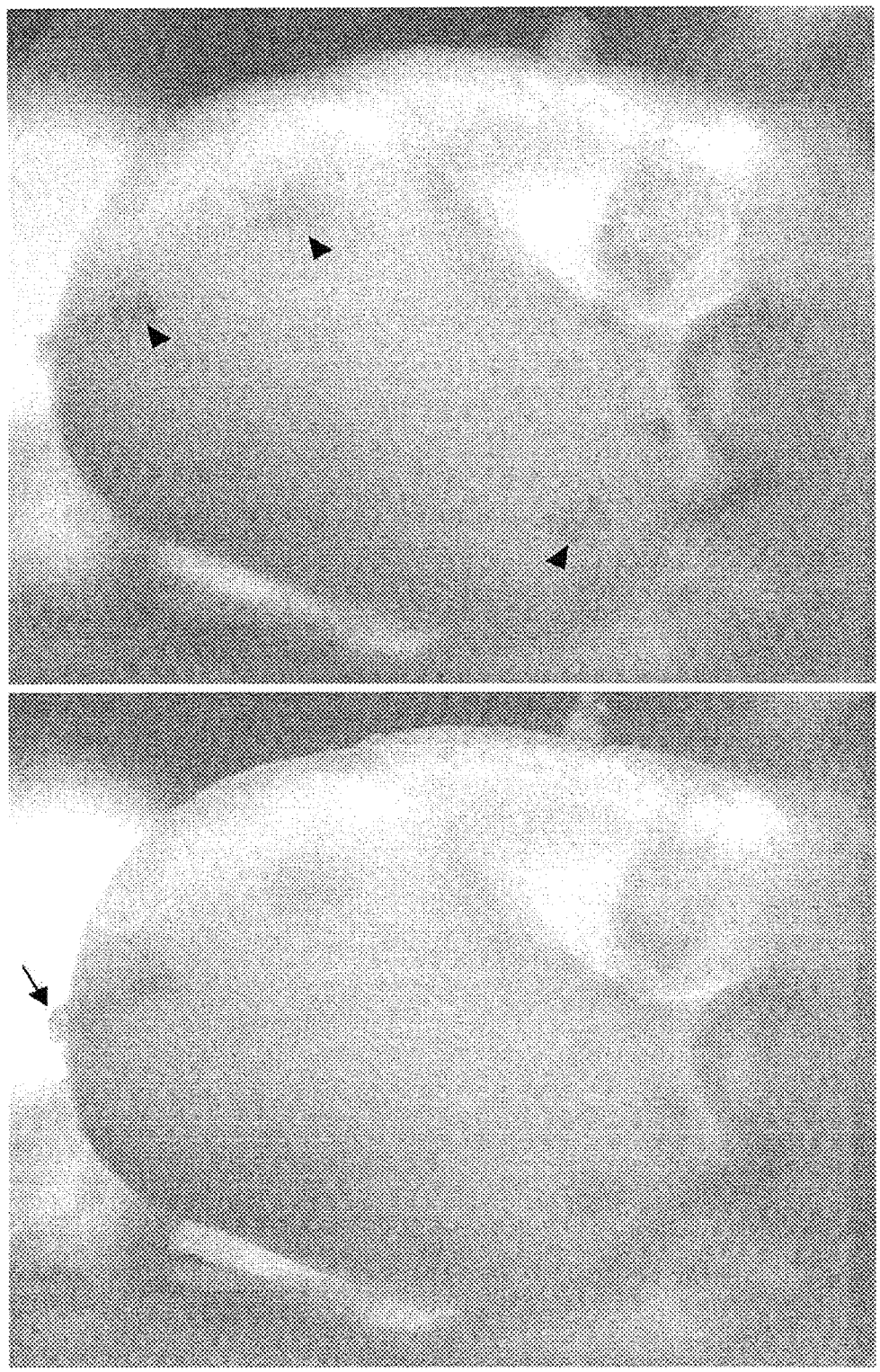

FIG. 55. These are two images of the same heart at different focal planes, visualizing D14 EPC aggregates three days following implantation in chicken embryos. Brown clusters of cells (GFP staining) are clearly visible (arrowheads). Arrow points to a cluster of PE cells that are attached but have not invaded.

Figure 8:
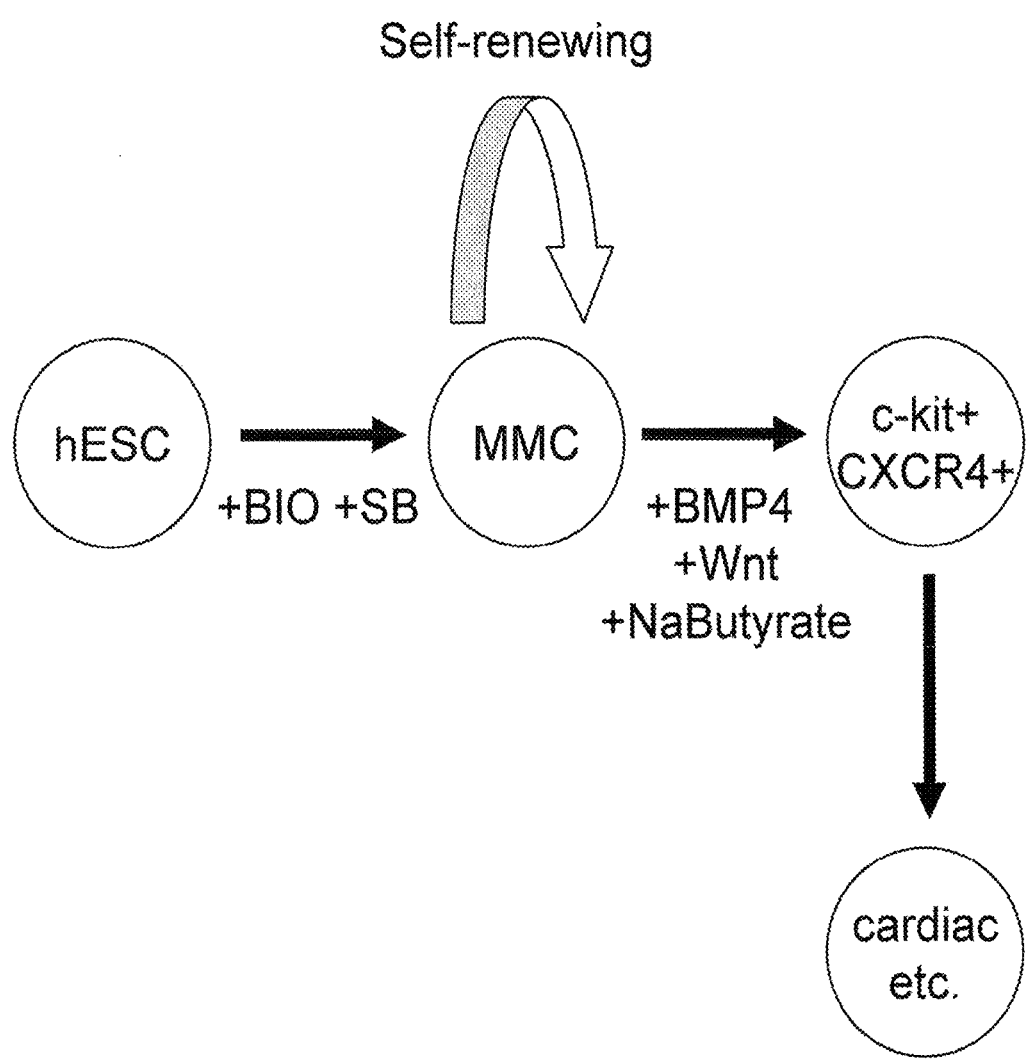
FIG. 8: Schematic showing the formation of MMC progenitor cells which can be maintained as a stable self-renewing population. MMS can be differentiated into a c-kit+ CXCR4+ progenitor cell type.
Figure 56:
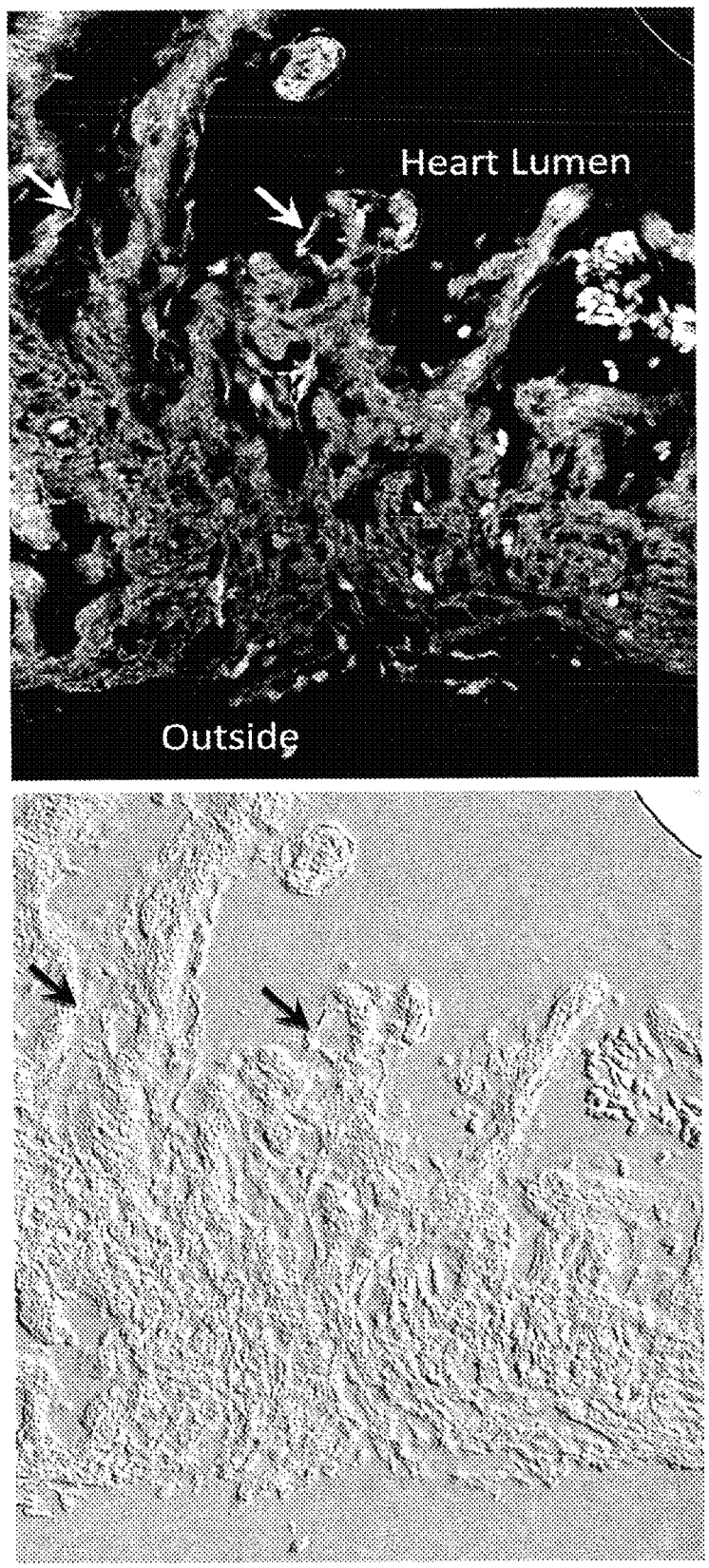

FIG. 56, 57. EPC aggregates were transplanted next to the developing chick heart (FIG. 8). Tissue was fixed with PFA, paraffin embedded and sectioned. Sections were then stained with an anti GFP antibody to detect GFP+ EPC cells in grafts. Immunofluorescence staining shows that EPCs migrate through the chick myocardium and are therefore highly invasive.

Figure 58:
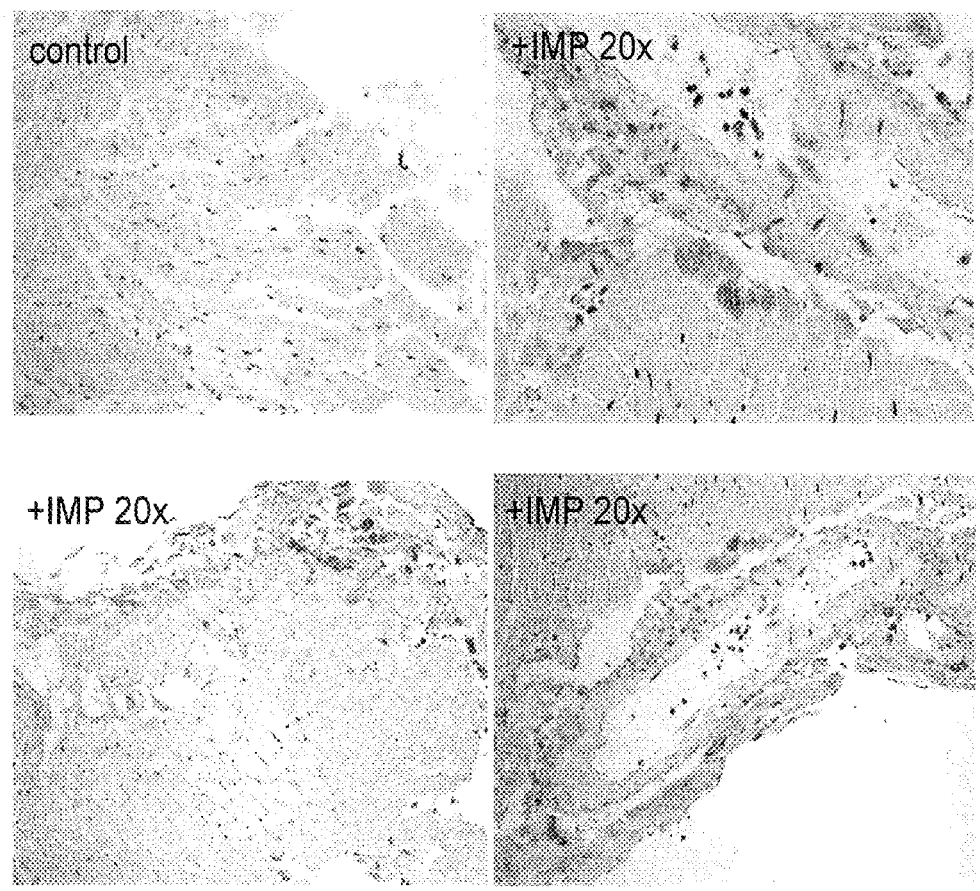

FIG. 58. IMP cells were grown as spheres then co-cultured with pieces of mouse, cardiac tissue. After 8 days co-culture, mouse heart tissue was fixed with PFA, paraffin embedded and sectioned. Sections were then probed with antibodies for anti-human beta myosin heavy chain (brown). Data indicates the presence of human, IMP-derived cardiomyocytes in the mouse cardiac tissue, indicating that IMP cells can differentiate into cardiomyocytes.

Figure 59:
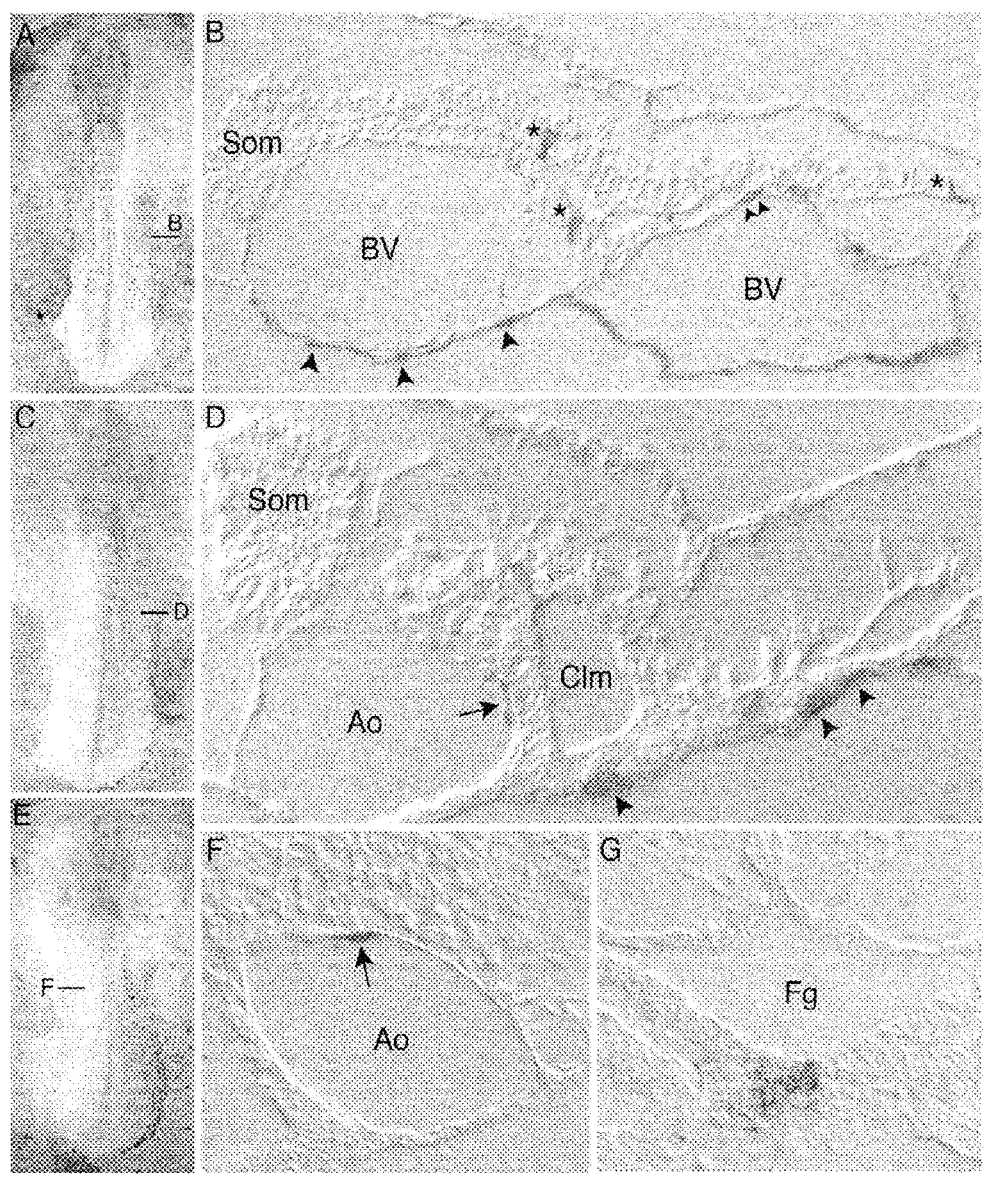

FIG. 59. GFP+ IMP cells incorporate into embryonic structures of chicken embryos. Whole mount images (A, C, E) and transverse embryo sections (B-G) localizing HES cells by GFP immunodetection. (A) Stage 12 embryo and corresponding transverse section (B), showing broad incorporation of HES cells into the endoderm (arrowheads) somatic and splanchnic mesoderm (asterisks), and perivascular cells (double arrowheads). (C) Stage 12 embryo and corresponding transverse section (D) showing IMP-derived endoderm (arrowheads), endothelial cell (arrow) and intermediate mesoderm (white arrow). (E) Stage 12 embryo and corresponding transverse section (F) showing and IMP-derived endothelial cells in the aorta. (G) Transverse section of a stage 13 embryo showing cells derived from IMPs incorporate into the liver primordium at the level of the anterior intestinal portal.

Figure 60:
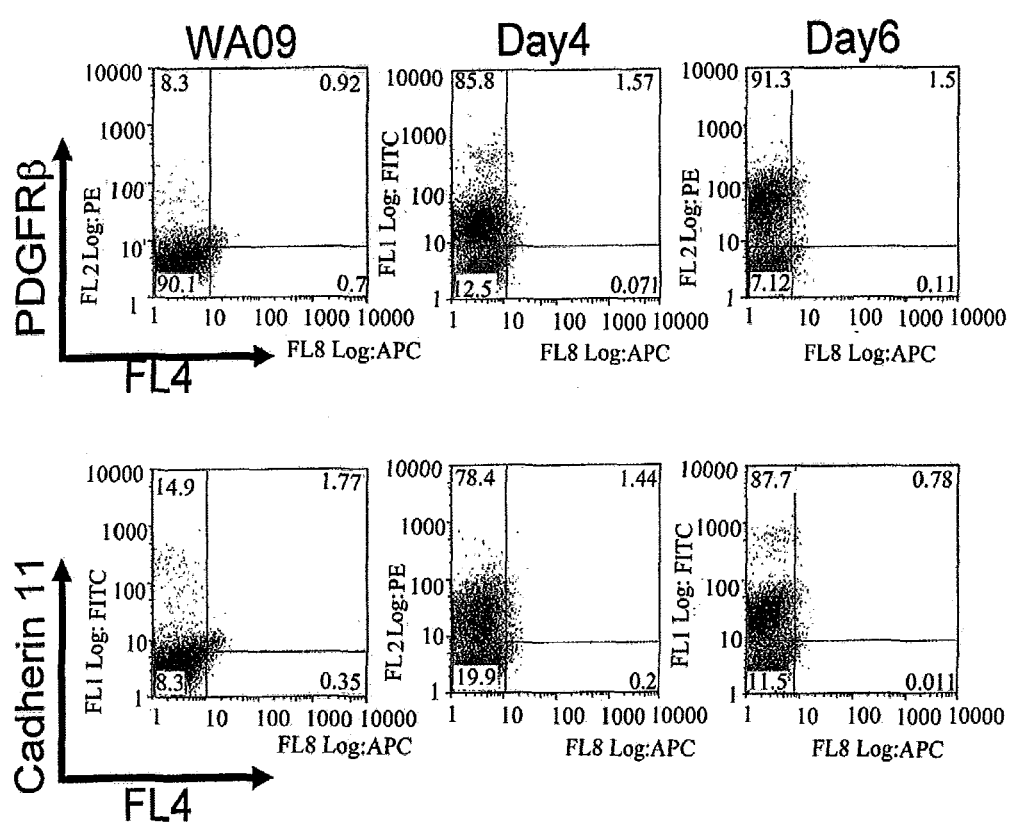

FIG. 60: Isl1+ cells are marked by the presence of Cadherin 11 and PDGFRβ. WA09 cells were differentiated in the presence of Wnt3a and BMP4 (as stated previously) for 4 and 6 days. WA09, day 4 and day 6 cells were Accutase treated to form single cell suspensions and stained for Cadherin 11 and PDGFRβ. In conjunction, cells were stained using donkey anti-goat 488 secondary antibody and IgG2aPE isotype control respectively. The cells were visualized using a Cyan flow cytometer (DAKO). Populations are visualized antibody versus FL4 with the red representing control populations and blue antibody stained populations.

Figure 61:
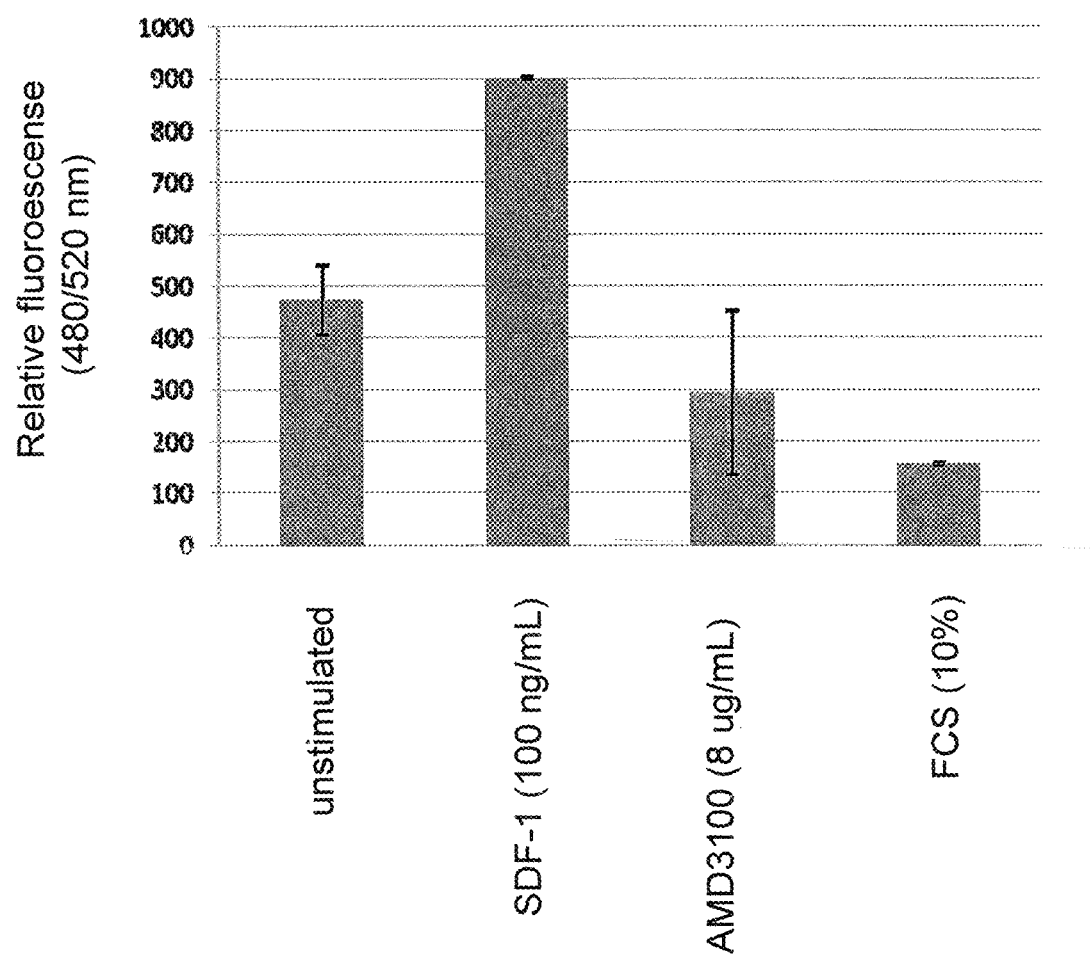

FIG. 61. To investigate the mechanisms by which C56Cs migrate towards ischemic/damaged tissue we assayed these cells in a Boyden chamber assay. 300,000 C56C cells were seeded in the upper chamber of a Boyden chamber. In the lower chamber these data demonstrate that C56C cells are responsive and migrate towards the SDF1 cytokine (FIG. 61). This migration is blocked with the antagonist AMD3100, indicating that migration is mediated through the CXCR4 receptor.

Figure 62:
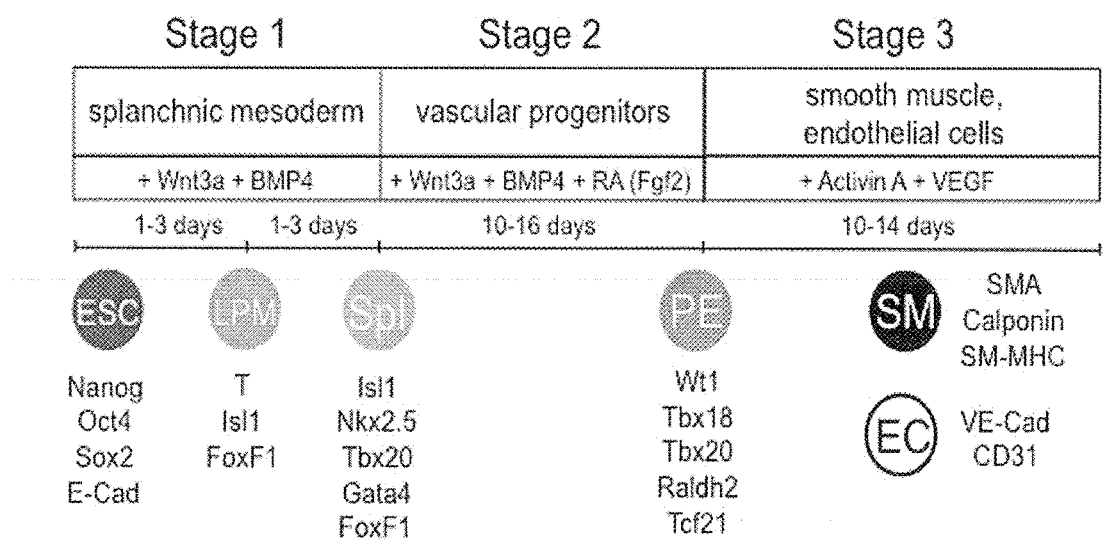

FIG. 62. Summary of differentiation pathways defined in this report. Human embryonic stem cells (ESC) treated with Wnt3a and BMP4 first transition through a lateral plate mesoderm stage (LPM), followed by splanchnic mesoderm (Spl-m); Stage 1. Spl-m are denoted by expression of Isl1 and Nkx2.5 (i.e., IMP Cells). Addition of Fgf2 or retinoic acid (RA) promotes formation of Wt1+ pro-epicardium (PE)-like vascular progenitor cells (EPCs-Stage 2) that can be further differentiated into smooth muscle and endothelial cells (Stage 3).

Figure 63:
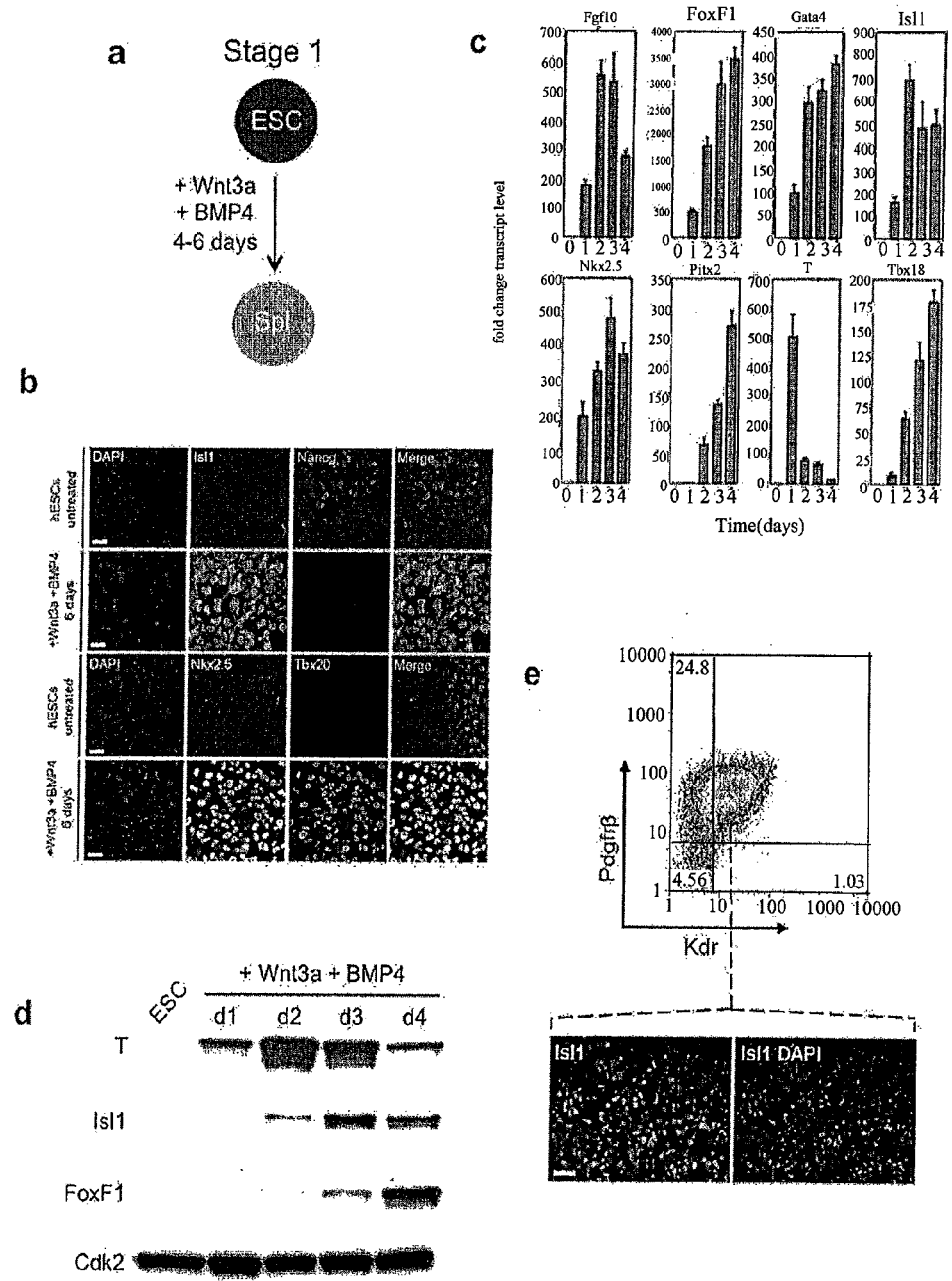

FIG. 63. Efficient differentiation of hESCs into Isl1+ splanchnic mesoderm (IMP cells) with defined factors. (a) The general approach to specify Isl1+ splanchnic mesoderm (Spl-m) cells from hESCs using Wnt3a and BMP4 (Stage 1 differentiation). (b) Immunostaining of untreated WA09 hESCs or, hESCs treated with Wnt3a (25 ng/ml) and BMP4 (50 ng/ml) for 6 days. Fixed cells were probed with antibodies for Isl1, Nanog, Nkx2.5 and Tbx20. DAPI was used to counter stain nuclei. Micron bar, 25 µm. (c) Q-PCR analysis of Wnt3a and BMP4 treated WA09 hESCs over 4 days. Assays for each transcript were performed in triplicate and fold-changes shown relative to untreated hESCs after normalization with Gapdh. Error bars, +/−standard deviation. (d) Immunoblot analysis of T, Isl1 and FoxF1 over a time-course of 4 days following treatment of WA09 hESCs with Wnt3a and BMP4. Cdk2 was used as a loading control. (e) Flow cytometry analysis following treatment of WA09 hESCs with Wnt3a and BMP4 for 6 days. Double staining for Pdgfrβ and Kdr is shown. The Pdgfrβ+ Kdr+ population (circled) was isolated by FACS, plated on Matrigel-coated slides and stained for Isl1 and DAPI. Micron bar, 100 µm.

Figure 64:
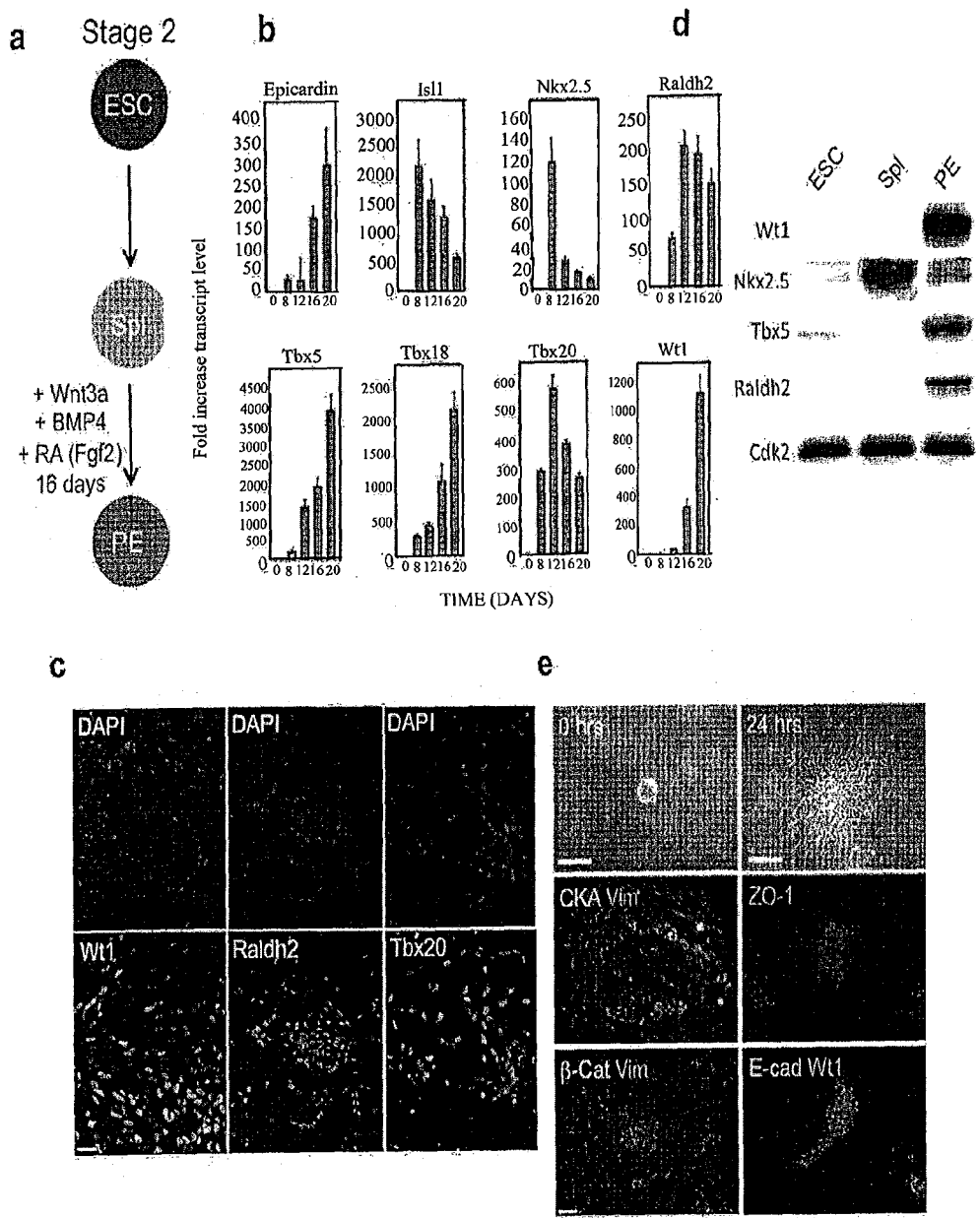

FIG. 64. Efficient differentiation of WA09 hESC-derived Spl-m (IMPs) into Wt1+ epicardium-like cells (EPCs). (a) Summary of the differentiation strategy used to derive epicardium-like cells (EPi) from hESCs (ESC); Stage 2 differentiation. (b) Q-PCR analysis as hESC-derived Spl-m cells transition towards Wt1+PE-like cells following RA (4 µM) treatment. Assays were performed in triplicate on samples at days 0, 8, 12, 16, 20. Fold-changes are relative to transcript levels in hESCs after normalization to Gapdh. Error bars, +/−standard deviation. (c) Immunofluorescence staining of hESC-derived PE-like cells after 20 days differentiation in the presence of Wnt3a, BMP4 and RA. Fixed cells were probed with antibodies for Wt1, Raldh2, Tbx20 and counter stained with DAPI (DNA). Micron bar, 50 µm. (d) Immunoblot analysis of cell lysates from hESCs (ESC), Isl1+ Splanchnic mesoderm (Spl) and PE-like cells (PE). Blots were probed with antibodies for Wt1, Nkx2.5, Tbx5 and Raldh2. Cdk2 was used as a load control. (e) Bright field Images showing Wt1+ cell aggregates plated on to Matrigel for 0 and 24 hours (top panels). Micron bar, 200 µm. Middle and lower panels: immunofluorescence images showing Wt1+PE-like cell aggregates 24 hours after plating on Matrigel. Cells are stained for antibodies raised against the epithelial markers cytokeratin A (CKA), ZO1, E-cadherin (E-cad), the mesenchymal marker vimentin (Vim), β-catenin, (β-cat) and Wt1. DAPI, DNA (blue). Micron bar, 25 μm.

Figure 65:
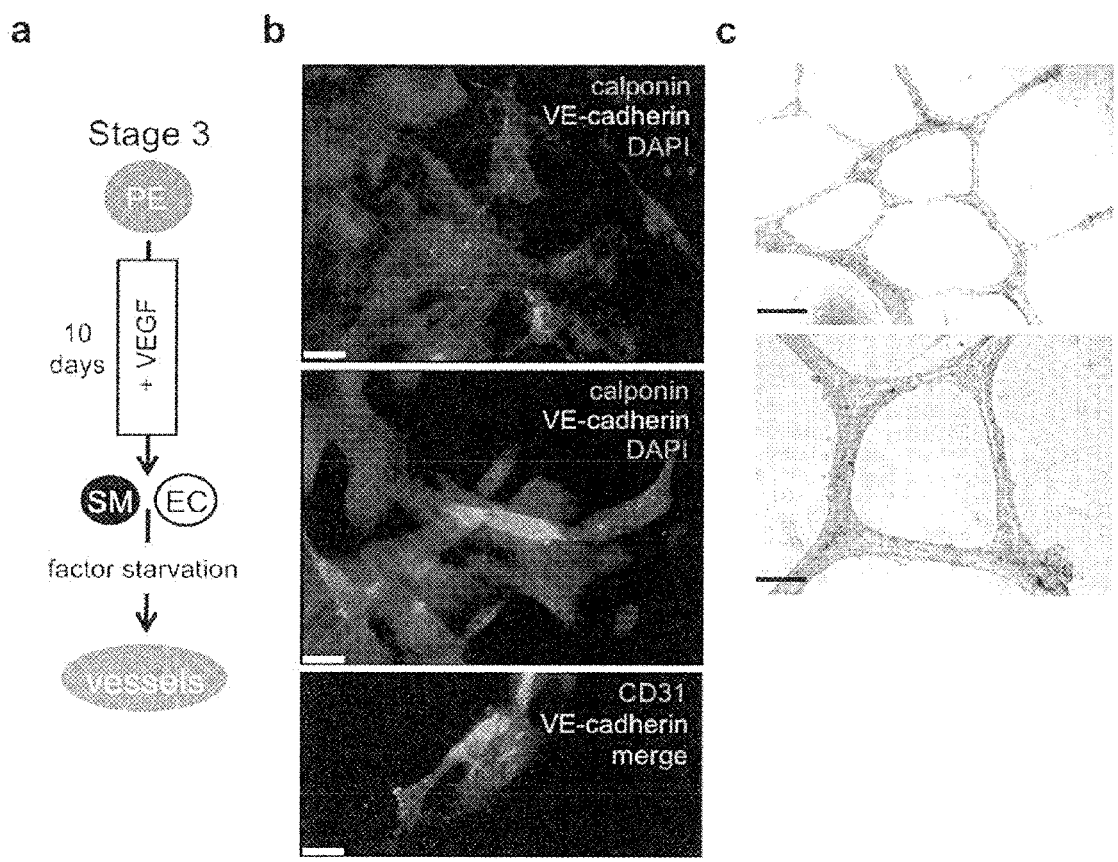

FIG. 65. hESC-derived pro-epicardium/epicardium (EPCs) differentiate into smooth muscle and endothelial cells invitro. (a) Summary of the approach used to generate smooth muscle and endothelial cells from PE-like cells (Stage 3) and their subsequent assembly into vessels. (b) Immunofluorescence images of Wt1+ cultures switched to VEGF (10 ng/ml) containing media for 10 days. Top and middle panels; VEGF treated cells were stained with antibodies for calponin (smooth muscle, red) and VE-cadherin (endothelial cells, green) and DAPI (DNA, blue). Micron bars; top, 50 μm, middle, 25 μm. Bottom panel: double staining for CD31 (red) and VE-cadherin (green). Cells were counterstained with DAPI (blue). Micron bar, 25 μm. (c) Bright field images representing vessels formed on Matrigel coated plates after 7 days culture under starvation conditions. Micron bar, 500 μm top panels, 200 μm bottom panels.

Figure 66:
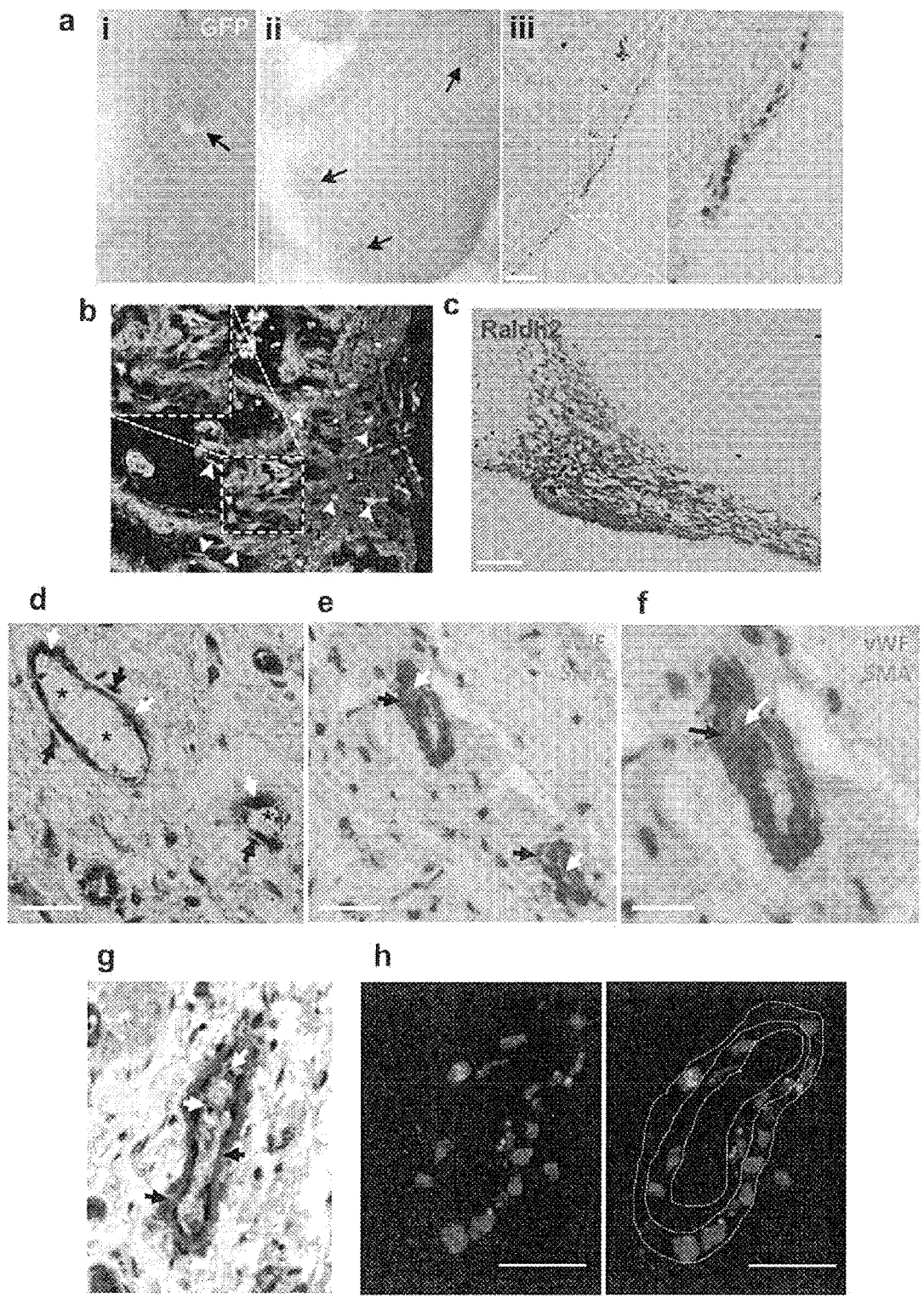

FIG. 66. hESC-derived epicardium generates fully invested vessels in vivo. (a[i]) Combined bright-field and immunofluorescence images of a HH stage 15 chicken embryo immediately following implantation of several GFP+ Wt1+ aggregates immediately adjacent to the heart (arrow). The looping heart is visible above the GFP+ cell aggregates. (ii) Immunocytochemical visualization of hESC-derived epicardium-like cells on a typical heart four days following implantation, using anti-GFP followed by HRP staining. Three aggregates of GFP+ cell are shown to be integrated in the chick epicardium (arrows). (iii) Immunocytochemical visualization of human Wt1+-derived GFP+ cells integrated into the chick epicardium following implantation As in (ii). The right-hand panel is a magnification of part of the left-hand panel. Micron bar, 50 μm. (b) Immunofluorescence localization of Wt1+-derived GFP+ cells (lavender) in a sectioned chick embryo heart five days following implantation. The myocardium appears green due to high levels of autofluorescence. The outer myocardial wall is to the right. Trabeculae extending into the heart lumen are on the left. GFP+ cells are visible throughout the myocardial wall, from the surface (right) to just beneath the endogenous endothelium on the luminal surface. Arrowheads point to representative GFP+ cells. A higher magnification view of the boxed area is shown at upper left. (c) Similar to (b) except that chick embryo sections were probed with antibody that recognizes human Raldh2 (no cross-reactivity with chick). The section shows a region of tissue where Raldh2+ cells (brown) are invading the underlying myocardium. Micron bar, 50 mm. (d) Immunohistochemistry of Wt1+-containing collagen type I plugs subcutaneously implanted into murine (SCID-beige) recipients. vWF+ endothelial cells are localized into vessels (white arrows), which are connected to host vasculature as indicated by the presence of luminal erythrocytes (star). Larger vessels are tightly surrounded by pericytic cells (black arrow). (e) Double staining revealed pericytic cells surrounding endothelial cells (brown) to be SMA+ smooth muscle cells (red). (f) At 40× magnification it is easy to identify a double layer of cells (endothelial cells inner and smooth muscle cells outer) surrounding a lumen. (g) as described for (e) and (f), but section in series with (h) demonstrating human origin of both cell layers as determined by fluorescence in situ hybridization (FISH) using a human-specific centromeric probe. Micron bars for (d), (e), (g) and (h) are 50 μm and 25 μm for (f).

FIG. 67. Table 3. Microarray analysis of hESC-derived Isl1+ splanchnic mesoderm (IMP cells). WA09 and BG02 cells were differentiated for 4 days in media containing Wnt3a (25 ng/ml) and BMP4 (50 ng/ml) and mRNA collected along with untreated WA09 and BG02 hESCs cultured for the same time in hESC media. Microarray analysis was performed using Affymetrix Human Genome U133 Plus 2.0 gene chips. Genes represented here have greater than and 8-fold increase in expression over hESC. Microarray analysis was performed in biological triplicate.

Figure 68:
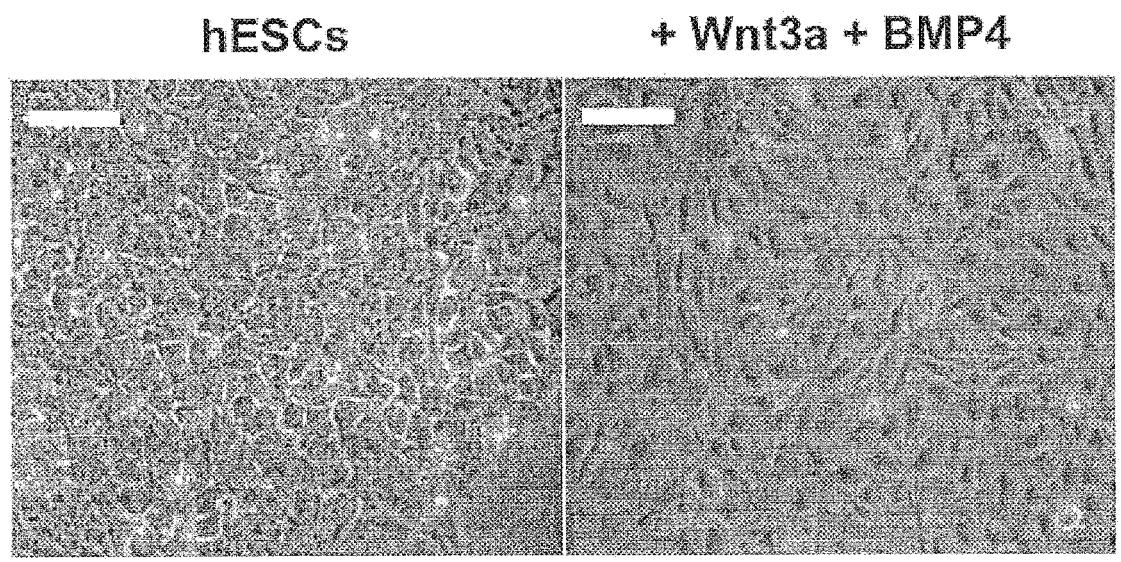

FIG. 68. Bright field images of untreated WA09 hESCs and hESCs treated with Wnt3a and BMP4 for 4 d. Micron bar, 100 μm.

Figure 69:
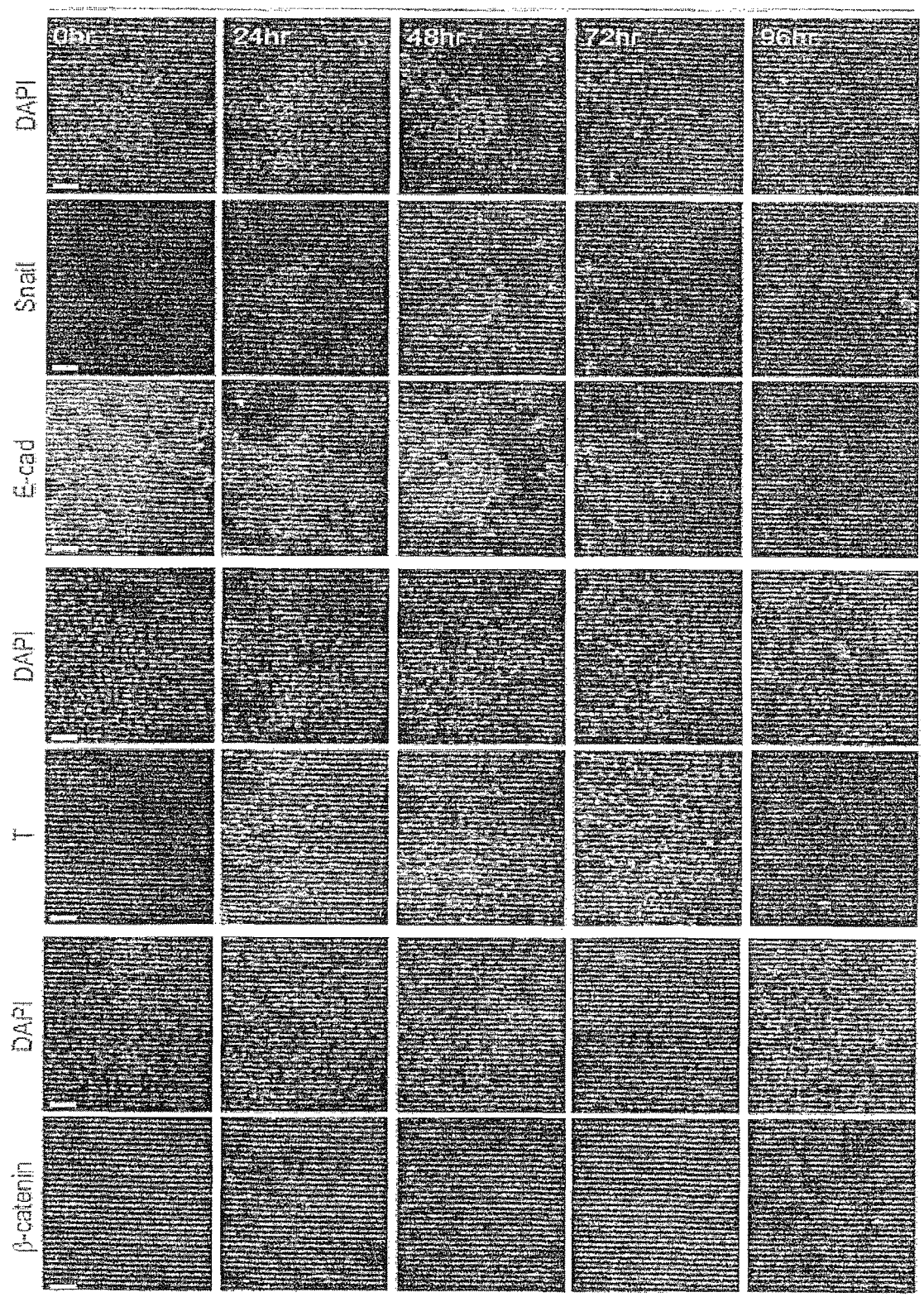

FIG. 69. WA09 hESC-derived splanchnic mesoderm (IMP cells) develops from a mesendoderm intermediate involving an epithelial to meschymal transition (EMT). Immunofluorescence staining of WA09 hESCs differentiated in the presence of Wnt3a (25 ng/ml) and BMP4 (50 ng/ml) for 96 h. Cells were fixed with 4% paraformaldehyde at 0, 24, 48, 72, 96 h and stained with antibodies raised against Snail, E-cadherin, T and 1-catenin. Mesendoderm is marked by T staining. Transition through an EMT is indicated by the accumulation of nuclear Snail and β-catenin and by down regulation of E-cadherin (E-cad). DAPI was used as a nuclear counterstain. Micron bar, 100 μm.

Figure 70:
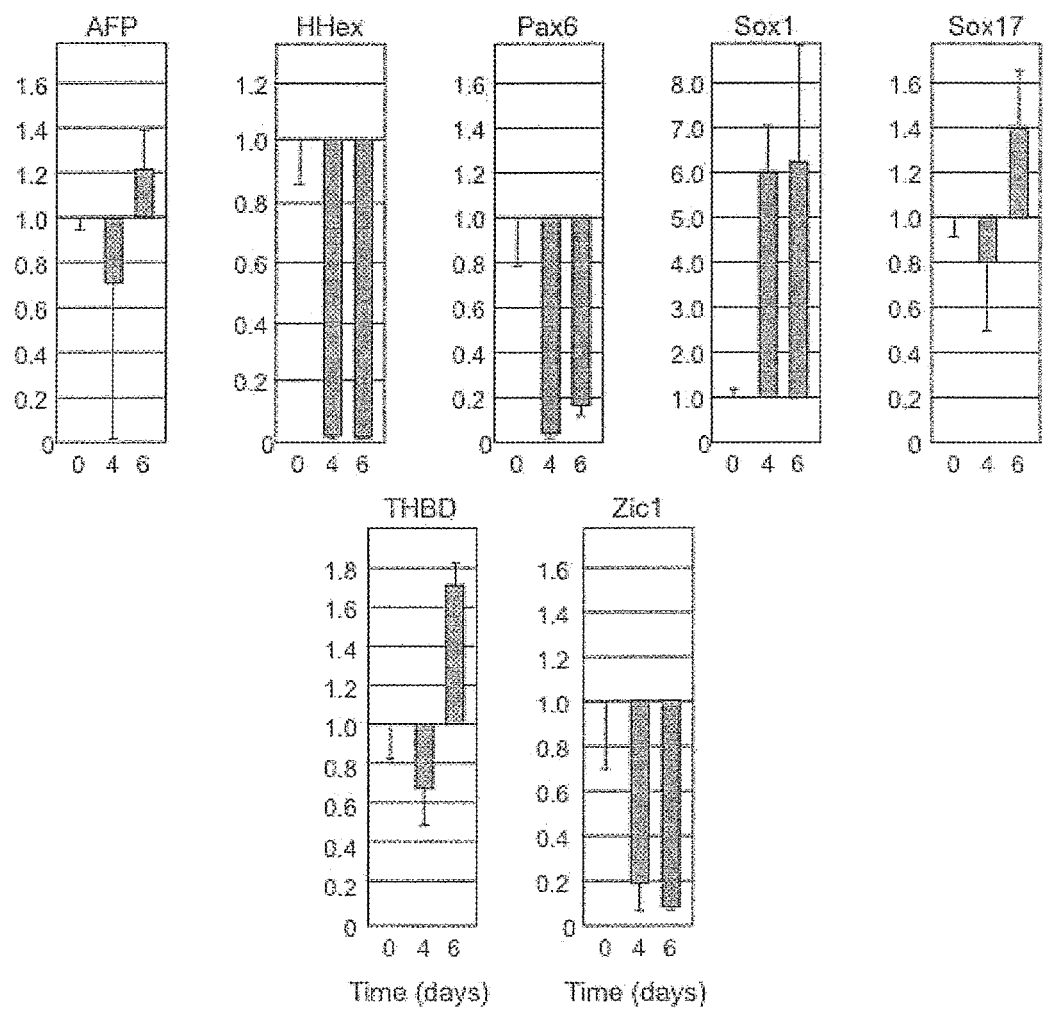

FIG. 70. Isl1+ mesoderm (IMP cells) forms at the exclusion of other lineages following Wnt3a/BMP4 treatment of hESCs. Q-PCR analysis of WA09 hESCs treated with Wnt3a (25 ng/ml) and BMP4 (50 ng/ml) for 0, 4, 6 d. Marker transcripts for endoderm (AFP, HHex, Sox17, THBD) and ectoderm (Pax6, Sox1, Zic1) are shown. Assays were performed in triplicate and shown relative to untreated hESC transcript levels following normalization to Gapdh. Error bars, +/−standard deviation.

Figure 71:
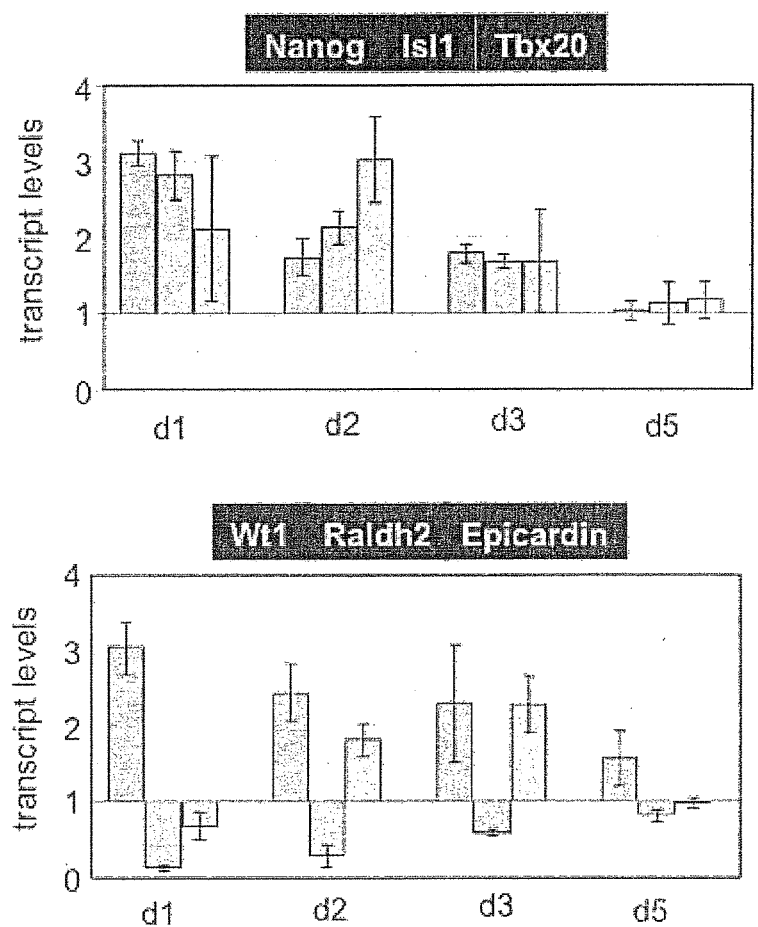

FIG. 71. Transcripts for splanchnic mesoderm (IMP cells) do not increase under hESC self-renewing conditions. WA09 cells were plated and maintained in media used to routinely maintain hESCs (see Methods section). Q-PCR analysis was then performed in triplicate on samples at day 1, 2, 3 and 5 d post-plating using probes for Nanog, Isl1, Tbx20, Wt1, Raldh2 and epicardin. Error bars, +/−standard deviation.

Figure 72:
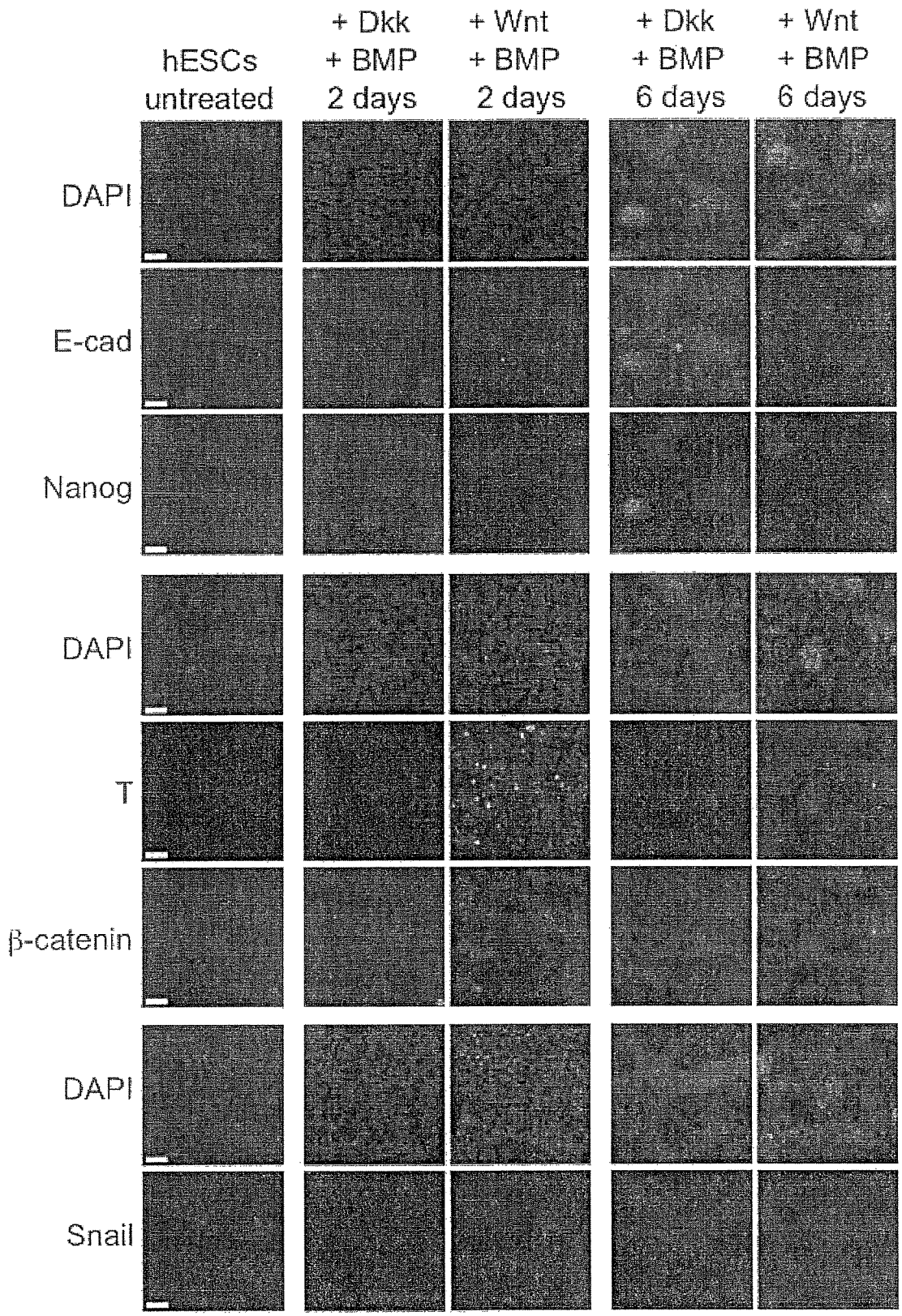

FIG. 72. Wnt signaling is critical for BMP4-dependent differentiation of hESCs. WA09 hESCs were cultured for 2 and 6 days in the presence of Wnt3a (25 ng/ml) and BMP4 (50 ng/ml) or, in the presence of BMP4 (50 ng/ml) and Dkk1 (150 ng/ml). Samples were fixed and probed with antibodies for E-cadherin (E-cad), Nanog, T, β-catenin and Snail. Micron bars, 100 μm FIG. 73. Isl1+ splanchnic mesoderm (IMPs) derived from hiPSCs. Fib-iPS4 hiPSCs were cultured for 4 d in hESC media (−) or differentiation media (+) containing Wnt3a (25 ng/ml) and BMP4 (50 ng/ml). (a) Q-PCR analysis of indicated mRNAs was performed in triplicate. Error bars, +/−standard deviation. Transcript changes are represented as the fold-increase over cells maintained in hESC media (−) following normalization to Gapdh. (b) Immunofluorescence analysis of 4% paraformaldehyde fixed cells probed with the indicated antibodies. Fib-iPS4; iPSCs maintained in self-renewal media for 4 d.+Wnt3a+BMP4; represents iPSCs cultured in media containing Wnt3a and BMP4 for 4 d. DAPI was used to stain nuclei. Micron bar, 100 μm.

Figure 74:
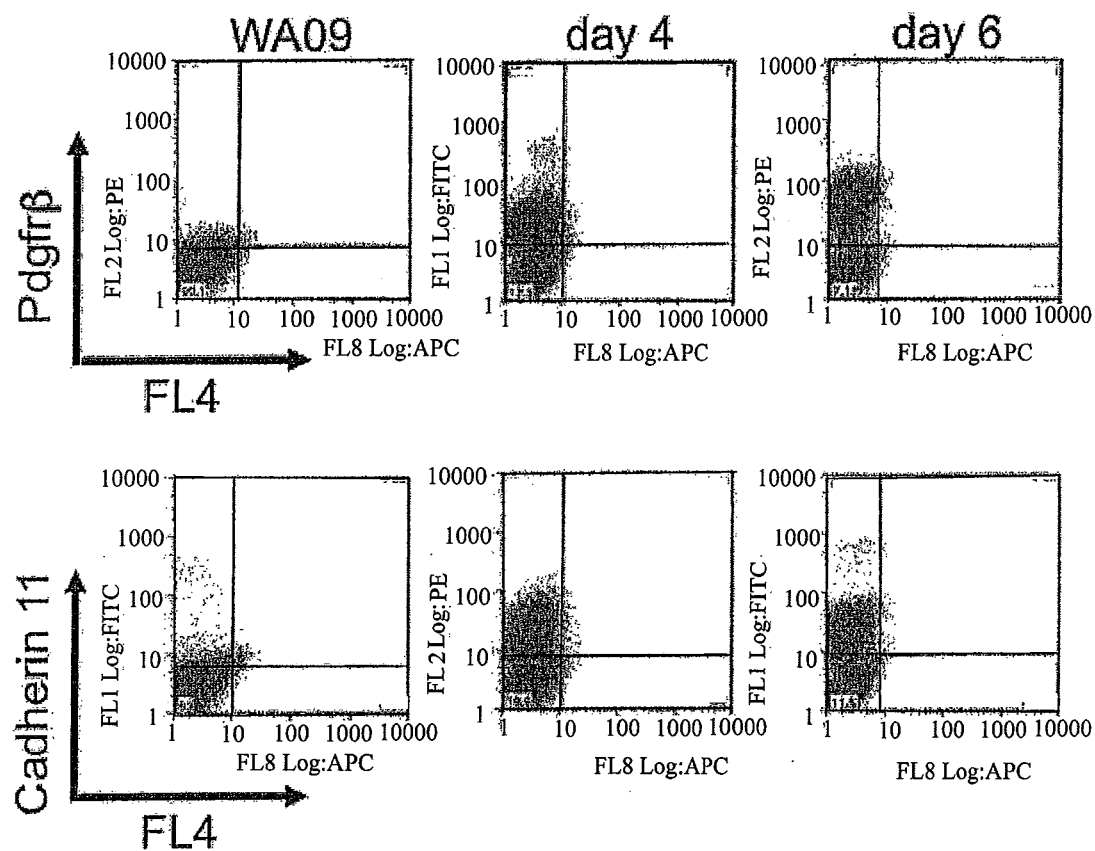

FIG. 74. Cadherin 11 and Pdgfrβ are surface markers of hESC-derived Isl1+ splanchnic mesoderm (IMP cells). WA09 hESCs were differentiated in the presence of Wnt3a (25 ng/ml) and BMP4 (50 ng/ml) for 4 and 6 d. Single cell suspensions were probed with antibodies for Pdgfrβ and Cadherin 11 then analyzed by flow cytometry. The dark gray population represents staining with isotype control antibody.

The light gray population represents Pdgfr+ (top panels) Cadherin 11+ (lower panels) cells, as indicated.

Figure 75:
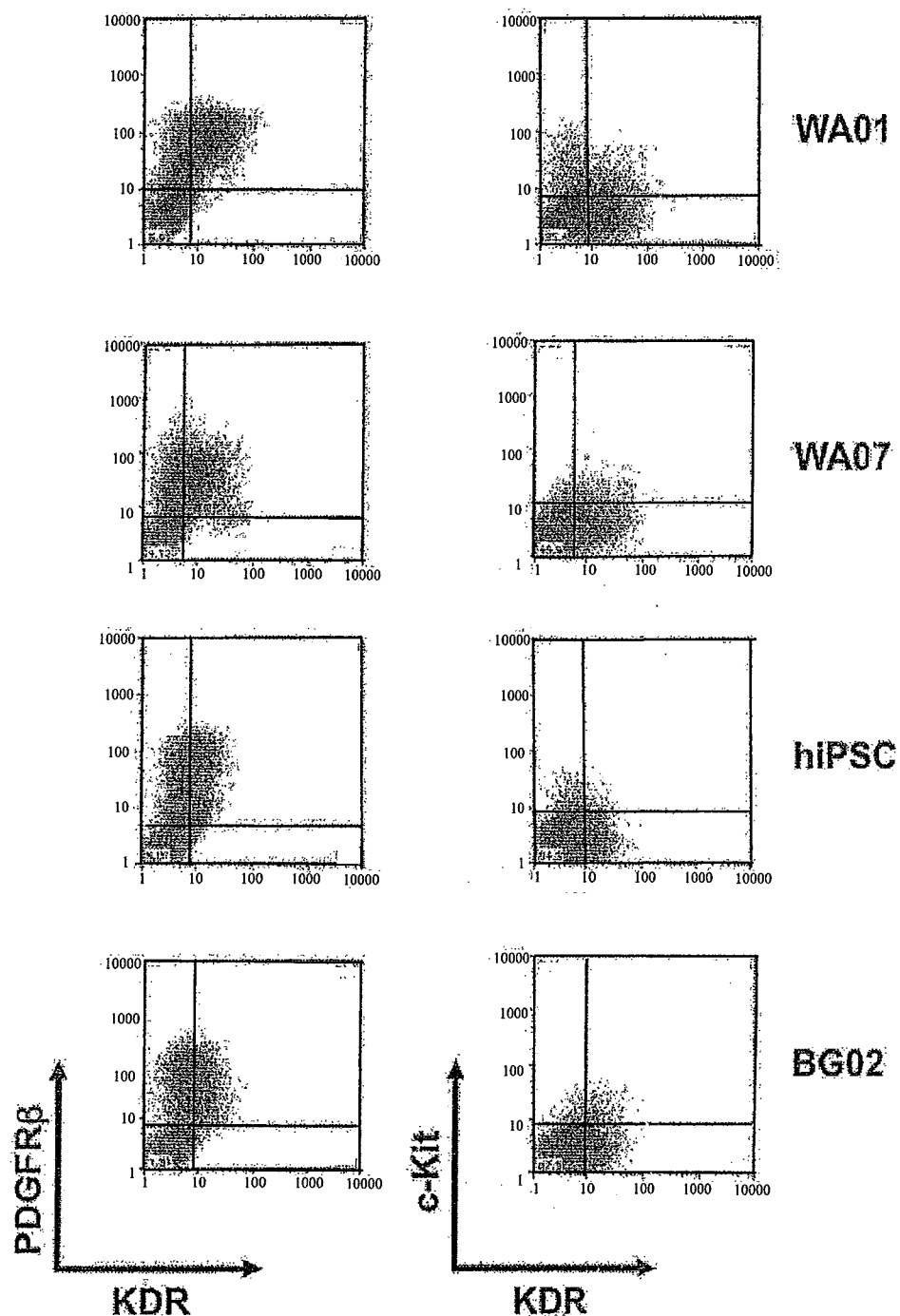

FIG. 75. WA01, WA07, BG02 hESCs and Fib-iPS4 hiPSCs were differentiated in the presence of Wnt3a (25 ng/ml) and BMP4 (50 ng/ml) for 4 d. Single cell suspensions were double probed with antibodies for Pdgfrβ and Kdr or, c-kit and Kdr then analyzed by flow cytometry.

FIG. 76. Fgf2 and retinoic acid (RA) can promote differentiation of Isl1+ splanchnic mesoderm (IMP cells) to Wt1+ PE-like cells. (a) Isl1+ cells were generated by treatment with Wnt3a (25 ng/ml) and BMP4 (50 ng/ml) for 4 d. Isl1+ cells were then treated with Fgf2 (100 ng/ml) or all-trans retinoic acid (4 µM) for a further 16 d. Q-PCR analysis was performed using probes for PE markers (Wt1, Raldh2, Tbx18 and Tbx5) on WA09 hESCs, Fgf2 and RA treated samples in triplicate. Error bars, +/−standard deviation. (b) Isl1+ cells were treated with RA or Fgf2 (as in [a]) for 2, 4, 6 and 24 h. Cell lysates were then subject to immunoblot analysis, probing with pan-Erk1,2 and phospho-Erk1,2 antibodies. Cdk2 was used as a load control.

FIG. 77. hiPSC-derived Isl1+ splanchnic mesoderm (IMP cells) differentiates into Wt1+ PE-like cells in response to Wnt3a (25 ng/ml), BMP4 (50 ng/ml), RA (4 µM) treatment. Q-PCR analysis of Fib-iPS4-derived Isl1+ PE (Stage 1) differentiated for a further 4 d or 14 d (Stage 2). Assays were performed in triplicate and expressed as the fold-change relative to untreated hiPSCs after normalization to Gapdh. Error bars, +/−standard deviation.

Figure 78:
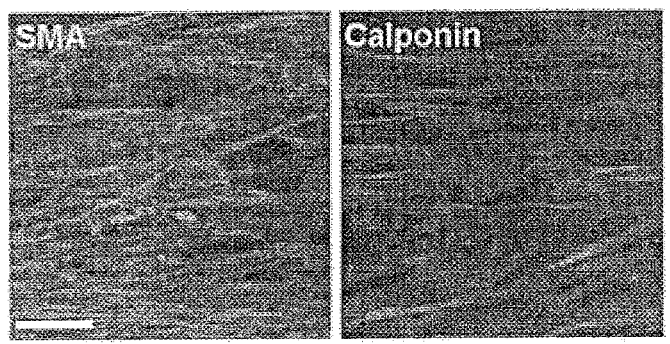

FIG. 78. hESC-derived Wt1+ PE-like cells differentiate into smooth muscle in vitro. Immunofluorescence images of Wt1+ cultures switched to VEGF (10 ng/ml) containing media after 10 d. A region of smooth muscle cells are shown, double probed with antibodies for smooth muscle actin (SMA, left panel) or calponin (right panel). Micron bar, 50 µm.

FIG. 79. Vasculogenic capacity of transplanted Wt1+ cells. (a) Representative collagen plugs recovered from mice after implantation for 21 days. Left plug, no cells; right plug, 5 million Wt1+ cells. Micron bar, 5 mm. (b) Control plug receiving no cells remained acellular within the collagen matrix compared with Wt1+ cell plug (c), which was consistently highly cellular throughout the plug as determined by H&E staining. Micron bar, 100 µm. (d) Plugs receiving Wt1+ cells also contrasted to control plugs in that they contained numerous organized structures containing lumens. Micron bar, 50 µm.

FIG. 80 Table 4. Microarray analysis of hESC-derived Isl1+ splanchnic mesoderm. WA09 and BG02 cells were differentiated for 4 d in media containing Wnt3a (25 ng/ml) and BMP4 (50 ng/ml) and mRNA collected along with untreated WA09 and BG02 hESCs cultured for the same time in hESC media. Microarray analysis was performed using Affymetrix Human Genome U133 Plus 2.0 gene chips, in biological triplicate. Fold-changes (log 2) are compared to parent hESCs. Represented genes show no significant increase or decrease during Wnt/BMP treatment.

FIG. 81 Table 5. Details of the antibodies used in this study.

FIG. 82 Table 6. Q-PCR assays used in this study from Applied Biosystems.

OBJECTS OF THE PRESENT INVENTION

It is an object of the invention to provide methods for the long-term maintenance of Islet 1+ multipotent precursors (IMPs) in order to provide practical approaches to culturing these cells before shipment and/or use.

It is another object of the invention to provide methods to enhance clonal passage and amplification of Islet 1+ multipotent precursors (IMPs).

It is still a further object of the invention to provide methods for the generation of endothelial cells, smooth muscle cells, cardiomyocytes and blood vessels from self-renewing IMPs.

Still an additional object of the invention relates to methods for the generation of endothelial cells, smooth muscle cells and cardiomyocytes from IMPs derived directly from hPSCs, including hESCs and hiPSCs.

Other objects of the invention relate to the fact that IMPs express a cell surface marker (PDGFRβ) in appreciable quantities that can be used to identify IMPs and separate these cells to significant purity.

Still other objects of the invention relate to methods and compositions of matter for the generation of MMCs and c-kit+ CXCR4+ multipotent progenitors (C56Cs) from MMCs and general approaches, where in combination with GSK3 inhibitors, inhibitors of Activin/Nodal signaling and/or BMP signaling can be used to generate different types of self-renewing progenitor cells.

Additional aspects of the present invention relate to methods which can be used to target C56Cs to damaged and/or inflamed tissue in a patient using the unexpected discovery that these cells home to damaged tissue areas and can be used to rebuild and/or treat such damaged/inflamed tissue.

Still further objects of the invention relate to methods for generating multipotent epicardial progenitor cells (EPCs) from hPSCs, including hESCs and hiPSCs. Other objects of the invention relate to these multipotent epicardial progenitor cells (EPCs) which are produced.

Still other objects of the invention relate to methods of using EPCs, including generating endothelial cells, smooth muscle and cardiac fibroblasts.

Any one or more of these and/or other objects of the invention may be readily gleaned from the description of the invention which follows.

BRIEF DESCRIPTION OF THE INVENTION

The present invention is directed, inter alia, to methods for generating multipotent migratory cell progenitors (MMCs), ISL1+ multipotent progenitors (IMPs), from human pluripotent stem cells, including human embryonic stem cells (hESCs) and human induced pluripotent stem cells (hiPSC), as otherwise described herein.

In particular aspects, the present invention relates to one or more of the following inventive aspects, among others.
1. Methods for the long-term maintenance (>10 passages) of Islet 1+ multipotent precursors (IMPs).
2. Methods and the utility of clonal passage and amplification of IMPs.
3. Methods for the generation of endothelial cells, smooth muscle cells and cardiomyocytes from self-renewing IMPs.
4. Methods for the generation of endothelial cells, smooth muscle cells and cardiomyocytes from IMPs derived directly from hPSCs, including hESCs and hiPSCs.
5. A cell surface marker (PDGFRβ) and a method that can be used to identify IMPs and separate these cells to significant purity.
6. (i) Methods and compositions of matter for the generation of CXCR4+CD56+ multipotent progenitors (C56Cs) from MMCs. (ii) General approaches, where in combination with GSK3 inhibitors, inhibitors of Activin/Nodal signaling and/ or BMP signaling can be used to generate different types of self-renewing progenitor cells.

7. Methods which can be used to target C56Cs to damaged and/or inflamed tissue in a patient using the unexpected discovery that these cells home to damaged tissue areas and can be used to rebuild and/or treat such damaged/inflamed tissue.

8. Methods for generating multipotent epicardial progenitor cells (EPCs) from hPSCs, including hESCs and hiPSCs.

9. Methods of generating EPCs from Isl1+ Multipotent Progenitor (IMPs).

10. Composition of matter for multipotent epicardial progenitor cells (EPCs).

11. Methods of using EPCs to i) identify secreted factors which are produced by epicardium which influence cardiomyocyte proliferation, survival function and differentiation; ii) as a source of cells that can be used in drug screens for cardiovascular applications; iii) as a source of cells that can be used for therapeutic purposes—to repair the ischemic heart, to regenerate the coronary vasculature; iv) for tissue engineering purposes where components of the heart or the coronary vasculature are required; and v) as a research tool for the study of cardiovascular development and disease.

12. Methods of generating endothelial cells, smooth muscle and cardiac fibroblasts from epicardial progenitor cells (EPCs).

13. Methods of producing blood vessels from endothelial and/or smooth muscle cells obtained EPCs.

Pharmaceutical compositions which comprise an effective number of MMCs, C56Cs or EPCs in combination with a pharmaceutically acceptable carrier, additive or excipient and optionally, an additional bioactive agent which is therapeutically appropriate for use in the proposed therapy along with MMCs, C56Cs or EPCs represent additional aspects of the present invention.

The present invention also relates to a method for treating one or more of the following disease states or conditions by administering an effective amount of a population of MMCs or preferably, a population of C56Cs or EPCs to a patient in need thereof. The method of treating is applicable to the following diseases states or conditions: cardiovascular disease (cardiomyopathy, ischemia), retinomyopathy, neuropathy, diabetes (type I and II), stroke, head trauma, autoimmune disease (lupus, arthritis, multiple sclerosis), immune suppression, graft versus host disease, bone repair, wound repair, inflammatory disease (arthritis, Crohn's disease, cystic fibrosis) and Parkinsons, Huntington's disease, among others. Systemic administration of MMCs, C56Cs or EPCs may be by intravenous administration, directly at the site of damage or disease where localized or by infusion. Because of the homing qualities of MMCs and more importantly, C56Cs and EPcs, these cells may be administered at a site far from the site of damage/inflammation and the cells will "home" to that site in the patient's body to effect therapy.

Methods of generating endothelial cells, smooth muscle cells, cardiac fibroblasts and blood vessel or vascular cells from EPCs either in vitro or in vivo as otherwise described herein, represent additional aspects of the present invention.

DETAILED DESCRIPTION OF THE INVENTION

The following terms shall be used to describe the present invention.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific conditions, or specific methods, etc., as such may, of course, vary, and the numerous modifications and variations therein will be apparent to those skilled in the art.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "patient" or "subject" is used throughout the specification within context to describe an animal, generally a mammal and preferably a human, to whom treatment, including prophylactic treatment (prophylaxis), with the cellular compositions according to the present invention is provided. For treatment of those infections, conditions or disease states which are specific for a specific animal such as a human patient, the term patient refers to that specific animal.

The terms "treat", "treating", and "treatment", etc., as used herein, refer to any action providing a benefit to a patient at risk for or afflicted by a disease state, condition or deficiency which may be improved using cellular compositions according to the present invention. Treating a condition includes improving the condition through lessening or suppression of at least one symptom, delay in progression of the effects of the disease state or condition, including the prevention or delay in the onset of effects of the disease state or condition, etc. Treatment, as used herein, encompasses both prophylactic and therapeutic treatment.

The term "primate Pluripotent Stem Cells", of which "human Embryonic Stem Cells" or hESCs and human induced pluripotent stem cells or hiPSCs are a subset, are derived from pre-embryonic, embryonic, fetal tissue or adult stem cells (in the case of human induced pluripotent stem cells) at any time after fertilization, and have the characteristic of being capable under appropriate conditions of producing progeny of several different cell types that are derivatives of all of the three germinal layers (endoderm, mesoderm and ectoderm), according to a standard art-accepted test, such as the ability to form teratomas in 8-12 week old SCID mice. The term includes both established lines of stem cells of various kinds, and cells obtained from primary tissue that are pluripotent in the manner described.

Included in the definition of pluripotent or pPS cells (pPSCs) are embryonic cells of various types, especially including human embryonic stem cells (hESCs), described by Thomson et al. (Science 282: 1145, 1998); as well as embryonic stem cells from other primates, such as Rhesus stem cells (Thomson et al., Proc. Natl Acad. Sci. USA 92: 7844, 1995). Other types of pluripotent cells are also included in the term. Human Pluripotent Stem Cells includes stem cells which may be obtained from human umbilical cord or placental blood as well as human placental tissue. Any cells of primate origin that are capable of producing progeny that are derivatives of all three germinal layers are included, regardless of whether they were derived from embryonic tissue, fetal, or other sources. The pPS cells are preferably not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells in the population will often be surrounded by neighboring cells that are differentiated.

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines WA01, WA07, and WA099 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.), as well as normal human embryonic stem cell lines such as WA01, WA07, WA09 (WiCell) and BG01, BG02 (BresaGen, Athens, Ga.).

Epiblast stem cells (EpiScs) and induced pluripotent stem cells (iPSCs), especially human induced pluripotent stem cells (hiPSCs) fall within the broad definition of pluripotent cells hereunder and in concept, the technology described in the present application applies to these and other pluripotent cell types (ie, primate pluripotent cells) as set forth above. EpiScs are isolated from early post-implantation stage embryos. They express Oct4 and are pluripotent. See, Tesar et al, *Nature*, Vol 448, p. 196 12 Jul. 2007. iPS cells are made by dedifferentiating adult somatic cells back to a pluripotent state by retroviral transduction of four genes (c-myc, Klf4, Sox2, Oct4). See, Takahashi and Yamanaka, Cell 126, 663-676, Aug. 25, 2006.

Human embryonic stem cells (hESCs) may be prepared by methods which are described in the present invention as well as in the art as described for example, by Thomson et al. (U.S. Pat. No. 5,843,780; *Science* 282:1145, 1998; *Curr. Top. Dev. Biol.* 38:133 ff., 1998; *Proc. Natl. Acad. Sci. U.S.A.* 92:7844, 1995).

The term "embryonic stem cell" refers to pluripotent cells, preferably of primates, including humans, which are isolated from the blastocyst stage embryo. Human embryonic stem cell refers to a stem cell from a human and are preferably used in aspects of the present invention which relate to human therapy or diagnosis. The following phenotypic markers are expressed by human embryonic stem cells:

SSEA-3, SSEA-4, TRA-1-60, TRA-1-81, CD9, alkaline phosphatase, Oct 4, Nanog, Rex 1, Sox2 and TERT. See Ginis, et al., *Dev. Biol*, 269(2), 360-380 (2004); Draper, et al., *J. Anat.*, 200(Pt. 3), 249-258, (2002); Carpenter, et al., *Cloning Stem Cells*, 5(1), 79-88 (2003); Cooper, et al., *J. Anat.*, 200(Pt.3), 259-265 (2002); Oka, et al., *Mol. Biol. Cell*, 13(4), 1274-81 (2002); and Carpenter, et al., *Dev. Dyn.*, 229(2), 243-258 (2004). While any primate pluripotent stem cells (pPSCs), including especially human embryonic stem cells can be used in the present methods to produce mesendoderm cells, mesoderm Isl1+ (IMP) cells, multipotent migratory cells (MMCs), a multipotent CXCR4+ CD56+ cells (C56Cs) or multipotent epicardial progenitor cells (EPCs) according to the present invention, preferred pPSCs for use in the present invention include human embryonic stem cells, including those from the cell lines BG01 and BG02, as well as numerous other available stem cell lines, including human induced pluripotent stem cells.

The term "differentiation" is used to describe a process wherein an unspecialized ("uncommitted") or less specialized cell acquires the features of a more specialized cell such as, for example, a multipotent migratory cell, a multipotent CXCR4+ CD56+ cell, a multipotent epicardial progenitor cells, a nerve cell, a muscle cell, a cardiomycete or other cell. The term "differentiated" includes the process wherein a multipotent stem cell, including a hESC, becomes a more specialized intermediate cell such as a progenitor cell, including where a more specialized intermediate cell (MMC, IMP mesendoderm cell, mesoderm cell, C56C or EPC) becomes an even more specialized cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

The terms "multipotent migratory cells" or "MMCs" are used interchangeably to refer to a cell or cells produced according to the present invention. MMCs are dynamic multipotent cells which are characterized as being E-cad-Oct4-Nanog-SSEA3-CXCR4+; they are of low to medium density and are migratory. They are storage stable and may be passaged for numerous generations and still remain viable. They have significant developmental plasticity. They are not hESCs based on marker profiling.

MMCs may be stabilized for storage in the presence of effective amounts of a GSK inhibitor and an Activin A inhibitor. BMP inhibitors, such as Noggin, can also be used in combination with GSK inhibitors and Activin A inhibitors. These cells may be differentiated to mesoderm cells or definitive endoderm cells, among numerous others. Further methods relating to MMCs are disclosed herein.

The multipotent migratory cells (MMCs) according to the present invention have one or more (at least 4, at least 5 at least 6, at least 10, preferably all) of the following characteristics:
  it can be cultured for at least 20 passages as a stable cell population
  cells appear mesenchymal when plated at low density and grow into a sheet at high density
  can be produced from a range of hESC lines including BG01, BG02, WA09
  MMCs can be frozen and cryogenically preserved by standard methods
  MMCs can be recovered after cryogenic storage, recovered and differentiated
  MMCs can be passaged with high plating efficiency (greater than 50% plating efficiency–50% of cells passaged successfully seed down and survive)
  do not exhibit the SSEA3 and SSEA4 antigens on their cell surface
  do not express hESC markers such as Oct4, Nanog
  MMCs can express CXCR4 on their surface
  MMCs express the following transcripts at high levels Zic1, HoxA9, HoxD4, HoxA5, HoxC10, HoxD3, Pax6, N-CAM, CXCR4
  MMCs are not mesendoderm because they do not express T/brachyury or eomesodermin
  E-cadherin negative
  MMCs do not express Sox17, Isl1, musashi, nestin at appreciable levels by Q-PCR analysis
  retain a normal karyotype during passaging
  exhibit a migratory, mesenchymal phenotype
  have multipotent differentiation capacity (including mesoderm, endoderm)
  do not form teratomas when injected into SCID mice
  can be isolated from inner cell mass embryos and fetal tissue
  see microarray data for a more complete description of MMC genes expression profiles As used herein the terms "mesoderm (Isl1+) cell", mesoderm-derived Isl1+ multipotent progenitor cell "ISL+ multipotent progenitor", "IMP", "Spl-m" or "IMP-Spl-m" are used interchangeably within context to describe mesoderm Isl1+ cells which are produced according to methods of the present invention from pPSCs (especially hESCs), mesendoderm cells or MMCs or as otherwise described herein (see examples section). IMP-Spl-m are IMP cells which are produced from pluripotent cells (including hESCs and hiESCs) as otherwise described herein and pass through lateral plate mesoderm cells (LPMs) before differentiating into IMP-Spl-m or splanchnic IMP cells.

Isl1 I+ multipotent progenitors or IMPs have the following characteristics:
  express Isl1, Nkx2.5, Fgf10, Gata4, FoxF1, PDGFRβ
  optionally express Tbx3 and/or Hand1
  karyotypically normal
  do not express Oct4, Nanog, T, eomesodermin
  may express PDGFRβ and cadherin 11 on the cell surface
  can differentiate into cardiomyocytes, smooth muscle cells and endothelial cells, among others.

The cell surface markers PDGFRβ and/or cadherin 11 for IMPs represent an immunogenic target which can be used in conjunction with a monoclonal antibody specific for said cell surface markers to isolate IMPs from a population of cells. Use of a monoclonal antibody which is linked to a reporter molecule (fluorescent, radioisotopic, etc.) may be used to identify the existence and relative numbers of cells in a sample of cells. Anti-PDGFRβ monoclonal antibodies are disclosed in US Patent Publication 2009/0053241 which is incorporated by reference in its entirety herein. Additional monoclonal antibodies which are anti-PDGFRβ and may be used in the present invention include IMC-2C5, among others.

As used herein, the term "multipotent CXCR4+CD56+ cells", "CXCR4+CD56+ cells" or "C56Cs" are used to describe pre-mesenchymal pluripotent cells which may be produced from hPSCs as well as MMCs according to methods as otherwise described herein. These calls may be used therapeutically to treat inflamed and/or damaged tissue by injecting an effective number of cells into a patient in need of treatment in an effective amount.

Figure 16:
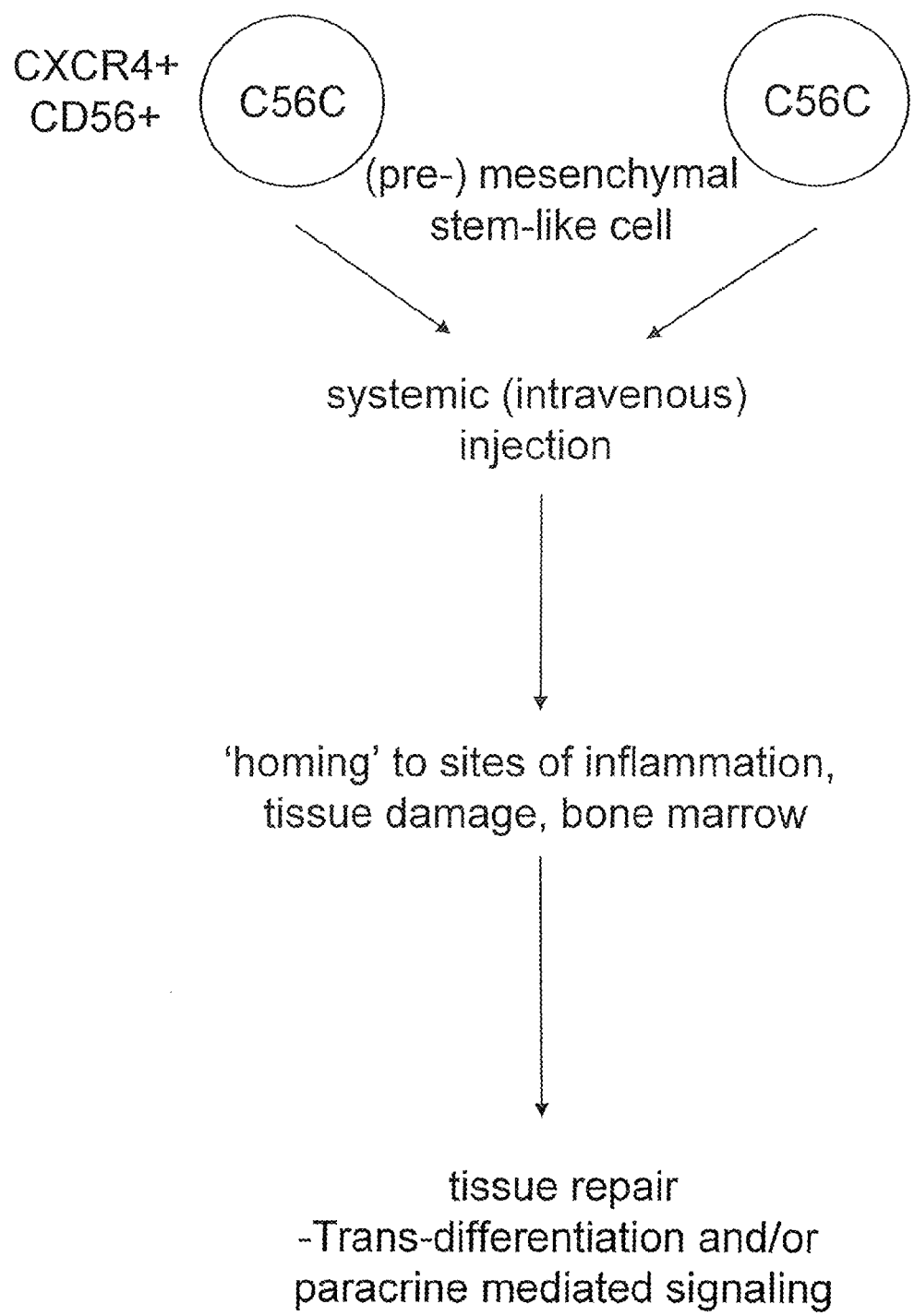
FIG. 16. Following 'homing' of C56Cs to sites of inflammation, tissue damage they could potentially participate in tissue regeneration-repair in several ways. First, through paracrine mechanisms where 'homed' C56Cs release cytokines, growth factors and other molecules to stimulate the repair process. This could involve recruitment of cells in the local environment that have some regenerative capacity. Second, these cells may trans-differentiate into functional cell types that directly contribute to tissue repair/regeneration.

Based on reports in the literature where bone marrow derived mesenchymal stem cells have been applied to disease models (Phinney and Prockop, 2007; Stem Cells 25: 2896-2902; Uccelli et al., 2008; Nature Reviews Immunol. 8: 726-736), we predict a number of applications for MMCs and C56Cs. This would be based on their ability to stimulate repair by a paracrine effect—through release of factors that stimulate other cells to repair damaged tissue or, by direct trans-differentiation into cell types that participate in the repair process (FIG. 16).

These applications include but are not restricted to therapies for:
- cardiovascular disease (cardiomyopathy, ischemia)
- retinomyopathy
- neuropathy
- diabetes (type I and II)
- stroke
- head trauma
- autoimmune disease (lupus, arthritis, multiple sclerosis)
- immune suppression
- graft versus host disease
- bone repair
- wound repair
- inflammatory disease (arthritis, Crohn's disease, cystic fibrosis)
- Parkinsons, Huntington's disease C56Cs according to the present invention have the following characteristics:
- They express CXCR4 and CD56 biomarkers (CXCR4+ and CD56+);
- They express CXCR4 at levels higher than MMCs;
- They express at least 3, at least 4 at least 5, at least 6 and preferably all of the following biomarkers at appreciable levels:
- c-kit, CD166, CD105, CD44, CD133, CD90;
- They do not express CD31;
- and in most instances:
- They express PDGFRα at low levels;
- They can exhibit a homing characteristic to sites of inflammation and tissue damage through the SDF-1/CXCR4 signaling axis (See for example, Dalton, *Regen. Med.*, 3, 181-188, 2008);
- These cells are physically smaller than hESCs and hiPSCs making them useful for intravenous administration.

C56Cs are prepared by exposing MMCs to effective amounts of a bone morphogenic protein (preferably, BMP4), a Wnt protein (preferably Wnt3a) and a butyrate salt (preferably, sodium butyrate) in a differentiation medium for a period ranging from about 1 to 8 or more days, preferably, about 2 to 7 days, about 3-6 days, about 4-6 days as otherwise described herein. In this aspect of the invention, differentiation of MMCs to C56Cs occurs in the absence of a GSK inhibitor (e.g. BIO) and Activin A inhibitor (e.g. SB431542).

Figure 14:
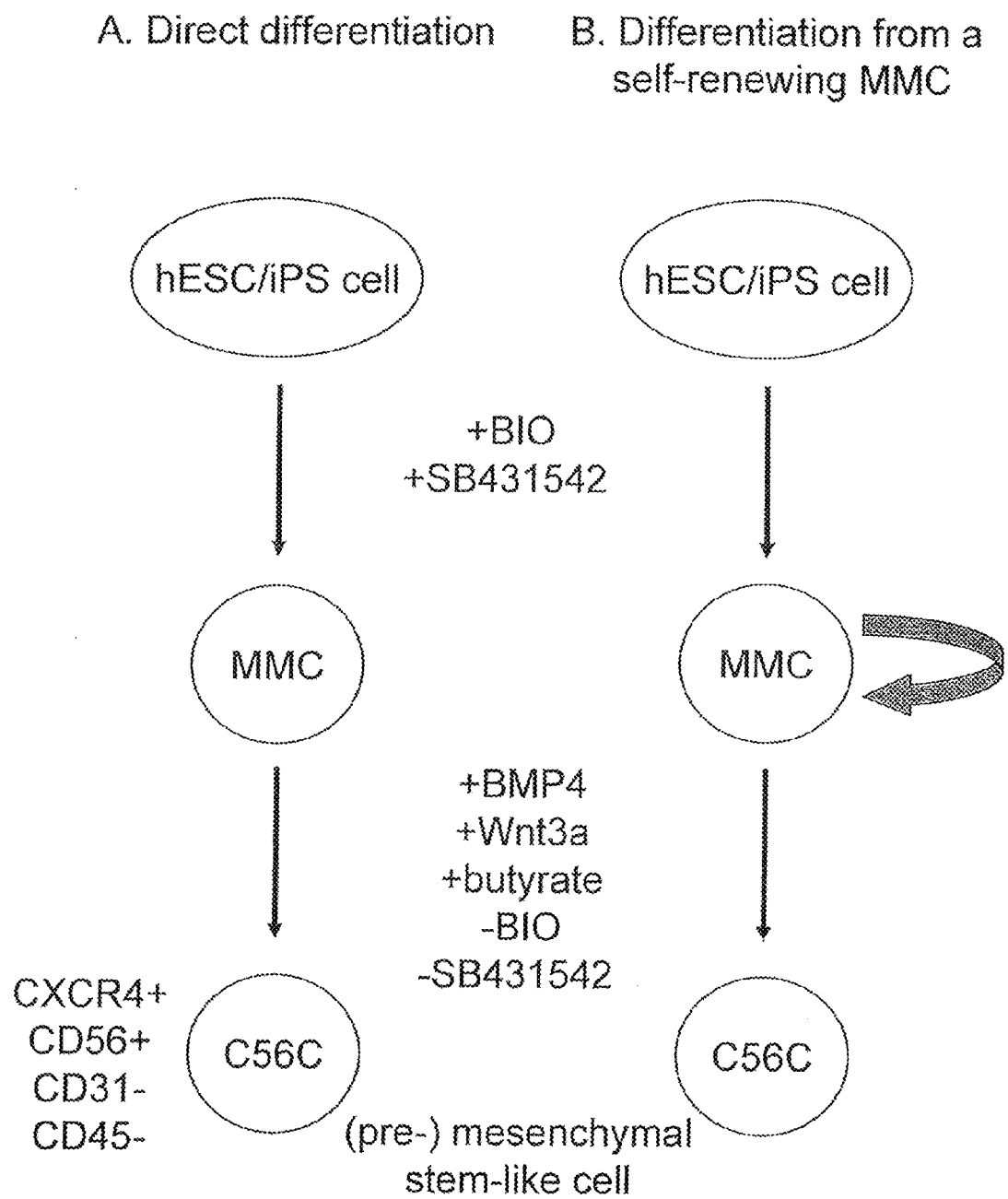
FIG. 14. Schematic diagram representing the differentiation of self-renewing human pluripotent stem cells (hESCs, iPS cells) into MMCs and then to CXCR4+ CD56+ cells (C56Cs). MMCs are generated as illustrated in FIG. 2. MMCs are then converted into C56Cs over a 3-6 day period by removal of BIO and SB431542 and by addition of BMP4, Wnt3a and sodium butyrate. C56Cs are similar to mesenchymal stem cells, express CXCR4 and CD56 but not markers for hematopoietic stem cells (CD45) or endothelial cells (CD31). C56Cs can be generated following direct differentiation of hESCs into MMCs or, from self-renewing MMCs.

The pathway for generation of C56Cs is indicated in FIG. 14. Generation of MMCs from hESCs is disclosed herein and has been described previously (see PCT/US2008/001222, published as WO2008/094597, Aug. 7, 2008, which is incorporated by referenced herein). hPSCs are generally differentiated in the presence of a GSK inhibitor (BIO) and an Activin A inhibitor (SB431542). Optionally, for producing MMCs, a BMP signaling inhibitor (Noggin, Compound C) may also be included. The method for generating C56Cs are applicable to any human pluripotent cell such as human induced pluripotent stem cells (hiPS cells) or similar human pluripotent stem cells. To generate MMCs, human pluripotent stem cells, especially including hESCs or hiPSCs are exposed to a differentiation medium which includes an effective amount of a GSK3 inhibitor such as BIO (between 0.25 and 10 µM, about 0.5 to about 5 µM, about 1 to 4 µM, about 1.5 to 3 µM, about 2 µM, and an Activin A inhibitor such as SB431542 (between about 2 to about 50 µM, about 5 to about 35 µM, about 10 to about 30 µM, preferably about 20 µM) as otherwise described herein. To generate C56Cs, MMCs are treated for around 1 to 8 days (preferably, 3-6 days) with BMP4 (about 10-250 ng/ml, preferably about 100 ng/ml), Wnt3a (about 5 to about 50 ng/ml, about 25 ng/ml), sodium butyrate (0.1 to about 5 mM, about 0.25 to about 1 mM, about 0.5 mM) in base media [DMEM/F12 [50/50]. The base media (differentiation media) preferably contains effective amounts of other components as described herein, including approximately 2% probumin [albumin], antibiotics [1× Pen/Strep 1×NEAA], Trace Elements A, B, C [1× from Mediatech], Ascorbic acid [about 10 to 100 µg/ml, ~50 µg/ml], Transferrin [~10 µg/ml], β-Mercaptoethanol [about 0.1 mM], bFGF [e.g. about 8 ng/ml], LR-IGF [e.g., about 200 ng/ml], Activin A [e.g., about 1 to 20 ng/ml, 10 ng/ml], Heregulin [e.g., about 1 to 20 ng/ml, about 10 ng/ml]). It is important that GSK inhibitors (in contrast to wingless or Wnt proteins) and Activin A inhibitors are absent when differentiating MMCs to C56Cs. Also, bone morphogenic protein inhibitors (noggin, compound c) should also be absent when MMCs are used to produce C56Cs.

Compositions which may be used for therapies as described above include an effective amount of C56C cells for carrying out the therapy. The composition comprises between about $5 \times 10^5$ and $5 \times 10^8$, preferably between about $10^6$ and $10^8$ cells suspended in saline solution. The amount of saline solution generally ranges from about 50 ul to about 10 ml, preferably about 100 ul to about 2 ml. The composition may be administered intravenously, directly into the site where therapy with the cells of the present invention is to occur or by infusion. The purity of the C56Cs cells which are used therapeutically ranges from at least about 50% to greater than about 99.5%, about 75% or greater, about 85% or greater, about 90% or greater, about 95% or greater, about 97.5% or greater, about 98% or greater, about 99% or greater, about 99.5% or greater. In general, the conditions of differentiating MMCs to produce C56Cs result in high purity of the resulting C56Cs so that there is not a further need to purify same. The cells may be administered in the absence of bioactive agents or including bioactive agents. Pharmaceutical compositions which comprise an effective number of C56Cs in combination with a pharmaceutically acceptable carrier, additive or excipient and optionally, an additional bioactive agent which is therapeutically appropriate for use in the proposed therapy along with C56Cs represent additional aspects of the present invention.

The term "epicardial progenitor cells", "epicardial pluripotent cells" or "EPCs" is used to refer to the multipotent cells which are produced from human pluripotent cells (hPCs), including hESCs or from Isl1+ pluripotent cells (IMPs) according to the present invention by exposing hPCs to conditions which produce IMPs, and then exposing the resulting IMPs to conditions which produce EPCs. As indicated EPCs are produced by exposing IMPs in a differentiation medium in the presence of effective amounts of a GSK inhibitor (e.g., a Wnt protein such as Wnt3a as otherwise described herein or a GSK inhibitor such as BIO), a bone morphogenic protein (e.g., BMP4) and retinoic acid (preferably, all-trans retinoic acid) for a period of time sufficient to convert IMPs to EPCs (e.g., about 8 to 20 days or more, about 10 to 18 days, about 15-17 days or more). EPCs may be produced directly from hPCs by exposing the cells initially to effective amounts of a GSK inhibitor (e.g., WNT3a or BIO), a bone morphogenic protein (e.g. BMP4) and optionally an Activin A inhibitor (e.g., SB431542) and then (generally, after about 2-8 days) further exposing the intermediate cells produced (which are IMPs) to the same conditions for converting IMPs to EPCs as presented above (e.g., Wnt3a or BIO, BMP4 and all-trans retinoic acid for a period up to about 16-20 days or more).

EPCs (pro-epicardium/epicardium cells) are characterized by their ability to spread over the surface of the myocardium forming an outer later and also by their capacity to migrate into the myocardium in an invasive manner (Olivey et al., 2004 Trends Cardiovasc Med. 14, 247-251;). A standard assay to evaluate the migratory properties of pro-epicardium/epicardium is to plate cells on a collagen I matrix.

Microarray analysis of EPCs generated from three hESC lines and a human iPSC line indicates that EPC cells express Wilm's tumor suppressor protein 1 (Wt1), Tcf21 (epicardin), Raldh2 (Aldh1a2). These transcripts/biomarkers are primary identifiers of EPCs, a pro-epicardial/epicardial cell type generated from pluripotent cells in culture.

In addition to the above, EPCs also can express one or more (2, 3, 4, or 5) of Tbx18, COL3A1, GATA6, Tbx3 and Tbx5. A table summarizing some of the most up-regulated genes is shown in FIG. 47, Table 2.

EPCs have a number of uses. They can be used for identification of secreted factors produced by the epicardium which influence cardiomyocyte proliferation, survival, function and differentiation; they provide a source of cells that can be used in drug screens for cardiovascular applications; they provide a source of cells that can be used for therapeutic purposes—to repair the ischemic heart and/or to regenerate the coronary vasculature; they can be used for tissue engineering purposes where components of the heart or the coronary vasculature are required; and they may serve as a research tool for the study of cardiovascular development and disease.

As described herein, EPCs may be further differentiated into endothelial cells (in the presence of effective amounts of $VEGF_{165}$ or $VEGF_{165}$ and SB431542 or other Activin A inhibitor); smooth muscle and cardiac fibroblasts (in the presence of effective amounts of $VEGF_{165}$ or $VEGF_{165}$ and platelet derived growth factor beta (PDGFβ) or $VEGF_{165}$ and hDkk1 in 10% fetal bovine serum) or blood vessels (in the presence of FGF2, LR-IGF, Heregulin β and VEGF) as otherwise described herein. These cells may also be used therapeutically to treat and/or reduce the likelihood of cardiovascular disease/damage to heart tissue or vascular disease/damage by administering an effective amount of EPCs to a patient in need of therapy.

As used herein, the terms "differentiation medium", "cell differentiation medium", "culture media", "basal cell medium", "basal cell media" or "basal media" or "stabilizing medium" are used synonymously to describe a cellular growth medium in which (depending upon the additional components used) the hESCs, mesoderm ISl1+ multipotent cells (IMPS), multipotent migratory cells (MMCs), C56Cs, EPC's or other cells are produced, grown/cultured or alternatively, differentiated into more mature cells. Specific examples of these are presented in the examples section which follows. Differentiation media are well known in the art and comprise at least a minimum essential medium plus one or more optional components such as growth factors, including fibroblast growth factor (FGF), ascorbic acid, glucose, non-essential amino acids, salts (including trace elements), glutamine, insulin (where indicated and not excluded), Activin A, transferrin, beta mercaptoethanol, and other agents well known in the art and as otherwise described herein. Preferred media includes basal cell media which contains between 1% and 20% (preferably, about 2-10%) fetal calf serum, or for defined medium (preferred) an absence of fetal calf serum and KSR, and optionally including bovine serum albumin (about 1-5%, preferably about 2%). Preferred differentiation medium is defined and is serum free. In certain embodiments wherein MMCs are produced and Activin A inhibitor is used, the medium may eliminate or substantially reduce the amount of Activin A.

Other agents which optionally may be added to differentiation medium according to the present invention include, for example, nicotinamide, members of TGF-β family, including TGF-β 1, 2, and 3, Activin A, nodal, serum albumin, members of the fibroblast growth factor (FGF) family, platelet-derived growth factor-AA, and -BB, platelet rich plasma, insulin growth factor (IGF-I, II, LR-IGF), growth differentiation factor (GDF-5, -6, -8, -10, 11), glucagon like peptide-I and II (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, heregulin, or combinations thereof, among a number of other components. Each of these components, when included, are included in effective amounts.

By way of further example, suitable media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Preferred embodiments of media used in the present invention are as otherwise described herein.

A particularly preferred differentiation medium for growing/culturing pPSCs (especially, hESCs) and for differentiating cells in the present invention (depending upon the components which are used) is DMEM/F12 (50:50) which contains about 2% proalbumin (albumin; Millipore/Serologicals), 1× Pen/Strep, 1×NEAA, 1× Trace Elements A, B, C (Mediatech), Ascorbic Acid (10-100 ng/ml, about 25-65 ng/ml, about 50 ng/ml), about 0.1 mM (0.025-0.5 mM) β-Mercaptoethanol (Gibco), about 2-10 ng/ml, about 5-9 ng/ml, about 8 ng/ml bFGF (Sigma), 200 ng/ml (5-500 ng/ml) LR-IGF (referred to as IGF-I; JRH Biosciences), 10 ng/ml Activin A (about Ing/ml to no more than about 20 ng/ml and in certain aspects is excluded) and 10 ng/ml (about 1-20 ng/ml or more) Heregulin. Each of the individual components used is an effective amount and such amount ranges for the individual components, as well as the preferred amounts applies for media used in the present invention, regardless of the cells to be produced. It is noted that Activin A or Activin A signaling is not required for the production of multipotent migratory cells MMCs, but may be included (where included, Activin A is preferably included in low concentrations, generally below about 20 ng/ml—in some cases it is preferably excluded), especially when producing mesoderm (Isl1+) cells. In contrast, about 20 ng/ml to about 100 ng/ml or more of Activin A or "high concentrations of Activin A" is used for producing other cells, as described herein. Alternatively, mouse embryonic fibroblast-conditioned media (MEF-CM) with similar componentry to DMEM/F12 may also be used to passage hESC and to produce Isl1+ mesoderm cells (IMPs) and multipotent migratory cells (MMCs), as well as CXCR4+ CD56+ (C56Cs) cells and epicardial progenitor cells (EPCs) according to the present invention.

Differentiation media useful in the present invention are commercially available and can be supplemented with commercially available components, available from Invitrogen Corp. (GIBCO), Cell Applications, Inc. and Biological Industries, Beth HaEmek, Israel, among numerous other commercial sources, including Calbiochem. In preferred embodiments at least one differentiation agent such as fibroblast growth factor (FGF), LR-IGF (an analogue of insulin-like growth factor), Heregulin and optionally, VEGF (preferably all three in effective amounts) is added to the cell media in which a stem cell is cultured and differentiated into a multipotent migratory cell or endothelial cells (vascular cells). One of ordinary skill in the art will be able to readily modify the cell media to produce any one or more of the target cells pursuant to the present invention. Cell differentiation medium is essentially synonymous with basal cell medium but is used within the context of a differentiation process and includes cell differentiation agents to differentiate cells into other cells. Stabilizing medium is a basal cell medium which is used either before or after a differentiation step in order to stabilize a cell line for further use. Culture media is essentially the same as stabilizing medium, but refers to media in which a pluripotent or other cell line is grown or cultured prior to differentiation. In general, as used herein, cell differentiation medium and stabilizing medium may include essentially similar components of a basal cell medium, but are used within different contexts and may include slightly different components in order to effect the intended result of the use of the medium. In the case of MMCs, especially MMCs which are storage stable, the inclusion of effective amounts of Activin A signaling inhibitors as otherwise disclosed herein in combination with an effective amount of a GSK inhibitor as otherwise described herein in cell media may be used to differentiate and to stabilize the MMCs, i.e., prevent their further differentiation and allow for storage stability of the cell populations. BMP inhibitors may be used in conjunction with Activin A inhibitors and GSK inhibitors for this purpose.

Pluripotent stem cells also may be cultured on a layer of feeder cells that support the pluripotent stem cells in various ways which are described in the art. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium. These approaches are well known in the art. In preferred aspects of the present invention, the cells are grown in feeder cell free medium.

Approaches for culturing cells on a layer of feeder cells are well known in the art. For example, Reubinoff et al. (*Nature Biotechnology* 18: 399-404 (2000)) and Thompson et al. (*Science* 6 Nov. 1998: Vol. 282. no. 5391, pp. 1145-1147) disclose the culture of pluripotent stem cell lines from human blastocysts using a mouse embryonic fibroblast feeder cell layer. Richards et al, (*Stem Cells* 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent". US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer. In another example, Wang et al (Stem Cells 23: 1221-1227, 2005) disclose methods for the long-term growth of human pluripotent stem cells on feeder cell layers derived from human embryonic stem cells. In another example, Stojkovic et al (Stem Cells 2005 23: 306-314, 2005) disclose a feeder cell system derived from the spontaneous differentiation of human embryonic stem cells. In a further example, Miyamoto et al (+22: 433-440, 2004) disclose a source of feeder cells obtained from human placenta. Amit et al (*Biol. Reprod* 68: 2150-2156, 2003) discloses a feeder cell layer derived from human foreskin. In another example, Inzunza et al (Stem Cells 23: 544-549, 2005) disclose a feeder cell layer from human postnatal foreskin fibroblasts.

Approaches for culturing pPSCs in media, especially feeder-free media, are well known in the art. U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure." In another example, WO2005014799 discloses conditioned medium for the maintenance, proliferation and differentiation of mammalian cells. In still another example, Xu et al (*Stem Cells* 22: 972-980, 2004) discloses conditioned medium obtained from human embryonic stem cell derivatives that have been genetically modified to over express human telomerase reverse transcriptase. In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (*BioReprod DOI*:10.1095/biolreprod. 105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal. In another example, Levenstein et al (*Stem Cells* 24: 568-574, 2006) disclose methods for the long-term culture of human embryonic stem cells in the absence of fibroblasts or conditioned medium, using media supplemented with bFGF. In still another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells. In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In still another example, WO2005086845 discloses a method for maintenance of an undifferentiated stem cell, said method comprising exposing a stem cell to a member of the transforming growth factor-beta (TGF.beta.) family of proteins, a member of the fibroblast growth factor (FGF) family of proteins, or nicotinamide (NIC) in an amount sufficient to maintain the cell in an undifferentiated state for a sufficient amount of time to achieve a desired result.

The cells are preferably grown on a cellular support or matrix, as adherent monolayers, rather than as embryoid bodies or in suspension. In the present invention, the use of Matrigel as a cellular support is preferred. Cellular supports preferably comprise at least one differentiation protein. The term "differentiation protein" or "substrate protein" is used to describe a protein which is used to grow cells and/or to promote differentiation (also preferably attachment) of an embryonic stem cell or mesendoderm, mesoderm or multipotent migratory cell (MMC). Differentiation proteins which are preferably used in the present invention include, for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting and differentiation activity. Other differentiation proteins which may be used in the present invention include for example, collagen, fibronectin, vibronectin, polylysine, polyornithine and mixtures thereof. In addition, gels and other materials such as methylcellulose of other gels which contain effective concentrations of one or more of these embryonic stem cell differentiation proteins may also be used. Exemplary differentiation proteins or materials which include these differentiation proteins include, for example, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others. The preferred material for use in the present invention includes Matrigel™ and Geltrex™.

A preferred composition/material which contains one or more differentiation or substrate proteins is BD Matrigel™ Basement Membrane Matrix. This is a solubilized basement membrane preparation extracted from the Engelbreth-Holm-Swarm (EHS) mouse sarcoma, a tumor rich in ECM proteins. Its major component is laminin, followed by collagen IV, heparan sulfate, proteoglycans, entactin and nidogen.

The pluripotent stem cells are preferably plated onto the differentiation or substrate protein. The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

As used herein, the term "activate" refers to an increase in expression of a marker such as Isl or an upregulation of the activity of Isl or a marker associated with a blood cell, vascular cells (endothelial cells), kidney cells, bone and muscle cells. These cells have utility in treating heart disease, kidney degeneration, the repair of bone and vascular degeneration.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide (including a marker) in a cell, such that levels of the molecule are measurably higher in or on a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "markers" or "biomarkers" describe nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, the term "contacting" (i.e., contacting a cell with a compound) is intended to include incubating the compound and the cell together in vitro (e.g., adding the compound to cells in culture). The term "contacting" is not intended to include the in vivo exposure of ("exposing") cells to a differentiation agent that may occur naturally in a subject (i.e., exposure that may occur as a result of a natural physiological process). The step of contacting the cell with differentiation medium and one or more growth factors (BMP or other) and/or inhibitors (inhibitors of GSK, Activin A (signaling) or BMP (signaling, etc.)) as otherwise described herein can be conducted in any suitable manner. For example, the cells may be treated in adherent culture as an adherent layer, as embryoid bodies or in suspension culture, although the use of adherent layers are preferred because they provide an efficient differentiation process oftentimes providing differentiation to a target cell population (mesendoderm, mesoderm or multipotent migratory cells) of 90% or more. It is understood that the cells contacted with the differentiation agent may be further treated with other cell differentiation environments to stabilize the cells, or to differentiate the cells further, for example to produce islet cells.

As used herein, the term "differentiation agent" refers to any compound or molecule that induces a cell such as hESC's, multipotent migratory cells (MMCs), C56Cs, Isl1+ multipotent progenitors (IMPs), EPCs, to partially or terminally differentiate, wherein said differentiation is due at least in part to inhibition of GSK, to the inclusion of bone morphogenic protein (BMP-2, BMP-4, BMP-6 or BMP-7) such as in the differentiation of hESCs to mesoderm Isl1+ cells (IMPs), or alternatively, the inhibition of GSK and the inhibition of Activin A and/or the inhibition of bone morphogenic protein to produce multipotent migratory cells (MMCs), or the addition of Wnt3a, BMP4 and sodium butyrate Activin A to produce C56Cs from MMCs, or the addition of Wnt3a, BMP4 and all-trans retinoic acid to IMPs produce EPCs, etc. While the differentiation agent may be as described below, the term is not limited thereto. The term "differentiation agent" as used herein includes within its scope a natural or synthetic molecule or molecules which exhibit(s) similar biological activity.

The term "effective" is used to describe an amount of a component, compound or compositions which is used or is included in context in an amount and/or for a period of time (including sequential times) sufficient to produce an intended effect. By way of example, an effective amount of a differentiation agent is that amount which, in combination with other components, in a differentiation medium for an appropriate period of time (including sequential times when different differentiation agents are exposed to cells to be differentiated) will produce the differentiated cells desired.

The term "bone morphogenic protein" or BMP is used to describe a differentiation agent which is used in the present invention, in combination with other components as otherwise described herein, to differentiate hESCs or mesendoderm cells to mesoderm Isl1+ cells. Any one of BMP-2, BMP-4, BMP-6 or BMP-7 (BMP-2 or BMP-4 being preferred) may be used in effective amounts to assist the differentiation process. BMP may be used in amounts ranging from about 1 ng/ml to about 500 ng/ml or more, about 25 to about 500 ng/ml, about 25 to about 250 ng/ml, about 50 to about 150 ng/ml, about 75 to about 125 ng/ml, about 100 ng/ml.

The term "GSK inhibitor" is used to describe a compound which inhibits GSK (especially GSK3, including GSK3α or GSK3β). Examples of preferred GSK inhibitors for use in the present invention include one or more of the following, all available from Calbiochem:

BIO (2'Z,3'E)-6-Bromoindirubin-3'-oxime (GSK3 Inhibitor IX);
BIO-Acetoxime (2'Z,3'E)-6-Bromoindirubin-3'-acetoxime (GSK3 Inhibitor X);
(5-Methyl-1H-pyrazol-3-yl)-(2-phenylquinazolin-4-yl) amine (GSK3-Inhibitor XIII);
Pyridocarbazole-cyclopenadienylruthenium complex (GSK3 Inhibitor XV);
TDZD-8 4-Benzyl-2-methyl-1,2,4-thiadiazolidine-3,5-dione (GSK3β Inhibitor I);
2-Thio(3-iodobenzyl)-5-(1-pyridyl)-[1,3,4]-oxadiazole (GSK3β Inhibitor II);
OTDZT 2,4-Dibenzyl-5-oxothiadiazolidine-3-thione (GSK3β Inhibitor III);
α-4-Dibromoacetophenone (GSK3β Inhibitor VII);
AR-A014418 N-(4-Methoxybenzyl)-N'-(5-nitro-1,3-thiazol-2-yl)urea (GSK-3β Inhibitor VIII);
3-(1-(3-Hydroxypropyl)-1H-pyrrolo[2,3-b]pyridin-3-yl]-4-pyrazin-2-yl-pyrrole-2,5-dione (GSK-3β Inhibitor XI);
TWS119 pyrrolopyrimidine compound (GSK3β Inhibitor XII);
L803 H-KEAPPAPPQSpP-NH$_2$ or its Myristoylated form (GSK3β Inhibitor XIII); and
2-Chloro-1-(4,5-dibromo-thiophen-2-yl)-ethanone (GSK3β Inhibitor VI).

In addition, numerous wingless proteins or Wnt proteins function similar to GSK inhibitors and in particular, GSK inhibitors according to the present invention. They are therefore subsumed under the term GSK inhibitors, but within context and in instances where GSK inhibitors as described above are excluded (e.g. in the case of the formation of C56Cs from MMCs as otherwise described herein, may be referred to specifically as wingless or Wnt proteins. Exemplary Wnt proteins which may be used in the present invention include one or more of Wnt1, Wnt2, Wnt3, Wnt3a, Wnt4, Wnt10, Wnt 14, Wnt14b, Wnt15, and Wnt16, among other Wnt proteins. The use of Wnt3a is preferred.

Preferred GSK inhibitors for use in the present invention include, BIO (GSK-3 IX) and Wnt3a.

GSK inhibitors are useful in all aspects of the invention which relate to the differentiation and formation of multipotent migratory cells (MMCs) and epicardial progenitor cells (EPCs). When used, they are used in effective amounts, in concentrations (depending upon the molecular weight of the inhibitors used) of about 0.001 to about 100 µM or more, about 0.05 to about 75 µM, about 0.1 to about 50 µM, about 0.25 to about 35 µM, about 0.5 to about 25 µM. In the case of the use of BIO, this GSK inhibitor is used in the differentiation medium in an amount ranging from about 0.05 to about 50M, about 0.1 to about 10 µM, about 0.5 to about 5 µM, about 1-3 µM. When a Wnt protein is used, the amount of Wnt which is used ranges from about 1 to about 100 ng/ml, about 5 to about 50 ng/ml, about 10 to about 35 ng/ml, about 20 to about 30 ng/ml, about 25 ng/ml.

The term "Activin A inhibitor" is used to describe compounds or components which optionally are added to a differentiation medium to inhibit the effects of Activin A (TGFβ signaling inhibitor) in the differentiation process and when used, produce multipotent migratory cells (MMCs) from hESCs or endothelial cells EPCs. In order to produce MMCs from hESCs, the differentiation agent comprises an effective amount of a GSK inhibitor (preferably, a GSK3 inhibitor, such as BIO or other GSK3 inhibitor) and an Activin A inhibitor plus or minus a bone morphogenic protein (BMP) inhibitor.

Exemplary Activin A inhibitors for use in the present invention include, for example, SB431542 (Sigma), follistatin, follistatin gene related protein (FGRP, available from R and D Systems), BMP and Activin Membrane Bound Inhibitor (BAMBI), anti-BAMBI (monoclonal antibody), Smad7 (Mothers Against Decapentaplegic Homolog 7) and TGF RI inhibitor (Calbiochem), among others. Activin A inhibitors are used in the present invention in effective amounts, generally within the range of about 0.001 to about 100 μM or more, about 0.05 to about 75 μM, about 0.1 to about 50 μM, about 0.25 to about 35 μM, about 0.5 to about 25 μM.

The term "bone morphogenic protein inhibitor" or "BMP inhibitor" is used to describe a compound or component which, when added in effective amounts to a differentiation medium to inhibit the effects of bone morphogenic protein (inhibits BMP signaling) in differentiating hESCs to multipotent migratory cells (MMCs). Exemplary BMP inhibitors include, for example, noggin, compound C, sclerostin, gremlin (Drm/Gremlin) and USAG-1, among others. The amount of BMP inhibitor used is an effective amount, generally (depending upon the molecular weight and effectiveness of the inhibitor used) falling within the range of about 0.01 ng/ml to about 500 ng/ml or more, about 0.1 to about 350 ng/ml, about 0.5 to about 250 ng/ml, about 1 to about 500 ng/ml, about 5 to about 250 ng/ml, about 50 to about 150 ng/ml, about 75 to about 125 ng/ml, about 100 ng/ml.

The term "inhibitor of the PI3-kinase pathway" or "inhibitor of PI3-kinase signaling" refers to any molecule or compound that decreases the activity of PI3-kinase or at least one molecule downstream of PI3-kinase in a cell contacted with the inhibitor. These inhibitors are preferred inhibitors for preparing definitive endoderm cells from mesendoderm cells and/or multipotent migratory cells according to the present invention. The term encompasses, e.g., PI3-kinase antagonists, antagonists of the PI3-kinase signal transduction cascade, compounds that decrease the synthesis or expression of endogenous PI3-kinase, compounds that decrease release of endogenous PI3-kinase, and compounds that inhibit activators of PI3-kinase activity. In certain embodiments of the foregoing, the inhibitor is selected from the group consisting of Rapamycin, LY 294002, wortmannin, lithium chloride, Akt inhibitor I, Akt inhibitor II (SH-5), Akt inhibitor III (SH-6), NL-71-101, and mixtures of the foregoing. Akt inhibitor I, II, Akt III, and NL-71-101 are commercially available from Calbiochem. In other embodiments, the inhibitor is selected from the group consisting of Rapamycin and LY 294002. In a further preferred embodiment, the inhibitor comprises LY 294002. In another embodiment, the inhibitor comprises Akt1-II. It is understood that combinations of inhibitors may be used to elicit the desired differentiation effect. The ultimate result is production of substantial quantities of definitive endoderm cells which may be used for the production of pancreatic endoderm cells and/or liver endoderm cells as disclosed in international application no. PCT/US2005/028829, filed 15 Aug. 2005, published as WO 2006/020919 (published 23 Feb. 2006) and PCT/US2008/001222, filed 30 Jan. 2008, published as WO2008/094597, Aug. 7, 2008, relevant portions of which are incorporated by reference herein.

As used herein when referring to a cell, cell line, cell culture or population of cells within context, the term "isolated" refers to being substantially separated from the natural source of the cells such that the cell, cell line, cell culture, or population of cells are capable of being cultured in vitro. Alternatively, and depending upon context, the term "isolated" means that a cell population is separated from the differentiation medium and culture flask so that the cell population may be stored (cryopreservation). In addition, the term "isolating" may be used to refer to the physical selection of one or more cells out of a group of two or more cells, wherein the cells are selected based on cell morphology and/or the expression of various markers.

The term "passaged" is used to describe the process of splitting cells and transferring them to a new cell vial for further growth/regrowth. The preferred adherent cells (or even embryoid bodies) according to the present invention may be passaged using enzymatic (Accutase™ or collagenase) passage, manual passage (mechanical, with, for example, a spatula or other soft mechanical utensil or device) and other non-enzymatic methods, such as cell dispersal buffer As used herein, the term "contacting" (i.e., contacting a hESC, multipotent migratory cell, C56Cs, IMPs or EPCs with a compound) or "exposing" is intended to include incubating the compound and the cell together in vitro (e.g., adding the compound to cells in culture). The term "contacting" is not intended to include the in vivo exposure of cells to growth factors and/or other differentiation agents or inhibitors that may occur naturally in a subject (i.e., exposure that may occur as a result of a natural physiological process). The step of contacting the cell with the growth factors and/or inhibitors in differentiation medium pursuant to the present invention can be conducted in any suitable manner. For example, the cells may be treated in adherent culture, as embryoid bodies or in suspension culture. It is understood that the cells contacted with the differentiation agent(s) and/or inhibitors may be further treated with other cell differentiation environments to stabilize the cells, or to differentiate the cells further, for example to produce endothelial cells, muscle cells, including cardiac muscle cells and vascular cells, including blood vessels. These cells have utility in regenerative medicine to treat heart disease, kidney degeneration, repair of bone and vascular degeneration.

In certain embodiments, the hESCs, (Isl1+) multipotent progenitors (IMPs), EPCs or MMCs to be further differentiated are plated at a concentration of less than approximately $2.5 \times 10^6$ cells/35 mm dish, of at least approximately $2.5 \times 10^4$ cells/35 mm dish, between approximately $2.5 \times 10^5$ to approximately $2 \times 10^6$ cells/35 mm dish, between approximately $5 \times 10^5$ to approximately $2 \times 10^6$ cells/35 mm dish, of less than approximately $2 \times 10^6$ cells/35 mm dish, or at a density of greater than $4 \times 10^5$ cells/35 mm dish. In certain preferred aspects, the cells to be differentiated are plated at a concentration of approximately $7.5 \times 10^5$ cells/35 mm dish.

In producing (Isl1+) multipotent progenitor cells (IMPs) or MMCs from hESCs, as a first step in certain embodiments of the present invention, the present invention further encompasses the use of a composition for culturing cells to produce an adherent monolayer of hESCs. The hESC's are grown as adherent monolayers on a cellular support, preferably Matrigel, in defined cellular media (no serum or KSR). The cellular media, in addition to typical components as otherwise described herein, also preferably comprise an effective amount of one or more of the following components in effective amounts: ascorbic acid, transferrin, β-Mercaptoethanol (Gibco), fibroblast growth factor (FGF), LR-IGF, Activin A, and heregulin, and preferably all of these components. The cellular media in which adherent layers (or embryoid bodies) of hESCs are grown to be used as starting cell populations for differentiation may be varied within the teachings of the art.

The hESC's produced above, are then plated onto cellular support and differentiated in a differentiation medium (as otherwise described herein) in effective amounts of differentiation agents and/or inhibitors. The cells are preferably grown as adherent monolayers. In the case of ISl1+ multipotent progenitors (IMPs), hESCs are contacted with a differentiation medium comprising an effective amount of a GSK inhibitor as otherwise herein (preferably BIO or Wnt3a) for an appropriate period of time to produce a stable IMP population. In the case of producing IMPs, hESCs are contacted with a differentiation medium comprising an effective amount of a GSK inhibitor as otherwise herein (preferably BIO or Wnt3a) in combination with a bone morphogenic protein (BMP-2, BMP-4, BMP-6, BMP-7) for an appropriate period of time to produce a (Isl1+) multipotent progenitor cell population (IMPs).

IMPs may be cloned and/or expanded in defined media in the presence of a GSK inhibitor (e.g. BIO, at 0.5-10 µM, 2 µM) and BMP4 and passaged (Accutase, other). These cells may then be plated at low density (20-200 cells/mm2 in methylcellulose (0.9% final concentration) or other thickener (e.g. cellulosic) for several (3) days on a substrate protein (Matrigel) and thereafter, the media is replaced daily. After about two weeks (14 days), individual colonies may be isolated and subcultured to generate stable, clonal IMP cell lines.

IMPs may be used directly to produce cardiomyocytes in the absence of Activin A+/−IGF in the presence of effective amounts of BMP (1-25 ng/ml, about 10 ng/ml); BMP (1-25 ng/ml, about 10 ng/ml)+DKK1 (25-500 ng/ml, 150 ng/ml); BMP (1-25 ng/ml, about 10 ng/ml)+DKK1 (25-500 ng/ml, 150 ng/ml)+VEGF (1-25 ng/ml, 10 ng/ml); DKK1 (25-500 ng/ml, 150 ng/ml) and VEGF (1-25 ng/ml, 10 ng/ml) for a period of about two weeks (about 10-20+ days).

IMPs may be used to generate smooth muscle cells, cardiomyocytes and endothelial cells as otherwise described herein in vitro and in vivo. IMPs may be injected/applied directly to sites of cardiac tissue damage and may participate in the repair process by differentiating into functional cardiomyocytes, endothelial cells and smooth muscle cells. In addition, IMPs can differentiate into cardiomyocytes when cultured with cardiac tissue.

IMPs may be differentiated into EPCs utilizing an effective amount of a wingless protein (Wnt3a), a bone morphogenic protein (BMP4) and all-trans retinoic acid in a defined media as otherwise described herein. EPCs produced according to methods of the present invention may be used to generate endothelial cells, smooth muscle cells and cardiac fibroblasts.

IMPs may be injected/applied directly to sites of cardiac tissue damage and may participate in the repair process by differentiating into functional cardiomyocytes, endothelial cells and smooth muscle cells. In addition, IMPs can differentiate into cardiomyocytes EPCs, like IMPs, may be used to generate smooth muscle cells, cardiomyocytes and endothelial cells as otherwise described herein in vitro and in vivo. IMPs may be injected/applied directly to sites of cardiac tissue damage and may participate in the repair process by differentiating into functional cardiomyocytes, endothelial cells and smooth muscle cells. EPCs also are believed to be able to incorporate into endoderm vascular tissue (chick embryo engraftment). Consequently, EPCs are believed to be capable of regenerating organs associated with endoderm such as the gut—which also has a lining derived from serosal mesothelium (where pro-epicardium comes from). Consequently, it is believed that EPCs may have utility in repair of endoderm derived organs in the body. EPCs according to the present invention thus have the ability to contribute to the gut vasculature and has roles outside of cardiac repair in a wide range of tissues that need to be revascularized (stroke, diabetes complications, etc.). See Wilm, et al., *Development*, 132(23) 5317-28, 2005.

In a further embodiment, the cell culture medium may be a conditioned medium (MEF-CM). The conditioned medium can be obtained from a feeder layer. It is contemplated that the feeder layer may comprise fibroblasts, and in one embodiment, comprises embryonic fibroblasts. Preferably, the medium is feeder cell free.

In a particularly preferred embodiment, the differentiation medium for producing mesoderm (Isl1+) cells (IMPs) or MMCs comprises DMEM/F12 (50/50), approximately 2% probumin (albumin), antibiotics (1× Pen/Strep 1×NEAA), Trace Elements A, B, C (e.g., 1× from Mediatech), Ascorbic acid (e.g. about 50 µg/ml), Transferrin (e.g. about 10 µg/ml), β-Mercaptoethanol (about 0.1 mM), bFGF (e.g. about 8 ng/ml), LR-IGF (e.g., about 200 ng/ml), Activin A (e.g., about 10 ng/ml) and Heregulin (e.g., about 10 ng/ml). Note that Activin A and Heregulin may be removed for production of multipotent migratory cells (MMCs). Of course, one or more of the above-components may be left out of the differentiation medium as taught by the art, but the full componentry as set forth is preferred for use in the present invention.

The present cells also provide potential for use in bioassays to identify molecules which impact (promote, inhibit or influence) differentiation of cells. The first step in the differentiation of the present cells provides a great chance to study epithelial to mesenchymal transition, especially in the progression of cancer, as part of tumor metastasis. Thus, the methods and populations of cells according to the present invention provide exceptional systems to both understand EMT at the molecular level and identify new drug targets and also to screen for small molecules that block EMT under conditions that promote EMT (BIO). Given that cells can be grown in 96/384 well plates this could easily be done, rapid drug-screening may be used to identify potential molecules which block or inhibit EMT and may represent potentially valuable anticancer agents.

With respect to MMCs, this is a stable population of cells growing in defined media with multi-potent differentiation capabilities. These cells may be particularly useful for screening for molecules that promote or inhibit differentiation or promote and specify differentiation to one lineage or another.

Therapies

The population of cells and/or methods which are described herein may provide useful therapies in the treatment of disease and/or conditions associated with the cells.

In a first aspect, the present invention provides a method for treating a patient suffering from a cardiovascular disorder. This method comprises culturing pluripotent stem cells, differentiating the pluripotent stem cells in vitro into cardiovascular muscle cells (cardiomyocytes) and implanting an effective amount of the cardiovascular muscle cells into a patient in need thereof. Alternatively, a method of treating cardiovascular disease, including an infarction, in a patient comprises administering into the heart tissue of a patient in need of therapy thereof an effective amount of epicardial progenitor cells (EPCs) or Isl1+ multipotent progenitor (IMPs) which may be administered systemically or directly onto or into cardiac tissue. These cells may also be used to treat stroke and complications of diabetes, especially vascular complications and to repair endoderm organs (liver, pancreas, digestive tract, etc.) in the patient.

In another aspect, the present invention provides a method for treating damaged or ischemic vascular tissue (blood vessels) in a patient in need thereof, comprising administering to the blood vessels to be repaired an effective amount of EPCs or IMPs. In an alternative embodiment, EPCs are differentiated to smooth muscle cells by passaging the cells for a period of at least about 5-6 days in a cell differentiation medium comprising an effective amount of a GSK inhibitor (preferably Wnt3a) in combination with BMP (BMP4) and the smooth muscle cells obtained therefore are administered (implanted) to the site of structural vascular damage in the patient in order to treat/repair same.

Therapeutic methods may utilize MMCs or preferably, C56Cs produced as described herein for homing to a site which has damaged/inflamed tissue. In this aspect, an effective number of C56Cs are administered to a patient in need thereof in order to treat a disease state or condition selected from the group consisting of cardiovascular disease (cardiomyopathy, ischemia), retinomyopathy, neuropathy, diabetes (type I and II), stroke, head trauma, autoimmune disease (lupus, arthritis, multiple sclerosis), immune suppression, graft versus host disease, bone repair, wound repair, inflammatory disease (arthritis, Crohn's disease, cystic fibrosis) and Parkinsons, Huntington's disease, among others. Systemic administration of MMCs or C56Cs may be by intravenous administration, directly at the site of damage or disease where localized or by infusion, including cardiovascular tissue (especially an ischemic heart) and bone tissue. Because of the homing qualities of MMCs and more importantly, C56Cs, these cells may be administered at a site far from the site of damage/inflammation and the cells will "home" to that site in the patient's body to effect therapy.

If appropriate, the patient can be further treated with pharmaceutical agents or bioactives that facilitate the survival and function of the transplanted cells. These agents may include, for example, insulin, members of the TGF-β family (TGF-β 1, 2, and 3) bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

Epicardial pluripotent cells (EPCs) according to the present invention may be used to generate endothelial cells, smooth muscle and cardiac fibroblast cells or to generate vascular cells in vivo in a patient. These cells may be used to treat cardiovascular disease and to repair or treat damaged tissue, including liver, pancreas and tissue in the gastrointestinal tract. This method comprises administering an effective number of EPCs systemically to a patient in order to influence and enhance cardiomyocyte proliferation, survival function and differentiation. In addition, EPCs may function as a therapy for the ischemic or damaged heart by regenerating coronary tissue, especially including coronary vasculature.

To enhance further differentiation, survival or therapeutic activity of the implanted cells, additional factors, such as growth factors, antioxidants, immunosuppressants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In another aspect, this invention provides a method for treating a patient suffering from, or at risk of developing cardiovascular disease or suffering ischemia. This method involves culturing pluripotent stem cells, differentiating the cultured cells in vitro into a population of epicardial pluripotent cells (EPCs) and injecting these cells into a patient in need or alternatively, incorporating the cells into a three-dimensional support to produce endothelial tissue, cardiomycetes and smooth muscle tissue. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells or which may otherwise be used to treat diabetes or cardiovascular disease or dysfunction.

The term "cardiovascular" agent is used to describe any number of cardiovascular agents which may be administered in combination with EPCs according to the present invention. A cardiovascular agent is used to describe agents which affect the rate and/or intensity of cardiac contraction, blood vessel diameter or blood volume and include anti-arrhythmic agents, anti-hypertensive agents, calcium channel blockers, cardioplegic agents, cardiotonic agent, fibrinolytic agents, nitric oxide donors, potassium channel blockers, sclerosing solutions, sodium channel blockers, vasoconstrictor agents and vasodilator agents, among others, all standard and well-known in the art.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945. The support may also be incorporated with at least one pharmaceutical compound that is an inhibitor of fibrosis, such as, for example, compounds disclosed in U.S. Pat. No. 6,331,298. The support may also be incorporated with at least one pharmaceutical compound that is capable of enhancing angiogenesis, such as, for example, compounds disclosed in U.S. Published Application 2004/0220393 and U.S. Published Application 2004/0209901. The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β 1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), LDkk1, platelet derived growth factor beta (PDGFβ), pleiotrophin, endothelin, among others. Other pharmaceutical compounds can include, for example, nicotinamide, hypoxia inducible factor 1-α, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

EXAMPLES

Figure 1:
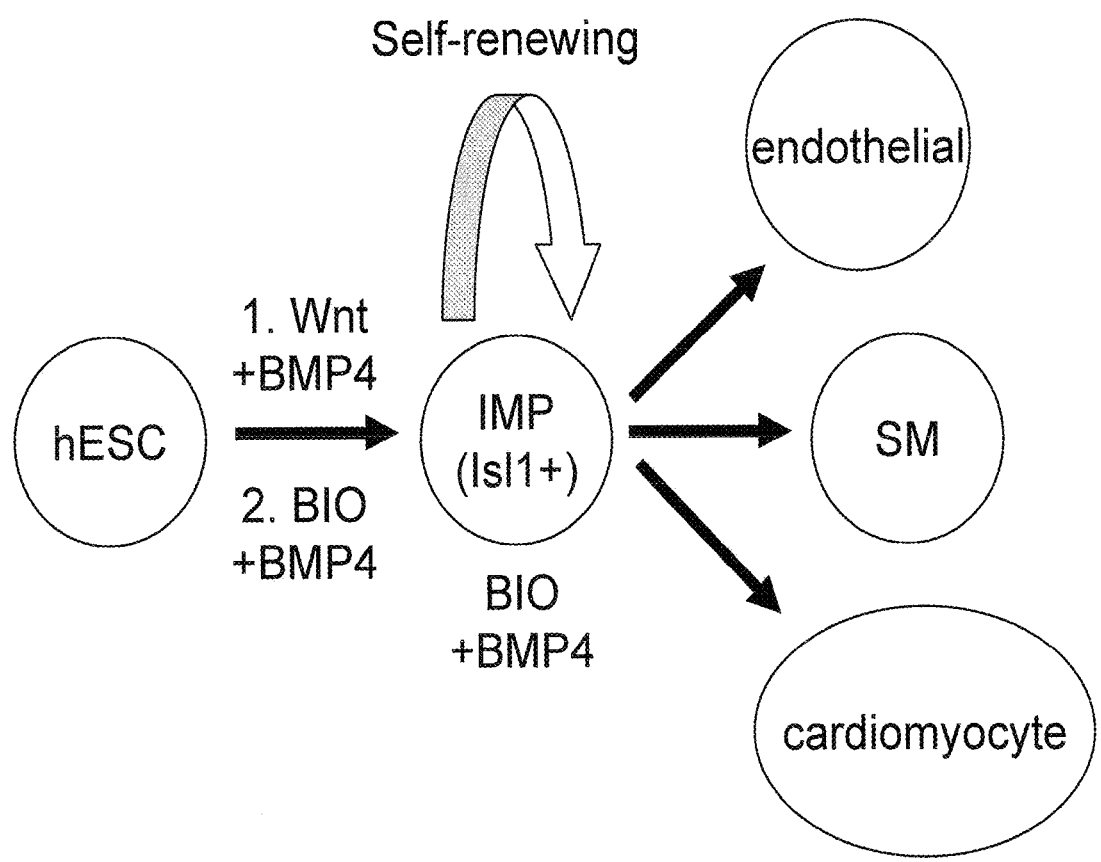
FIG. 1: Scheme illustrating the generation of Isl1+ IMPs from hESCs following treatment with (1) Wnt3a (25 ng/ml)+BMP4 (100 ng/ml) over 4-6 days or (2) BIO (2 μM)+BMP4 (100 ng/ml) over 4-6 days. IMP cells represent lateral plate/splanchnic mesoderm and can be maintained in a stable self-renewing state for at least 10 passages without loss of IMP marker expression and differentiation potential and have potential for differentiation into a wide-range of mesoderm derived cell types including cardiovascular and hematopoietic lineages.

All components, where used, are used in effective amounts.
1. Methods for Generation and Maintenance of Mesoderm-Derived Isl1+ Multipotent Progenitors (IMPS)
This Example describes a method for generation and maintenance for multiple passages of a mesoderm-derived Isl1+ multipotent progenitor (IMP) cell type that has ability to differentiate into cardiomyocytes, smooth muscle cells or endothelial cells (FIG. 1).
a) Generation and Maintenance of IMP's
IMP's were generated as in Example 3 from WA09 hESCs (PCT/US2008/001222, published as WO2008/094597). See below.

Example 3 (PCT/US2008/001222, Published as WO2008/094597): Methods for Generation of Mesoderm-Derived Isl1+ Multipotent Progenitors (IMPs)

Figure 11:
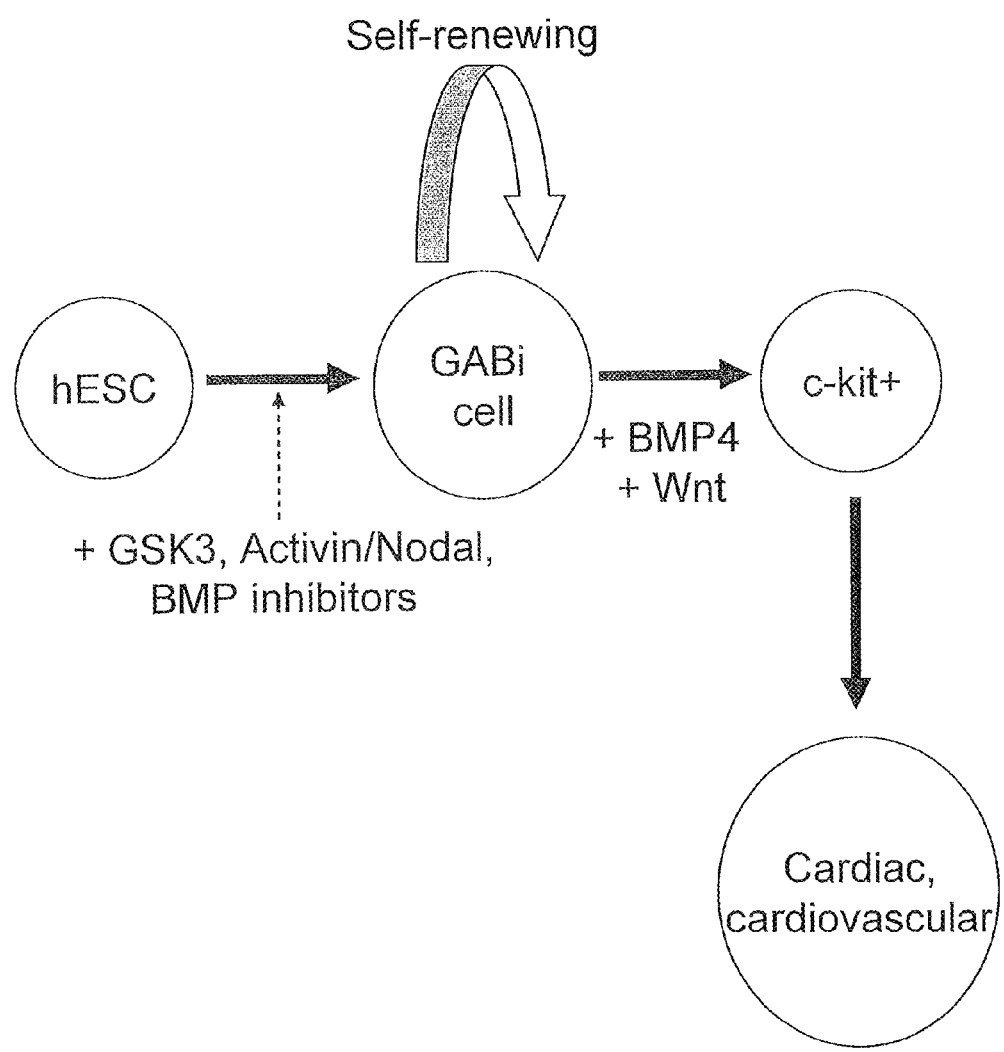
FIG. 11: A general model to illustrate the principle of generating a variety of multipotent mesenchymal progenitors from hESCs, cultured in defined media, by exposure to GSK3 inhibitors (such as BIO) in the presence of inhibitors of Activin/Nodal signaling and/or BMP signaling (Noggin, Compound C for example). These cells are generically called GABi cells—for GSK3, Activin/Nodal signaling, BMP signaling inhibitor cells.
Figure 12:
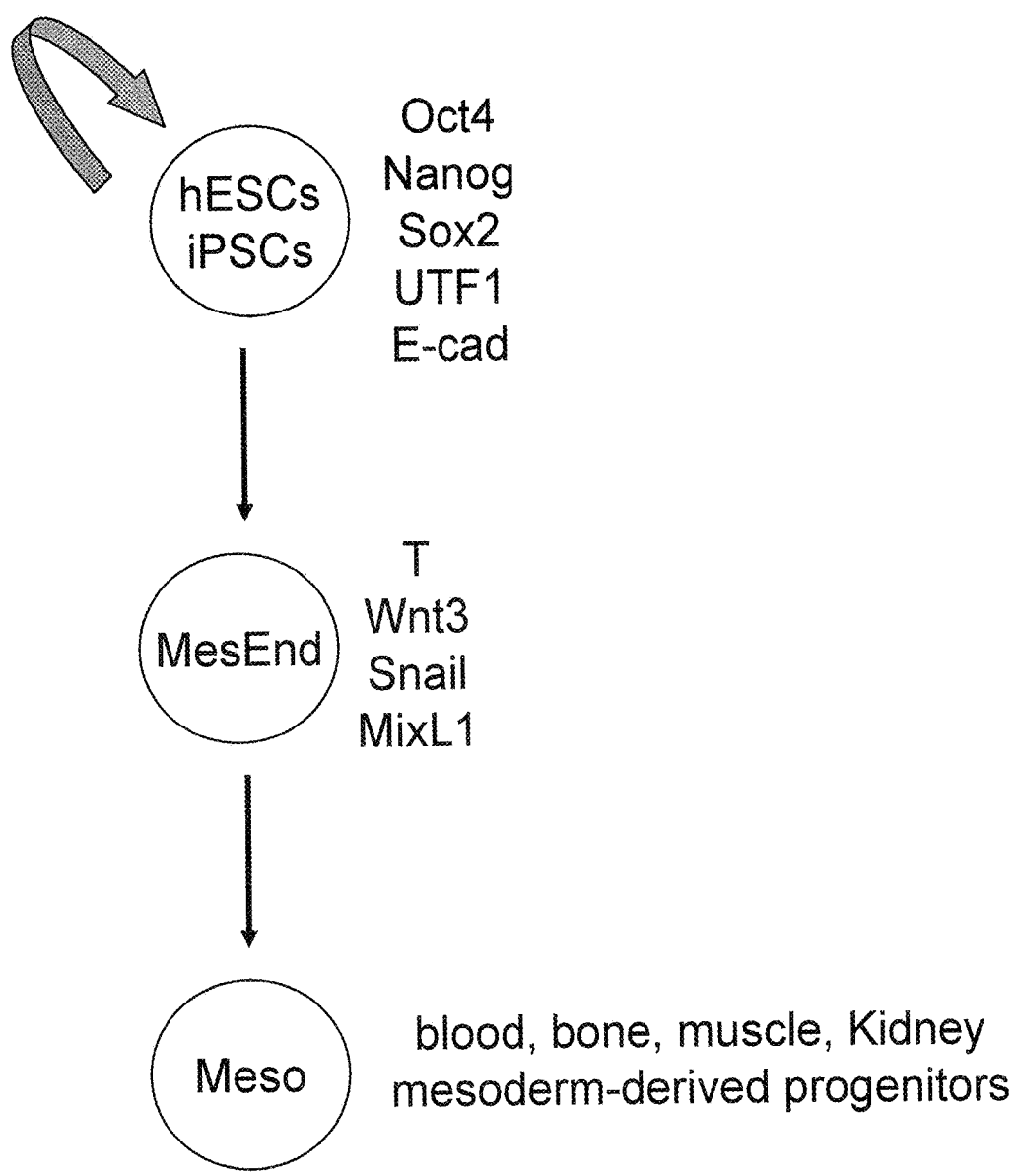
FIG. 12. Schematic diagram representing the differentiation of self-renewing human pluripotent stem cells (hESCs, iPS cells) into mesendoderm (MesEnd) and then mesoderm (Meso). Markers for pluripotent cells and mesendoderm are indicated as are the types of lineages that can be generated in the mesoderm lineage. The initial types of mesoderm formed include lateral plate and splanchnic mesoderm that under the appropriate conditions further differentiate into different mesoderm lineages.
Figure 13:
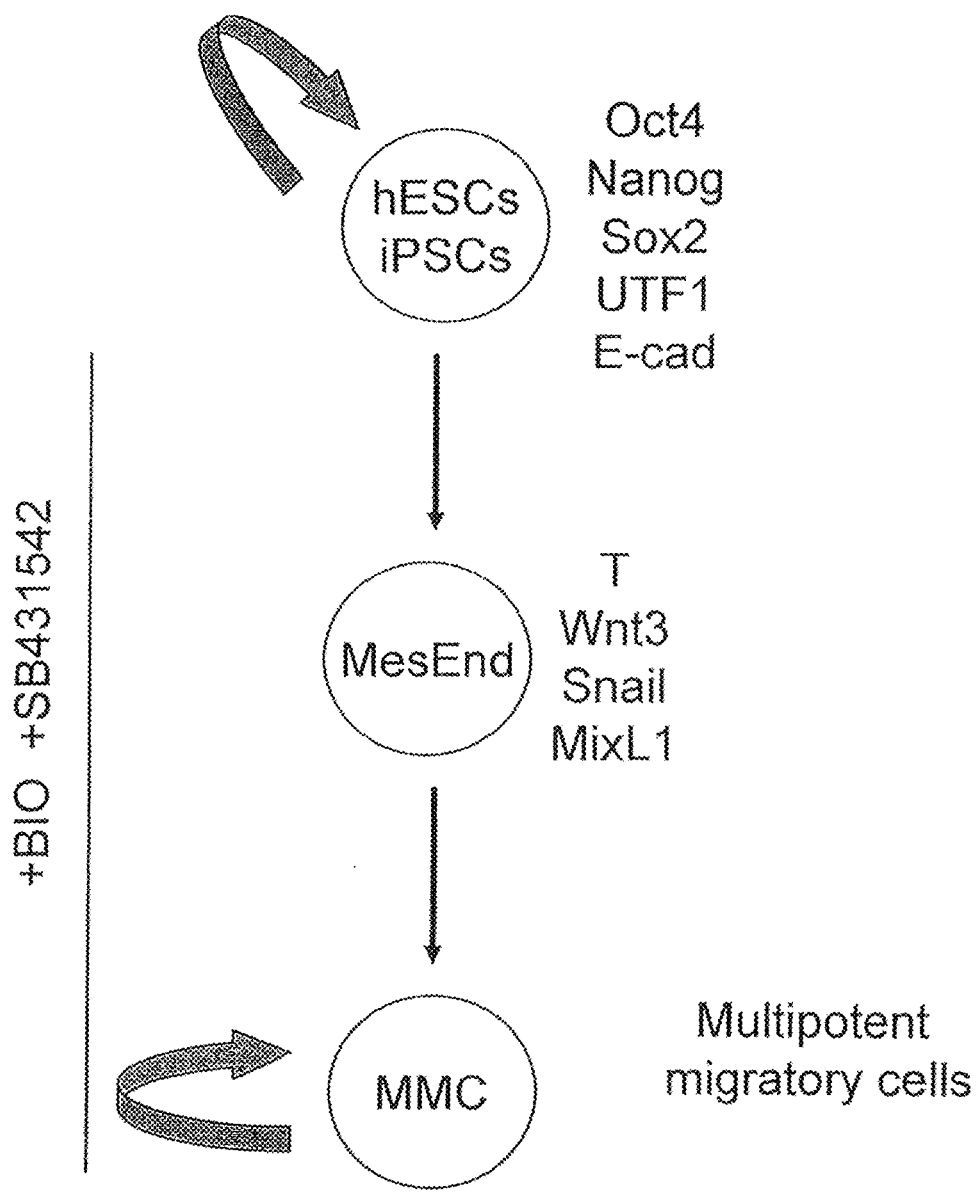
FIG. 13. Schematic diagram representing the differentiation of self-renewing human pluripotent stem cells (hESCs, iPS cells) into a mesoderm derived progenitor known as a multipotent migratory cell (MMC). Small molecule inhibitors such as BIO and SB431542 are added to hESCs to promote the cellular transition to MMCs. MMCs can be maintained as a stable cell population and therefore self-renew.

This Example describes a method for generation of a mesoderm-derived Isl1+ multipotent progenitor (IMP) cell type that has ability to differentiate into cardiomyocytes, smooth muscle cells or endothelial cells. This cell type differentiates along a pathway through the mesendoderm state and then to mesoderm.
(a) Generation of an Isl1+ Multipotent Progenitor (IMP) by Addition of Wnt3a and BMP4 to hESC Cultures.
BG02 hESCs grown in StemPro® defined media were passaged with Accutase™ and plated onto Matrigel coated dishes ($1.0 \times 10^6$ cells per 60 mm dish) as described in Example 1, except that media was supplemented with BMP4 (100 ng/ml, R&D Systems) plus human Wnt3a (R&D Systems). Media was replaced every day. Q-PCR analysis was performed over 240 hours (10 days) to evaluate differentiation. This analysis showed that mesendoderm markers such as T were elevated at 24 hours post-treatment but decreased thereafter (FIG. 11). After 24 hours treatment, transcript markers indicative of mesoderm differentiation were significantly upregulated (Isl1, PDGFRalpha, KDR, Tbx20, GATA4) (FIG. 11). Immunostaining revealed that over 24-96 hours post-treatment, most cells stained positive for T but this decreased by 144 hours. After 6 days treatment (144 hours) with BMP4 and Wnt3a, >90% of cells stained positive for Nkx2.5, Isl1 and Tbx20. This gene expression profile is indicative of multipotent Isl1+ progenitor cells of the secondary heart field (Laugwitz et al., Development 135: 193-205). Differentiation to Isl1+ cells is accompanied by a distinctive cell morphology change.
(b) Generation of an Isl1+ Multipotent Progenitor (IMP) by Addition of Wnt3a for Days 1-3 Followed by Addition of BMP4.
Isl1+ mesoderm cells can be generated by treatment of hESCs, grown in either MEF-CM or defined media, with Wnt3a for the initial 1-3 days followed by addition of BMP4 for a further 2-4 days.
(c) Generation of an Isl1+ Multipotent Progenitor (IMP) by Addition of BMP4 and GSK Inhibitors Such as BIO to hESCs in MEF-CM.
BG02 hESCs grown on Matrigel in MEF-CM were passaged with trypsin and $1.5 \times 10^6$ cells per 60 mm dish seeded back onto Matrigel in MEF-CM supplemented with BIO (2 µM) plus BMP4 (100 ng/ml). Media was replaced every day. Q-PCR analysis was performed over 240 hours (10 days) to evaluate differentiation. Compared to hESCs, treated cells underwent a change in morphology indicative of differentiation. Analysis of transcript levels by Q-PCR showed that hESC markers Nanog, Oct4, Lefty A declined by ~48 hours and mesendoderm markers (T, MixL1) peaked at 48 hours but declined by 96 hours. As mesendoderm marker levels decreased, markers for early mesoderm (FoxF1, GATA4, Isl1, Tbx20, PDGFRalpha, PDGFRbeta) became elevated from 24-48 hours onwards. These markers are indicative of the formation of IMPs.

(d) Generation of an Isl1+ Multipotent Progenitor (IMP) by Addition of BMP4 and GSK Inhibitors Such as BIO to hESCs Cultured in Defined Media.

hESCs can be differentiated to an Isl1+ progenitor by addition of BMP4 and BIO to hESCs cultured in defined media. 6 days of treatment with BMP4 and BIO.

(e) Generation of an Isl1+ Multipotent Precursor by Addition of GSK Inhibitors, Such as BIO, for 1-3 Days Followed by Addition of BMP4.

Isl1+ mesoderm cells can be generated from hESCs grown in MEF-CM or defined media by addition of GSK inhibitors, such as BIO, for 1-3 days followed by addition of BMP4 for a further 2-4 days.

(f) Generation of an Isl1+ Multipotent Progenitor (IMP) by Addition of Wnt3a and BMP4 and TGFβ Signaling Inhibitors (Such as SB431542) to hESC Cultures.

Isl1+ mesoderm cells can be generated from hESCs, grown in MEF-CM or defined media, by addition of Wnt3a, BMP4 and TGFβ inhibitors (such as SB431542) for 1-4 days followed by the removal of TGFβ inhibitors and continued culture with Wnt3a and BMP4 for a further 2-4 days.

(g) Generation of an Isl1+ Multipotent Progenitor (IMP) by Addition of Wnt3a and TGFβ Signaling Inhibitors (Such as SB431542) for Days 1-4 Followed by Addition of BMP4.

Isl1+ mesoderm cells can be generated from hESCs, grown in MEF-CM or defined media, by addition of Wnt3a and TGFβ inhibitors (such as SB431542) for 1-4 days followed by addition of BMP4 for a further 2-4 days.

(h) Generation of an Isl1+ Multipotent Progenitor (IMP) by Addition of Wnt3a for Days 1-3 Followed by Addition of BMP4 and SB431542.

Isl1+ mesoderm cells can be generated from hESCs, grown in mEF-CM or defined media, by addition of Wnt3a and SB431542 for 1-3 days followed by addition of BMP4 for a further 2-4 days.

Figure 2A:
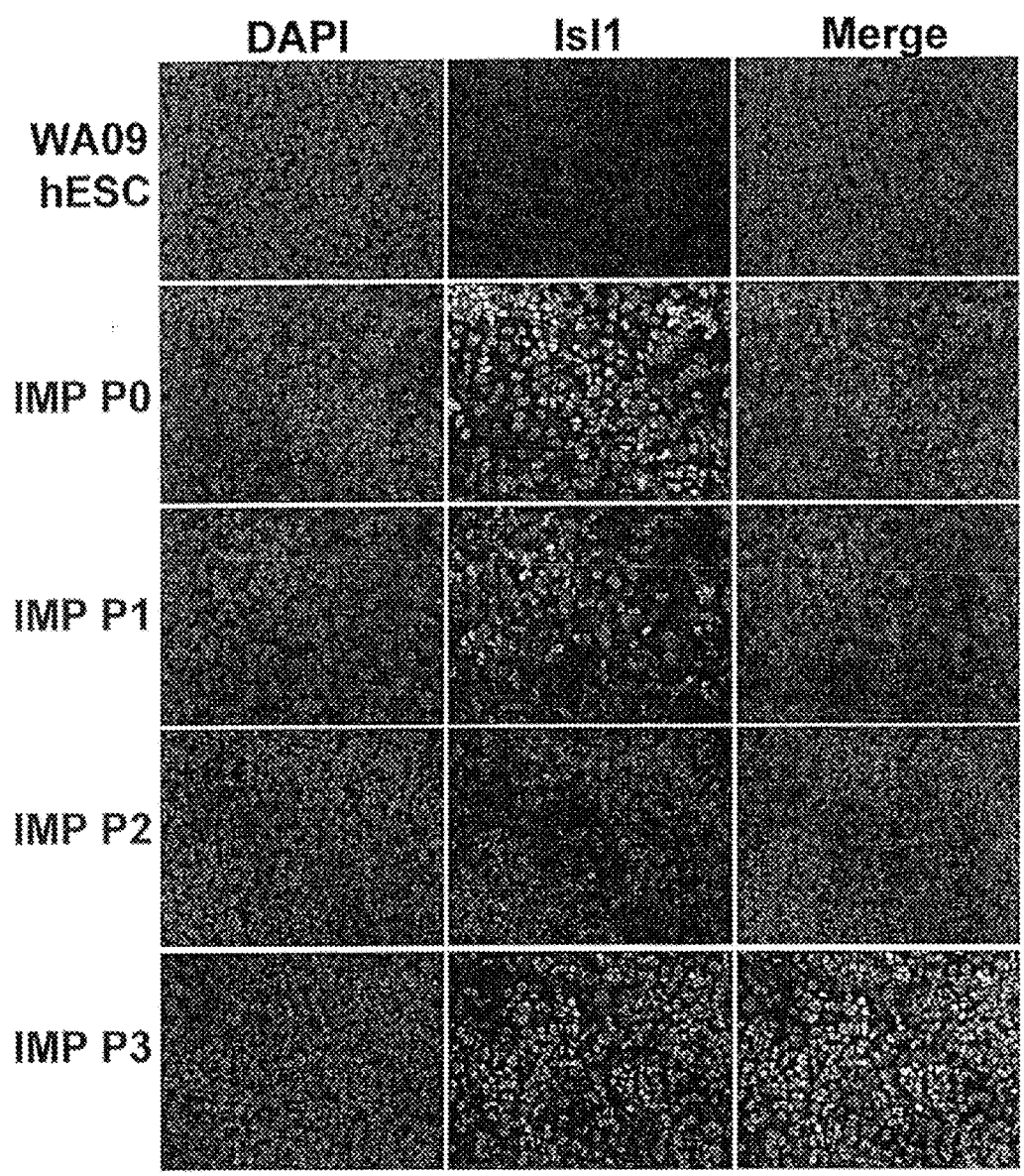
FIGS. 2A, 2B, 2C, 2D: Generation of a self-renewing IMP population following treatment of IMP's with Bio (2 μM) and BMP4 (100 ng/ml) in defined media. WA09 hESCs were passaged every 4-6 days at a ratio 1:6 and fixed at passage (P) 0-3 with 4% paraformaldehyde. Immunostaining at each passage was performed using A) Isl1, B) Nkx2.5, C) E-cadherin and D) β-catenin and Nanog. Isl1 and Nkx2.5 was expressed at all passages. β-catenin started to localize to the nucleus at P0 and became more diffuse over the passaging. E-cadherin (a marker for epithelial cells was lost along with the hESC marker Nanog. Merge images are shown along with DAPI (nuclear stain). Images were at 20× magnification.
Figure 2B:
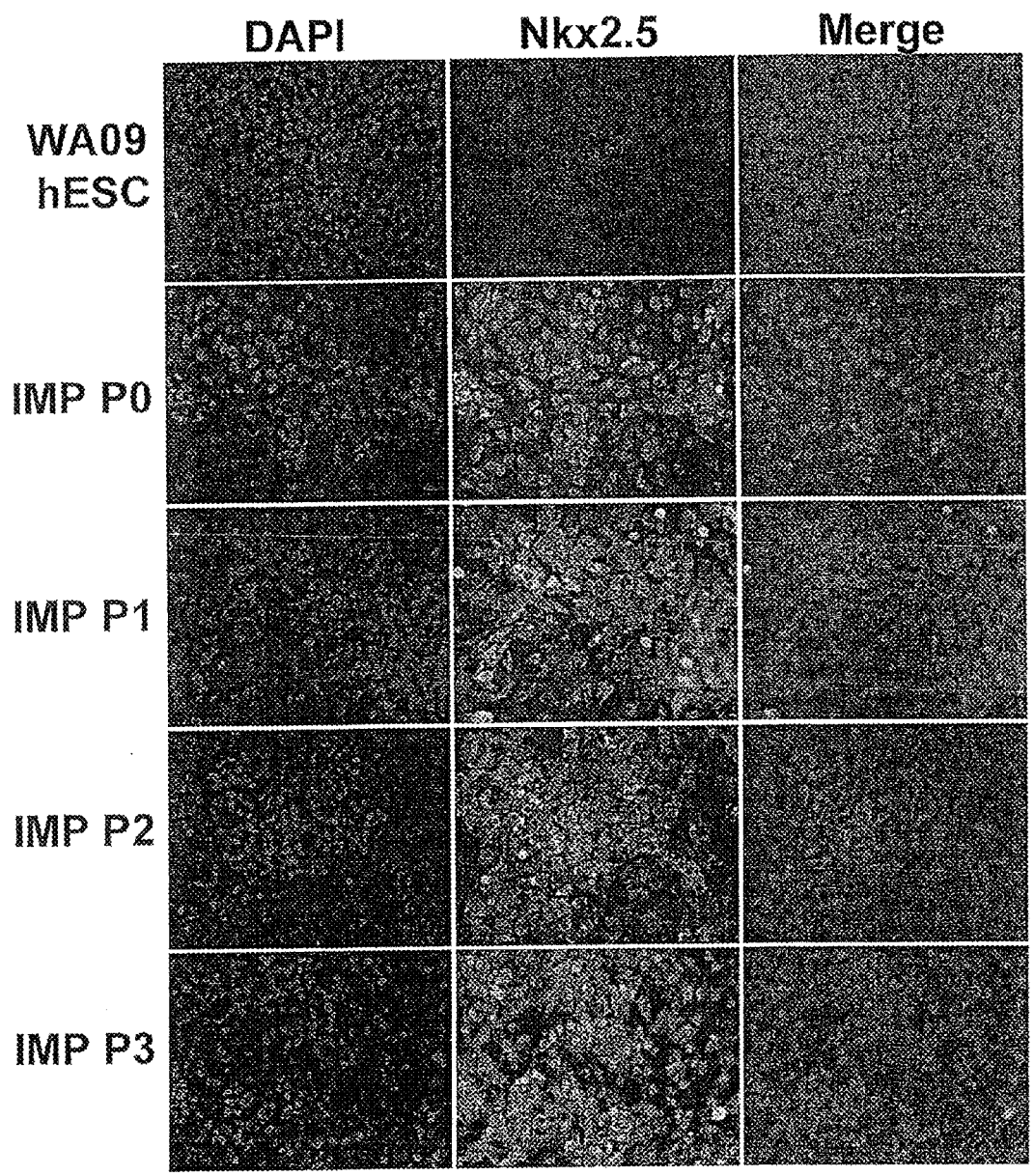
Figure 2C:
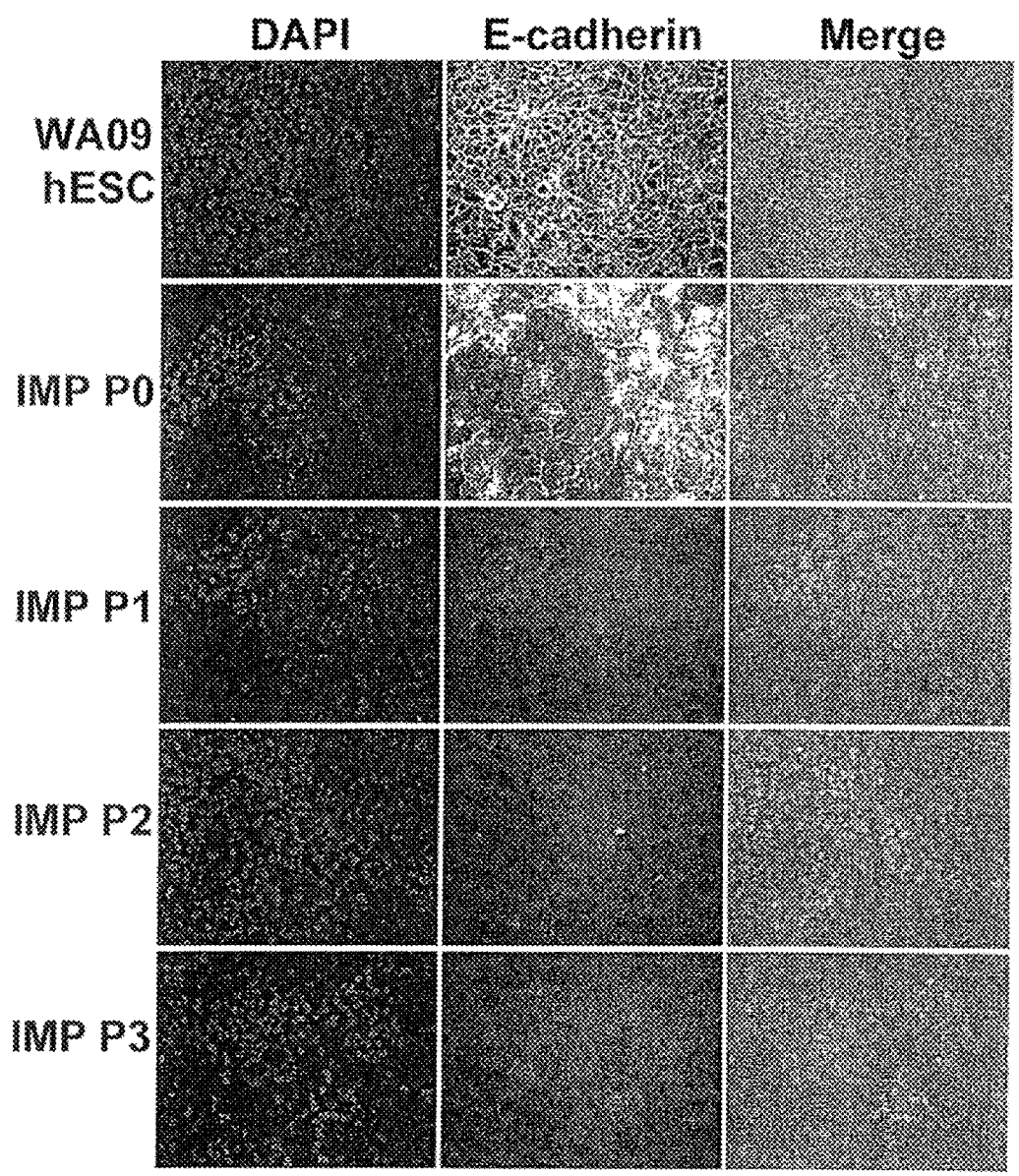
Figure 2D:
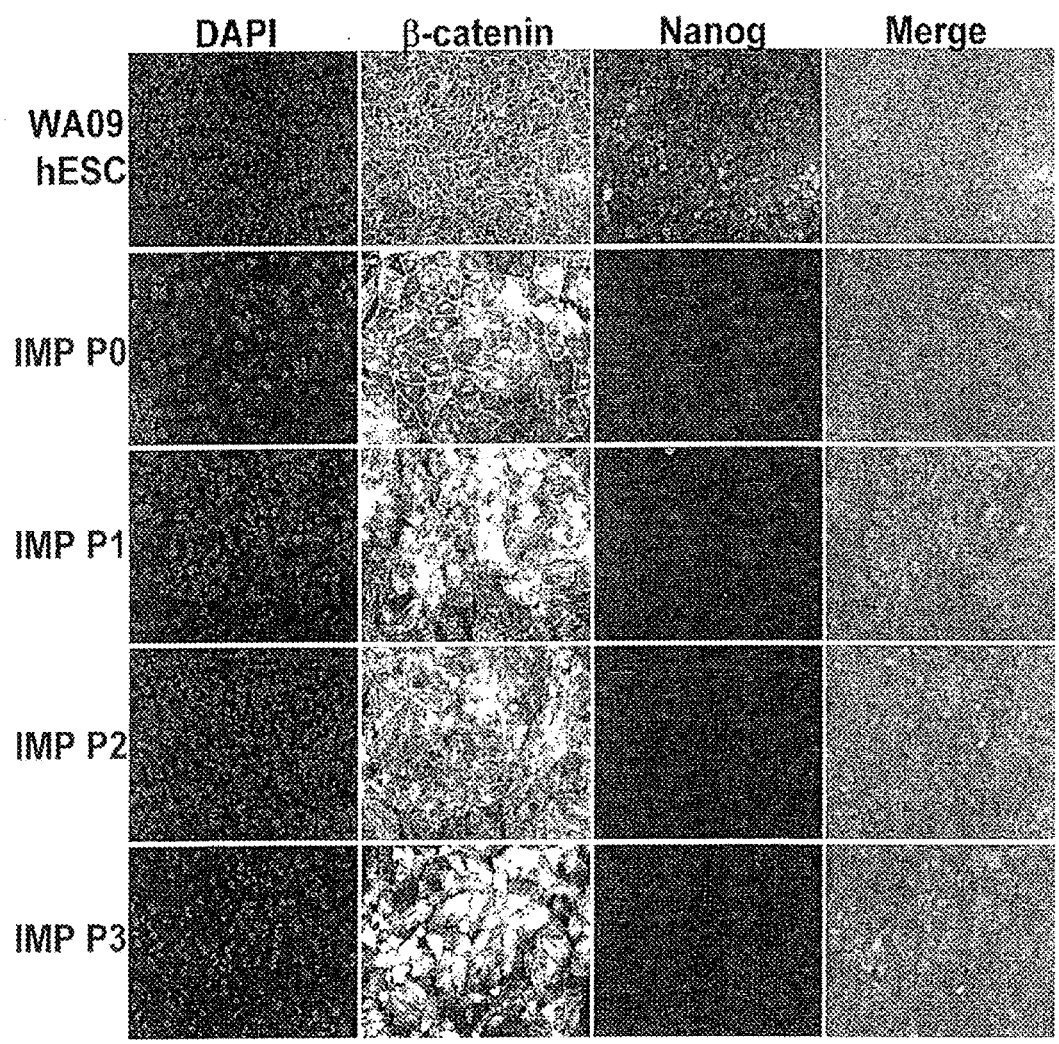

Following the method of the present invention, at days 3-6 the cells obtained following the method described above were split 1:6 into defined media containing Bio (2 μM) and BMP4 (100 ng/ml). The cells were maintained in this media indefinitely and split every 4-6 days at a 1:4-1:6 ratio. The resultant cells maintained their Isl1+ expression over subsequent passages along with Nkx2.5 (FIG. 2 A-B). These cells lost the hESC pluripotent marker Nanog and the epithelial marker E-cadherin, whereas β-catenin was found to defuse throughout the cell including localizing to the nucleus (FIG. 2C-D).

2. Clonal Expansion of Self-Renewing Isl1+ Multipotent Progenitors (IMPs).

Figure 3:
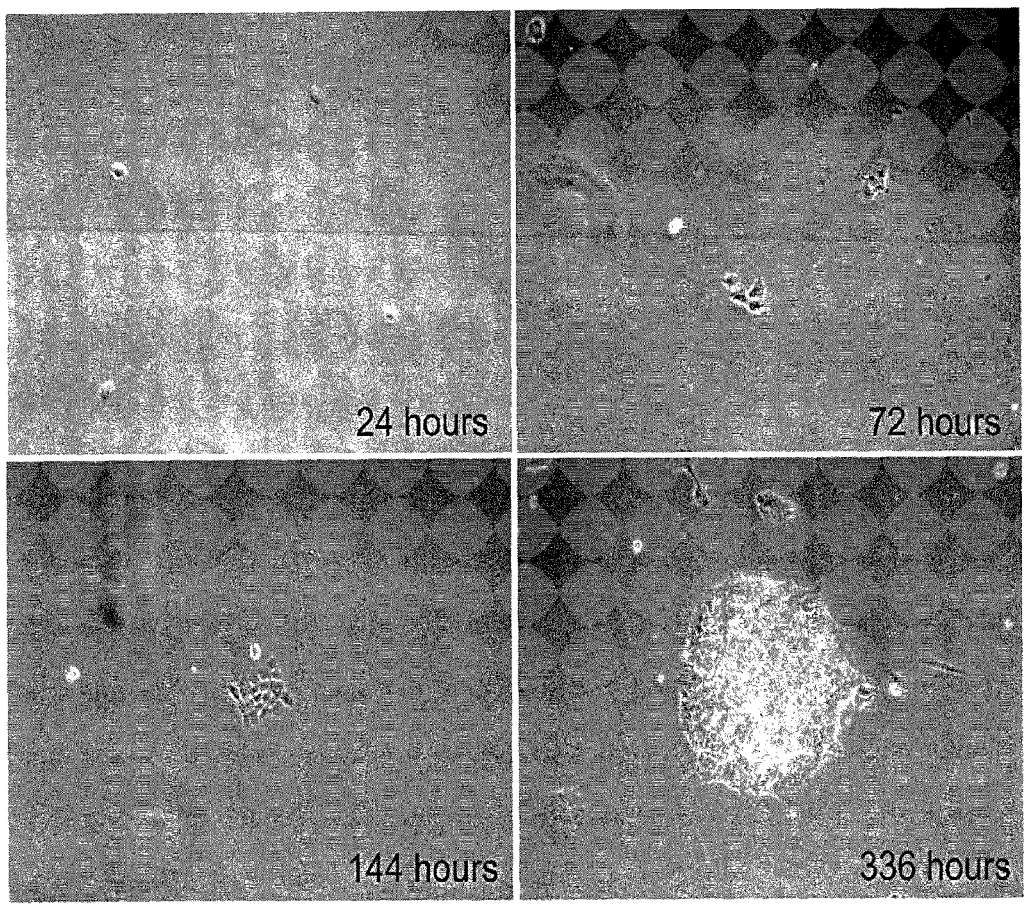
FIG. 3. Clonal propagation of Isl1+ multipotent progenitors (IMPs). Bright-field images of Accutase™ passaged IMP cells at 24-336 hours grown in BIO (2 μM) and BMP4 (100 ng/ml), with methylcellulose (0.9% final concentration) for the first 72 hours at 10× magnification.

This invention further encompasses a method for the clonal propagation of mesoderm (Isl1+ multipotent progenitor, IMP) cells under self-renewing conditions containing a GSK inhibitor and BMP comprising (a) mesoderm (Isl11+ multipotent progenitor) cells, (b) grown in methylcellulose (0.9% final concentration, purchased from Stem Cell Technologies) and self-renewal media for 1-5 days, (c) grown further in self-renewal media 3-20 days to form a single colony. The single colony may be collected, expanded, and differentiated further (FIG. 3). Refer to example 3 of PCT/US2008/001222 (WO2008/094597) for information relating to the generation of IMP cells from hESCs.

The ability to passage and amplify IMPs at clonal density allows for the potency of these cells to be rigorously tested but also allows these cells to be used for high-density/high-throughput screening assays. For example, since Isl1+ cells are resident in the adult heart, it would be of importance to identify small molecules that impact on IMP cell proliferation/amplification and differentiation into functional cell types. IMP cells represent a model for identifying drugs/compounds that could be used to control the behavior of Isl1+ cells in the heart. An anticipated outcome would be that this could stimulate Isl1+ cells to participate in cardiac repair/regeneration.

Method for Generating Clonal IMP (Isl1+ Multipotent Progenitor) Cell Lines

This example describes a procedure for the generation of clonal IMP cell lines (ie. cell lines derived from a single cell) and for their low density plating, suitable for high-throughput drug screens. IMP cells can be maintained (self-renewed) in defined media with the addition of a GSK inhibitor (for example, BIO at 2 μM) and BMP4 (for example, 100 ng/ml) and passaged by Accutase™ (FIG. 3). These cells can be plated at "low density" (10-500, preferably 20-200 cells/mm$^2$) in a biologically compatible thickener, preferably a cellulosic thickener, preferably methylcellulose (0.9% final concentration) for 3 days on Matrigel™ coated plates. After 3 days, media is replaced daily. After 14 days, individual colonies may be isolated and subcultured to generate stable, clonal cell lines. Alternatively, clonally amplified IMP cells can be passaged as clumps using enzymes such as collagenase.

3. Methods for Generation of Endothelial, Smooth Muscle and Cardiomyocyte Cells from Self-Renewed Isl1+ Multipotent Progenitors (IMPs)

a) Generation of Cardiomyocytes from Self-Renewed IMP's

This refers to methods for the generation of cardiomyocytes from self-renewing IMP cells (see above and also PCT/US2008/001222, WO2008/094597). In principle, these cells could be generated from Isl1+ cells derived directly from hESCs.

Several approaches for the generation of cardiomyocytes are described below.

Self-renewed IMP's were split and seeded at 25-250×10$^3$ cells/cm$^2$ and grown in defined media minus Activin A and +/−IGF, in the presence of either i) BMP (10 ng/ml)
ii) BMP (10 ng/ml)+DKK1 (150 ng/ml)
iii) BMP (10 ng/ml)+DKK1 (150 ng/ml)+VEGF (10 ng/ml) (FIG. 4)
iv) DKK1 (150 ng/ml)+VEGF (10 ng/ml)

Figure 4:
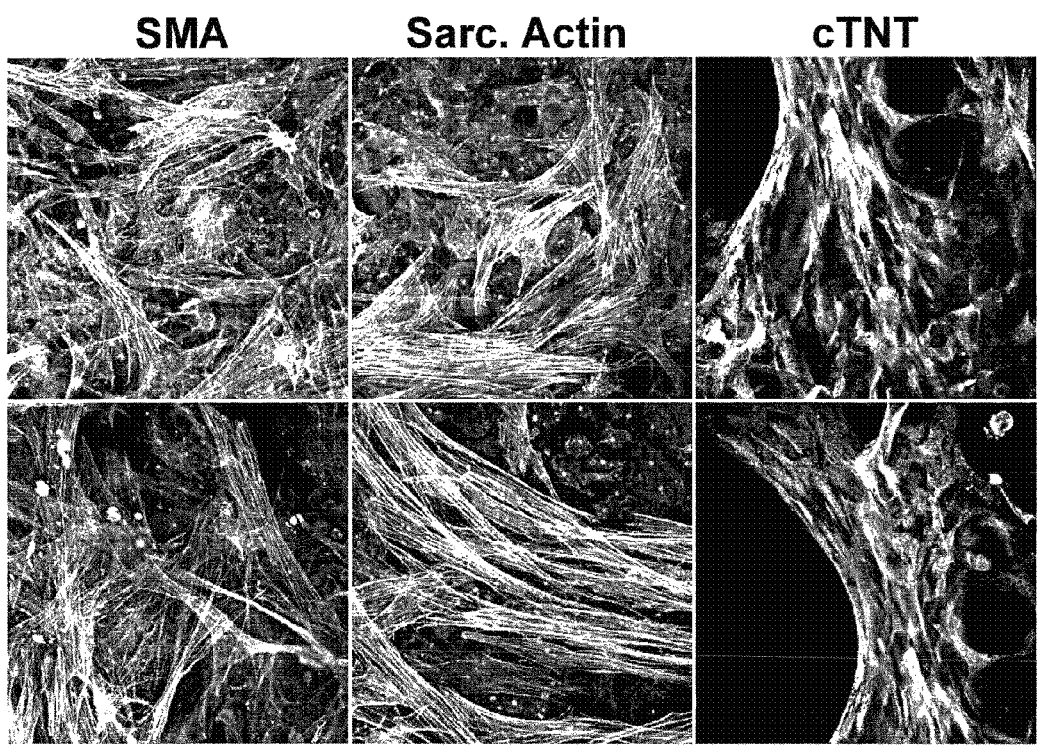
FIG. 4: Generation of cardiomyocytes from self-renewed IMP's (originally derived from WA09 hESCs). Passage 5 IMP's were grown in defined media minus Activin A, IGF and with the addition of VEGF (10 ng/ml) and DKK1 (150 ng/ml) for 14 days. The cells were fixed in 4% paraformaldehyde and immunostained for smooth muscle actin (SMA), sarcomeric actin (Sarc. Actin) and cardiac troponin T (cTNT). Confocal images taken at 40× magnification.

The cells were grown for a further 14 days in these media. The resultant culture contained 10-30% cardiomyocytes as defined by expression of cTNT, SM-actin and sarcomeric actin (FIG. 4).

As an alternate strategy, Isl1+ IMP cells can be converted to cardiomyocytes by treatment with:

v) B27 supplement (1×; Invitrogen) in RPMI media

In addition to the above (i-v) individual conditions can be supplemented with all-trans retinoic acid (0.1-5 μM) to enhance cardiomyocyte differentiation.

b) Generation of Endothelial Cells from Self-Renewing IMPs

This refers to methods for the generation of endothelial cells from self-renewing IMP cells. In principle, these cells could be generated from Isl1+ cells derived directly from hESCs.

Several approaches for the generation of endothelial cells are described below.

Self-renewed IMP's are split and seeded at 25-250×10$^3$ cells/cm$^2$ and grown in defined media minus Activin A and +/−IGF, in the presence of either v) BMP (10 ng/ml)
vi) BMP (10 ng/ml)+DKK1 (150 ng/ml)

vii) BMP (10 ng/ml)+DKK1 (150 ng/ml)+VEGF (10 ng/ml)
viii) DKK1 (150 ng/ml)+VEGF (10 ng/ml)

The cells are grown for a further 14 days in these media.

c) Generation of Smooth Muscle Cells from Self-Renewing IMPs

Self-renewing IMPs can be grown in defined media in the presence of Wnt3a (25 ng/ml) and BMP4 (100 ng/ml) for 21 days.

4. Formation of Endothelial Cells, Smooth Muscle and Cardiomyocytes from hESCs Through an IMP Progenitor Intermediate.

(i) Generation of Smooth Muscle Cell from IMPs.

hESCs were grown in defined media in the presence of Wnt3a (25 ng/ml) and BMP4 (100 ng/ml) for 6 days. The cells are split at 1:4-1:6 into the same media for a further 4 days. The cells are fixed and stained for smooth muscle markers smooth muscle actin, calponin, caldesmin and SM-MHC. The majority of the cells did stain for these smooth muscle markers.

(ii) Generation of Cardiomyocytes and Endothelial Cells from IMPs.

Figure 21:
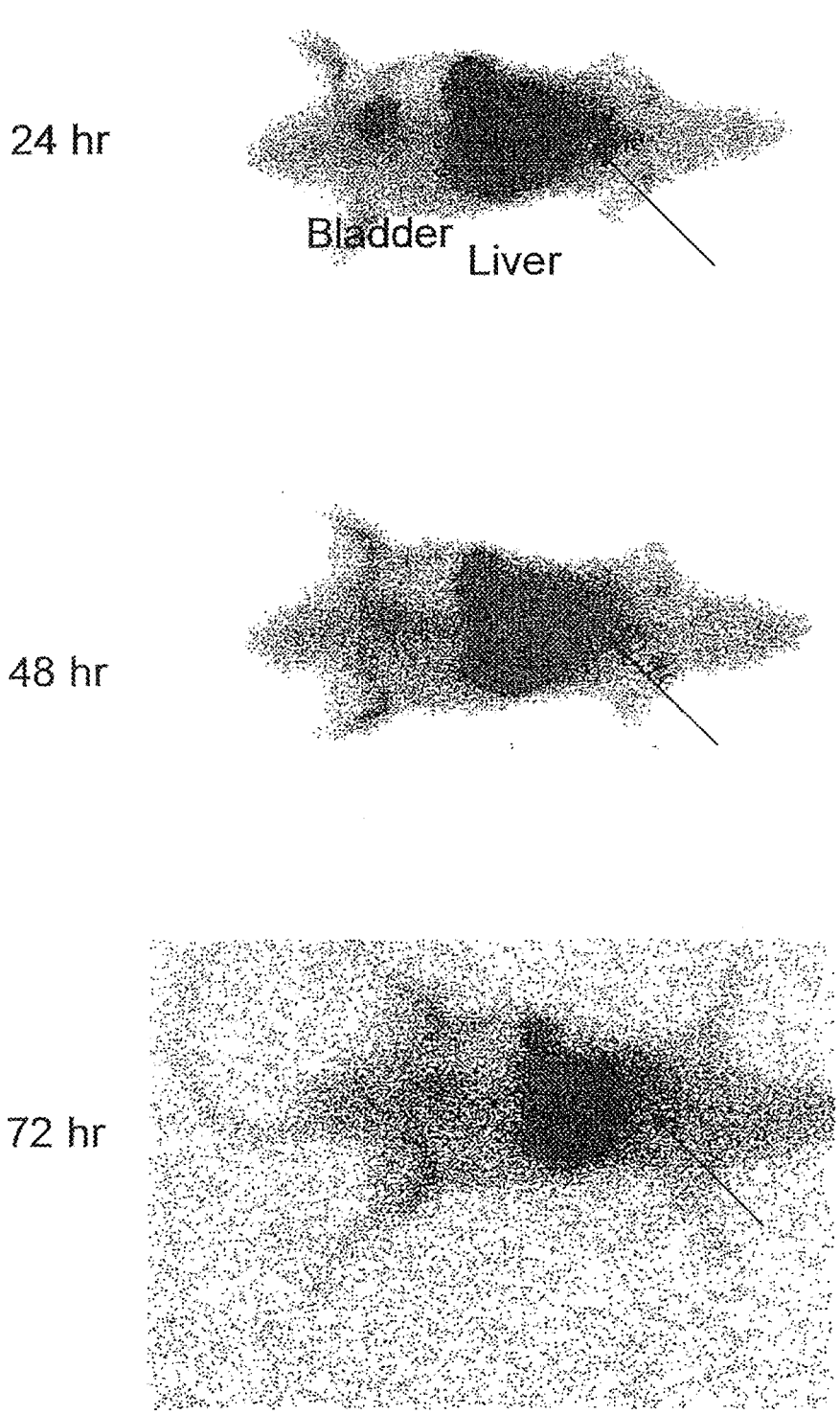
FIG. 21. 'Homing' of [$^{111}$In]oxime-labeled cells to the ischemic heart, bone and liver-lungs. C56Cs were labeled with [$^{111}$In]oxime for 5 minutes, washed with 10% rat serum to remove unbound radioactive label (Caveliers et al., 2007 Q J Nucl Med Mol 51: 61-66), then injected (~2-4×10$^6$ cells in 0.1 ml saline) into the tail vein of Sprague Dawley rats with a cardiac ischemia resulting from a surgically ligated left anterior descending coronary artery. Animals were then subject to 'live' nuclear imaging with a gamma camera at 24, 48 and 72 hours post-infusion. The labeled cardiac region is indicated by arrows. Regions of other accumulation are indicated. By 72 hours the signal decreases due to radioactive decay and clearance. Whole body planar images are shown.

IMPs were made via three different treatments. Treatment one; hESCs were grown in defined media with Activin A (100 ng/ml) for the first 24 hrs, Wnt3a (25 ng/ml) for Day 1-4 and BMP4 (100 ng/ml) for Day 2-6. Treatment two; hESCs (BG02) were grown in defined media minus IGF-I, Heregulin and FGF2 with Wnt3a (25 ng/ml) for days 1-2 and BMP4 (100 ng/ml) for days 2-6. Treatment 3; hESCs were grown in defined media with Activin A (100 ng/ml) for the first 24 hrs, Wnt3a (25 ng/ml) for Day 1-2 and BMP4 (10 ng/ml) for Day 2-6. At the end of day 6 the cells were put into defined media for a further 14 days. The cells were collected and Q-PCR analysis showed treatment 2 produced endothelial cell markers (CD31/Pecam1 and CDH5/VE-cadherin) and treatment 3 cardiomyocyte markers (ACTC1/Cardiac Alpha Actin and cTNT) (FIG. 21). These results show that IMP cells can differentiate into cardiomyocytes and endothelial cells.

a) Generation of Endothelial Cells from IMP's.

hESCs were grown in defined media in the presence of Wnt3a (25 ng/ml) and BMP4 (100 ng/ml) for 4-6 days. The cells were split at $25\text{-}250\times10^3$ cells/cm$^2$ and grown in defined media minus Activin A and +/−IGF, in the presence of either ix) BMP (10 ng/ml)
x) BMP (10 ng/ml)+DKK1 (150 ng/ml) (FIG. 5)
xi) BMP (10 ng/ml)+DKK1 (150 ng/ml)+VEGF (10 ng/ml)
xii) DKK1 (150 ng/ml)+VEGF (10 ng/ml)

Figure 5:
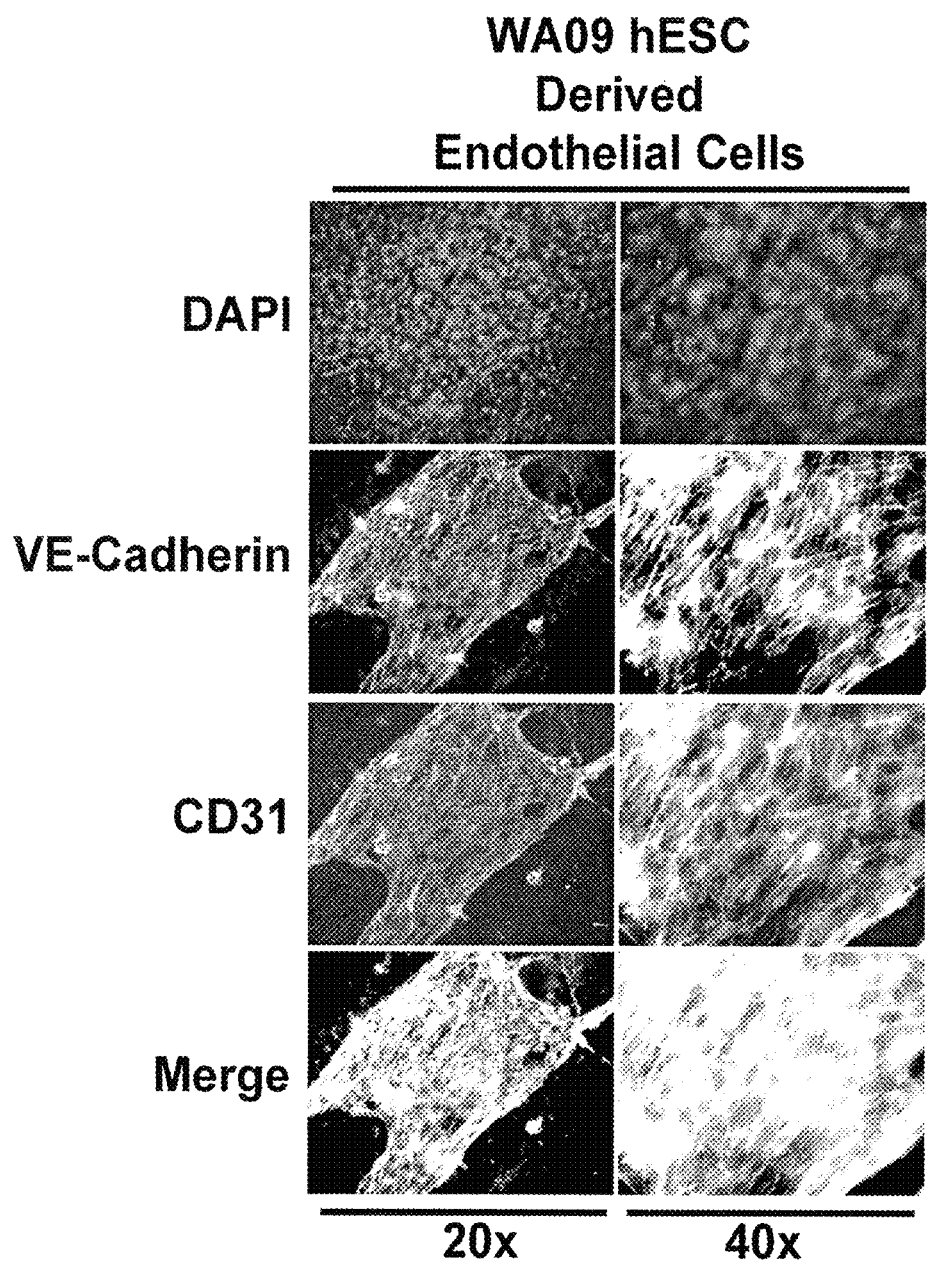
FIG. 5: Generation of endothelial cells from (WA09-derived) IMP's following treatment with BMP4 (10 ng/ml) and DKK1 (150 ng/ml) in defined media minus Activin A and IGF. Cells were fixed in 4% paraformaldehyde and immunostained for VE-Cadherin and CD31. Dapi was used as a nuclear stain. Merge pictures of Dapi/VE-cadherin/CD31 are shown. The fluorescent images were taken at 20 and 40× magnification.

The cells were grown for a further 14 days in these media. 20-40% of the resultant culture was of endothelial origin (FIG. 5).

Figure 6B:
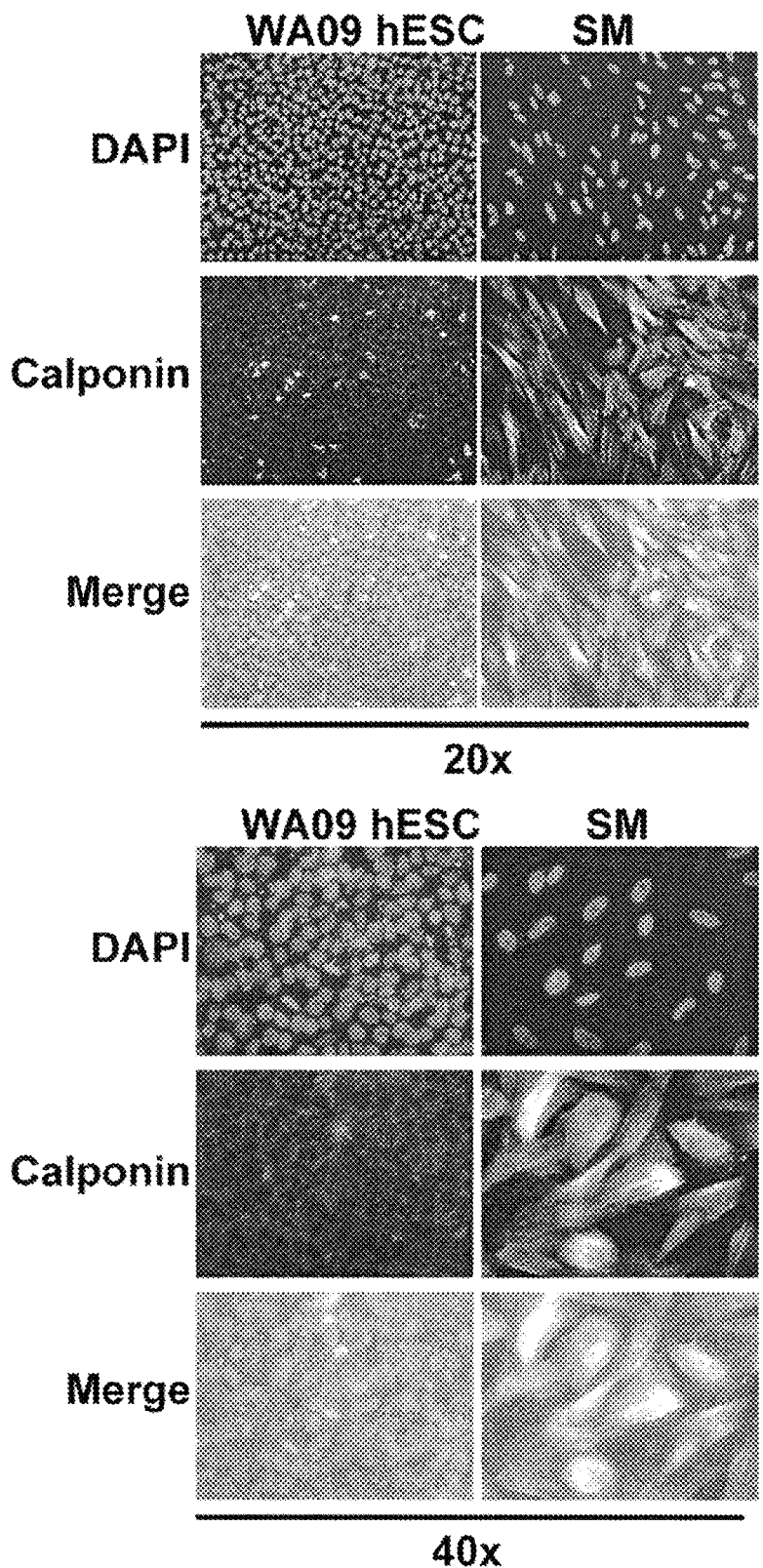

Alternatively, rather than splitting the initial IMP cultures, they were maintained and treated as described in (ix-xii) without passaging.

b) Generation of Smooth Muscle Cells from IMP's.

hESCs were grown in defined media in the presence of Wnt3a (25 ng/ml) and BMP4 (100 ng/ml) for 21 days. The cells were split 1:4-1:8 and grown for a further 24 hours in the same media. The resultant culture was >90% Smooth Muscle (FIG. 6A-C).

c) Generation of Cardiomyocytes from Self-Renewed IMP's

This refers to methods for the generation of cardiomyocytes from IMP cells generated directly from hESCs (see also PCT/US2008/001222, WO2008/094597).

Several approaches for the generation of cardiomyocytes are described below.

IMP's are split and seeded at $25\text{-}250\times10^3$ cells/cm$^2$ and grown in defined media minus Activin A and +/−IGF, in the presence of either
i) BMP (10 ng/ml)
ii) BMP (10 ng/ml)+DKK1 (150 ng/ml)
iii) BMP (10 ng/ml)+DKK1 (150 ng/ml)+VEGF (10 ng/ml)
iv) DKK1 (150 ng/ml)+VEGF (10 ng/ml)

The cells are grown for a further 14 days in these media. The resultant culture contains 10-30% or more cardiomyocytes as defined by expression of cTNT, SM-actin and sarcomeric actin.

As an alternate strategy, Isl1+ IMP cells can be converted to cardiomyocytes by treatment with:
v) B27 supplement (1×; Invitrogen) in RPMI media In addition to the above (i-v) individual conditions can be supplemented with all-trans retinoic acid (0.1-5 μM) to enhance cardiomyocyte differentiation.

5. Further Definition of IMP Cells by Cell Surface Marker Analysis

Figure 7:
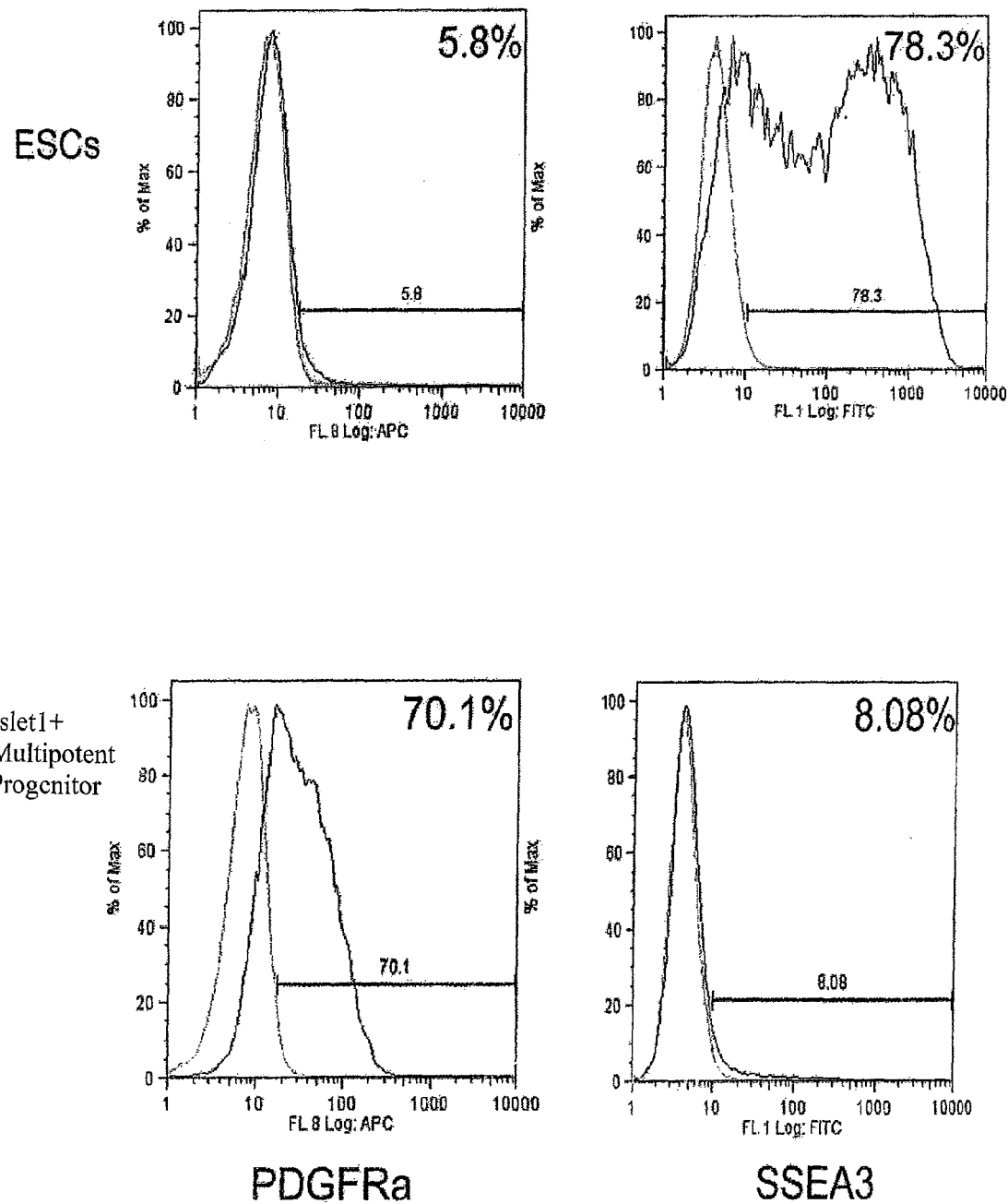
FIG. 7: WA09 hESCs were differentiated to Islet1+ multipotent progenitor (IMP) cells in defined media with Wnt3a (25 ng/ml) and BMP4 (100 ng/ml) over 4 days. hESCs and IMP cells stained with antibodies for SSEA3 or PDGFRα and subject to flow cytometry analysis. The % of cells positive for either SSEA3 or PDGFRα at each stage are indicated.

Following the observation in our laboratory that increases in PDGFRα transcripts are associated with IMP formation, we now show that this is also associated with detection of PDGFRα on the cell surface by flow cytometry (FIG. 7). As hESCs differentiate towards IMP cells in the presence of Wnt3a and BMP4 they down-regulate the hESC marker SSEA3 and upregulate PDGFRα.

6. Differentiation of MMCs into C-Kit+ Cardiovascular Progenitors

Figure 15:
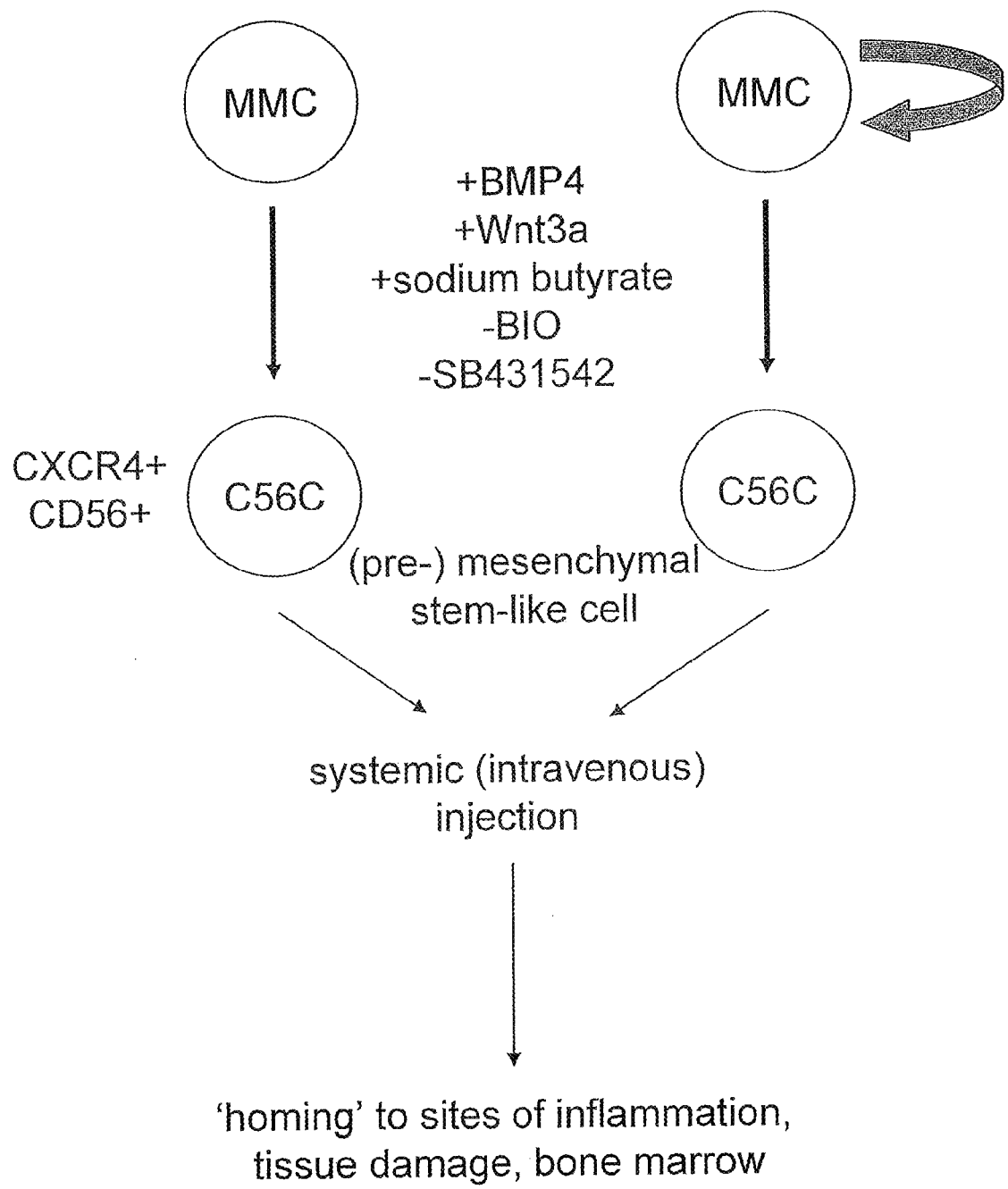
FIG. 15. A strategy to use C56Cs as part of a cell therapy strategy where they are administered systemically by intravenously injection, for example. Cells then 'home' to sites of tissue damage, inflammation and bone marrow (for example) where they would then stimulate tissue repair/regeneration. This does not preclude the direct application of these cells to sites of tissue damage/inflammation.

MMCs are a self-renewing, multipotent population derived from hESCs that are mesoderm-derived progenitors with potential for differentiation into a wide range of cell types, in particular, cardiovascular lineages such as cardiac myocytes, smooth muscle and endothelial cells (PCT/US2008/001222, published as WO2008/094597, which is incorporated by reference herein). MMCs can be frozen, recovered and then grown over extended periods of time while retaining their multipotent differentiation potential. Here, the differentiation of MMCs into a c-kit+ CXCR4+ cell type is described (see FIG. 8). This cell type has utility for, but is not restricted to, repair of damaged cardiac and cardiovascular tissue. Cells could be used as a cell therapeutic by direct injection into the site of damaged tissue or by systemic administration where the cells can 'home' to sites of damaged tissue. FIG. 15. The repair function of these cells is not restricted to cardiovascular applications and could be used for the control of inflammatory diseases and repair of other damages tissues/organs due to the multipotent nature of these cells.

Culture of Human Embryonic Stem Cells (as Described in WO2008/094597)

Methods for Growing hESC.

Methods:

hESCs expressing markers such as the POU domain transcription factor Oct4 are preferably grown in mouse embryonic feeder conditioned medium MEF-CM or defined media using Matrigel as a growth matrix (for example). Cells are typically plated at $1\text{-}1.5\times10^6$ per 60 mm dish. Cells are passaged every 4-5 days at a split of ~1:4 to 1:10.

(i) Mouse Embryo Fibroblast Conditioned Media (MEF-CM)

hESCs can be grown on Matrigel (BD Biosciences; 1:20-1:200 dilution is preferred) or other matrices that support hESC maintenance in mouse embryo fibroblast conditioned media (MEF-CM) in the presence of Fgf2 (McLean et al. Stem Cells 25: 29). Cells can be passaged by a variety of methods using enzymatic (trypsin, Accutase™, collagenase), manual passage (mechanical) and non-enzymatic methods. Cells are plated at a density of 1.5×10⁶ per 60 mm dish and passaged every 4-5 days at a split of 1:4-1:10.

(ii) Defined Conditions (DC)

(a) Defined media for routine culture of hESCs is purchased from Invitrogen as StemPro® (Wang et al., Blood 110: 4111). The media is used according to the manufacturer's recommendations except that Accutase™ is used for passaging cells as single cell suspensions. The following formulation is capable of maintaining hESCs in a pluripotent state. The following defined, serum free media conditions work well but are not restricted to this specific formulation and involves feeder-free culture: DMEM:F12 (Gibco), 2% BSA (Seriologicals, #82-047-3), 1× Pen/Strep (Gibco), 1× non-essential amino acids (Gibco), 1× Trace Elements A, B and C (Cellgro; #99-182-C1, #99-176-C1, #99-175-C1), 50 ug/ml Ascorbic Acid (Sigma, #A4034), 10 ug/ml Transferrin (Gibco, #11107-018), 0.1 nM beta-mercaptoethanol, 8 ng/ml Fgf2 (Sigma, #F0291), 200 ng/ml LR-IGF (JRH Biosciences, #85580), 10 ng/ml Activin A (R&D Systems, #338-AC), 10 ng/ml Heregulin beta (Peprotech; #100-03).

(b) hESCs can also be cultured in additional commercially available media formulations such as mTeSR1 (BD/Stem Cell Technologies; Ludwig et al., Nat Biotechnol. 24:185), according to the manufacturer's recommendations. Accutase™ passaging is also used in conjunction with this media.

Generation of Multipotent Migratory Cells (MMCs)
Based Upon Example 8 of PCT/US2008/001222, WO2008/094597

BG02 hESCs grown in StemPro® defined media were passaged with Accutase™ and plated onto Matrigel coated dishes (1.0×10⁶ cells per 60 mm dish) as described above, except that media was supplemented with BIO (2 μM) plus SB431542 (20 μM; Sigma). Media was replaced every day and cells were passaged every 5-6 days with Accutase™, with a 1:5-1:10 split at each passage. When cultured under these conditions, the pluripotency marker Nanog decreased during the first passage (P0) and T transcript levels increased whereas Sox17, FoxF1, CXCR4 and PDGFRalpha remained low. ~90% of cells stained +ve for T 4 days after treatment with BIO and SB431542, indicating they transitioned through a mesendoderm state at some point. During this time Nanog, Oct4 and E-cad were significantly downregulated, as indicated by immunostaining. The disappearance of E-cadherin is indicative that cells underwent an epithelial to mesenchymal transition, consistent with the differentiation into mesendoderm. Upon continued passage, T expression (as determined by Q-PCR) decreased over P1-P10 and the pluripotency marker Nanog did not reappear. This was confirmed by immunostaining where P7 cells did not express Nanog, Oct4 or E-cadherin, in contrast to hESCs. Mesoderm and endoderm markers did not increase during this time frame. The cells were continually passaged under the same conditions and they maintained robust proliferative activity for over 20 passages (using the same medium as described above containing BIO and SB431542) with maintenance of morphology. The MMCs produced were cryopreserved, using standard methods, and recovered with a plating efficiency of >10%. The growth characteristics and morphology of cryorecovered MMCs were indistinguishable from that of the precryopreserved MMCs.

Generation of Additional Self-Renewing Progenitors of Mesoderm Origin Using Combinations of GSK3 Inhibitors, Activin/Nodal Signaling Inhibitors and BMP Signaling Inhibitors (GABi Cells).

As an extension of the principles already defined in the present application as well as the previously filed PCT application (PCT/US2008/001222, WO2008/094597), which is incorporated by reference in its entirety herein, it is possible to generate self-renewing progenitors of mesodermal origin from hESCs, that can be maintained over extended periods in culture (>10 passages) and which exhibit multipotent differentiation potential. These progenitors can be derived from hESCs grown under conditions described already in this document (Example above and PCT/US2008/001222, WO2008/094597).

These progenitors can be generated by treating hESCs with GSK3 inhibitors in combination with inhibitors of Activin/Nodal signaling (such as SB431542) and/or inhibitors of BMP signaling (such as Noggin or Compound C). Due to the action of GSK3 inhibitors, hESCs differentiate through an EMT, become mesendoderm and following culture convert to a progenitor phenotype in the presence of the chemical inhibitors specified above (FIG. 11).

Additional examples of how progenitors can be generated from hESCs include:

(i) GSK3 inhibitors such as BIO (2 μM) plus inhibitors of Activin/Nodal signaling (for example, SB431542)—these are known as MMCs (as described in PCT/US2008/001222, the entire contents of which is incorporated by reference herein)

(ii) GSK3 inhibitors such as BIO plus inhibitors of BMP signaling (Noggin, Compound C for example)—prophetic example hESC cells are plated in Matrigel dishes at a density of 2.0×10⁶/60 mm dish. The differentiation media comprises DMEM/F12 (50/50), approximately 2% probumin (albumin), antibiotics (1× Pen/Strep 1×NEAA), Trace Elements A, B, C (e.g., 1× from Mediatech), Ascorbic acid (e.g. about 50 μg/ml), Transferrin (e.g. about 10 μg/ml), β-Mercaptoethanol (about 0.1 mM), bFGF (e.g. about 8 ng/ml), LR-IGF (e.g., about 200 ng/ml), Heregulin (e.g., about 10 ng/ml), BIO (e.g., about 2 μM) and Compound C (e.g., about 1 μM). Noggin can also be used in place of Compound C.

Cells were continually grown and passaged every 5-7 days with Accutase™ (Innovative Cell Technologies) at a split of 1:5. These cells can be frozen, thawed with high recovery and differentiated into multiple lineages. Cells can also be passaged with other dispersal reagents (enzymatic and non-enzymatic) as single cell suspensions or as clumps.

(iii) GSK3 inhibitors such as BIO plus BMP signaling inhibitors plus inhibitors of Activin/Nodal signaling (prophetic example)

hESC cells are plated in Matrigel dishes at a density of 2.0×10⁶/60 mm dish. The differentiation media comprises DMEM/F12 (50/50), approximately 2% probumin (albumin), antibiotics (1× Pen/Strep 1×NEAA), Trace Elements A, B, C (e.g., 1× from Mediatech), Ascorbic acid (e.g. about 50 μg/ml), Transferrin (e.g. about 10 μg/ml), β-Mercaptoethanol (about 0.1 mM), bFGF (e.g. about 8 ng/ml), LR-IGF (e.g., about 200 ng/ml), Heregulin (e.g., about 10 ng/ml), BIO (e.g., about 2 μM), Compound C (for example; about 1 μM) and SB431542 (for example).

Cells were continually grown and passaged every 5-7 days with Accutase™ (Innovative Cell Technologies) at a split of 1:5. These cells can be frozen, thawed with high recovery and differentiated into multiple lineages. Cells can also be passaged with other dispersal reagents (enzymatic and non-enzymatic) as single cell suspensions or as clumps.

Example (i) has been described extensively in this document and the resulting multipotent lineage is known as multipotent migratory cells (MMCs).

The progenitor described in Example (ii) can in principle be generated from several hESC lines including BG02, WA09, WA07 and can be maintained as a self-renewing population for over 10 passages.

The progenitor described in Example (iii) in principle, can be generated from several hESC lines including BG02, WA09, WA07 and can be maintained as a self-renewing population for over 10 passages.

Differentiation of MMCs to a c-Kit+ CXCR4+ Progenitor Population (C56Cs)

To further differentiate MMCs, MMC cells, obtained according to the description above, are plated in Matrigel dishes at a density of 2.5×10⁶/60 mm dish. The differentiation involves removal of GSK3 inhibitors (ie. BIO) and SB431542 that are used to maintain MMCs. Differentiation media comprises DMEM/F12 (50/50), approximately 2% probumin (albumin), antibiotics (1× Pen/Strep 1×NEAA), Trace Elements A, B, C (e.g., 1× from Mediatech), Ascorbic acid (e.g. about 50 µg/ml), Transferrin (e.g. about 10 µg/ml), β-Mercaptoethanol (about 0.1 mM), bFGF (e.g. about 8 ng/ml), LR-IGF (e.g., about 200 ng/ml), Activin A (e.g., about 10 ng/ml), Heregulin (e.g., about 10 ng/ml), BMP4 (e.g., about 100 ng/ml), Wnt3a (e.g., about 25 ng/ml) and the histone deacetylase inhibitor Sodium Butyrate (e.g., about 0.5 mM). It is important that GSK3 (ie BIO) inhibitors and SB431542 are removed for this differentiation step and that BMP4 (or other BMP such as BMP2 with similar activity) and Wnt3a (or other Wnt with similar activity) are added (along with the sodium butyrate) for a period ranging from about 1 day to 8 days or longer, 2 to 7 days, 2 to 6 days. Cells were assayed by quantitative RT-PCR (FIG. 9) and flow cytometry (FIG. 10A-C) analysis at days 2, 4 and 6.

Figure 9:
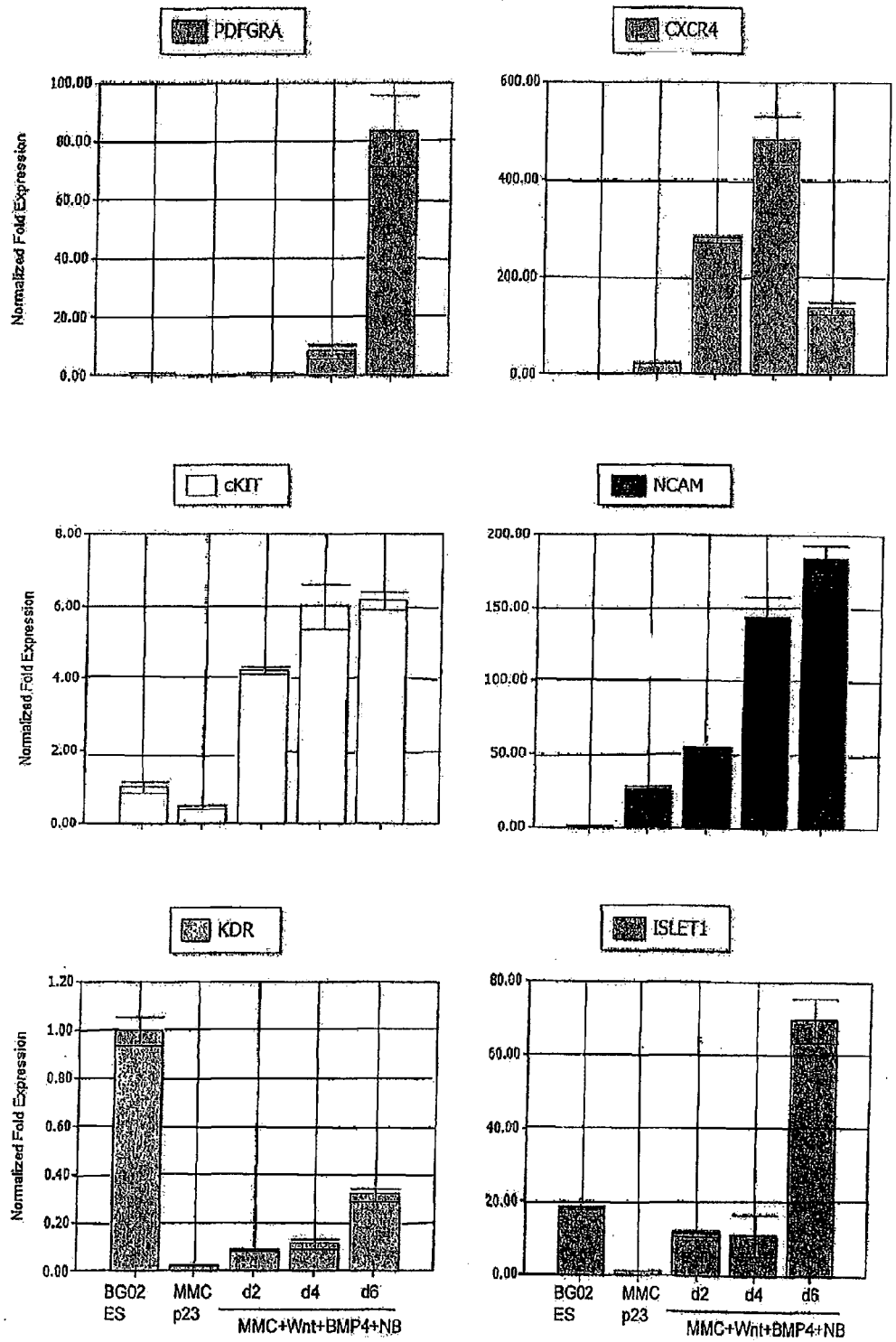
FIG. 9: Differentiation of BG02 hESC-derived MMCs under defined media conditions following addition of BMP4, Wnt3a and Sodium Butyrate (NB) over a 6 day course. Q-PCR transcript analysis of PDGFRα, CXCR4, KDR, c-KIT, CD56 (N-CAM) and Islet1 transcripts over a 6 day period is shown for BG02 ES cells, MMCs at passage 23 (MMC p23), and differentiated MMC p23 at days 2 (d2), 4 (d4) and 6 (d6).
Figure 10A:
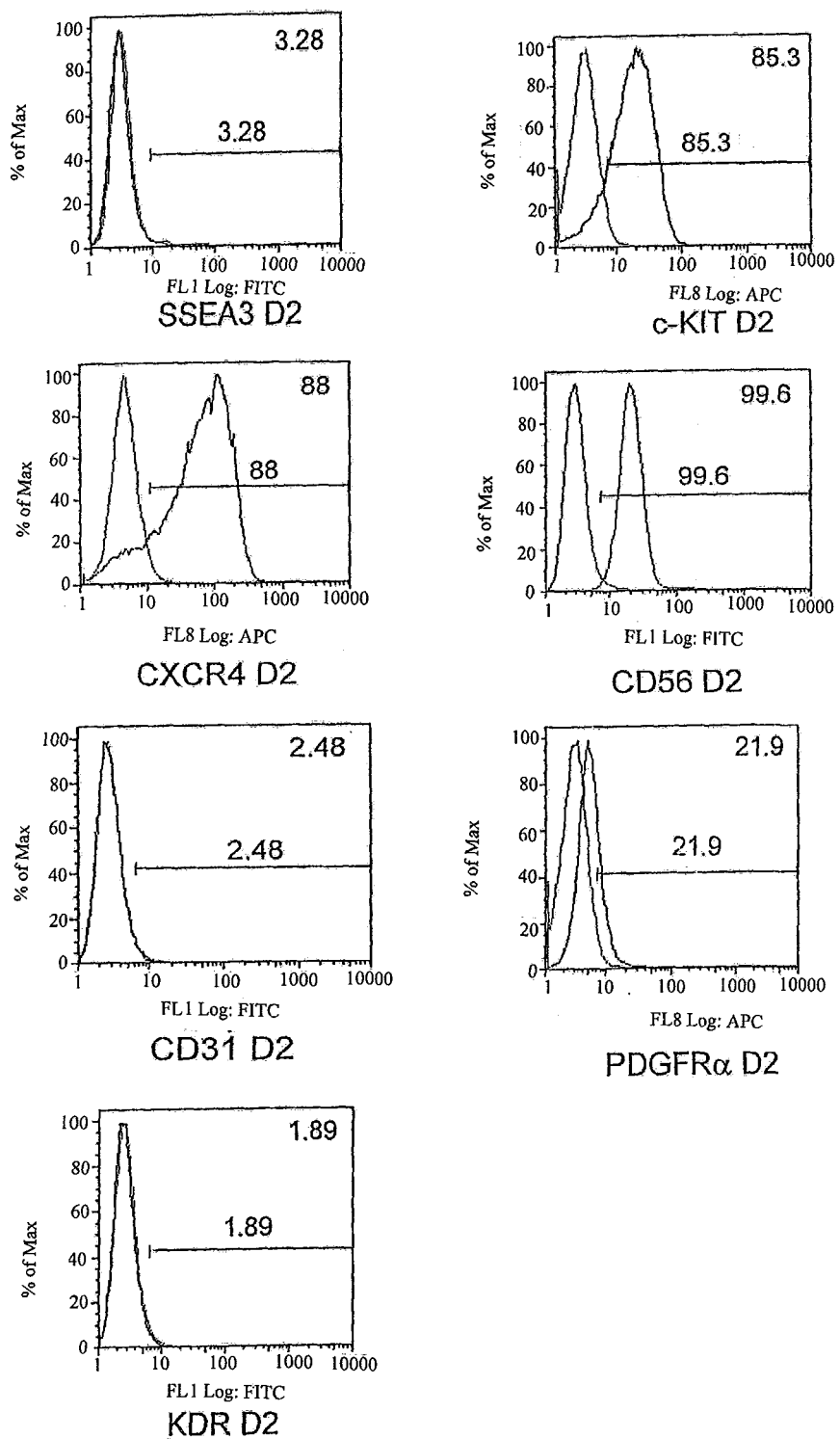
FIGS. 10A, 10B, 10C, 10D: Histogram of flow cytometry analysis of BG02-derived MMC differentiated under defined media conditions following addition of BMP4, Wnt3a and Sodium Butyrate for 2 (A), 4 (B) and 6 (C) days. Percentage of SSEA3, c-KIT, CXCR4, CD56, CD31, PDGFRα and KDR positive cells is calculated respectively to the isotype control for each antibody. (D) Bright field pictures of MMCs differentiated for 2, 4 and 6 days (c-KIT+ CXCR4+) as described for (A-C). Magnification 10×, 20×.
Figure 10B:
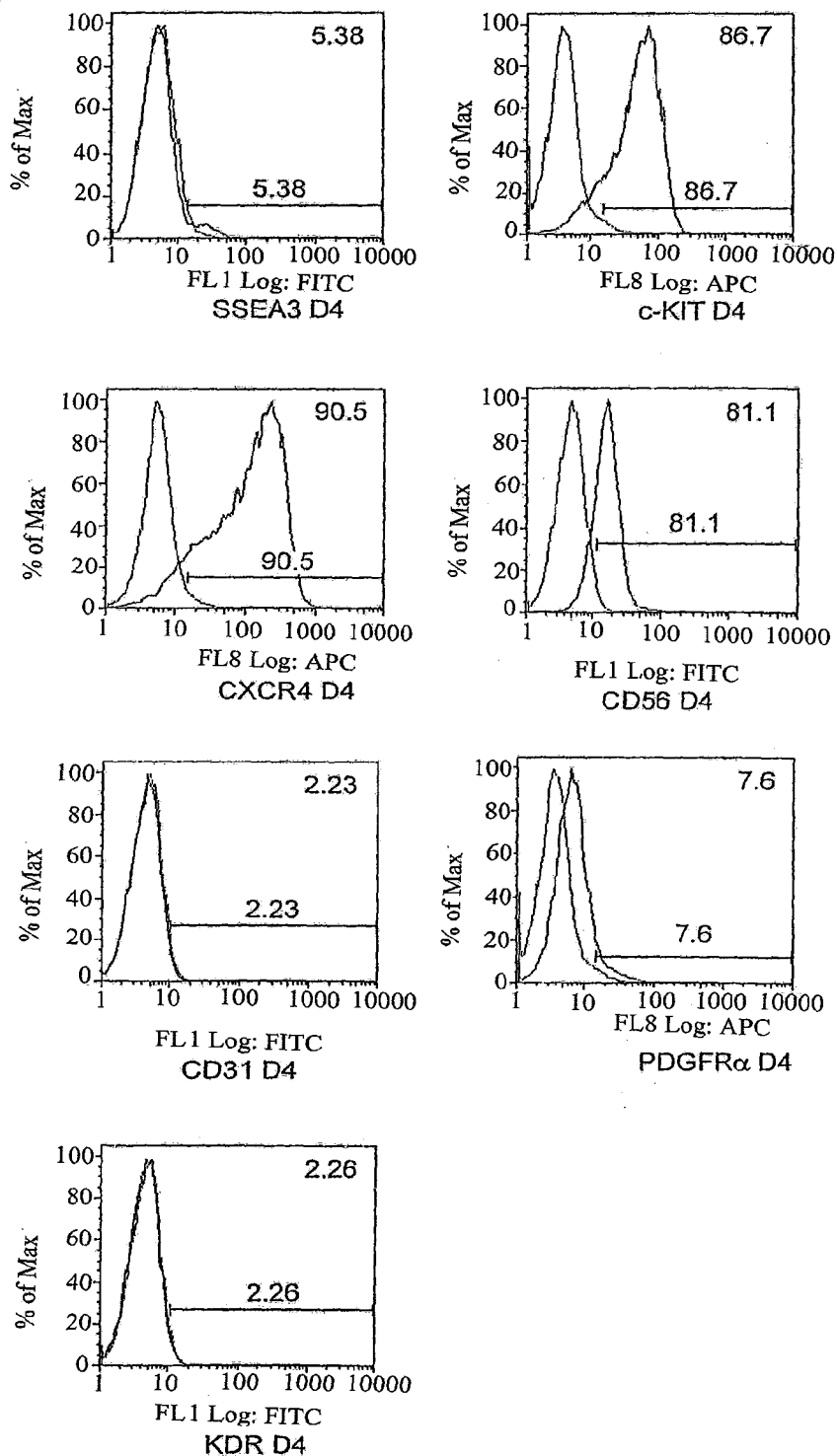
Figure 10C:
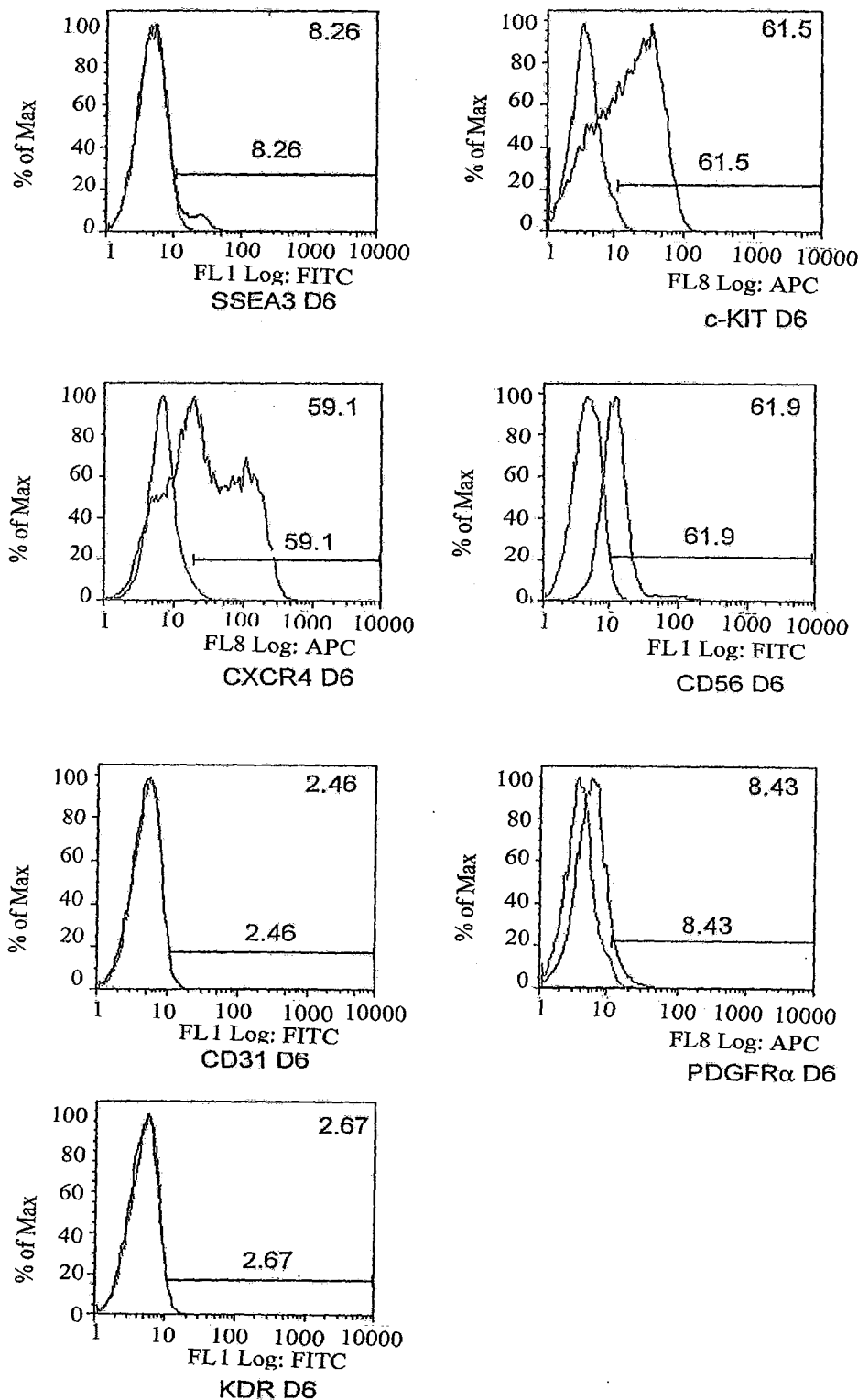
Figure 10D:
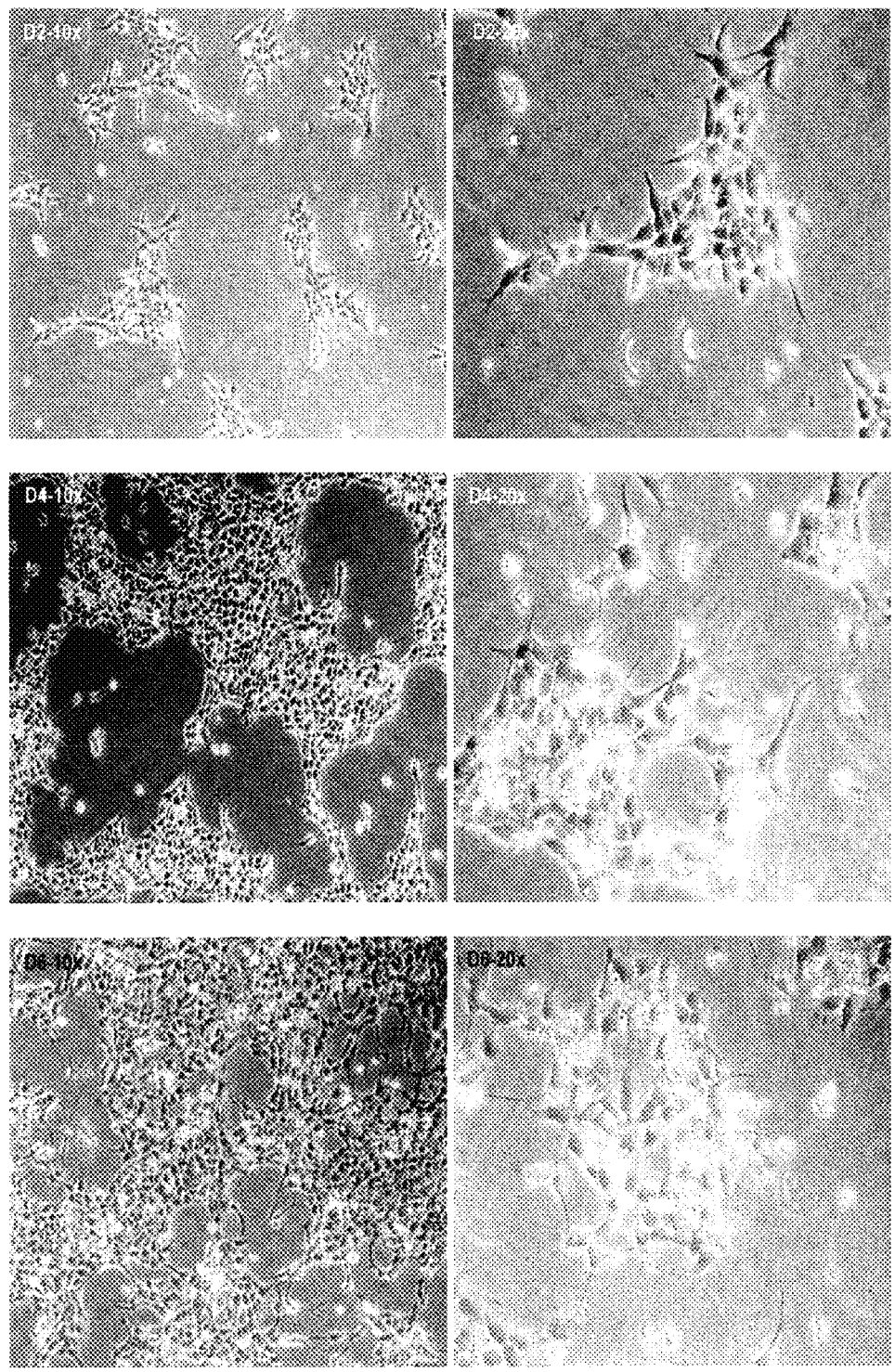

Over a 4-6 day differentiation time course, CXCR4, c-Kit, CD56 (N-CAM) were found to be elevated, as judged by quantitative real time PCR analysis of transcript levels and flow cytometry analysis (FIG. 9,10). Flow cytometry analysis showed undetectable amounts of CD31, KDR (Flk1) and SSEA3, but a slight increase of PDGFR□□ over the 4-6 day differentiation (FIG. 10). Isl1 also increased at the transcript level in these experiments (FIG. 9). Bright field pictures of c-kit+ CXCR4+ cells generated from MMCs by treatment with BMP4, Wnt3a and sodium butyrate over 2-6 days are shown in FIG. 10D.

Alternatively, C56Cs may be obtained from pluripotent stem cells by first exposing the pluripotent stem cells, especially hESCs to conditions for producing MMC's and once the MMC's are obtained, exposing the MMC's to differentiation conditions CXCR4+CD56+ Cells (C56Cs)
Methods for the Generation of C56Cs The pathway for generation of C56Cs is indicated in FIG. 14. Generation of MMCs from hESCs has been described previously. The approach to provide MMCs is applicable to any human pluripotent cell such as induced pluripotent stem cells (iPS cells) or similar human pluripotent stem cells. The general method which describes the production of hESCs to MMCs applies to pluripotent stem cells as otherwise described herein in general. To generate C56Cs, MMCs are treated for around 1 to 8 days (preferably, 3-6 days) with BMP4 (100 ng/ml), Wnt3a (25 ng/ml), sodium butyrate (0.5 mM) in base media [DMEM/F12 [50/50], approximately 2% probumin [albumin], antibiotics [1× Pen/Strep 1×NEAA], Trace Elements A, B, C [1× from Mediatech], Ascorbic acid [~50 µg/ml], Transferrin [~10 g/ml], β-Mercaptoethanol [about 0.1 mM], bFGF [e.g. about 8 ng/ml], LR-IGF [e.g., about 200 ng/ml], Activin A [e.g., about 10 ng/ml], Heregulin [e.g., about 10 ng/ml]). C56Cs are thereafter passaged. The resulting C56Cs are highly pure and may be used therapeutically without further purification.

Conceivably, MMCs could also be used for the therapeutic applications described herein, but since CXCR4 levels are generally higher in C56Cs, experiments were performed in this cell type.

Biomarkers CXCR4+ CD56+ Cells (C56Cs)

Figure 17:
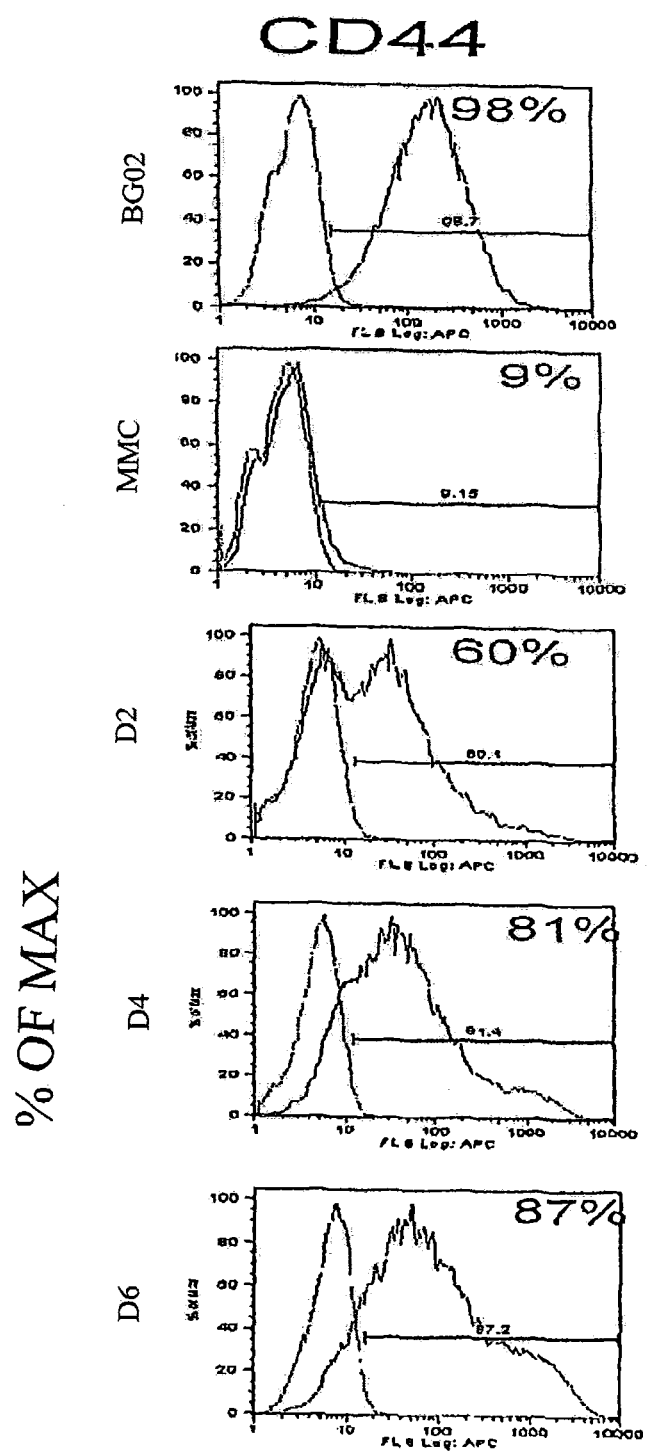
FIG. 17, 18. Flow cytometry analysis of WA09 hESCs, MMCs generated from WA09 hESCs and C56Cs generated by treatment of MMCs with BMP4, Wnt3a and sodium butyrate for 2, 4 and 6 days.
Figure 17:
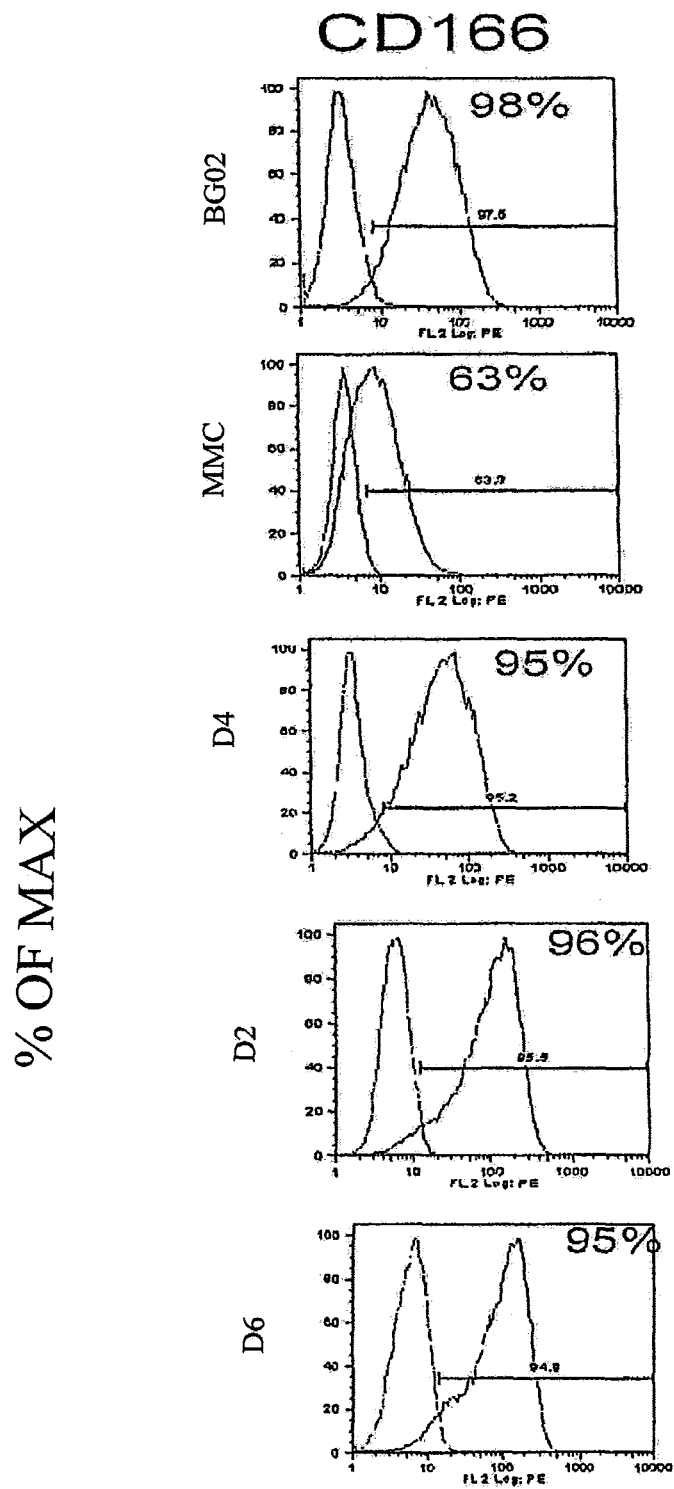
Figure 17:
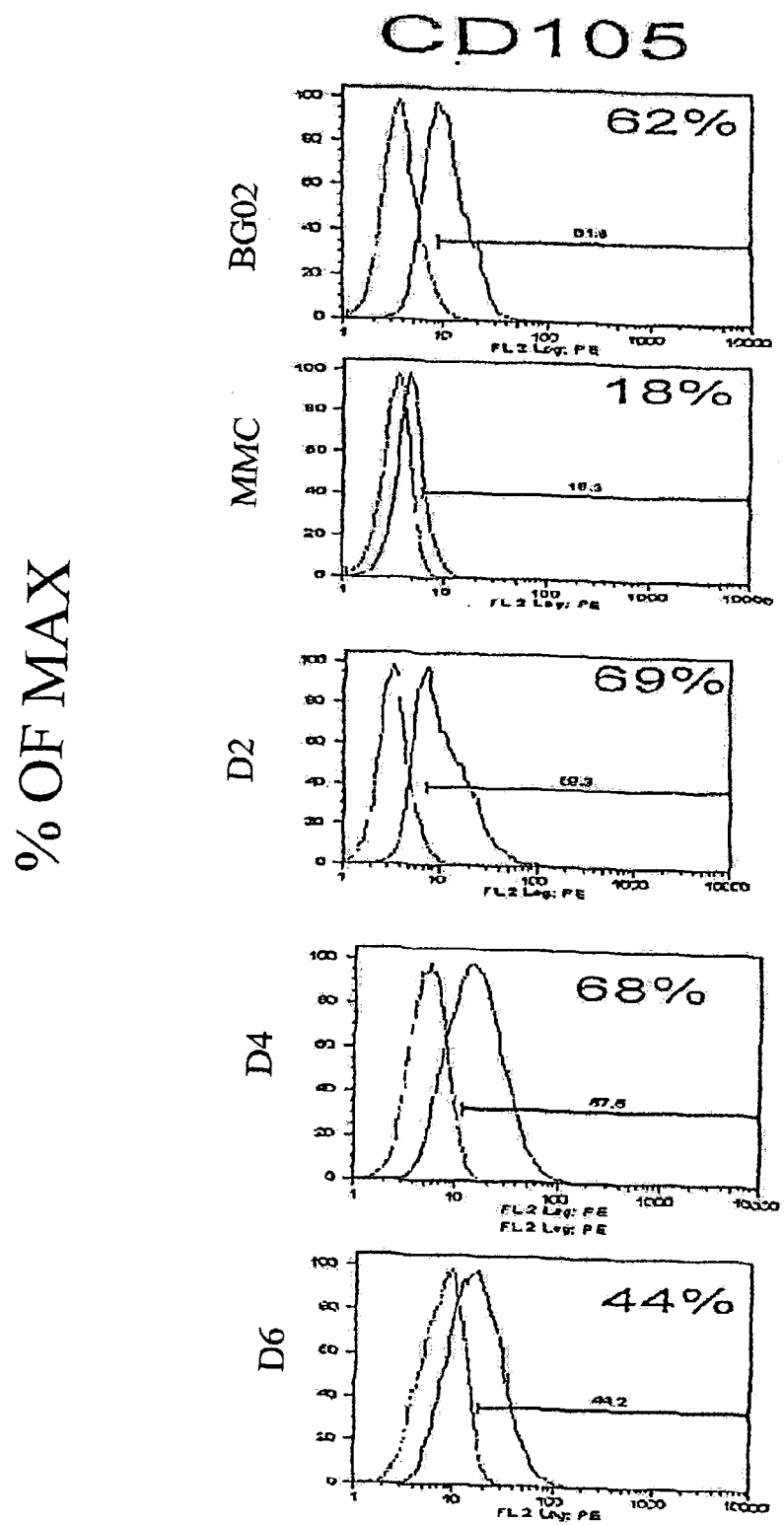
Figure 17:
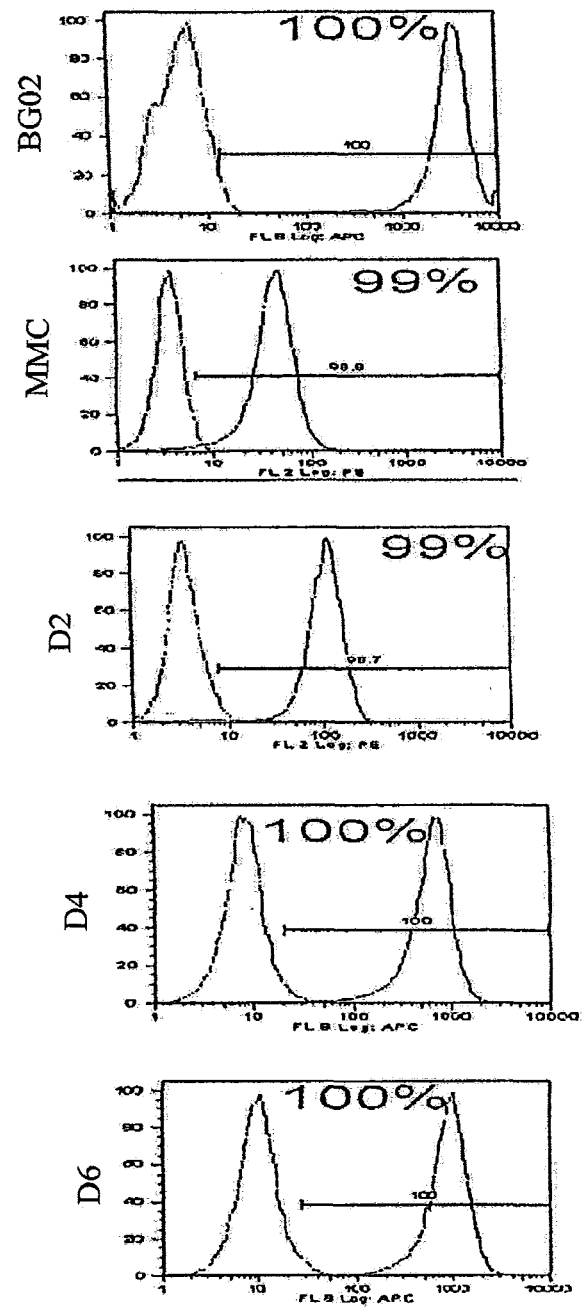
Figure 17:
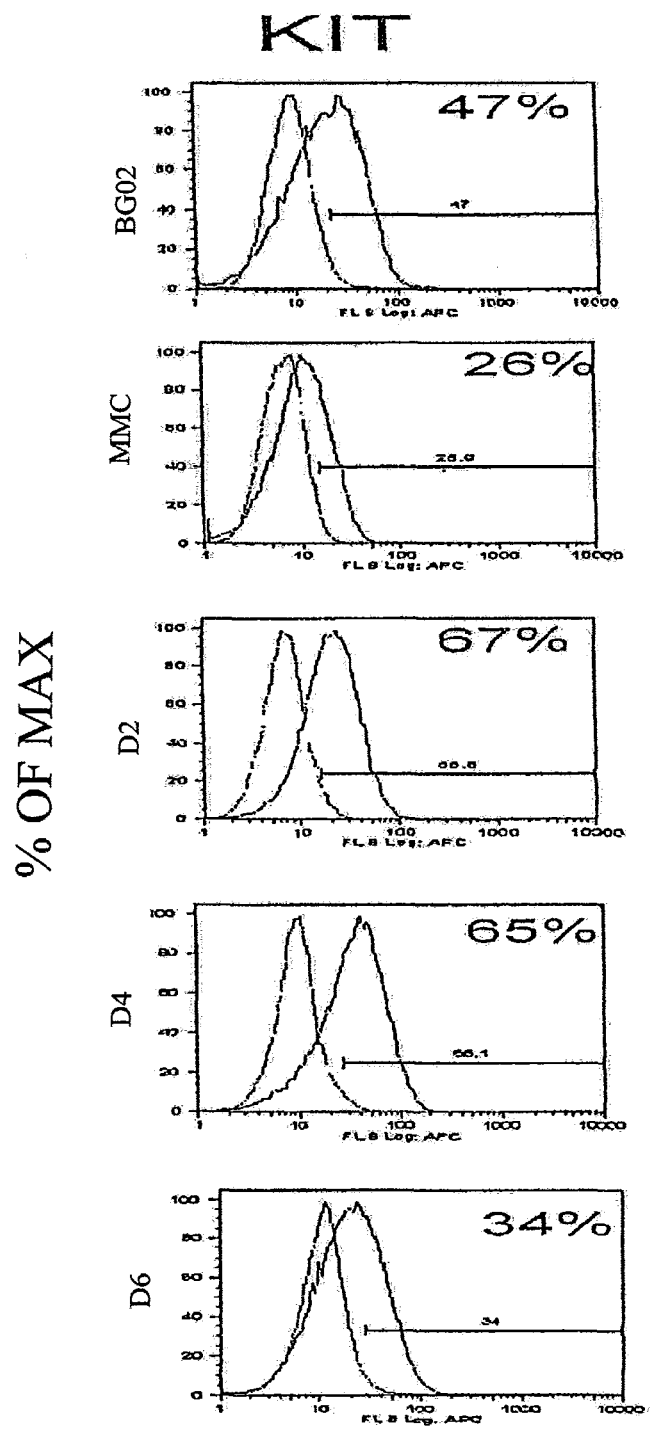
Figure 17:
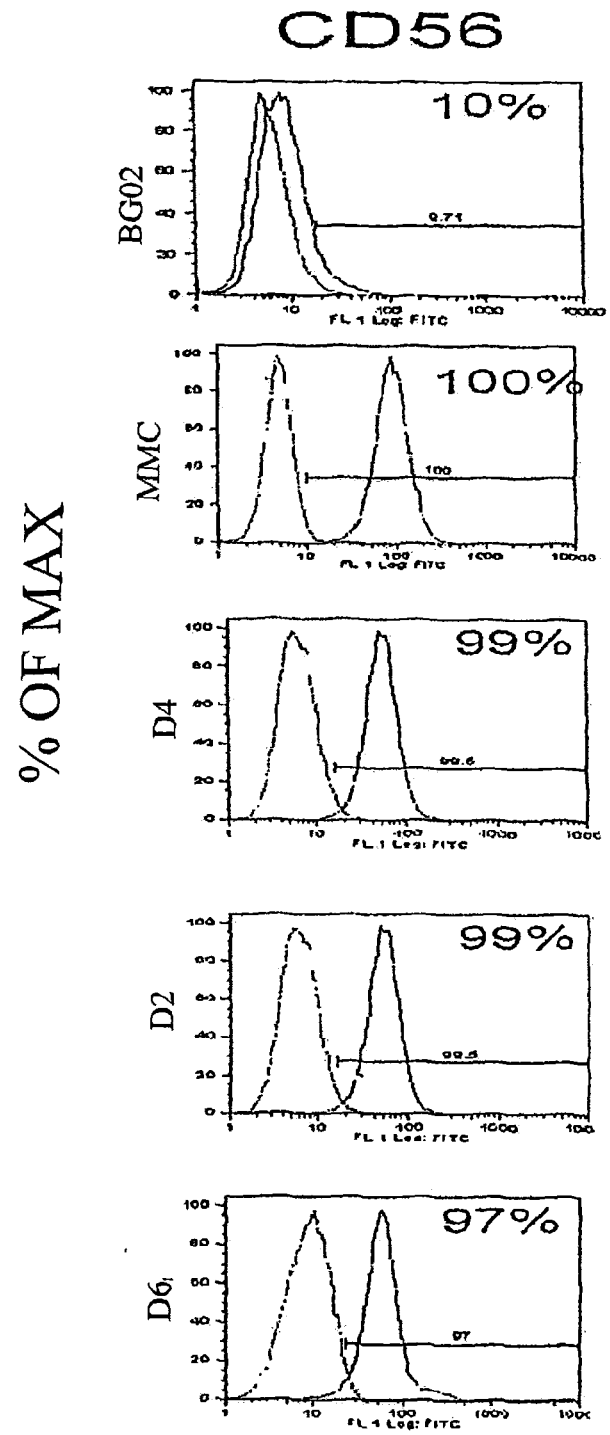
Figure 17:
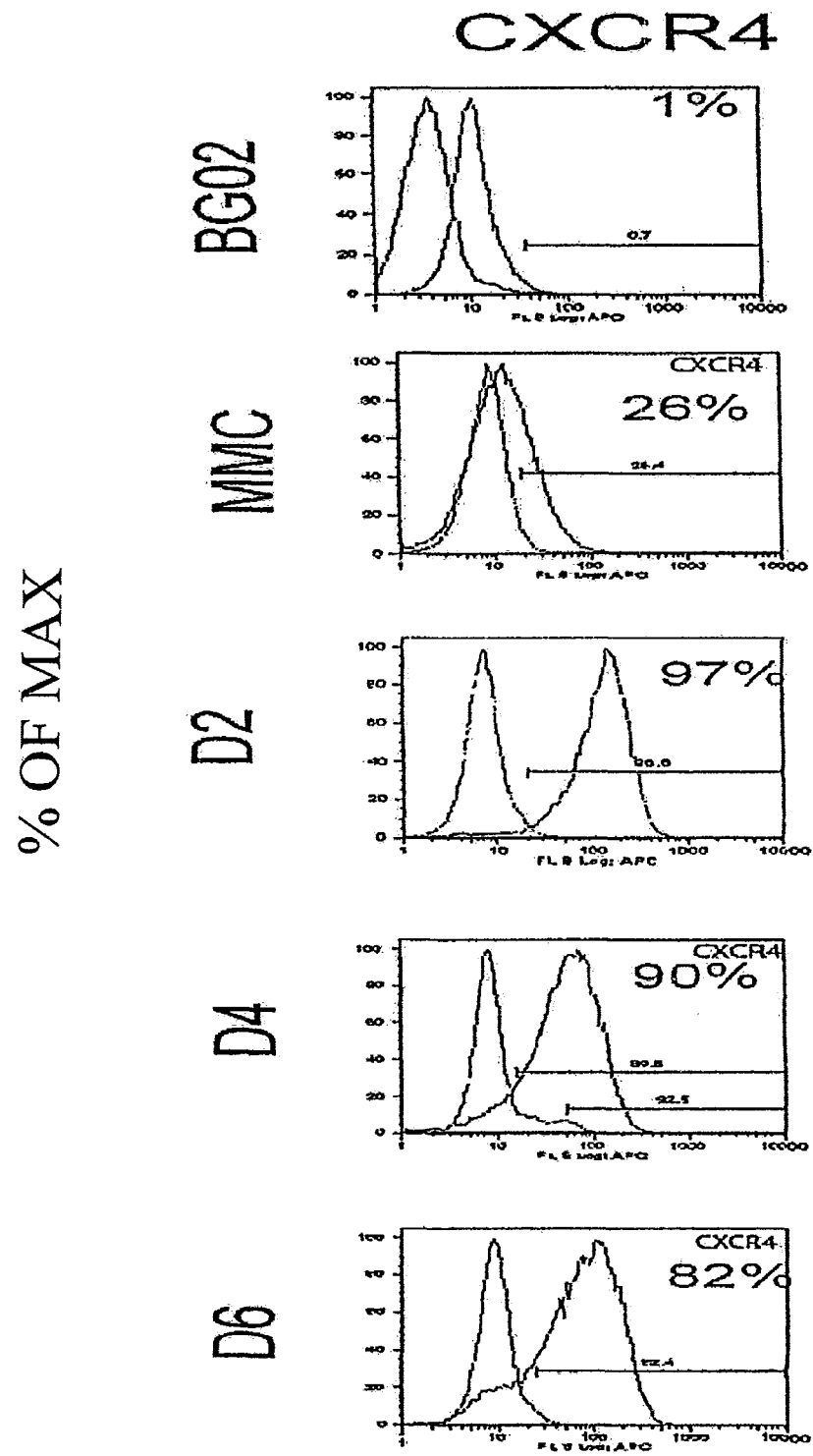
Figure 18:
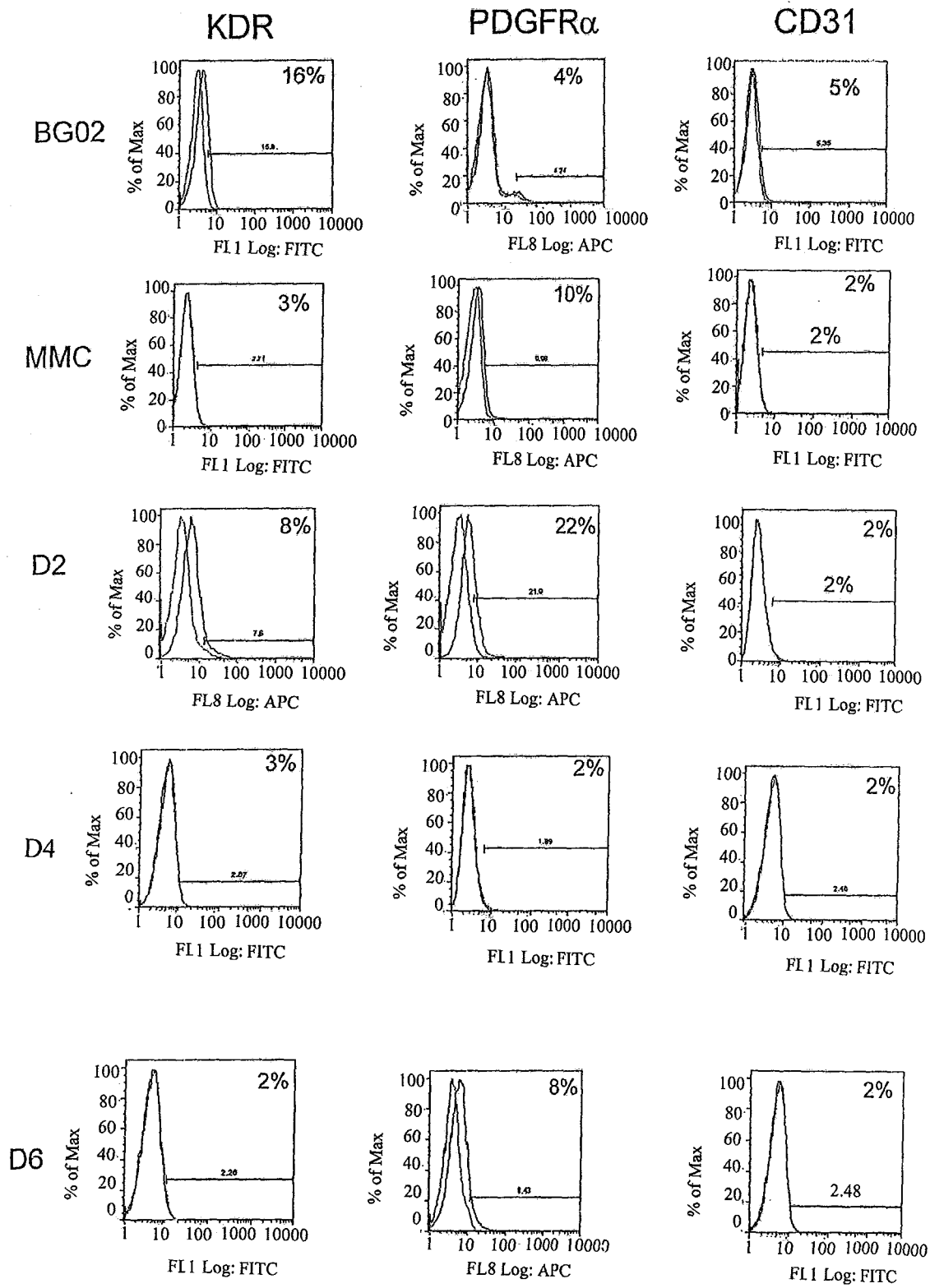

A more detailed survey of cell surface markers associated with C56Cs reveals the following. These cells exhibit high levels of CXCR4 and CD56 on their cell surface. Consequently, these cells have been named C56Cs, for CXCR4+ CD56+ cells. This cell population can also exhibit c-kit, CD56, CD166, CD105, CD44, CD133 and CD90 biomarkers. Representative flow cytometry profiles are shown in FIGS. 17, 18 and a summary of these findings in FIG. 19. Briefly, although MMCs are also CXCR4+, the amount of CXCR4 expression, as judged by flow cytometry, increases in C56Cs. MMCs and C56C cells are uniformly positive for CD56, CD133. c-Kit levels increase as MMCs transition to C56Cs as does CD105—the entire population is not definitively positive for these 2 markers however, all of the time. CD105, CD166 and CD104 also have a tendency to increase as MMCs transition to C56Cs. Flk1/KDR does not appear to be positive in MMCs or C56C cells, although some transcript is detected (data not shown). MMCs and C56Cs also appear to be low for PDGFRα and negative for CD31. Based on their properties, C56Cs are similar although not identical to mesenchymal stem cells and are believed to represent a pre-mesenchymal stem cell-like state.

Homing of CXCR4+ CD56+ Cells (C56Cs) to Ischemic Tissue and Bone

Figure 20:
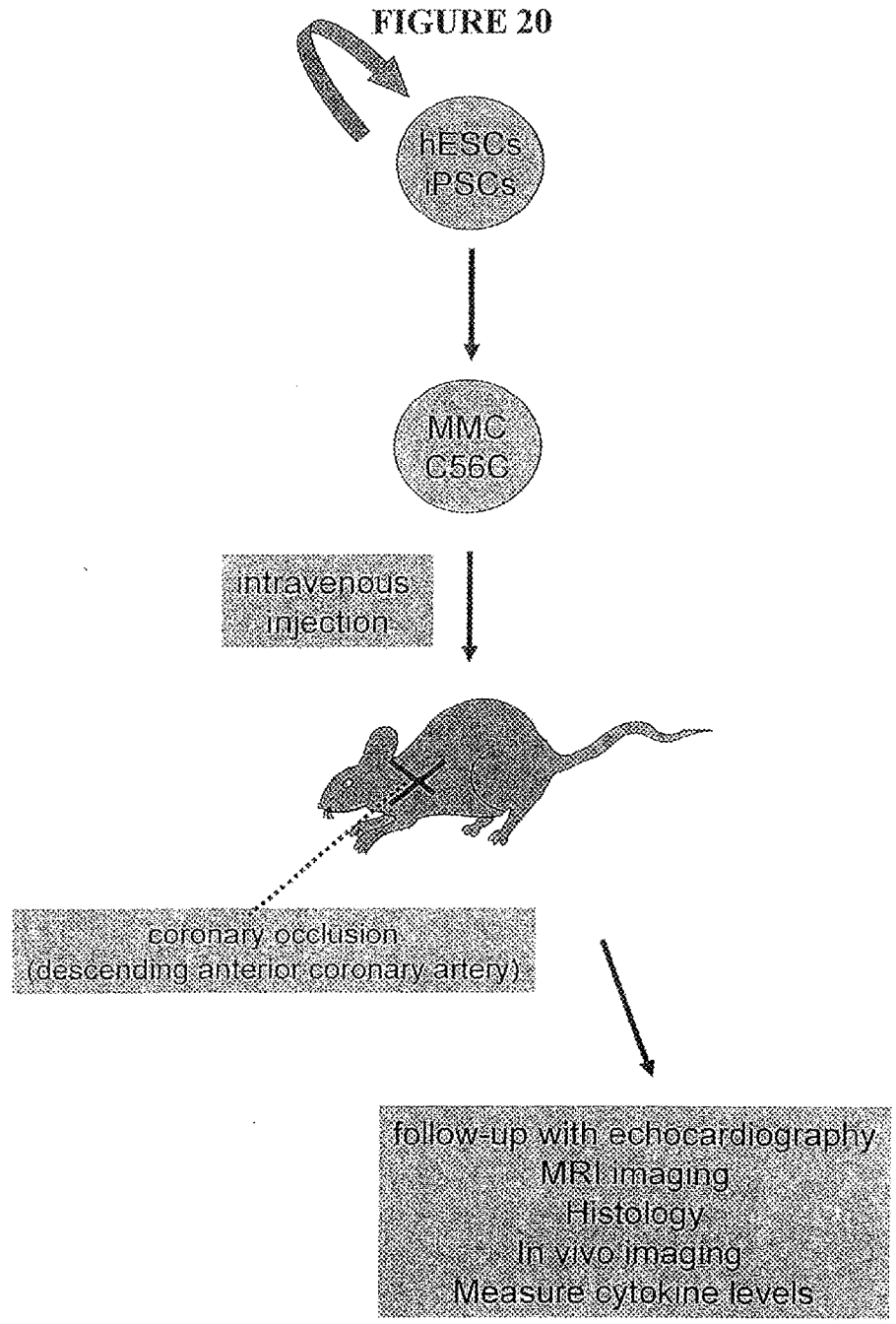
FIG. 20. The general scheme by which MMCs and C56Cs can be used to regenerate ischemic heart tissue. MMCs and C56Cs (both CXCR4+) are administered intravenously (for example) into an animal. Cells then 'home' to sites of ischemia and inflammation. Animals are evaluated for restoration of function by the approaches indicated.
Figure 22:
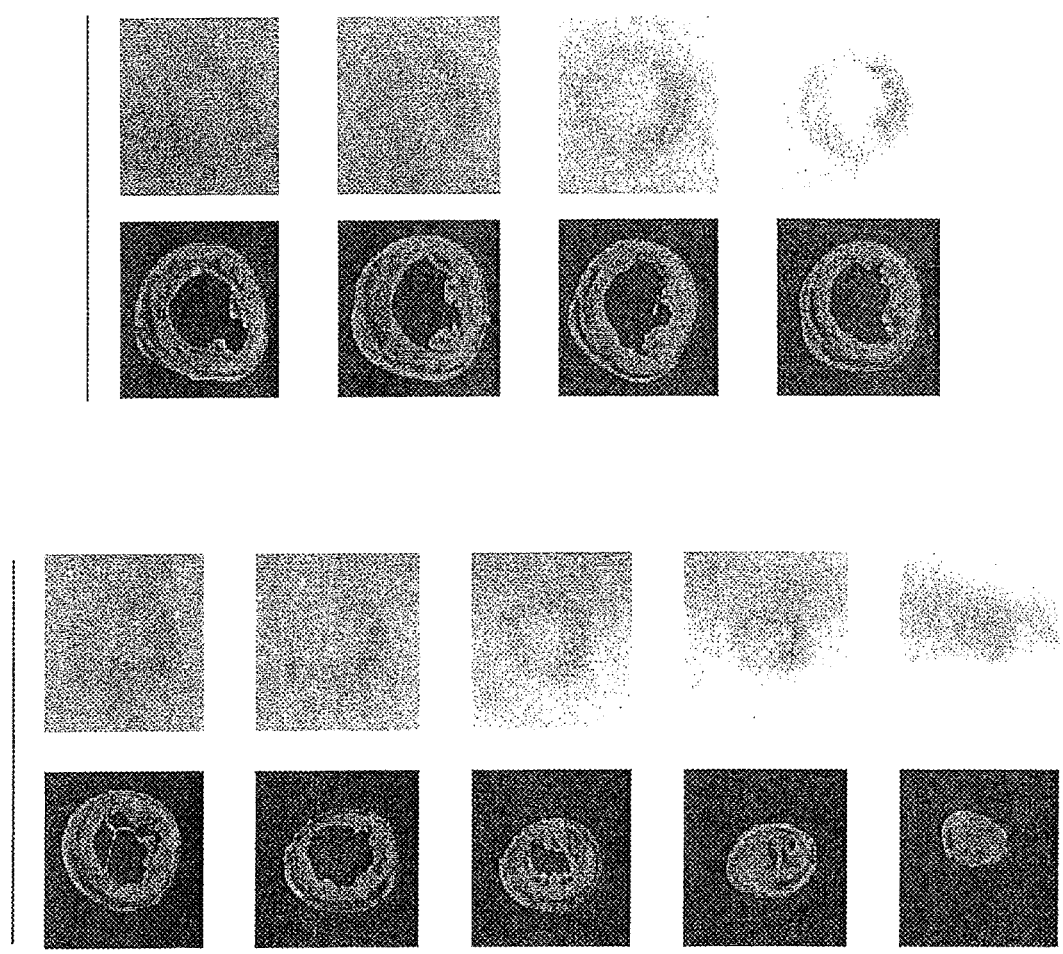
FIG. 22. Autoradiography of consecutive short-axial sections of the heart from the same rat as shown in FIG. 10. The heart was harvested at 72 hr after cell infusion, the tissue was fixed (shown in lower panels) and exposed to autoradiography film for 8 days (upper panels).
Figure 26:
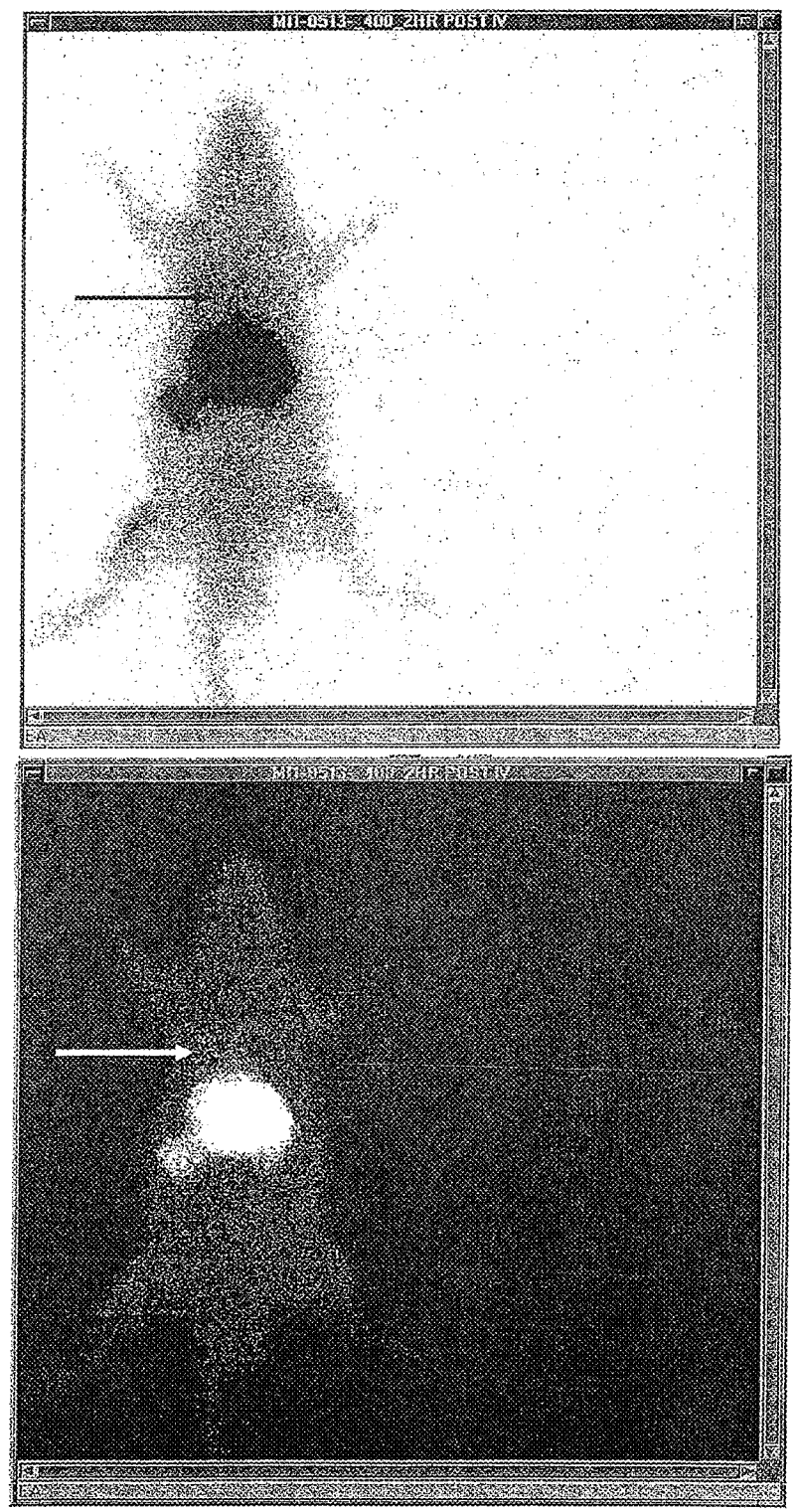

Since C56Cs express CXCR4, we proposed that they can home to sites of inflammation and tissue damage, through the SDF-1/CXCR4 signaling axis (reviewed in Dalton, 2008; Regen Med., 3: 181-188). This is similar to what has been described previously for bone marrow derived mesenchymal stem cells mobilized into peripheral blood (Kucia et al. 2005, Stem Cells 23: 879-894). A scheme for how MMCs and C56Cs can be administered as a systemic cell therapeutic is illustrated in FIG. 20. Cells could also be administered in conjunction with other compounds or cell types (ie. Isl1+ multipotent cardiovascular progenitors, for example) systemically or, directly to the site of tissue injury. FIG. 21 and FIGS. 23-26 show images where [$^{111}$In]oxime radio-labeled cells (Caveliers et al., 2007 Q J Nucl Med Mol 51: 61-66) were systemically administered through the tail vein into Sprague Dawley rats that previously received a ligation of the coronary artery. Injection into the femoral vein would also suffice. Whole animal 'live' images were captured with a gamma camera for up to 3 days. During this time cells were shown to localize to organs such as liver and lungs, bone and importantly, the ischemic heart (FIGS. 21, 23-16). Injected cells were retained immediately by the lungs then migrated partially to the liver within a 2 hour acquisition period. Initially, background accumulation in the lung obscured labeling in the cardiac region—this cleared after 10-24 hours revealing distinct accumulation of cells in the heart. Following fixation and axial sectioning of heart tissue from a rat that had been infused with labeled cells, autoradiography confirmed that 'homing' of C56Cs had occurred (FIG. 22).

Functional Recovery of a Cardiac Ischemia Using C56Cs in a Rodent Model

To establish if C56Cs could promote functional recovery in a rodent cardiac ischemia model, they were injected into the tail vein of nude rats following a surgically induced cardiac ischemia. Acute myocardial infarction was generated in male athymic Sprague Dawley rats (rh, rnu-rnu, 240-300 g, Harlon) following an open thoracotomy and occlusion of the left descending anterior coronary artery with a suture for 30-60 minutes, followed by reperfusion for 24 hours (Laflamme et al., 2007, Nat. Biotechnol. 25: 1015-1024).

Cells (typically $1-3 \times 10^6$ in 0.1 ml) were injected into the tail vein at each day, over a 3-4 day period, beginning ~24 hours after infarction. 24 hours before cell infusion and then for the first seven days thereafter, animals received cyclosporin A (0.75 mg/day) as an immunosuppressant. Animals were then imaged by trans-thoracic echocardiography (FIGS. 16,17; Zhu et al., 2008, Nucl. Med. Commun. 29: 764-769) and by high-resolution magnetic resonance imaging (MRI), using a Bruker Biospec 94/30 9.4T scanner, at various times post-injection (Laflamme et al., 2007, Nat. Biotechnol. 25: 1015-1024; FIGS. 18,19). Left ventricular ejection fraction (LVEF) was calculated by published methods (Laflamme et al., 2007, Nat. Biotechnol. 25: 1015-1024).

Overview of Results for C56C Administration:

Injection fractions (EFs) were calculated as described by LaFlamme et al. (2007, Nat. Biotechnol. 25: 1015-1024) in rats with acute myocardial infarctions. The average injection fractions after infarction for cells receiving saline (n=3) alone was 56.33+/−7.4 and 59.7+/−16.4 at 2 and 4 weeks post injection, respectively. EFs for infarcted rats receiving C56Cs (n=4) were 80.8+/−5.9 and 82.8+/−4.4 at 2 and 4 weeks post-injection, respectively.

Figure 27:
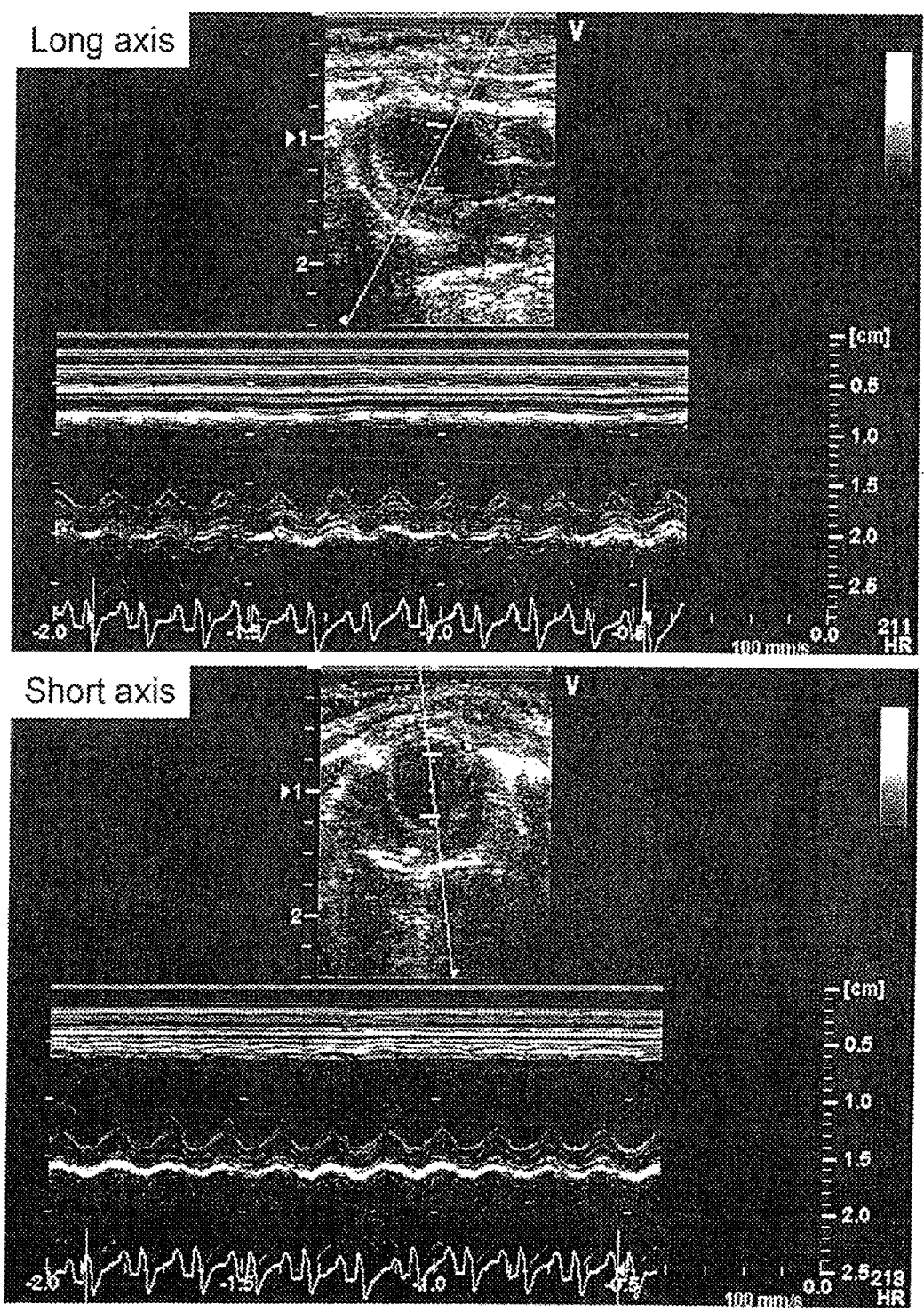
FIG. 27. Trans-thoracic echocardiography of an athymic rat with an acute myocardial infarction that received saline (0.1 ml) administered into the tail vein. Saline was administered each day over a 3 day period post-infarction. Echocardiography was performed 2 weeks post-infusion.

Echocardiography (FIGS. 27,28) and MRI analysis (FIGS. 29, 30) showed significant and reproducible functional recovery in all of the animals receiving infused C56Cs (n=4). It was evident from MRI analysis that re-muscularization of the ischemic cardiac tissue had occurred following infusion of C56Css at 2 weeks (FIGS. 29, 30). Thickening of the heart wall and restoration of beating cardiac muscle in the infarct zone was easily observed by echocardiography and MRI imaging.

By all measures used, administration of C56Cs has a major therapeutic effect on cardiac regeneration following acute myocardial infarction.

Homing of C56Cs to a Stroke Lesion in the Rodent Model

In addition to the ischemic heart model, another application for MMCs and C56Cs are in recovery/repair of cerebral stroke. To investigate the ability of GFP+ C56Cs to 'home' to a cerebral stroke a rodent model was employed. C57Bl mice received a craniotomy and a photo-thrombotic stroke. Each animal received ~$3-4 \times 10^6$ cells by tail-vein injection ~24 hours after the photo-thrombotic cerebral stroke. Cells were re-suspended in Texas Red solution and injected. GFP+ cells were observed in the circulation almost immediately after injection but nor after 48 hours. Using 2-photon microscopy GFP+ cells were identified in the ischemic penumbra and in the choroid plexus (FIG. 31,32).

Further Examples

Generation of IMPs from hiPSCs

The generation of IMP cells from hiPSCs follows similar methods described for the generation of IMP cells from hESCs as set forth above and as described herein.

(a) Methods for Growing hESCs and hiPSCs hESCs and hiPSCs expressing markers such as Oct4 and Nanog are preferably grown in mouse embryonic feeder conditioned medium (MEF-CM) or defined media (DM) using Matrigel as a growth matrix. Cells are typically plated at $1-1.5 \times 10^6$ per 60 mm dish. Cells are passaged every 4-5 days at a split of ~1:4 to 1:10.

(i) Mouse Embryo Fibroblast Conditioned Media (MEF-CM)

hESCs and hiPSCs (such as hFib2-iPS4) can be grown on Matrigel (BD Biosciences; 1:20-1:200 dilution is preferred) or other matrices that support maintenance of pluripotent cells in mouse embryo fibroblast conditioned media (MEF-CM) in the presence of Fgf2 (McLean et al., 2007; Stem Cells 25, 29-38; Park et al., 2008; Nature 451, 141-146). Cells can be passaged by a variety of methods using enzymatic (trypsin, accutase, collagenase), manual passage (mechanical) and non-enzymatic methods. Cells are plated at a density of $1.5 \times 10^6$ per 60 mm dish and passaged every 4-5 days at a split of 1:4-1:10.

(ii) Defined Media Conditions (a) Defined media (DM), for routine culture of hESCs and hiPSCs, is purchased from Invitrogen as StemPro (see Wang et al., Blood 110: 4111-4119). The media is used according to the manufacturer's recommendations except that Accutase (Chemicon) is used for passaging cells as single cell suspensions. The following represents this formulation and is capable of maintaining hESCs and hiPSCs in a pluripotent state. The following defined, exemplary serum free media conditions work well but are not restricted to this specific formulation and involves feeder-free culture: DMEM:F12 (Gibco), 2% BSA (Seriologicals, #82-047-3), 1× Pen/Strep (Gibco), 1× non-essential amino acids (Gibco), 1× Trace Elements A, B and C (Cellgro; #99-182-C1, #99-176-C1, #99-175-C1), 50 ug/ml Ascorbic Acid (Sigma, #A4034), 10 ug/ml Transferrin (Gibco, #11107-018), 0.1 nM beta-mercaptoethanol, 8 ng/ml Fgf2 (Sigma, #F0291), 200 ng/ml LR-IGF (JRH Biosciences, #85580), 10 ng/ml Activin A (R&D Systems, #338-AC), 10 ng/ml Heregulin beta (Peprotech; #100-03).

(b) hESCs and hiPSCs can also be cultured in additional commercially available defined media formulations such as mTeSR1 (BD/Stem Cell Technologies; Ludwig et al., Nat Biotechnol. 24:185-187), according to the manufacturer's recommendations. Accutase passaging is also used in conjunction with this media.

(a) Generation of an Isl1+ Multipotent Progenitor (IMP) by Addition of Wnt3a and BMP4 to hiPSC Cultures.

hFib2-iPS4 hiPSCs grown in StemPro defined media as described above were passaged with Accutase and plated onto Matrigel coated dishes ($1.0 \times 10^6$ cells per 60 mm dish) as described in above, except that media was supplemented with BMP4 (100 ng/ml, R&D Systems) plus human Wnt3a (25 ng/ml; R&D Systems). Media was replaced every day. Immunostaining was performed after 4 days (96 hours). In hiPSCs were positive for Oct4 and Nanog, two markers of pluripotent stem cells, as judged by immunostaining (FIG. 37). After 4 days treatment with BMP4 and Wnt3a, immunostaining showed that these markers were severely down-regulated (FIG. 37). In addition, E-cadherin expression was lost and expression of Snail became elevated (FIG. 37). This indicates that hiPSCs have lost their epithelial architecture and have gone through an epithelial to mesenchymal transition following BMP-Wnt treatment. Coinciding with loss of Nanog and Oct4, Isl1 transcript levels increased by almost 400-fold by 4 days of differentiation (FIG. 38). Hand2, GATA4, mRNAs also increase ~7,500 and 175-fold, respectively, over this time period.

In total, this expression profile is characteristic of IMP cells derived from hESCs, as described previously (see above and also, PCT/US2008/001222, published as WO2008/094597). To summarize, hiPSCs respond to the combined treatment of effective amounts of BMP4 and Wnt3a to generate a cell type indistinguishable from that of Isl1+ multipotent progenitors (IMPs).

(b) Generation of an Isl1+ Multipotent Progenitor (IMP) by Addition of Wnt3a for Days 1-3 Followed by Addition of BMP4. (Prophetic Example)

Isl1+ mesoderm cells could be generated by treatment of hiPSCs, grown in either MEF-CM or defined media, with Wnt3a for the initial 1-3 days followed by addition of BMP4 for a further 1-5, preferably 2-4 days.

(c) Generation of an Isl1+ Multipotent Progenitor (IMP) by Addition of BMP4 and GSK3 Inhibitors Such as BIO to hiPSCs in MEF-CM. (Prophetic Example)

Same as in (b) except that an inhibitor of GSK3 can be used in place of or in combination with Wnt3a.

(d) Generation of an Isl1+ Multipotent Progenitor (IMP) by Addition of BMP4 and GSK3 Inhibitors Such as BIO to hiPSCs Cultured in Defined Media. (Prophetic Example)

hiPSCs could be differentiated to an Isl1+ progenitor by addition of BMP4 and BIO to hESCs cultured in defined media. 6 days of treatment with BMP4 and BIO.

(d) Generation of an Isl1+ Multipotent Precursor by Addition of GSK3 Inhibitors, Such as BIO, for 1-3 Days Followed by Addition of BMP4.

Isl1+ mesoderm cells could be generated from hiPSCs grown in MEF-CM or defined media by addition of GSK3 inhibitors, such as BIO, for 1-3 days followed by addition of BMP4 for a further 2-4 days.

(e) Generation of an Isl1+ Multipotent Progenitor (IMP) by Addition of Wnt3a and BMP4 and TGFβ Signaling Inhibitors (Such as SB431542) to hiPSC Cultures.

Isl1+ mesoderm cells could be generated from hiPSCs, grown in MEF-CM or defined media, by addition of Wnt3a, BMP4 and TGFβ inhibitors (such as SB431542) for 1-4 days followed by the removal of TGFβ inhibitors and continued culture with Wnt3a and BMP4 for a further 2-4 days.

(f) Generation of an Isl1+ Multipotent Progenitor (IMP) by Addition of Wnt3a and TGFβ Signaling Inhibitors (Such as SB431542) for Days 1-4 Followed by Addition of BMP4.

Isl1+ mesoderm cells could be generated from hiPSCs, grown in MEF-CM or defined media, by addition of Wnt3a and TGFβ inhibitors (such as SB431542) for 1-4 days followed by addition of BMP4 for a further 2-4 days.

(g) Generation of an Isl1+ Multipotent Progenitor (IMP) by Addition of Wnt3a for Days 1-3 Followed by Addition of BMP4 and SB431542.

Isl1+ mesoderm cells could be generated from hiPSCs, grown in MEF-CM or defined media, by addition of Wnt3a and SB431542 for 1-3 days followed by addition of BMP4 for a further 2-4 days.

Generation of EPCs from (Isl1+) IMPs

The following describes a method for differentiation of IMP cells, generated from hESCs or hiPSCs, into multipotent pro-epicardium/epicardium progenitors (EPCs). This cell type has importance due to its ability to generate lineages comprising the coronary vasculature. FIGS. 34, 35, 43.

(a) Generation of Pro-Epicardium/Epicardium (EPCs) from Isl1+ Multipotent Progenitors (IMPs) by Addition of Wnt3a, BMP4 and all-Trans Retinoic Acid in Effective Amounts hESC/hFib2-iPS4 hiPSCs grown in StemPro defined media/defined media were differentiated into IMPs (as described above and elsewhere). At day 4, IMP cell stage, the defined media was supplemented with BMP4 (50 ng/ml, range about 2-100 ng/ml, R&D Systems), Wnt3a (25 ng/ml, range about 1-100+ng/ml, R&D Systems) and all-trans retinoic acid (4 μM, range about 0.25-25 μM Sigma), media changed every 2 (1-4 days) days, for about 10-16 days (about 7-25 days) (FIG. 39). The expression of Wt-1, Tbx18, Raldh2 and Tcf21 (epicardin) were confirmed by Q-PCR (FIGS. 40, 42) and Wt-1 by immunofluorescence (FIG. 41). This method typically gives cultures that are >80% positive for Wt1.

Generation of Pro-Epicardium/Epicardium from IMPs by Addition of Effective Amounts of Wnt Mimetics, Such as GSK3α/β Inhibitors (ie. BIO), BMP4/Other BMP and all-Trans Retinoic Acid Pro-epicardium/epicardium could be generated from IMPs by the addition of BIO (GSK3α/β Inhibitor), BMP4 and all-trans retinoic acid to defined media for up to ~16 or more days.

Generation of Endothelial Cells, Smooth Muscle and Cardiac Fibroblasts from EpCs a) Generation of Endothelial Cells from EPCs IMPs were grown in defined media in the presence of Wnt3a (25 ng/ml), BMP4 (50 ng/ml) and all-trans retinoic acid (Sigma; 4 μM) for 16 days. The cells were passaged and seeded 125 000 cells/cm$^2$ and grown in defined media+/− Activin A (R&D Systems), in the presence of either;

v) VEGF$_{165}$ (R&D Systems #293-VE; 10 ng/ml)

vi) VEGF$_{165}$ (10 ng/ml)+SB431542 (Tocris Biosciences; 20 μM)

The cells were grown for a further ~10-14 days in these media. 20-30% of the resultant culture was of endothelial origin as judged by immunostaining for CD31 and VE-cadherin (FIG. 44a).

(b) Generation of Smooth Muscle and Cardiac Fibroblasts Cells from Epicardium.

Figure 44B:
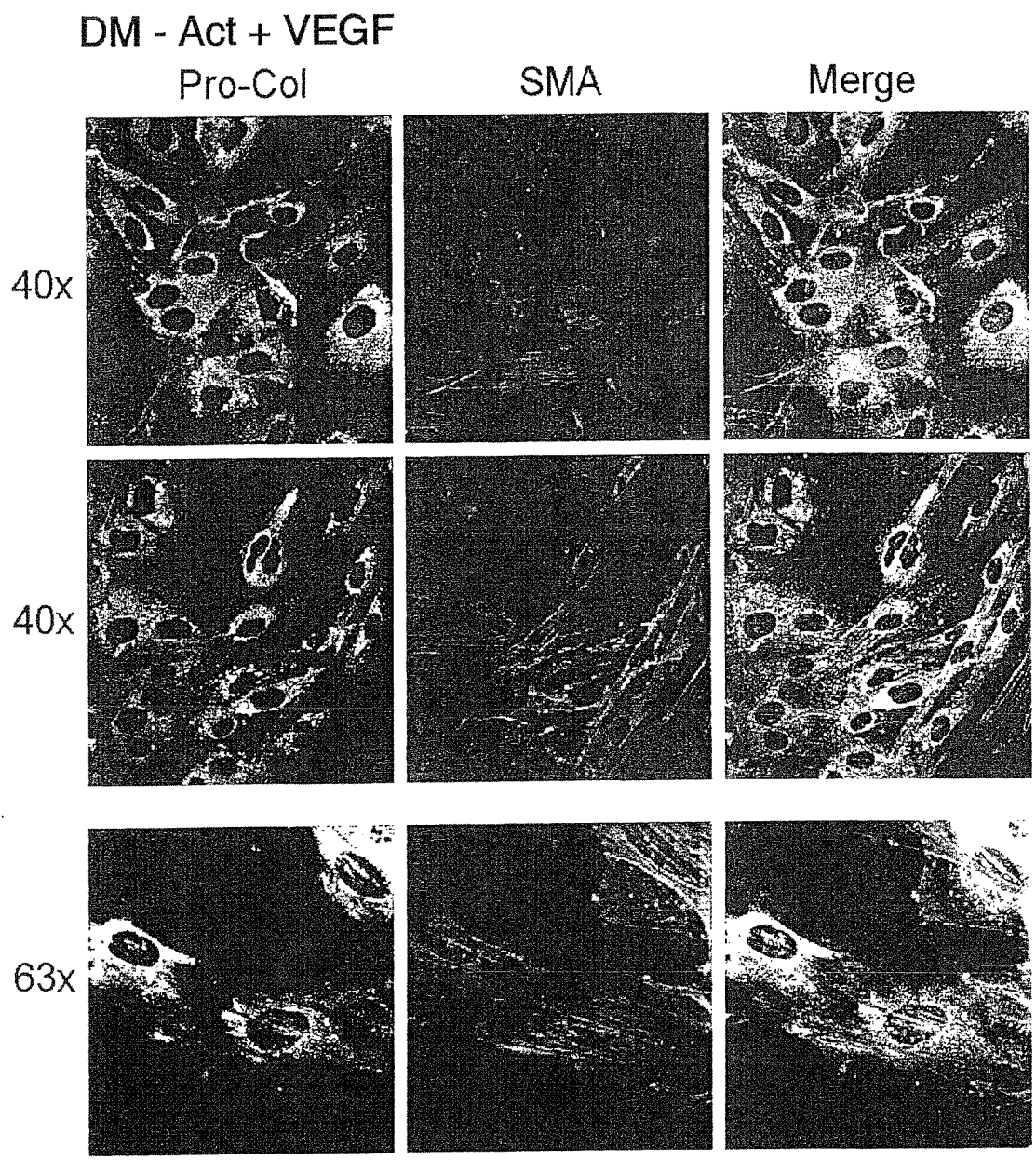

IMPs were grown in defined media in the presence of Wnt3a (25 ng/ml) and BMP4 (100 ng/ml) for 16 days. The cells were passaged and seeded 125 000 cells/cm$^2$ and grown in 10% FBS, DMEM, 1× Pen/Strep (Gibco), 1× sodium pyruvate (Mediatech) and L-Alanyl-L-Glutamine (Mediatech). The resultant culture was >90% smooth muscle as determined by immunostaining for smooth muscle actin (FIG. 45). Cardiac fibroblasts were detected by staining with an anti-procollagen antibody (FIGS. 44b, 45). These cells consisted of 5-10% of these cultures.

Smooth Muscle was also made using defined media supplemented with;

i) VEGF$_{165}$ (10 ng/ml)

ii) VEGF$_{165}$ (10 ng/ml)+PDGFB (R&D Systems; 5 ng/ml)

iii) VEGF$_{165}$ (10 ng/ml)+hDKK1 (R&D Systems; 150 ng/ml)

iv) 10% fetal bovine serum FBS

Composition of Matter for Imps Derived from Human iPSCs and hESCs

Microarray analysis of IMP cells generated from hiPSCs indicate that;

IMP cells derived from hiPSCs always express Isl1

IMP cells derived from hiPSCs express Pdgfrα, FoxF1, Nkx2.5, Gata4

IMP cells derived from hiPSCs optionally also express Tbx3 and Hand1

A table summarizing some of the most up-regulated genes is shown in FIG. 46, Table 1.

Composition of Matter for EPCs Derived from Human Pluripotent Cells

Microarray analysis of EPCs generated from three hESC lines and a human iPSC line indicates that EPC cells express;
Wilm's tumor suppressor protein 1 (Wt1), Tcf21 (epicardin), Raldh2 (Aldh1a2)

These transcripts are primary identifiers of EPCs, a pro-epicardial/epicardial cell type generated from pluripotent cells in culture.

EPCs also can express;
One or more (two, three, four or five) of Tbx18, COL3A1, GATA6, Tbx3, Tbx5

A table summarizing some of the most up-regulated genes is shown in FIG. 47, Table 2.

Utility of EPCs:
1. EPCs can be used for identification of secreted factors produced by the epicardium which influence cardiomyocyte proliferation, survival, function and differentiation
2. EPCs can be used as a source of cells that can be used in drug screens for cardiovascular applications
3. EPCs can be used as a source of cells that can be used for therapeutic purposes—to repair the ischemic heart, to regenerate the coronary vasculature
4. EPCs can be used for tissue engineering purposes where components of the heart or the coronary vasculature are required
5. EPCs can be as a research tool for the study of cardiovascular development and disease Method for Generating Blood-Vessel Like Tubes from EPCs We followed a strategy to generate blood vessels containing endothelial cells and smooth muscle cells as shown in FIG. 48. This involved generating IMP cells (Isl1+) from hESCs. IMP cells were then converted into EPCs (Wt1+) and then into vascular structures, comprising smooth muscle and endothelial cells.

WA09 cells were differentiated to Wt1+ epicardial progenitor cells (EPCs) for ~20 days as previously described. The cells were then harvested using 0.25% trypsin-EDTA to form a single cell suspension. The cells were then plated at a density of ~1.25×10$^5$ cells/cm$^2$ in defined conditioned media containing 8 ng/mL FGF2 (invitrogen), 200 ng/mL LR-IGF (Sigma), 10 ng/mL Heregulin β (Peprotech) and 10 ng/ml VEGF (R&D Systems). The cells were grown for a further 10-14 days at 37° C. in 5% $CO_2$ changing media every 2 days. VEGF was removed from the media and cultures allowed to stay at 37° C. in 5% $CO_2$ for a further 5-7 days without media change to allow tube formation (FIG. 49). The tubes were then fixed with 4% paraformaldehyde and stained with CD31 and CDH5 (R&D Systems). The resultant immunofluorescence images showed the formation of tubes as evidences by the presence of a visible lumen and 3-dimensional structure constructed from a Z stack (FIG. 50). Images were taken on a Zeiss confocal microscope.

FURTHER ASPECTS OF THE PRESENT INVENTION

In addition aspects, the present invention relates to a method of producing a population of ISL+ multipotent progenitor cells/splanchnic mesoderm cells (IMP/Spl-m) from pluripotent stem cells (PSCs) comprising exposing said pluripotent stem cells to a combination of an effective amount of a wingless (Wnt) protein and a bone morphogenic protein (BMP) in a cell differentiation medium and optionally, isolating aid IMP/Spl-m cells. Generally, in this method the pluripotent stem cells first differentiate into lateral plate mesoderm cells before differentiating into IMP/Spl-m cells. Differentiation from a pluripotent cell to a IMP/Spl-m cell will occur over a period ranging from about 3 to 10 days, preferably about 4 to 6 days. The preferred wingless protein is Wnt3a and the preferred bone morphogenic protein is BMP4, each of which agents is used in cell differentiation medium at concentrations ranging from about 10 ng/ml to about 150 ng/ml, with a preferred range for Wnt3a being about 10 ng/ml to about 35 ng/ml, more preferably about 20 to about 30 ng/ml, about 25 ng/ml and with a preferred range for BMP4 falling within the range of about 25 ng/ml to about 135 ng/ml, about 75 ng/ml to about 125 ng/ml, about 100 ng/ml. Preferably, the pluripotent cells which are used in this aspect of the invention are human embryonic stem cells (hESCs) or human induced stem cells (hISCs).

Further embodiments of the present invention relate to a method of producing a population of Wt+ epicardium-like cells (PE progenitor cells) comprising exposing a population of IMP/Spl-m cells to an effective amount of a wingless (Wnt) protein in combination with an effective amount of a bone morphogenic protein (BMP) in a cell differentiation medium in combination with at least one additional agent selected from the group consisting of a fibroblast growth factor, retinoic acid and mixtures thereof, and optionally, isolating the PE progenitor cells. In preferred aspects of this invention, the Wnt protein is Wnt3a and the bone morphogenic protein is BMP4, the fibroblast growth factor is Fgf2 and the retinoic acid used is trans-retinoic acid, even more preferably all trans-retinoic acid. In further preferred aspects of the invention, Wnt3a included in the cell differentiation medium at a concentration of about 10 to about 50 ng/ml, about 15 to 35 ng/ml, about 25 ng/ml, and the BMP4 is included in said differentiation medium at a concentration of about 25 ng/ml to about 100 nb/ml, about 35 to about 75 ng/ml, about 50 ng/ml. Fibroblast growth factor 2, when used, is included in the cell differentiation medium at a concentration of about 25 to about 150 ng/ml, about 75 to about 125 ng/ml, about 100 ng/ml and the retinoic acid, when used is preferably all trans-retinoic acid included in the cell differentiation medium at a concentration of about 1 to 10 μM, about 2 to 8 μM, about 4 μM. The method of differentiating IMP-Spl-m cells to PE cells occurs over a period of about 7 to 15 days, about 10-16 days, about 12-14 days.

In a further aspect of the invention, smooth muscle cells and/or endothelial cells are produced from PE progenitor cells by exposing a population of PE progenitor cells to a cell differentiation medium in the absence of Activin A (or, optionally in the presence of an Activin A inhibitor) comprising an effective amount of VEGF, preferably VEGF-A165 ($VEGF_{165}$) included in said cell differentiation medium (preferably CDM) at a concentration of about 1 to about 20 ng/ml, about 5 to about 15 ng/ml, about 10 ng/ml. The smooth muscle cells and/or endothelial cells produced above may be assembled into blood vessels under serum starvation conditions (grown in cell medium in fetal calf serum, preferably DMEM/20% fetal calf serum to stabilize the population of cells and then the stabilized cells are grown in cell medium with substantially reduced or no serum, preferably DMEM/0.2% fetal calf serum) for a period of about 4 to 10, about 5 to 9, about 7 days to produce blood vessels/vascular cells.

A further method according to the present invention is directed to producing a population of Wt+ epicardium-like cells (PE progenitor cells) from pluripotent stem cells comprising a first step of exposing the pluripotent stem cells to a combination of an effective amount of a wingless (Wnt)

protein and a bone morphogenic protein (BMP) in a cell differentiation medium and optionally, isolating the IMP/Spl-m cells produced and a second step which involves exposing the IMP/Spl-m cells obtained in step 1 to an effective amount of a wingless (Wnt) protein in combination with an effective amount of a bone morphogenic protein (BMP) in a cell differentiation medium further in combination with at least one additional agent selected from the group consisting of a fibroblast growth factor, retinoic acid and mixtures thereof, and optionally, isolating said PE progenitor cells. In this aspect of the invention, the pluripotent stem cells first differentiate into lateral plate mesoderm cells before differentiating into IMP/Spl-m cells in step 1 and the exposing step occurs over a period ranging from about 3 to 10 days, preferably about 4 to about 6 days. In this aspect in step 1, the preferred wingless protein is Wnt3a and the preferred bone morphogenic protein is BMP4, each of which agents is used in cell differentiation medium at concentrations ranging from about 10 ng/ml to about 150 ng/ml, with a preferred range for Wnt3a being about 10 ng/ml to about 35 ng/ml, more preferably about 20 to about 30 ng/ml, about 25 ng/ml and with a preferred range for BMP4 falling within the range of about 25 ng/ml to about 135 ng/ml, about 75 ng/ml to about 125 ng/ml, about 100 ng/ml. Preferably, the pluripotent cells which are used in this aspect of the invention are human embryonic stem cells (hESCs) or human induced stem cells (hISCs).

In step 2 of the above-described method, the wingless protein used is preferably Wnt3a, the bone morphogenic protein used is preferably BMP4, the fibroblast growth factor, when used, is fibroblast growth factor 2 (Fgf2) and the retinoic acid is all trans-retinoic acid. In step 2, the Wnt protein is Wnt3a included in said cell differentiation medium at a concentration of about 10 to about 50 ng/ml, about 15 to 35 ng/ml, about 25 ng/ml, the bone morphogenic protein is BMP4 included in the differentiation medium of step 2 at a concentration of about 25 ng/ml to about 100 nb/ml, about 35 to about 75 ng/ml, about 50 ng/ml. Fibroblast growth factor 2, when used, is included in the cell differentiation medium at a concentration of about 25 to about 150 ng/ml, about 75 to about 125 ng/ml, about 100 ng/ml and the retinoic acid, when used is preferably all trans-retinoic acid included in the cell differentiation medium at a concentration of about 1 to 10 µM, about 2 to 8 µM, about 4 µM. The method of differentiating IMP-Spl-m cells to PE cells of step 2, occurs over a period of about 7 to 15 days, about 10-16 days, about 12-14 days.

A further aspect of the invention relates to a method of inducing vascular formation in vivo comprising implanting into the epicardium of a patient or subject an effective amount of PE progenitor cells which are produced and described above.

Characterizing the Migratory Properties of EPCs In Vitro and In Vivo

Pro-epicardium/epicardium has the ability to spread over the surface of the myocardium forming an outer later and also the capacity to migrate into the myocardium in an invasive manner (Olivey et al., 2004 Trends Cardiovasc Med. 14, 247-251;). A standard assay to evaluate the migratory properties of pro-epicardium/epicardium is to plate cells on a collagen I matrix.

(i) In Vitro Migration of EPCs:

Pro-epicardium/epicardium isolated from cardiac tissue explants then has the capacity to become mesenchymal and migrate away from the site of attachment (Gaudix et al., 2006 Dev Dyn. 235, 1014-1026; Olivey et al., 2006 Dev Dyn. 235, 50-59; Dettman et al., 1998 Dev Biol. 193, 169-181). This is a typical feature of authentic pro-epicardium/epicardium and involves an epithelial to mesenchymal transition.

A standard assay to evaluate the migratory properties of pro-epicardium/epicardium is to plate cells on a collagen matrix. To evaluate the ability of EPCs to migrate on collagen gels the following was performed. IMP cells were treated with retinoic acid, BMP4 and Wnt3a for 6 days to generate Wt1+ EPCs. Single cell suspensions ($1 \times 10^6$ cells) were plated in 60 mm tissue culture dishes coated with PHEMA (polyhydroxyethylmethacrylate) and left for 24 hours to generate spheres. Spheres were then plated on Geltrex or collagen I (10 µg/ml)-coated dishes in defined media (HAIF) and photographed at various times (see FIG. 51). For immunofluorescence analysis, cells were fixed with 4% paraformaldehyde and permeabilized with 0.25% Triton X100. hESCs (FIG. 52-54) or EPC spheres (FIG. 53,54) were then blocked and probed with antibodies for cytokeratin or vimentin to establish the epithelial versus mesenchymal state of cells. This analysis shows that EPC spheres undergo an epithelial to mesenchymal transition following plating onto a collagen-based matrix such as Geltrex or collagen 1. This is very similar to the behavior of pro-epicardium/epicardium cells isolated from tissue explants (Gaudix et al., 2006 Dev Dyn. 235, 1014-1026; Olivey et al., 2006 Dev Dyn. 235, 50-59; Dettman et al., 1998 Dev Biol. 193, 169-181).

(ii) In Vivo Migration of EPCs

Pro-epicardium/epicardium tissue explants grafted onto the developing chick cardiac tube display very distinctive properties. Grafted pro-epicardium/epicardium undergoes an epithelial to mesenchymal transition forms and invades the myocardium (Guadix, et al., *Developmental Dynamics*, 235, 1014-1026 (2006). To establish that EPC spheres could also invade the developing chick heart in a manner reminiscent of tissue explant-derived pro-epicardium/epicardium, transplantation experiments were performed.

Figure 57:
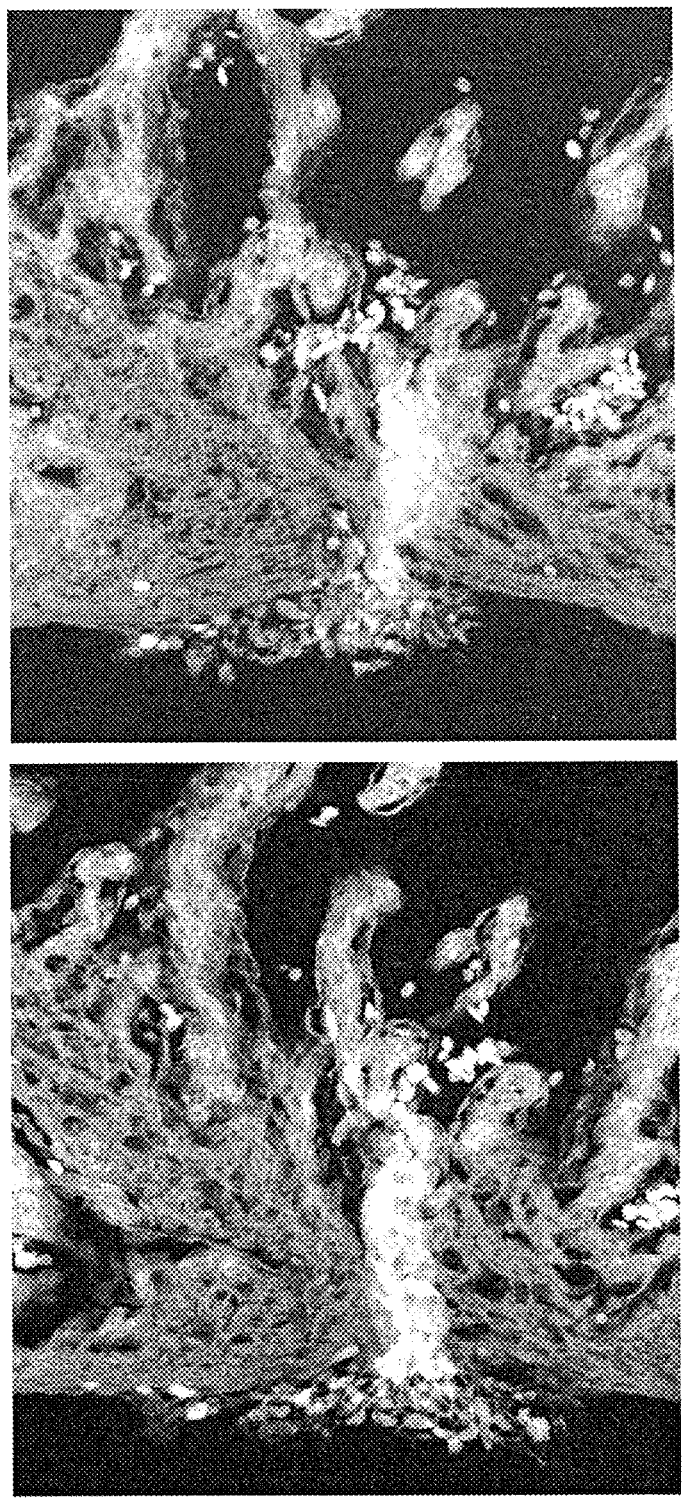

To evaluate the developmental potential of HES derived proepicardial cells, PE aggregates were implanted into HH stage 14-16 chick embryos immediately adjacent to the heart in the vicinity of the endogenous pro-epicardium. Embryos were incubated for three to six days and hESC/EPC-derived transplanted cells visualized by immunodetection with GFP antibody (FIG. 55-57). This analysis showed that transplanted EPC spheres engrafted into the chick tissue and invaded the chick myocardium. EPC cells therefore behave in a manner consistent with them being authentic pro-epicardium/epicardium in vivo 3. Demonstration that (Isl1+) IMPs can Integrate and Differentiate into Myosin Heavy Chain+ (MHC+) Cardiomyocytes when Co-Cultured with Rodent Cardiac Tissue Several reports have documented the ability of cells in the epicardium to differentiate into cardiomyocytes (see Zhou et al., 2008 Nature 454, 109-113). To establish the ability or EPCs to differentiate into cardiomyocytes, a co-culture assay was performed where EPC spheres were incubated with cardiac tissue explants.

Right and left ventricle from the hearts of 8 month old CD1 male mice were dissected into small pieces (~2 mm squares×1 mm thick) and cultured in DMEM/M199/FBS/PSF in gelatin coated 96 well plates for 24 hours. EPC spheres were then added and incubated for various times. Tissue was fixed with paraformaldehyde, paraffin-embedded, sectioned and probed with antibodies raised against human beta-myosin heavy chain to detect the presence of human cardiomyocytes. Large, beta-MHC+ cells were detected in tissue sections receiving Isl1+ cells but, not in sections that did not receive Isl1+ IMP cells (FIG. 58).

Demonstration that IMP Cells can Integrate into Tissue Including Mesoderm and Vasculature Structures Following Transplantation into Chick Embryos To investigate the developmental potential of GFP+ IMP cells, individual cells were implanted into the mesodermal layer of gastrula stage chicken embryos. This was accomplished ex ovo by peeling back the endoderm of Hamburger and Hamilton (HH) stage 4-5 embryos and layering a single cell suspension of 50-100 IMP cells onto the mesoderm. The endoderm was then replaced and embryos incubated for an additional 20-28 hours. IMP cells were identified by immunodetection of GFP.

Analysis of intact embryos and embryo sections showed that HES cells had incorporated broadly into embryonic structures, acquiring the morphology of the endogenous chicken cells (FIG. 59). IMP cells contributed to several mesodermal derivatives, including the epithelial layers of the somatic and splanchnic mesoderm, blood vessel endothelium, the perivascular mesoderm surrounding newly formed endothelial tubes (FIG. 59A-F), and occasionally in the somites (not shown). IMP cells also contributed in large numbers to the endoderm. IMP cells were observed throughout the lateral and medial endoderm, in the foregut and in the liver primordium (FIG. 59A-D, F). These data indicate that IMP cells have vasculature potential when transplanted in vivo.

Further Defining Composition of Matter for IMP Cells

No defining cell surface markers had been previously defined on the surface of IMP cells. Although KDR (Flk1) can be expressed on the surface of IMP cells, it is not a strictly defining cell surface marker as it is expressed on a wide range of stem and progenitor cell types. We now provide additional characterization. Transcript microarray analysis indicated that platelet derived growth factor beta receptor and cadherin 11 transcripts are significantly up-regulated in IMP cells derived from several hESC lines and hiPSCs (data not shown). To establish these as cell surface markers for IMP cells we performed flow cytometry and show that that IMPs can express PDGFRβ and cadherin 11 on their cell surface (FIG. 60). In contrast, hESCs (WAO9) are not positive for these markers.

Defining the Migratory Mechanisms Operating in C56C Cells

To investigate the mechanisms by which C56Cs migrate towards ischemic/damaged tissue we assayed these cells in a Boyden chamber assay. 300,000 C56C cells were seeded in the upper chamber of a Boyden chamber. In the lower chamber these data demonstrate that C56C cells are responsive and migrate towards the SDF1 cytokine (FIG. 61). This migration is blocked with the antagonist AMD3100, indicating that migration is mediated through the CXCR4 receptor.

Further Examples Related to the Further Aspects of the Invention—Inter Alia, Production of IMP-Spl-m Cells, PE Cells, Smooth Muscle and Endothelial Cells from PE Cells, Blood Vessels/Vascular Cells from Same and In Vivo Vascular Formation Differentiation of Human Pluripotent Cells into Coronary Vascular Progenitor-Like Cells Generation of cardiac lineages begins with the migration of pluripotent cells into the primitive streak where they transition through a T+ (brachyury+) mesendoderm intermediate stage. Specification towards cardiac fates is then determined by exposure of pre-cardiac mesoderm to Wnt, TGFβ, BMP and FGF family signaling molecules[1-3]. As early mesoderm precursor cells emerge from the streak, they migrate laterally and cranially until localizing either side of the embryonic midline as part of the lateral plate mesoderm (LPM)[4-6]. LPM then segregates into somatic and splanchnic mesoderm (Spl-m) layers, the latter of which contain the progenitor cells required for cardiovascular development.

Spl-m contributes to bilateral cardiogenic regions that fuse at the ventral midline, forming a crescent shaped epithelium known as the cardiac crescent. Cells within this domain represent what is often referred to as the first heart field (FHF) and contributes to the left ventricle and atria of the developing heart. Contiguous with the FHF but more medial, lies the secondary heart field which contributes to the cardiac outflow tract, right ventricle and atria[7]. Soon after the heart tube forms following morphogenic events involving both the FHF and SHF, an outer epithelial lining known as the epicardium is formed. The epicardium forms by the pro-epicardium (PE) contacting and then spreading over the heart tube[8, 9]. Although the PE was originally thought to originate from the septum transversum, its origin has been re-evaluated following the identification of pro-epicardial progenitors in the sinus venosus (SV)[10, 11]. Following contact of the PE with the heart tube and spreading to form an outer epithelial layer, a subset of epicardial cells undergo an epithelial to mesenchymal transition (EMT), thereby invading the myocardium. A subset of these invasive cells seed the developing heart with progenitors for the coronary vasculature[12-15] while others contribute to the interstitial layer between the epicardium and the myocardium[13, 14]. Other studies have reported contribution of the epicardium to the myocardium[16-18] but this remains controversial[19].

The myocardium and coronary vasculature originate from Isl1+ Nkx2.5+ cells in the cranial LPM. Cells contributing to the coronary vasculature segregate away from those giving rise to the major heart fields and become positioned in the SV, coinciding with loss of Isl1 Nkx2.5 expression and upregulation of Tbx18[10, 11]. At least some of these progenitors are retained by the developing PE and have been shown to contribute to smooth muscle and endothelial lineages in the coronary vasculature after contact with the heart tube[13, 48, 49]. Detailed lineage analysis of PE-derived vascular progenitors has not been performed however, leaving many questions unanswered[9].

In this report we describe efficient approaches for lineage-specific differentiation of human pluripotent cells into Wt1+ cells that follow a pathway consistent with them being coronary vascular progenitors. Details of how Spl-m resolves into progenitor cell populations within the PE are not fully understood but clearly important because of their roles in cardiac development, such as in formation of the coronary vasculature[8, 9]. These studies therefore lay foundations for understanding development of the PE and coronary vasculature from pluripotent-derived mesoderm progenitor cells. Moreover, our work provides a platform upon which to develop cell therapies for cardiac regeneration and tissue revascularization.

Methods

Culture and Differentiation of hESCs and hiPS Cells.

WA01, WA07, WA09, BG01 and BG02 hESCs and Fib-iPS4 hIPSCs[28] were adapted from mouse embryo fibroblast feeder-based culture conditions to feeder-free growth in chemically defined media (CDM) using single cell suspensions[50]. Briefly, CDM is composed of DMEM/F12 (Mediatech), 2% probumin (Bovine Serum Albumin fraction V)

biotech grade (Millipore), 1× nonessential amino acids, 50 U/mL penicillin, 50 µg/mL streptomycin, 1× trace elements A, B, C (all from Mediatech), 10 µg/mL transferrin, 0.1 mM 3-mercaptoethanol (Gibco), 50 µg/mL ascorbic acid (Sigma), 8 ng/mL bFGF (Invitrogen), 200 ng/mL LR-IGF (Sigma), 10 ng/mL Activin A (R and D Systems) and 10 ng/mL Heregulin 13 (Peprotech). Cells were passaged every 4-5 d using Accutase (Innovative Cell Technologies) to form a single cell suspension and then plated onto plates coated with 1:200 Geltrex (Invitrogen) at a cell density of $7.5 \times 10^4$ cells/cm$^2$ at 37° C. in 5% $CO_2$. Media was changed every 24 h. To differentiate hESC in Stage 1 (FIG. 62), cells were plated at a density of $5.1 \times 10^4$ cells/cm$^2$ into CDM containing 25 ng/mL rmWnt3a and 100 ng/mL rhBMP4 (R&D Systems). Cells were cultured at 37° C. in 5% $CO_2$ and media changed every 24 h for 4-6 d. CDM for Stage 2 of differentiation was supplemented with 25 ng/mL rmWnt3a, 50 ng/mL rhBMP4 with either 100 ng/ml Fgf2 or 4 µM all-trans retinoic acid (Sigma), changing media every 48 h for 10-16 d. For Stage 3 differentiation, Stage 2 cells were passaged at day 16 into CDM without Activin A, supplemented with 10 ng/mL rhVEGF-A$_{165}$ (R&D Systems). All bright field images were acquired on a Leica DMIL microscope.

Flow Cytometry, Q-PCR Analysis, Western Analysis and Immunofluorescence.

Cells were collected as single cell suspensions following harvesting with Accutase and then analyzed using a Cyan flow cytometer (Dako). Cells were blocked with species-specific serum for 30 min followed by blocking with CD16/32 (eBiosciences) for a further 15 min then, with specific antibodies shown in FIG. 81, Table 4. Immunofluorescence was performed on 4% paraformaldehyde-fixed cells in the presence of 10% donkey serum and 0.25% Triton X100 followed by visualization using 2.5% donkey serum in PBS with fluorescent conjugated secondary antibodies. Antibodies used herein are shown in FIG. 81, Table 4. DAPI (Sigma) was used to counterstain nuclei. Cells were visualized on a DM6000 B fluorescent microscope (Leica) and confocal images were performed on a LSM510 (Zeiss). mRNA was isolated using RNeasy kit (Qiagen), cDNA was made using iSCRIPT cDNA kit (BioRad) and Q-PCR was performed using TaqMan universal PCR master mix and assays on demand (Applied Biosystems) on a MyIQ (BioRad). Assays on demand are listed in FIG. 82, Table 5. Analysis of Q-PCR data was performed using a iQ5 instrument and Genex software (BioRad) and shown as Delta Delta Ct, normalized to Gapdh and referenced as a fold-change relative to hESCs (untreated). hESC lysates were prepared using RIPA buffer (50 mM Tris-HCl, pH7.5, 150 mM NaCl, 1% Nonidet P40, 0.5% sodium deoxycholate, 0.5% SDS), then resolved on a 8-10% polyacrylamide gels. Following transfer to nitrocellulose membranes (0.45 µm; BioRad), blots were probed with primary (FIG. 81, Table 4 online) followed by HRP conjugated secondary antibodies (Dako) and developed using Amersham ECL reagents (Amersham Biosciences).

In Silico Gene Expression Analysis.

Embryonic patterns of gene expression were evaluated by interrogating the GEISHA chick database http://geisha.arizona.edu[35, 36] and the mouse Genepaint database http://www.genepaint.org[37]. Details for individual entries used to establish gene expression patterns are available on request.

In Vivo Vascular Forming Assays.

Collagen plugs were generated by rapidly mixing cold HEPES (25 mM), 18 mM sodium bicarbonate, EBM-2 (Lonza, # cc-3156), 10% fetal bovine serum, human plasma fibronectin (100 µg/ml), collagen I (1.5 mg/ml), pH 7.6. 5 million hESC-derived Wt1$^+$ cells in 0.34 ml EBM-2 were added to the collagen plug mixture and transferred to a well in a 12-well plate at 37° C. for 30 mins. Polymerized plugs were overlaid with 1 ml EBM-2 and incubated overnight. Collagen plugs were bisected and subcutaneously implanted into the flanks of SCID-beige mice and harvested 21 d later for histological analysis.

Implantation and Detection of Human PE-Derived Cells.

PE aggregates were implanted into HH stage 14-16 embryos in ovo. Windows were cut into the egg shells using a Dremel tool, and a small slit was made in the vitelline membrane directly over the heart region using an electrolytically sharpened tungsten needle. One to four GFP$^+$ PE aggregates, each containing approximately 30-200 cells, were positioned between the heart and the ventral body wall under a fluorescence stereomicroscope, leaving the endogenous pro-epicardium intact. In some cases, aggregates were treated for 2-3 min with Accutase immediately prior to implantation to weaken intercellular contacts. Egg windows were sealed with transparent tape and embryos incubated for 3-6 d, after which embryos were examined under a fluorescence stereomicroscope for the localization of GFP cells. Embryos in which aggregates had remained in contact with the heart were analyzed further. The heart, adjacent body wall and organs were dissected away from the embryos in 123 mM NaCl and fixed overnight in freshly prepared 4% paraformaldehyde in PBS at 4° C. Tissue fragments were washed in PBS, dehydrated in a graded methanol series and then processed for immunodetection of GFP in intact tissue fragments or following paraffin sectioning. For whole mount analysis, endogenous peroxidases were quenched and embryos processed for visual immunodetection of GFP as described above. For sectioning, 10-12 µm sections were cut and processed for immunocytochemistry and immunohistochemistry according to standard procedures. Immunocytochemistry: following dewaxing and rehydration, antigen retrieval was performed using 0.1M glycine in PBS for 15 min. Sections were blocked in 5% normal goat serum in PBT for 30-60 min, then incubated for 2 h in a 1:500 dilution of rabbit anti-GFP (Invitrogen). Following washing in PBT, sections were incubated for 1 h with Alexa-flour conjugated Donkey anti-rabbit (Jackson ImmunoResearch Laboratories). Sections were washed in PBS and cover-slipped. Immunohistochemistry: following deparafinization and rehydration, antigen retrieval was performed using antigen retrieval buffer, high pH (Dako) at 120° C. for 20 min and cooled overnight. Sections were blocked with methanol/$H_2O_2$, avidin/biotin block (Dako) and protein block serum free (Dako). Sections were then incubated with the primary antibody at 37° C. for 2 h in a humid chamber, washed in PBS 3 times (5 min each), then incubated with the biotinylated secondary antibody (1:100 dilution, ABC Elite Kit, Vector Laboratories) in a humid chamber for 30 min at 37° C. and washed in PBS 3 times (5 min each). Finally, sections were incubated with horseradish peroxidase-streptavidin (ABC Elite kit, Vector Labs) for 15 min at RT in a humid chamber and washed in PBS 3 times (5 min each). As the last staining step, 3,3-iaminobenzidine (DAB; Vector Labs) was added to the sections and incubated at RT until a macroscopically appreciable light brown color developed in the sections (generally 30 s to 5 min) and washed in water. Sections were then counterstained with Gill's hematoxylin, dehydrated and mounted in Permount (Fisher).

Results

Efficient Differentiation of hESCs into Lateral Plate and then Splanchnic Mesoderm The pro-epicardium (PE) and epicardium play critical roles in cardiac development, homeostasis and repair. In this report, we describe the highly efficient differentiation of human pluripotent cells into vascular progenitors through a splanchnic mesoderm (Spl-m) intermediate. By marker analysis, the developmental pathway these cells follow closely resembles formation of the PE, a mesoderm-derived tissue that forms epicardium and seeds the developing heart tube with progenitors for the coronary vasculature. PE derived from pluripotent cells differentiate into smooth muscle and endothelial cells in vitro which together assemble into vascular networks. When transplanted in vivo, vascular progenitors incorporate into the host epicardium and invade the underlying myocardium. Fully invested vessels comprised of smooth muscle and endothelial cells are formed in vivo, indicating that these PE-like vascular progenitors can initiate vasculogenesis. These findings have major implications for our understanding of human cardiovascular development, for the generation of cell therapies and drug discovery.

Generation of cardiovascular lineages from pluripotent cells is one important approach towards the development of cardiac cell therapies. Although several groups have reported the differentiation of hESCs into cardiomyocytes[20, 21], the generation of other important cell types associated with heart development such as the SV and PE, has been elusive. To address this issue, we set out to establish methods for the efficient differentiation of human pluripotent cells towards PE vascular progenitor cells in chemically defined media (see FIG. 62). Data presented is for WA09 hESCs but experiments were reproduced in several hESC and iPSC lines. Since PE-derived vascular progenitors are derived after transitioning through LPM and then Spl-m intermediates[10, 11] (Stage 1 differentiation; see FIG. 62), we set out to establish culture conditions that reproduce these initial developmental steps, using recombinant growth factors with known mesoderm inducing activity[22]. As part of this specification, it was to be expected that cells would undergo an EMT and pass through a $T^+$ mesendoderm stage, reminiscent of events associated with gastrulation. The most effective factor cocktail tested was Wnt3a combined with BMP4 (FIG. 63a), both of which have well-established roles in early cardiac mesoderm specification[22, 23].

Following Wnt/BMP treatment, the epithelial architecture of pluripotent cells was lost and cells adopted a mesenchymal morphology within 24 h (FIG. 68). This was accompanied by nuclear accumulation of T, Snail and β-catenin and loss of the pluripotency markers Nanog and E-cadherin (FIG. 63b and FIG. 69). Q-PCR analysis also showed that T and MixL1 transcript levels increased 500 and 60-fold, respectively, by day 1 (FIG. 63c and data not shown). Together, these observations are consistent with the initial differentiation of pluripotent cells through a $T^+$ mesendoderm intermediate, reminiscent of events associated with primitive streak formation during early embryonic development. Shortly after this, markers characteristic of LPM (T, Isl1, FoxF1) and splanchnic mesoderm (Nkx2.5, Fgf10, Gata4, Pitx2) are up-regulated (FIG. 63b). Tbx18 transcripts also increased but with slightly delayed kinetics to that of Isl1 and Nkx2.5. An extended list of transcripts upregulated in both BG02 and WA09-derived Spl-m is shown in Table 3, FIG. 67. Western blot analysis also confirmed the transition of hESCs through LPM and then Spl-m states (FIG. 63d). T protein increased by day 1 following Wnt/BMP treatment, shortly followed by increased Isl1 and FoxF1. Immunostaining showed that ~95% of Wnt/BMP-treated hESCs were positive for Isl1, Nkx2.5 and Tbx20 within 6 days (FIG. 63b). These observations were reproducible in human iPSCs (FIG. 73).

Transcripts associated with somatic (Irx3)[24], paraxial (Foxc2, Tbx6)[25, 26] intermediate (Foxc2, Tbx6, Pax2)[25-27] and axial mesoderm (Pax3,6)[25] were not upregulated in Wnt/BMP treated cultures (FIG. 81, Table 4). Furthermore, Q-PCR analysis showed no consistent up-regulation of markers for ectoderm (Pax6, Sox1, Zic1) or primitive/definitive endoderm (AFP, HHex, Sox17, THBD; FIG. 70). We conclude that under the conditions used, Wnt/BMP treatment of hESCs results in the efficient formation of Spl-m through a LPM intermediate, at the exclusion of other lineages.

None of the gene expression changes associated with Wnt/BMP treatment are observed when pluripotent cells are maintained in normal self-renewal media (FIG. 71) or, following addition of Wnt3a alone (data not shown). Addition of BMP4 alone promoted differentiation in the absence of exogenous Wnt3a (data not shown), but addition of the Wnt antagonist Dkk1 blocked this, indicating that Wnt ligands produced by hESCs promote differentiation (FIG. 72). We routinely found however, that addition of exogenous Wnt3a promoted more uniform differentiation in conjunction with BMP4 and so was incorporated into our standard procedure. Further comments on the respective roles of Wnt3a and BMP4 are made in the Discussion. These observations indicate that the combined actions of Wnt3a and BMP4 are required for Spl-m specification from human pluripotent cells.

Figure 73:
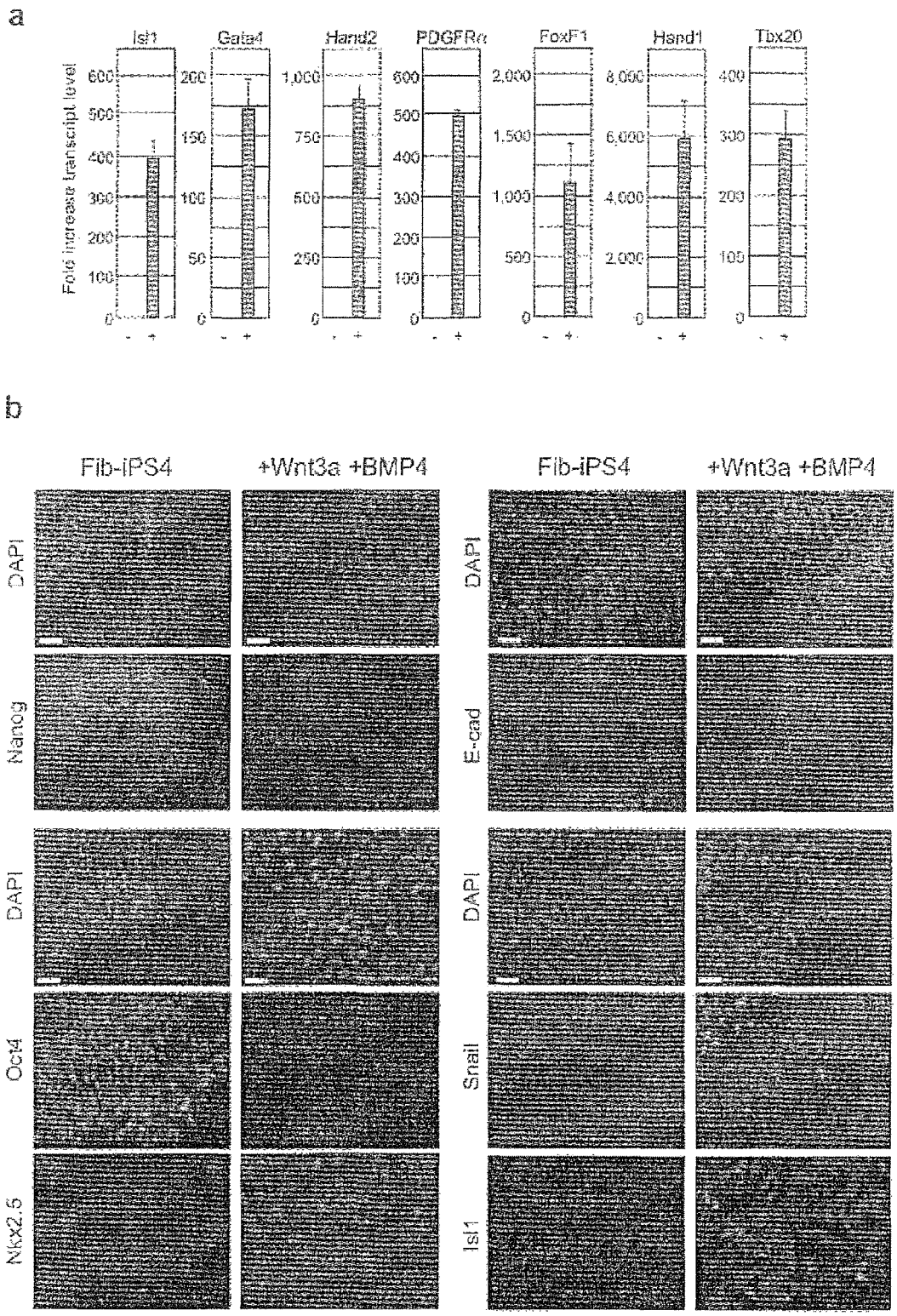

Microarray profiling identified two potential cell surface markers, PDGFRβ and CAD 11, that were validated by flow cytometry in WA09 hESCs (FIG. 63e and FIG. 73). Flow cytometry showed that ~95% of Wnt/BMP treated WA09 hESCs were Pdgfrβ$^+$. Approximately 75% of Pdgfrβ$^+$ cells were also Kdr$^+$ (Flk-1+; FIG. 63e). Pdgfrβ$^+$ cells isolated by FACS were shown to be >95% Isl1$^+$ (FIG. 63e), indicating that Pdgfrβ is a useful marker for Isl1$^+$ Spl-m. The general applicability of Wnt/BMP treatment as a method for converting other pluripotent cell lines into Spl-m was evaluated by flow cytometry, using Pdgfrβ and Kdr as markers. High efficiency generation of Pdgfrβ$^+$ Kdr Spl-m was reproduced following Wnt/BMP treatment in multiple hESC lines (BG01, BG02, WA01, WA07 and WA09) and in the human iPSC line, Fib-iPS4[28] (FIG. 74 and data not shown). The approach for generating Spl-m is therefore generally applicable to a wide range of human pluripotent cell lines.

Efficient Differentiation of hESC-Derived Spl-m to PE-Like Cells

Progenitor cells of the coronary vasculature are believed to reside in the PE and after forming the epicardium, seed the myocardium for future vessel formation. Many unanswered questions remain as to the characteristics of these progenitor cells but clearly, a better understanding of PE development will provide significant insight into this question. Lineage tracing studies in vivo indicate that PE and epicardium forms from an Isl1$^+$ Nkx2.5$^+$ progenitor[6, 18, 29]. This progenitor resides in Spl-m and transitions through a Tbx18$^+$ state in the SV before progressing to the PE[10, 11]. Only a few reports however, have addressed the sequence of events surrounding the development of PE at the molecular level and how it is specified from an Isl1$^+$ Nkx2.5$^+$ Spl-m intermediate. One clue to understanding this process comes from observations linking Fgf2-dependent Erk signaling to the formation of murine PE/epicardium[11, 30]. To determine if Fgf2 signaling could direct differentiation of Isl1$^+$ Spl-m along a pathway reminiscent of PE development (Stage 2 differentiation), Fgf2 levels were elevated to 100 ng/ml after 4 days of treatment with Wnt/BMP (FIG. 64a). This resulted in dramatic increases in transcripts expressed in PE/epicardium such as Wt1, Raldh2, Tbx18 and Tbx5 (FIG. 75). In addition to the up-regulation of PE/epicardial markers, the expression of Isl1 and Nkx2.5 diminish following Fgf2 treatment (data not shown). All-trans retinoic acid (RA), which also activates Erk signaling in many cell types[31-34], also promoted the up-regulation of PE/epicardium markers (FIG. 64b-d). Like Fgf2, RA activated Erk in Isl1+ Spl-m (FIG. 76) and was used in place of Fgf2 for further experiments. RA exposure was accompanied by diminished expression of Isl1 and Nkx2.5 mRNA (FIG. 64b). More than 90% of RA treated cells express Wt1, Raldh2 and Tbx20, indicating that highly enriched populations of Wt1+ PE-like cells are produced by this approach (FIG. 64c). The formation of these cells was recapitulated in hiPSC-derived Isl1+ Spl-m, demonstrating the general utility of this approach (FIG. 77).

To establish the specific type of Wt1+ cell being produced we asked whether the 'PE/epicardium cohort' of transcripts was associated with other types of mesothelial serosa. Consistent with published data, analysis of the GEISHA chick[35, 36] and GenePaint mouse in situ hybridization gene expression databases[37] shows that Wt1[38] and epicardin[39] are expressed in gut serosa. In contrast, Tbx18 and Tbx20 are only expressed in the PE/epicardium and so, represent markers that distinguish different types of mesothelia. Another possibility is that the mesothelial-like cell being produced is analogous to cells of the SV. This is suggested because SV arises from Spl-m and because it also expresses Tbx18[10, 11] and Tbx5[40]. This possibility is eliminated however, as cells in the SV do not express Wt1[41]. Based on the developmental lineage and patterns of gene expression described, the Wt1+ cell type produced is post-SV but, lies along the PE developmental pathway (see Discussion).

Next, we sought to characterize the in vitro properties of hESC-derived Wt1+ cells in relation to known characteristics of primary PE/epicardium explants and transformed cell lines derived from epicardium. In vitro, invasiveness of the epicardium is commonly evaluated by plating on a collagen matrix and assaying for cell migration as a read-out for an EMT[42]. To establish if hESC-derived Wt1+ cells behave in a similar manner to explanted PE/epicardium, Wt1+ cells were harvested as single cell suspensions, cultured for a further 2 d as aggregates in suspension, plated onto collagen 1-coated dishes and allowed to adhere. As is seen with primary epicardial explants[38], plated Wt1+ cells form an epithelial core that transitions to a migratory, mesenchymal phenotype at the edges (FIG. 64e). Migratory cells down-regulate the epithelial markers cytokeratin, ZO-1, membrane associated β-catenin and E-cadherin but up-regulated the mesenchymal marker, vimentin (FIG. 64e). This is consistent with the plated cells undergoing an EMT in a manner indistinguishable from how a primary epicardium and mesothelial serosal lines behave in similar assays[38, 42, 43].

hESC-Derived PE Differentiates into Smooth Muscle and Endothelial Cells In Vitro The analysis so far indicates that Wt1+ cells being produced lie along the PE pathway, however their vascular forming properties have not been addressed. Lineage tracing studies indicate that progenitor cells in the PE and epicardium contribute at various extents to the coronary vasculature[12-15]. Vascular forming progenitors with a disposition for smooth muscle formation have also been identified in gut mesothelium[44]. To establish the capacity of hESC-derived Wt1+ PE to generate vascular lineages, cells were plated in defined media supplemented with VEGF (Stage 3 differentiation), because of its known ability to promote endothelial differentiation (FIG. 65a). Over 10 days, cells transitioned to a mixed population that were ~80-90% positive for SMA and calponin, indicative of smooth muscle cells (FIG. 64b, FIG. 78). The residual 10-20% of cells stained positive for CD31 and VE-cadherin, indicative of endothelial cells (FIG. 65b). CD31+ VE-cadherin+ cells show clear intercalated membrane staining characteristic of inter-endothelial cadherent junctions. When VEGF-treated cultures were starved of fresh factors, following the formation of smooth muscle and endothelial cells (see FIG. 65a), networks of vessel-like structures formed over the following 7 days (FIG. 65c). hESC-derived Wt1+ cells therefore efficiently differentiate into vascular lineages and form vascular-like structures in vitro.

Vascular Potential of hESC-Derived Wt1+ PE Cells In Vivo

Pro-epicardium in vivo spreads over the heart tube forming an outer epicardial layer and in conjunction with this, some cells undergo an EMT resulting in the invasion of underlying myocardium[9]. To evaluate the invasive properties of hESC-derived Wt1+ cells and their ability to integrate into the epicardial layer cell aggregates were implanted into HH stage 14-16 chick embryos, immediately adjacent to the heart and in the vicinity of the endogenous PE (FIG. 66ai). This implantation stage corresponds to when the heart begins to loop and when the epicardium forms in the chick. The chick was used as model of choice because the mouse embryo can not be used for this type of experimentation due to technical barriers relating to embryo accessibility and size.

Embryos containing implanted Wt1+ cells marked with GFP were incubated for 3-6 d and following visual inspection, approximately half (N=53) remained in contact with the heart. In most embryos, several patches of GFP cells were observed on the heart surface, indicative of integration into the host epicardium (FIG. 66aii-iii). In some regions of the heart, extensive invasion of the underlying myocardium by GFP cells was also observed (FIG. 66b). Transplanted cells retained Raldh2 expression even as they invaded the underlying myocardium (FIG. 66c). These properties are consistent with the transplanted cells being PE-like.

In order to assess the vasculogenic activity of Wt1+ cells in vivo we utilized a collagen-based tube-forming plug assay[45]. hESC-derived Wt1+ cells were mixed into collagen I plugs and surgically implanted into the flanks of SCID-beige mice. Each plug was bisected and half was implanted into one flank and a control plug (no cells) was implanted into the opposite flank. After 21 d plugs were recovered, fixed and mounted in paraffin for immunohistochemistry. Collagen I was used in plug assays as it has been demonstrated to act as a barrier preventing the infiltration of host cells into plugs compared to that of the more traditional Matrigel[46]. Harvested plugs that did not receive donor cells were clearly smaller than those which received cells (FIG. 79). Moreover, sections from Hematoxylin-Eosin (H&E)-stained control plugs contained fewer cells and these were limited to invaginations and folds of the gel and were excluded from the gelatinized collagen. In contrast, collagen I plugs mixed with Wt1+ cells were all highly cellularized (8/8 mice) and contained many vessel-like structures throughout the collagen matrix (FIG. 79).

Tissue sections were stained for von Willebrand Factor (vWF) to identify endothelial cells in vascular structures. This analysis showed the presence of vWF cells within lumenized, vascular structures containing erythrocytes, indicative of connectivity with the host vasculature (FIG. 66d). Around 75% of these vessels appeared to be surrounded by a pericytic layer (FIG. 66d), subsequently identified by double staining as smooth muscle actin positive (Sma+) smooth muscle cells (FIG. 66e-g). These observations demonstrate the formation of not only capillaries (vessels lacking smooth muscle), but also fully invested vessels (containing smooth muscle and endothelial cells). In order to confirm the source of vessel-associated cells as being of human origin, fluorescent in situ hybridization (FISH) was performed using a human centromeric probe. This analysis confirms that cells contributing to the endothelial and smooth muscle layer in these tubes were of human origin (FIG. 66g,h). In conclusion, hESC-derived Wt1+ cells have high vasculogenic potential in vivo and assemble into fully invested vessels.

DISCUSSION

In these examples and in this application, the inventors describe efficient methods for the conversion of human pluripotent cells into Spl-m and then along a pathway reminiscent of SV and PE development. In terms of its molecular profile and vasculogenic potential, the Wt1+ cell type being produced is most closely related to coronary angioblasts associated with the PE.

Wnt3a and BMP4 were used to specify pluripotent cells into Isl1+ Spl-m. These factors have been implicated previously in early mesoderm induction[22] but this is the first report where pluripotent cells have been efficiently converted into a highly enriched Isl1+ Nkx2.5+ Spl-m population. BMP4 was essential for this differentiation step (Stage 1) and although exogenous Wnt3a was not required, it improved differentiation efficiencies (data not shown). Addition of Dkk, a Wnt antagonist, blocked BMP-dependent differentiation over the time course assayed, even in the absence of exogenous Wnt3a. This can be explained by the ability of hESCs to produce and secrete Wnts[47]. In the absence of exogenous Wnt, there is likely to be sufficient Wnt made by hESCs to synergize with BMP4 to promote mesoderm differentiation.

Fgf2 is thought to play a role in promoting differentiation of Tbx18+ progenitors in the SV and to promote formation of the PE/epicardium[11, 30]. Addition of Fgf2 to hESC-derived Isl1+ Spl-m promoted changes in gene expression that were consistent with formation of PE (Stage 2 differentiation). We were able to reproduce the latter developmental transition seen following Fgf2 addition using retinoic acid. Mechanistically, retinoic acid is known to be a potent activator of Mek/Erk signaling, a pathway required for Fgf2 dependent formation of PE/epicardium during embryonic development[11, 30]. The signaling pathways required for PE formation in the hESC differentiation model (Stage 2) therefore seem to be similar to that which occurs during development. The Tbx18+ progenitor arising from Isl1+ Spl-m would be anticipated to have the capacity to produce inflow tract cardiomyocytes. In this case, Tbx18 progenitors need to be exposed to BMP signals in the absence of high Fgf2/Erk signaling[11, 30] We have not tested the ability of hESC-Tbx18+ cells to generate myocytes but this will be the focus of future work.

Stage 3 of differentiation involved treatment with VEGF, a known vascular inducing factor[9, 48]. Once smooth muscle and endothelial cells were formed from hESC-derived Wt1+ cells, they self-assembled into vessels in vitro. The approach of factor deprivation has been used in other contexts to generate endothelial cell-containing vessels but the mechanism underpinning vessel formation in this context is not understood. Although PE contributes to smooth muscle and endothelial cells in the coronary vasculature, the characteristics of progenitors within the PE are not well-defined[13, 48,] [49]. A major question relates to whether there is a common bipotent progenitor in the PE or epicardium that contributes to all coronary vascular lineages? Lineage analysis in chick and quail for example, has failed to identify a common progenitor in the PE that generates all lineages of the coronary vasculature. Instead, a common progenitor has been proposed that segregates into smooth muscle and endothelial potential sometime before the PE contacts the heart[9, 13]. While transplant experiments have unambiguously located smooth muscle progenitors within the PE, endothelial potential seems to be restricted to the most proximal portion of the PE (dorsal mesocardium), adjacent to the liver. The exact identity of the common progenitor that gives rise to smooth muscle and endothelial progenitors has not been fully established in our studies but we propose that it lies along the Stage 2 phase of differentiation that we describe within this report (FIG. 62). We argue this because Wt1+ cells give rise to smooth muscle and endothelial cells, which assemble into invested vessels. Second, the developmental pathway we describe is consistent with formation of coronary vascular progenitors in the context of PE development. What is unclear however, is whether the hESC-derived Wt1+ cells being produced are bipotent or, if they have already segregated into smooth muscle and endothelial lineages, while retaining a similar marker profile. Our data indicates that these progenitors can not be discriminated using currently used markers and that further experiments will be required to address this question.

Throughout this report, we have argued that hESC-derived Wt1+ cells follow a pathway closely resembling that of PE development in terms of marker expression (Stage 2 differentiation). PE and epicardium express a cohort of transcription factors that are often used for their identification in the embryo. Some of these markers such as Wt1 and epicardin, are also expressed in other vasculogenic mesothelial serosa. In general, these mesothelial cells only contribute to smooth muscle and not endothelium (Wilm et al. 2005). By careful interrogation of published expression patterns included in the GEISHA and Genepaint databases, we are able to define a set of characteristic genes expressed in the PE/epicardium but not in other mesothelial serosa. Two developmentally regulated markers, Tbx18 and Tbx20, are expressed in PE/epicardium and in hESC-derived Wt1+ cells, but not in gut serosa. The molecular profile that we describe (Wt1+, Tbx18+, Tbx20+, Tbx5+, Raldh2+ and epicardin+) can therefore be used to discriminate between different Wt1+ mesothelia of different origins. The signaling pathways used to promote Stage 2 differentiation from Spl-m is analogous to what is known about PE development in the embryo. For example, Fgf2 is an inducer of PE development in the sinus venosus[11, 30]. In this report, we used Fgf2 or RA, to promote differentiation which gives rise to a pattern of gene expression characteristic of PE development. Other signaling pathways are likely to be required for PE formation but currently these await detailed characterization. One known determinant in the embryo is the liver bud[27] but it is unclear how signaling from this impacts on the developing pro-epicardial organ. We anticipate that the hESC model we have developed will be a useful tool to address this question.

The ability of hESC-derived Wt1+ PE cells to generate fully invested vessels, comprising smooth muscle and endothelial cells, makes them an exciting option for repair and revascularization of damaged tissue, including the heart. The invasive nature of these cells opens up many options in terms of how these cells could be used to revascularize damaged tissue.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set forth in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified. Examples which are described in the present or future tense generally are prophetic examples.

REFERENCES

1. Abu-Issa, R. & Kirby, M. L. Heart field: from mesoderm to heart tube. *Annu Rev Cell Dev Biol* 23, 45-68 (2007).
2. Rossant, J. & Tam, P. P. Emerging asymmetry and embryonic patterning in early mouse development. *Dev Cell* 7, 155-164 (2004).
3. Tam, P. P., Parameswaran, M., Kinder, S. J. & Weinberger, R. P. The allocation of epiblast cells to the embryonic heart and other mesodermal lineages: the role of ingression and tissue movement during gastrulation. *Development* 124, 1631-1642 (1997).
4. Buckingham, M., Meilhac, S. & Zaffran, S. Building the mammalian heart from two sources of myocardial cells. *Nat Rev Genet* 6, 826-835 (2005).
5. Kelly, R. G. & Buckingham, M. E. The anterior heart-forming field: voyage to the arterial pole of the heart. *Trends Genet* 18, 210-216 (2002).
6. Yang, L. et al. Isl1Cre reveals a common Bmp pathway in heart and limb development. *Development* 133, 1575-1585 (2006).
7. Laugwitz, K. L., Moretti, A., Caron, L., Nakano, A. & Chien, K. R. Islet1 cardiovascular progenitors: a single source for heart lineages? *Development* 135, 193-205 (2008).
8. Manner, J., Perez-Pomares, J. M., Macias, D. & Munoz-Chapuli, R. The origin, formation and developmental significance of the epicardium: a review. *Cells Tissues Organs* 169, 89-103 (2001).
9. Olivey, H. E., Compton, L. A. & Barnett, J. V. Coronary vessel development: the epicardium delivers. *Trends Cardiovasc Med* 14, 247-251 (2004).
10. Mommersteeg, M. T. et al. The sinus venosus progenitors separate and diversify from the first and second heart fields early in development. *Cardiovasc Res* 87, 92-101 (2010).
11. van Wijk, B. et al. Epicardium and myocardium separate from a common precursor pool by crosstalk between bone morphogenetic protein- and fibroblast growth factor-signaling pathways. *Circ Res* 105, 431-441 (2009).
12. Dettman, R. W., Denetclaw, W., Jr., Ordahl, C. P. & Bristow, J. Common epicardial origin of coronary vascular smooth muscle, perivascular fibroblasts, and intermyocardial fibroblasts in the avian heart. *Dev Biol* 193, 169-181 (1998).
13. Mikawa, T. & Fischman, D. A. Retroviral analysis of cardiac morphogenesis: discontinuous formation of coronary vessels. *Proc Natl Acad Sci USA* 89, 9504-9508 (1992).
14. Mikawa, T. & Gourdie, R. G. Pericardial mesoderm generates a population of coronary smooth muscle cells migrating into the heart along with ingrowth of the epicardial organ. *Dev Biol* 174, 221-232 (1996).
15. Perez-Pomares, J. M. et al. Experimental studies on the spatiotemporal expression of WT1 and RALDH2 in the embryonic avian heart: a model for the regulation of myocardial and valvuloseptal development by epicardially derived cells (EPDCs). *Dev Biol* 247, 307-326 (2002).
16. Cai, C. L. et al. A myocardial lineage derives from Tbx18 epicardial cells. *Nature* 454, 104-108 (2008).
17. Limana, F. et al. Identification of myocardial and vascular precursor cells in human and mouse epicardium. *Circ Res* 101, 1255-1265 (2007).
18. Zhou, B. et al. Epicardial progenitors contribute to the cardiomyocyte lineage in the developing heart. *Nature* 454, 109-113 (2008).
19. Christoffels, V. M. et al. Tbx18 and the fate of epicardial progenitors. *Nature* 458, E8-9; discussion E9-10 (2009).
20. Laflamme, M. A. et al. Cardiomyocytes derived from human embryonic stem cells in pro-survival factors enhance function of infarcted rat hearts. *Nat Biotechnol* 25, 1015-1024 (2007).
21. Yang, L. et al. Human cardiovascular progenitor cells develop from a KDR+ embryonic-stem-cell-derived population. *Nature* 453, 524-528 (2008).
22. Lindsley, R. C., Gill, J. G., Kyba, M., Murphy, T. L. & Murphy, K. M. Canonical Wnt signaling is required for development of embryonic stem cell-derived mesoderm. *Development* 133, 3787-3796 (2006).
23. van Wijk, B., Moorman, A. F. & van den Hoff, M. J. Role of bone morphogenetic proteins in cardiac differentiation. *Cardiovasc Res* 74, 244-255 (2007).
24. Mahlapuu, M., Ormestad, M., Enerback, S. & Carlsson, P. The forkhead transcription factor Foxf1 is required for differentiation of extra-embryonic and lateral plate mesoderm. *Development* 128, 155-166 (2001).
25. Sakurai, H., Okawa, Y., Inami, Y., Nishio, N. & Isobe, K. Paraxial mesodermal progenitors derived from mouse embryonic stem cells contribute to muscle regeneration via differentiation into muscle satellite cells. *Stem Cells* 26, 1865-1873 (2008).
26. Wilm, B., James, R. G., Schultheiss, T. M. & Hogan, B. L. The forkhead genes, Foxc1 and Foxc2, regulate paraxial versus intermediate mesoderm cell fate. *Dev Biol* 271, 176-189 (2004).
27. Ishii, Y., Langberg, J. D., Hurtado, R., Lee, S. & Mikawa, T. Induction of proepicardial marker gene expression by the liver bud. *Development* 134, 3627-3637 (2007).
28. Park, I. H. et al. Reprogramming of human somatic cells to pluripotency with defined factors. *Nature* 451, 141-146 (2008).
29. Zhou, B., von Gise, A., Ma, Q., Rivera-Feliciano, J. & Pu, W. T. Nkx2-5- and Isl1-expressing cardiac progenitors contribute to proepicardium. *Biochem Biophys Res Commun* 375, 450-453 (2008).
30. Kruithof, B. P. et al. BMP and FGF regulate the differentiation of multipotential pericardial mesoderm into the myocardial or epicardial lineage. *Dev Biol* 295, 507-522 (2006).

31. Kampmann, E. & Mey, J. Retinoic acid enhances Erk phosphorylation in the chick retina. *Neurosci Lett* 426, 18-22 (2007).
32. Li, Z., Theus, M. H. & Wei, L. Role of ERK 1/2 signaling in neuronal differentiation of cultured embryonic stem cells. *Dev Growth Differ* 48, 513-523 (2006).
33. Lu, J. et al. All-trans retinoic acid promotes neural lineage entry by pluripotent embryonic stem cells via multiple pathways. *BMC Cell Biol* 10, 57 (2009).
34. Smith, J. et al. Retinoic acid induces nuclear accumulation of Raf1 during differentiation of HL-60 cells. *Exp Cell Res* 315, 2241-2248 (2009).
35. Bell, G. W., Yatskievych, T. A. & Antin, P. B. GEISHA, a whole-mount in situ hybridization gene expression screen in chicken embryos. *Dev Dyn* 229, 677-687 (2004).
36. Darnell, D. K. et al. GEISHA: an in situ hybridization gene expression resource for the chicken embryo. *Cytogenet Genome Res* 117, 30-35 (2007).
37. Visel, A., Thaller, C. & Eichele, G. GenePaint.org: an atlas of gene expression patterns in the mouse embryo. *Nucleic Acids Res* 32, D552-556 (2004).
38. Kawaguchi, M., Bader, D. M. & Wilm, B. Serosal mesothelium retains vasculogenic potential. *Dev Dyn* 236, 2973-2979 (2007).
39. Hidai, H., Bardales, R., Goodwin, R., Quertermous, T. & Quertermous, E. E. Cloning of capsulin, a basic helix-loop-helix factor expressed in progenitor cells of the pericardium and the coronary arteries. *Mech Dev* 73, 33-43 (1998).
40. Hatcher, C. J. et al. A role for Tbx5 in proepicardial cell migration during cardiogenesis. *Physiol Genomics* 18, 129-140 (2004).
41. Norden, J. et al. Wt1 and retinoic acid signaling in the subcoelomic mesenchyme control the development of the pleuropericardial membranes and the sinus horns. *Circ Res* 106, 1212-1220 (2010).
42. Guadix, J. A., Carmona, R., Munoz-Chapuli, R. & Perez-Pomares, J. M. In vivo and in vitro analysis of the vasculogenic potential of avian proepicardial and epicardial cells. *Dev Dyn* 235, 1014-1026 (2006).
43. van Tuyn, J. et al. Epicardial cells of human adults can undergo an epithelial-to-mesenchymal transition and obtain characteristics of smooth muscle cells in vitro. *Stem Cells* 25, 271-278 (2007).
44. Wilm, B., Ipenberg, A., Hastie, N. D., Burch, J. B. & Bader, D. M. The serosal mesothelium is a major source of smooth muscle cells of the gut vasculature. *Development* 132, 5317-5328 (2005).
45. Montesano, R., Orci, L. & Vassalli, P. In vitro rapid organization of endothelial cells into capillary-like networks is promoted by collagen matrices. *J Cell Biol* 97, 1648-1652 (1983).
46. Schechner, J. S. et al. In vivo formation of complex microvessels lined by human endothelial cells in an immunodeficient mouse. *Proc Natl Acad Sci USA* 97, 9191-9196 (2000).
47. Paige, S. L. et al. Endogenous Wnt/beta-catenin signaling is required for cardiac differentiation in human embryonic stem cells. *PLoS One* 5, e11134 (2010).
48. Perez-Pomares, J. M. et al. Origin of coronary endothelial cells from epicardial mesothelium in avian embryos. *Int J Dev Biol* 46, 1005-1013 (2002).
49. Poelmann, R. E., Gittenberger-de Groot, A. C., Mentink, M. M., Bokenkamp, R. & Hogers, B. Development of the cardiac coronary vascular endothelium, studied with anti-endothelial antibodies, in chicken-quail chimeras. *Circ Res* 73, 559-568 (1993).
50. Wang, L. et al. Self-renewal of human embryonic stem cells requires insulin-like growth factor-1 receptor and ERBB2 receptor signaling. *Blood* 110, 4111-4119 (2007).

The invention claimed is:

1. A method of producing a population of human epicardial pluripotent cells (EPCs) from human ISL1+ multipotent progenitor cells (IMPs) comprising providing a population of human IMPs produced from differentiating human pluripotent stem cells; exposing said population of IMPs in a differentiation media to an effective amount of Wnt3a, BMP4 and retinoic acid to produce a population of human EPCs; and optionally, isolating said human EPCs.

2. The method according to claim 1 wherein said IMPs are produced from human embryonic stem cells (hESCs).

3. The method according to claim 1 wherein said IMPs are produced from human induced pluripotent stem cells (hiPSCs).

* * * * *